US012790290B2

(12) United States Patent
Jiang et al.

(10) Patent No.: US 12,790,290 B2
(45) Date of Patent: Nov. 10, 2026

(54) DITERPENOID COMPOUNDS THAT ACT ON PROTEIN KINASE C (PKC)

(71) Applicant: K-Gen, Inc., Burlingame, CA (US)

(72) Inventors: Chun Jiang, Hillsborough, CA (US); Ruihong Chen, Burlingame, CA (US)

(73) Assignee: K-GEN THERAPEUTICS INC., San Mateo, CA (US)

( * ) Notice: Subject to any disclaimer, the term of this patent is extended or adjusted under 35 U.S.C. 154(b) by 1202 days.

(21) Appl. No.: 17/763,611

(22) PCT Filed: Sep. 24, 2020

(86) PCT No.: PCT/US2020/052545

§ 371 (c)(1),
(2) Date: Mar. 24, 2022

(87) PCT Pub. No.: WO2021/062030

PCT Pub. Date: Apr. 1, 2021

(65) Prior Publication Data

US 2022/0411362 A1 Dec. 29, 2022

Related U.S. Application Data

(60) Provisional application No. 62/905,253, filed on Sep. 24, 2019.

(51) Int. Cl.

| | |
|---|---|
| ***A61P 11/00*** | (2006.01) |
| ***A61P 35/00*** | (2006.01) |
| ***A61P 35/02*** | (2006.01) |
| ***C07C 49/727*** | (2006.01) |
| ***C07C 69/21*** | (2006.01) |
| ***C07C 69/33*** | (2006.01) |
| ***C07C 69/34*** | (2006.01) |
| ***C07C 69/587*** | (2006.01) |
| ***C07C 69/608*** | (2006.01) |
| ***C07C 69/612*** | (2006.01) |
| ***C07C 69/67*** | (2006.01) |
| ***C07C 69/732*** | (2006.01) |
| ***C07C 69/75*** | (2006.01) |
| ***C07C 69/757*** | (2006.01) |
| ***C07C 219/12*** | (2006.01) |
| ***C07C 219/22*** | (2006.01) |
| ***C07C 229/08*** | (2006.01) |
| ***C07C 229/28*** | (2006.01) |
| ***C07C 229/34*** | (2006.01) |
| ***C07C 229/36*** | (2006.01) |
| ***C07C 317/48*** | (2006.01) |
| ***C07C 321/14*** | (2006.01) |
| ***C07C 323/57*** | (2006.01) |

(Continued)

(52) U.S. Cl.

CPC ............ *C07C 229/36* (2013.01); *A61P 11/00* (2018.01); *A61P 35/00* (2018.01); *A61P 35/02* (2018.01); *C07C 49/727* (2013.01); *C07C 69/21* (2013.01); *C07C 69/608* (2013.01); *C07C 69/75* (2013.01); *C07C 69/757* (2013.01); *C07C 229/34* (2013.01); *C07C 317/48* (2013.01); *C07C 321/14* (2013.01); *C07D 205/12* (2013.01); *C07D 209/20* (2013.01); *C07D 213/55* (2013.01); *C07D 231/12* (2013.01); *C07D 263/32* (2013.01); *C07D 277/30* (2013.01); *C07D 303/14* (2013.01); *C07D 471/04* (2013.01); *C07C 2603/40* (2017.05)

(58) Field of Classification Search

CPC ........... A61P 11/00; A61P 35/00; A61P 35/02; C07C 49/727; C07C 69/21; C07C 69/608; C07C 69/75; C07C 69/757; C07C 229/34; C07C 317/48; C07C 321/14; C07C 2603/40; C07C 69/33; C07C 229/08; C07C 229/28; C07C 323/58; C07C 2601/02; C07C 2601/04; C07C 2601/10; C07C 2601/14; C07C 2602/08; C07C 2603/74; C07C 69/34; C07C 69/587; C07C 69/612; C07C 69/732; C07C 69/67; C07C 2601/08; C07C 2603/08; C07C 219/12; C07C 219/22; C07C 323/57; C07C 49/77; C07C 229/36; C07D 205/12; C07D 209/20; C07D 213/55; C07D 231/12; C07D 263/32; C07D 277/30; C07D 303/14; C07D 471/04; C07K 5/06026; C07K 5/06043; C07K 5/06052; C07K 5/0804

See application file for complete search history.

(56) References Cited

U.S. PATENT DOCUMENTS

| | | | |
|---|---|---|---|
| 2011/0014699 | A1 | 1/2011 | Wender |
| 2014/0315990 | A1 | 10/2014 | Alkon et al. |

(Continued)

FOREIGN PATENT DOCUMENTS

| | | | |
|---|---|---|---|
| WO | 2017156350 | A1 | 9/2017 |

OTHER PUBLICATIONS

"Photoaffinity labeling of PKC with a phorbol derivative: Importance of the 13-acyl group in phorbol ester-PKC interaction" M. Sodeoka K. Uotsu, M. Shibasaki Tetrahedron Letters, vol. 36, and No. 48, pp. 4795-4798 (Year: 1995).*

(Continued)

*Primary Examiner* — Valerie Rodriguez-Garcia
*Assistant Examiner* — Sophia P Hirakis
(74) *Attorney, Agent, or Firm* — Susan J. Myers Fitch

(57) ABSTRACT

This present disclosure relates to protein kinase C (PKC) modulating compounds, methods of treating a subject with cancer using the compounds, and combination treatments with a second therapeutic agent.

35 Claims, 11 Drawing Sheets

(51) Int. Cl.

| | |
|---|---|
| ***C07C 323/58*** | (2006.01) |
| ***C07D 205/12*** | (2006.01) |
| ***C07D 209/20*** | (2006.01) |
| ***C07D 213/55*** | (2006.01) |
| ***C07D 231/12*** | (2006.01) |
| ***C07D 263/32*** | (2006.01) |
| ***C07D 277/30*** | (2006.01) |
| ***C07D 303/14*** | (2006.01) |
| ***C07D 471/04*** | (2006.01) |

(56) References Cited

U.S. PATENT DOCUMENTS

2018/0311209 A1 11/2018 Alkon
2024/0197666 A1* 6/2024 Jiang ..................... C07C 69/635

OTHER PUBLICATIONS

"Bioisosterism: A Rational Approach in Drug Design" GS Patani, EJ LaVoie. Chem Rev vol. 96, Issue 8, pp. 3147-3176 (Year: 1996).*
"Photoaffinity labeling of PKC with a phorbol derivative: Importance of the 13-acyl group in phorbol ester-PKC interaction" M Sodeoka, K Uotsu, M Shibasaki Tetrahedron Letters vol. 36, Issue 48, pp. 8795-8798 (Year: 1995).*
Irie, K. et al., Synthesis and Characterization of New Photolabile Phorbol Esters for Affinity Labeling of Protein Kinase C. J.Organic Chem. Mar. 22, 1996, 61(6):2164-2173. Scheme 1; compound 8b.
Koichiro Uotsu, Mikiko Sodeoka and Masakatsu Shibasaki. (1998), Bioorganic & Medicinal Chemistry 6(7):1117-1126.Scheme 1: compound 4.
PubChem CID 58108372 created on Aug. 19, 2012; modified Nov. 21, 2020 (8 pages).

* cited by examiner

DITERPENOID COMPOUNDS THAT ACT ON PROTEIN KINASE C (PKC)

1. CROSS-REFERENCE TO RELATED APPLICATIONS

This application claims the benefit under 35 U.S.C. § 119(e) of U.S. Provisional Application No. 62/905,253, filed Sep. 24, 2019, the contents of which are incorporated herein in their entireties by reference thereto.

2. BACKGROUND

Diterpenoid Protein Kinase C (PKC) modulating compounds display anti-cancer and cytotoxic activities. Most studied of these compounds are tigliane diterpenoids, such as phorbol esters and prostratin. The biological effects of these compounds are thought to be mediated by transactivation, translocation and suppression of PKC enzymes, which play important roles in regulating signaling pathways that regulate or modulate cellular structure and gene expression.

Association of PKC enzyme activation and its inhibitory effect on cancer cell growth is supported by studies of PKC mutations in human cancers, which found that most of the PKC mutations are loss-of function mutations (Antal et al., 2015, Cell 160:489-502). This presence of PKC loss-of-function mutations in various cancer types suggests that PKC enzymes may act as tumor suppressors. Studies with prostratin suggest that its anti-tumor effect occurs by activation of PKC enzymes that specifically target oncogene K-RAS (see Wang et al., 2015, Cell 163(5):1237-1251). A different tigliane diterpenoid compound, phorbol myristate 13-acetate (PMA) also displays inhibitory effects on tumor growth by its action on PKC enzymes but also non-PKC involved mechanisms (Bond et al., 2007, Int. J. Cancer 121:1445-1454).

In view of the therapeutic potential of diterpenoid PKC modulating compounds, it is desirable to further develop these class of compounds in applications for treating diseases and disorders capable of being affected by modulation of PKC activity.

3. SUMMARY

The present disclosure provides novel protein kinase C (PKC) modulating compounds. The compounds are diterpenoid PKC modulating compounds displaying enhanced pharmacological properties, including among others, potent PKC enzyme binding activity and anti-proliferative activity against different cancer cells. The PKC modulating compounds also have substituents that can enhance solubility and pharmacokinetic profiles. In one aspect, the compounds have the structure of formula (I):

(I)

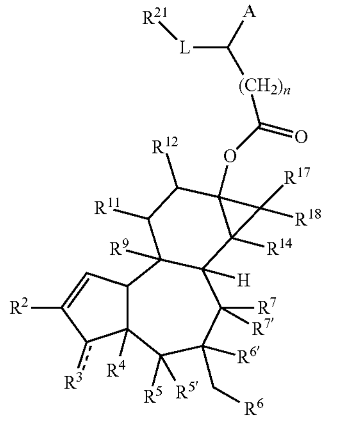

or a pharmaceutically acceptable salt, tautomer, or stereoisomer thereof;

wherein

A is —OH, —C(O)OR$^1$, or —NR$^{13}$R$^{13'}$;

R$^1$ is H or a M+ counterion;

R$^2$ is a $C_1$-$C_4$alkyl;

R$^3$ is O double bonded to the ring carbon when ( - - - ) is a bond, or —OR$^a$; wherein R$^a$ is H or —C(O)R$^{a1}$, wherein R$^{a1}$ is $C_1$-$C_6$alkyl, $C_2$-$C_6$alkenyl, $C_0$-$C_6$alkylaryl, or $C_0$-$C_6$alkylheteroaryl;

R$^4$ and R$^5$ are each independently H or —OR$^b$, wherein R$^b$ is H, $C_1$-$C_6$alkyl, $C_2$-$C_6$alkenyl, $C_0$-$C_6$alkylaryl, or $C_0$-$C_6$alkylheteroaryl;

R$^{5'}$ and R$^{6'}$ are H, or R$^{5'}$ and R$^{6'}$ form a bond or are bonded to a common O atom to form an epoxide ring as permitted by valency;

R$^6$ is OH, halo, or —OC(O)R$^c$, wherein R$^c$ is —$C_1$-$C_6$alkyl, —$C_1$-$C_6$alkyl-(NR$^{c1}$)$_2$ or —$C_1$-$C_6$alkylC(O)OR$^k$, R$^{c1}$ is H, $C_1$-$C_6$alkyl, or two R$^{c1}$ together with the N atom form a 5 to 7 membered heterocyclyl containing 1 to 3 heteroatoms selected from N, O, and S; or R$^6$ is

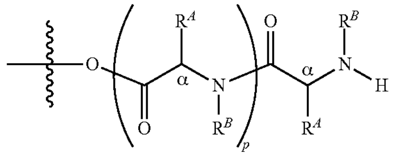

wherein, each occurrence of R$^A$ is independently selected from a side chain of a natural or non-natural amino acid, wherein each occurrence of R$^A$ is same or different;

each occurrence of R$^B$ is independently H, or R$^B$ together with the adjacent R$^A$ and the N atom to which it is attached form a heterocyclic ring of a natural or non-natural amino acid, wherein each occurrence of R$^B$ is same or different; and p is 0, 1, or 2;

R$^{6'}$ and R$^{7'}$ are H, or R$^{6'}$ and R$^{7'}$ form a bond or are bonded to a common O atom to form an epoxide ring, as permitted by valency;

R$^7$ is H or OH;

R$^9$ is OR$^e$, wherein R$^e$ is H, $C_1$-$C_6$alkyl, or aryl;

R$^{11}$ is $C_1$-$C_4$alkyl;

$R^{12}$ is H, —OH, —OC(O)$R^f$, wherein $R^f$ is $C_1$-$C_{12}$alkyl, $C_2$-$C_{12}$alkenyl, —$C_0$-$C_{12}$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_2$alkylene, or $C_2$-$C_{12}$alkenylene, wherein the $C_1$-$C_2$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclic, adamantyl, or —C(O)$OR^k$, wherein the $C_3$-$C_7$cycloalkyl, heterocyclyl, aryl, heteroaryl, spiro$C_5$-$C_{12}$ cycloalkyl, bridged bicyclic, or adamantyl is optionally substituted with 1 to 3 of $J^1$, and wherein optionally 1 to 2 carbon atoms of the spiro$C_5$-$C_{12}$cycloalkyl or bridged bicyclic is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, A is —OH. In some embodiments, A is —C(O)$OR^1$, wherein $R^1$ is H or a $M^+$ counterion. In some embodiments, A is —$NR^{13}R^{13'}$, wherein $R^{13}$ and $R^{13'}$ are each independently H or $C_1$-$C_4$alkyl.

In some embodiments, the present disclosure provides a compound of formula (II):

(II)

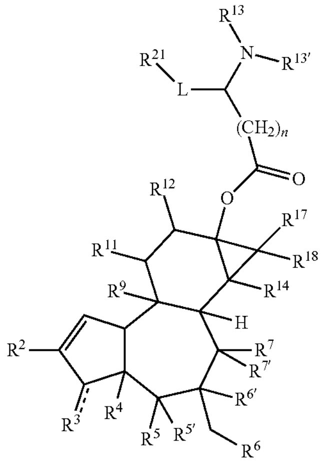

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —C(O)$R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^{5'}$ and $R^{6'}$ are H, or $R^{5'}$ and $R^{6'}$ form a bond or are bonded to a common O atom to form an epoxide ring as permitted by valency;

$R^6$ is OH, halo, or —OC(O)$R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

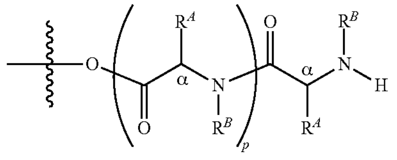

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{6'}$ and $R^{7'}$ are H, or $R^{6'}$ and $R^{7'}$ form a bond or are bonded to a common O atom to form an epoxide ring, as permitted by valency;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —OC(O)$R^f$, wherein $R^f$ is $C_1$-$C_2$alkyl, $C_2$-$C_2$alkenyl, —$C_0$-$C_{12}$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)$OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, the compound has the structure of formula (IIc):

(IIc)

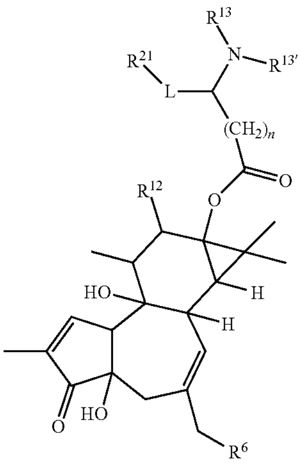

or a pharmaceutically acceptable salt, tautomer, or stereoisomer thereof;

wherein $R^6$ is OH, halo, or —OC(O)$R^c$, wherein $R^c$ is —$C_1$-$C_6$alkyl, —$C_1$-$C_6$alkyl-($NR^{c1}$)$_2$ or —$C_1$-$C_6$alkylC(O)O$R^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

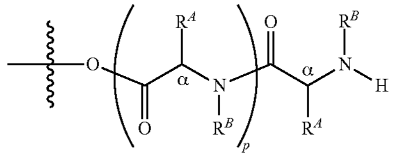

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{12}$ is H, —OH, —OC(O)$R^f$, wherein $R^f$ is $C_1$-$C_{12}$alkyl, $C_2$-$C_{12}$alkenyl, —$C_0$-$C_{12}$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{13}$ and $R^{13'}$ are each independently H or $C_1$-$C_4$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —S(O)$_2R^j$, —S$R^j$, —N($R^j$)$_2$, —Si($R^j$)$_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)O$R^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In another aspect, the present disclosure provides a compound of formula (IV):

(IV)

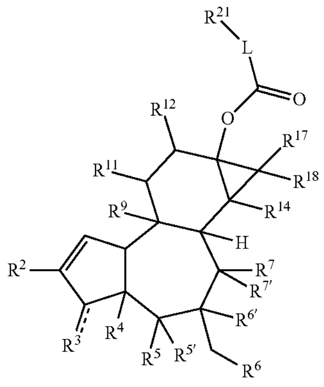

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —O$R^a$; wherein $R^a$ is H or —C(O)$R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —O$R^b$, wherein $R^B$ is H, $C_1$-$C_6$alkyl, $C_2$-$C_6$alkenyl, $C_0$-$C_6$alkylaryl, or $C_0$-$C_6$alkylheteroaryl;

$R^{5'}$ and $R^{6'}$ are H, or $R^{5'}$ and $R^{6'}$ form a bond or are bonded to a common O atom to form an epoxide ring as permitted by valency;

$R^6$ is OH, halo, or —OC(O)$R^c$, wherein $R^c$ is —$C_1$-$C_6$alkyl, —$C_1$-$C_6$alkyl-($NR^{c1}$)$_2$ or —$C_1$-$C_6$alkylC(O)O$R^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

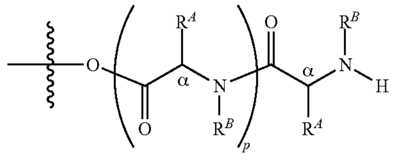

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2;

$R^{6'}$ and $R^{7'}$ are H, or $R^{6'}$ and $R^{7'}$ form a bond or are bonded to a common O atom to form an epoxide ring, as permitted by valency;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —OC(O)$R^f$, wherein $R^f$ is $C_1$-$C_{12}$alkyl, $C_2$-$C_{12}$alkenyl, —$C_0$-$C_2$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is $C_0$-$C_6$alkylarylene, $C_0$-$C_6$alkylheteroarylene, $C_0$-$C_6$alkyl$C_3$-$C_7$cycloalkylene, $C_1$-$C_6$alkylene or $C_2$-$C_{12}$alkenylene, wherein the $C_1$-$C_{12}$alkylene or $C_2$-$C_{12}$alkenylene is optionally substituted with OH or $C_1$-$C_4$alkyl; and $R^{21}$ is H, —OH, —SH, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)$OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$; and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl or, when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$J^1$ is selected from OH, CN, halo, $C_1$-$C_4$alkyl, and halo$C_1$-$C_4$alkyl; and $R^k$ is H or $M^+$ counterion.

In some embodiments, the compounds can be used in a method to activate protein kinase C, comprising contacting a mammalian cell with an effective amount of a compound disclosed herein. In some embodiments, the mammalian cell is a cancer cell.

In some embodiments, the compounds are used for treating cancer by administering a therapeutically effective amount to a subject in need thereof a compound disclosed herein.

In some embodiments, the cancer for treatment is adrenocortical cancer, anal cancer, biliary cancer, bladder cancer, bone cancer, brain cancer, breast cancer, cervical cancer, colon cancer, endometrial cancer, esophageal cancer, head and neck cancer, intestinal cancer, liver cancer, lung cancer, oral cancer, ovarian cancer, pancreatic cancer, renal cancer, prostate cancer, salivary gland cancer, skin cancer, stomach cancer, testicular cancer, throat cancer, thyroid cancer, uterine cancer, vaginal cancer, sarcoma, or soft tissue carcinomas.

In some embodiments, the cancer for treatment is a hematological cancer, such as leukemia or lymphoma. In some embodiments, the hematological cancer is lymphoblastic leukemia (ALL), acute myeloid leukemia (AML), lymphoma (e.g., Hodgkin's lymphoma, Non-Hodgkin's lymphoma, Burkitt's lymphoma), chronic lymphocytic leukemia (CLL), chronic myelogenous leukemia (CML), Hairy Cell chronic myelogenous leukemia (CML), and multiple myeloma.

4. BRIEF DESCRIPTION OF THE DRAWINGS

5. DETAILED DESCRIPTION

Figure 1:
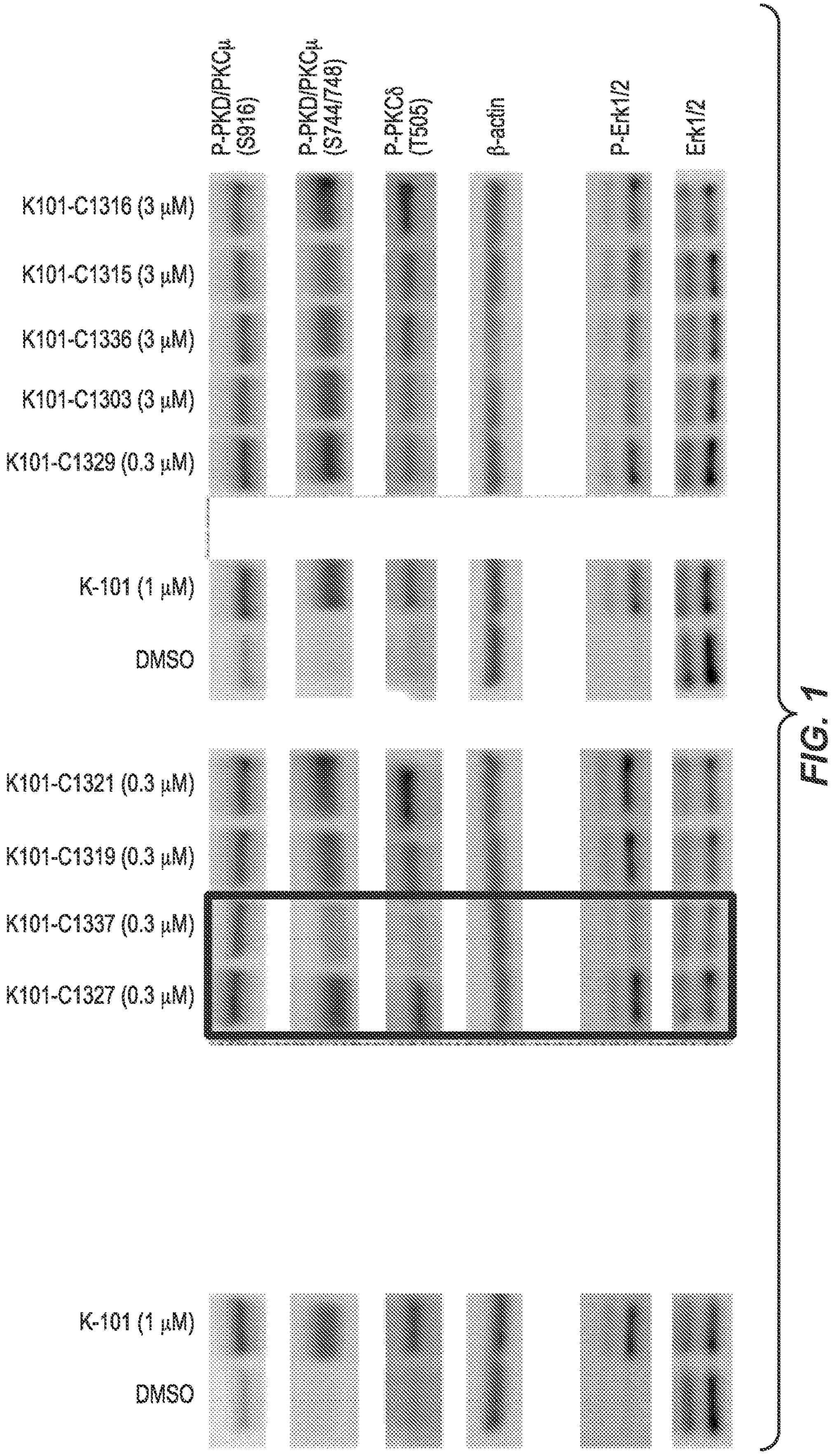
FIG. 1 shows PKC activation in A549 non-small cell lung cancer cells by diterpenoid compounds as assessed by measuring levels of phosphorylated PKC (p-PKC) and phosphorylated ERK1/2 proteins (p-ERK1/2).
Figure 2:
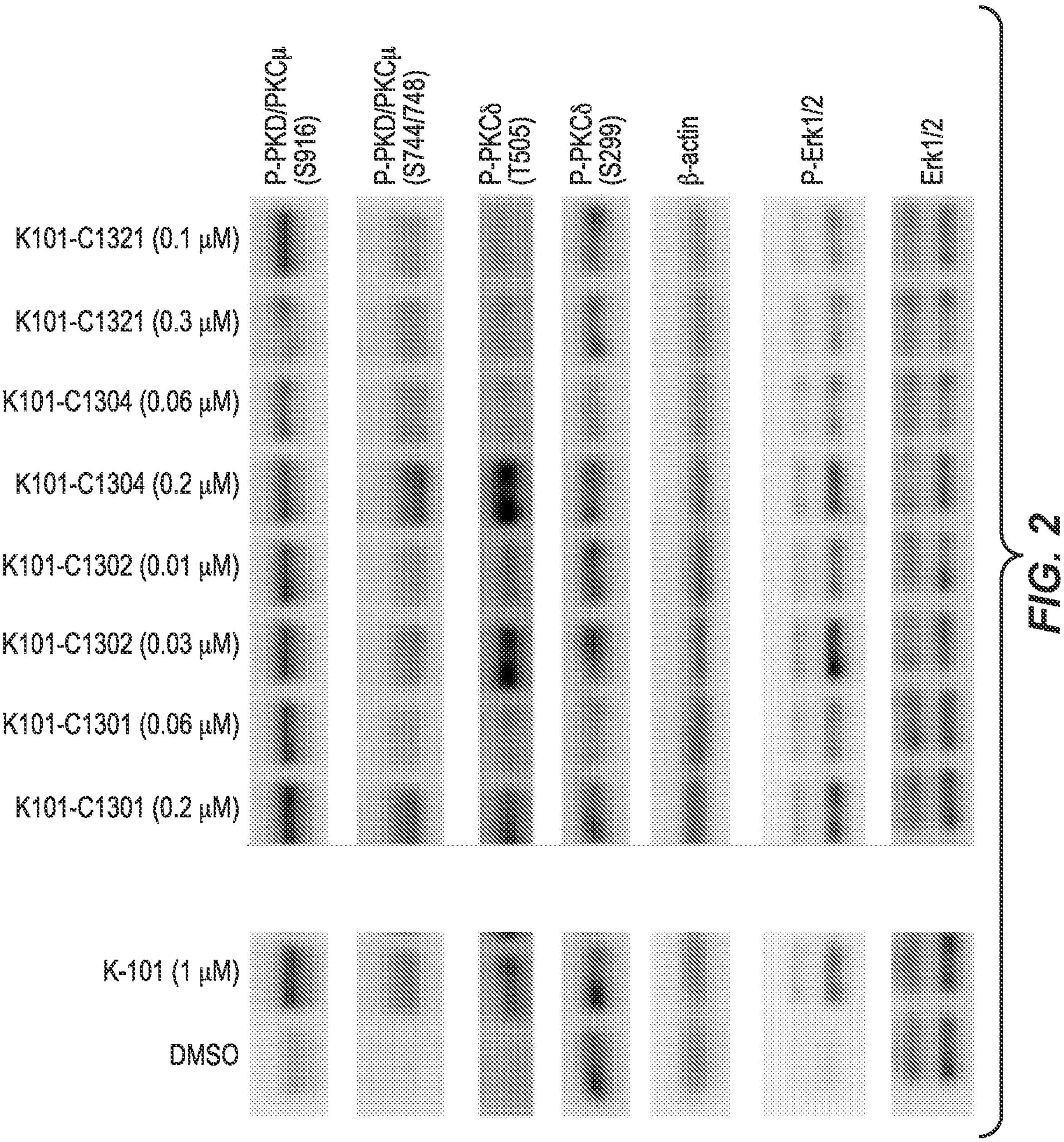
FIG. 2 shows PKC activation in A549 non-small cell lung cancer cells by diterpenoid compounds as assessed by measuring levels of phosphorylated PKC (p-PKC) and phosphorylated ERK1/2 proteins (p-ERK1/2).
Figure 3:
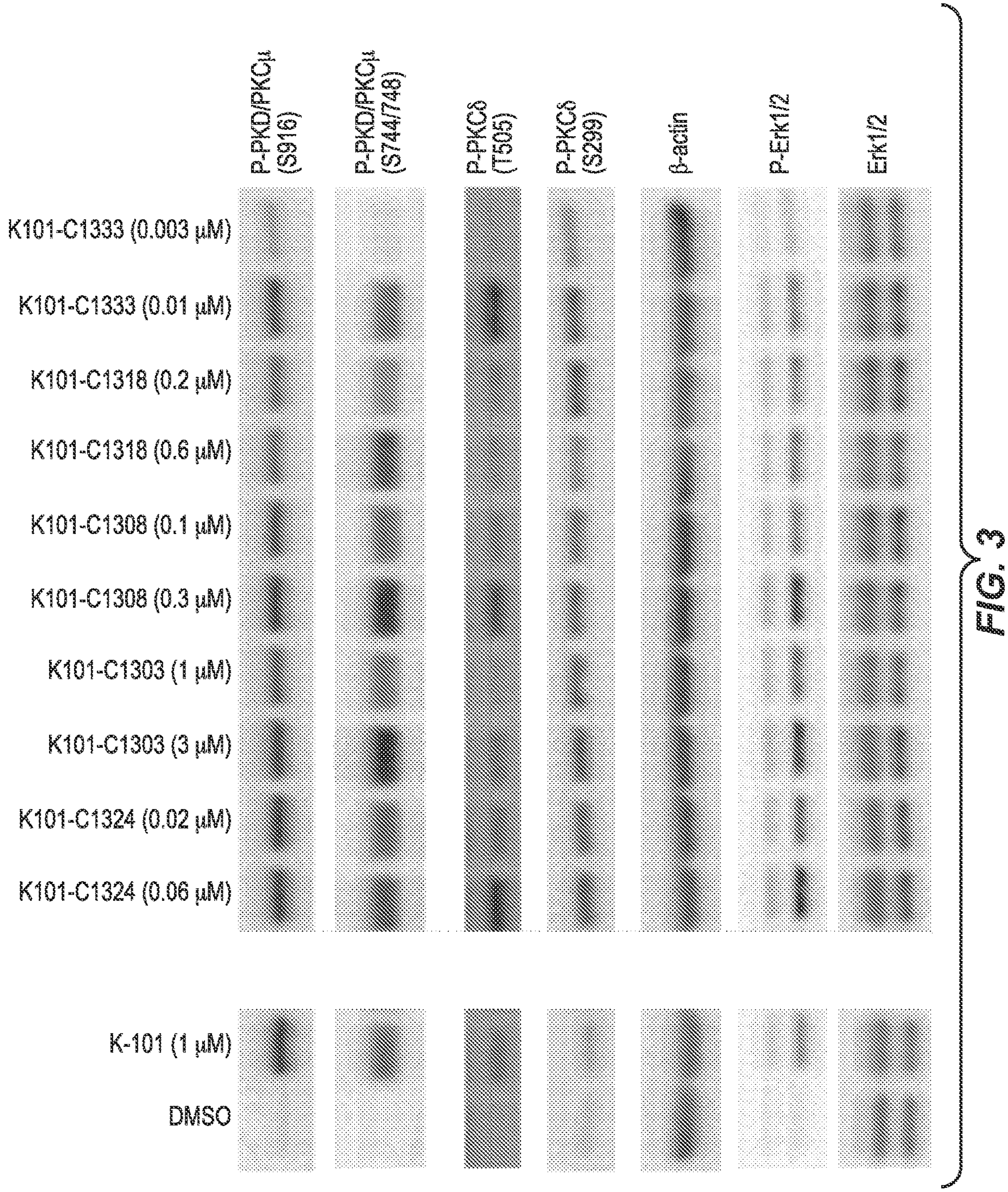
FIG. 3 shows PKC activation in A549 non-small cell lung cancer cells by diterpenoid compounds assessed by measuring levels of phosphorylated PKC (p-PKC) and phosphorylated ERK1/2 proteins (p-ERK1/2), with prostratin (K101) provided for comparison.
Figure 4A:
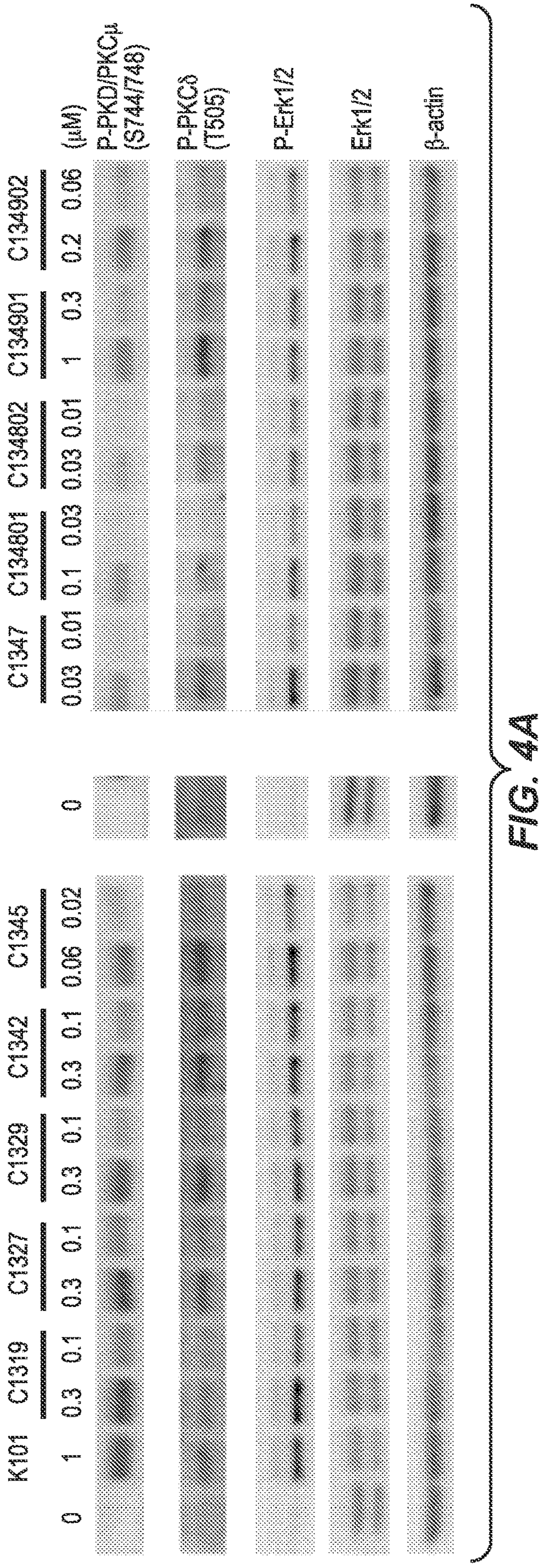
FIG. 4A shows PKC activation in A549 non-small cell lung cancer cells by diterpenoid compounds based on levels of phosphorylated PKC (p-PKC) and phosphorylated ERK1/2 proteins (p-ERK1/2).
Figure 4B:
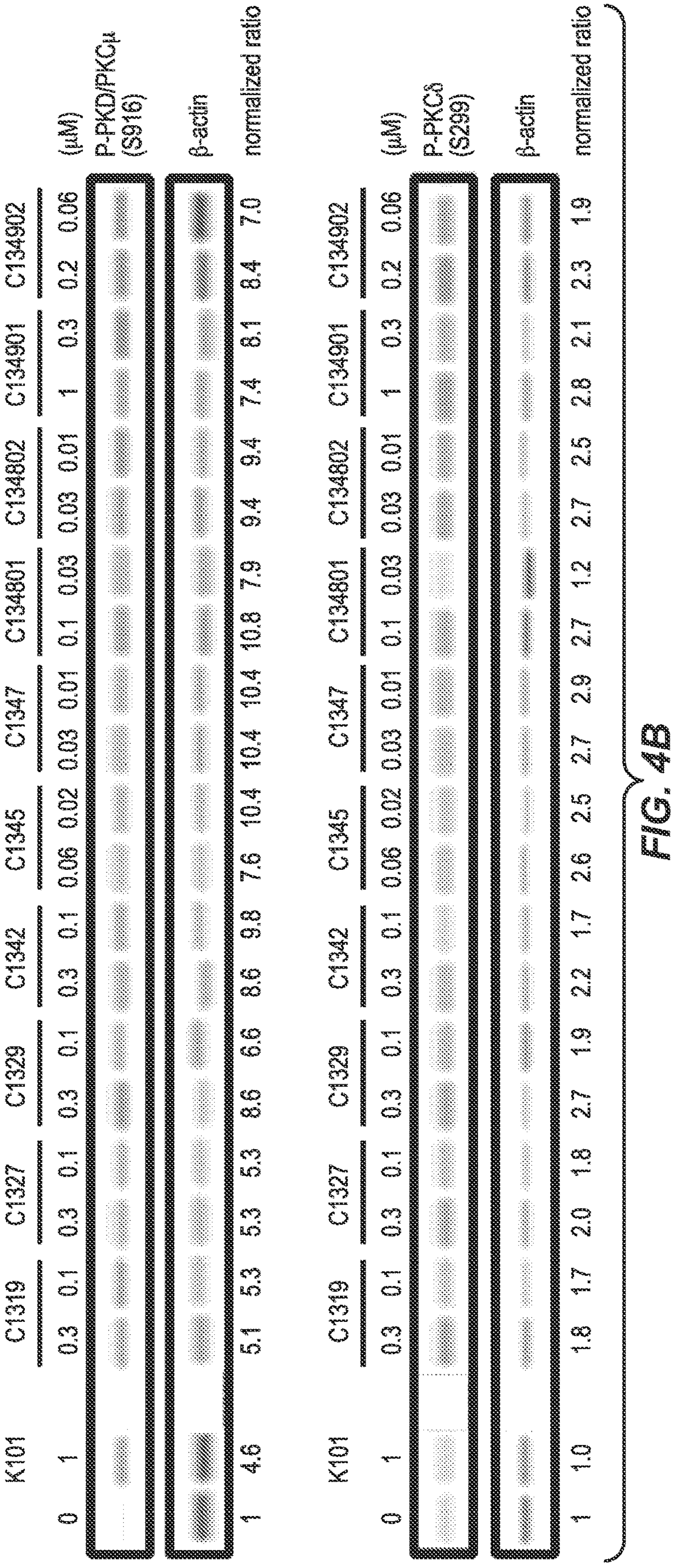
FIG. 4B shows PKC activation in A549 non-small cell lung cancer cells by diterpenoid compounds assessed by measuring levels of phosphorylated PKD/PKCμ (p-PKC) and phosphorylated PKCδ.

As used in this specification and the appended claims, the singular forms "a", "an" and "the" include plural referents unless the context clearly indicates otherwise. Thus, for example, reference to "a protein" includes more than one protein, and reference to "a compound" refers to more than one compound.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be understood that both the foregoing general description, including the drawings, and the following detailed description are exemplary and explanatory only and are not restrictive of this disclosure. The section headings used herein are for organizational purposes only and not to be construed as limiting the subject matter described.

5.1. Definitions

In reference to the present disclosure, the technical and scientific terms used in the descriptions herein will have the meanings commonly understood by one of ordinary skill in the art, unless specifically defined otherwise. Accordingly, the following terms are intended to have the meanings as described below.

"Alkyl" refers to straight or branched chain hydrocarbon groups of 1 to 20 carbon atoms, particularly 1 to 12 carbon atoms ($C_1$-$C_{12}$ or $C_{1-12}$), and more particularly ($C_1$-$C_8$ or $C_{1-8}$) carbon atoms.

Exemplary "alkyl" includes, but are not limited to, methyl, ethyl, n-propyl, i-propyl, n-butyl, s-butyl, t-butyl, n-pentyl, and s-pentyl.

"Alkenyl" refers to straight or branched chain hydrocarbon group of 2 to 20 carbon atoms, particularly 2 to 12 carbon atoms ($C_2$-$C_{12}$ or $C_{2-12}$), and most particularly 2 to 8 ($C_2$-$C_8$ or $C_{2-8}$)carbon atoms, having at least one double bond. Exemplary "alkenyl" includes, but are not limited to, vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

"Alkynyl" refers to a straight or branched chain hydrocarbon group of 2 to 12 carbon atoms ($C_2$-$C_{12}$ or $C_{2-12}$), particularly 2 to 8 carbon atoms ($C_2$-$C_8$ or $C_{2-8}$), containing at least one triple bond. Exemplary "alkynyl" includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"Alkylene", "alkenylene" and "alkynylene" refers to a straight or branched chain divalent hydrocarbon radical of the corresponding alkyl, alkenyl, and alkynyl, respectively. The "alkylene", "alkenylene" and "alkynylene" may be optionally substituted, for example with alkyl, alkyloxy, hydroxyl, carbonyl, carboxyl, halo, nitro, and the like.

"Aliphatic" refers to an organic compound characterized by substituted or unsubstituted, straight or branched, and/or cyclic chain arrangements of constituent carbon atoms. Aliphatic compounds do not contain aromatic rings as part of the molecular structure of the compounds. Aliphatic compound can have 1-20 ($C_1$-$C_{20}$ or $C_{1-20}$) carbon atoms, 1-12 ($C_1$-$C_{12}$ or $C_{1-12}$) carbon atoms, or particularly 1-8 ($C_1$-$C_8$ or $C_{1-8}$) carbon atoms.

"Lower" in reference to substituents refers to a group having between one and six carbon atoms.

"Cycloalkyl" refers to any stable monocyclic or polycyclic system which consists of carbon atoms, any ring of which being saturated. "Cycloalkenyl" refers to any stable monocyclic or polycyclic system which consists of carbon atoms, with at least one ring thereof being partially unsaturated. Examples of cycloalkyls include, but are not limited to, cyclopropyl, cyclobutyl, cyclopentyl, cyclohexyl, cycloheptyl, cyclooctyl, bicycloalkyls and tricycloalkyls (e.g., adamantyl).

"Heterocycloalkyl" or "heterocyclyl" refers to a substituted or unsubstituted 3 to 14 membered, mono- or bicyclic, non-aromatic hydrocarbon, wherein 1 to 3 carbon atoms a (e replaced by a heteroatom. Heteroatoms and/or heteroatomic groups which can replace the carbon atoms include, but are not limited to, —O—, —S—, —S—O—, —NR'—, —PH—, —S(O)—, —$S(O)_2$—, —S(O) NR'—, —$S(O)_2NR'$—, and the like, including combinations thereof, where each R' is independently hydrogen or lower alkyl. Examples include oxiranyl, oxetanyl, azetidynyl, oxazolyl, thiazolidinyl, thiazolyl, morpholinyl, pyrrolidinonyl, pyrrolidinyl, piperidinyl, piperazinyl, 2,3-dihydrofuranyl, dihydropyranyl, tetrahydrofuranyl, tetrahydropyranyl, dihydropyridinyl, tetrahydropyridinyl, tetrahydropyrimidinyl, tetrahydrothiophenyl, tetrahydrothiopyranyl, azapanyl, and the like.

"Carbocycle," "carbocyclyl," and "carbocyclic," as used herein, refer to a non-aromatic saturated or unsaturated ring in which each atom of the ring is carbon. The ring may be monocyclic, bicyclic, tricyclic, or even of higher order. Thus, the terms "carbocycle", "carbocyclyl", and "carbocyclic", encompass fused, bridged and spirocyclic systems: Preferably a carbocycle ring contains from 3 to 14 atoms, including 3 to 8 or 5 to 7 atoms, such as for example, 6 atoms.

"Aryl" refers to a six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Examples of "aryl" groups include phenyl, naphthyl, indenyl, biphenyl, phenanthrenyl, naphthacenyl, and the like.

"Heteroaryl" refers to an aromatic heterocyclic ring, including both monocyclic and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In some embodiments, the heteroaryl can be a 5 to 6 membered monocyclic, or 7 to 11 membered bicyclic ring systems. Examples of "heteroaryl" groups include pyrrolyl, pyrazolyl, imidazolyl, pyrazinyl, oxazolyl, isoxazolyl, thiazolyl, furyl, thienyl, pyridyl, pyrimidyl, benzoxazolyl, benzisoxazolyl, benzothiazolyl, purinyl, benzimidazolyl, indolyl, isoquinolyl, quinoxalinyl, quinolyl, and the like.

"Bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 5 to 12 ring members and 0-4 heteroatoms independently selected from nitrogen, oxygen, and sulfur. Such bridged bicyclic groups include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

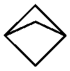 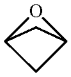 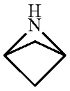 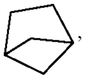, 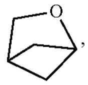,

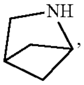, 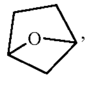, 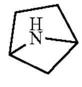, 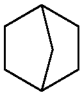,

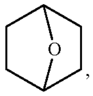, 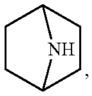, 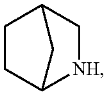 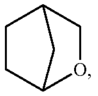

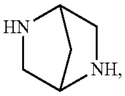 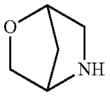 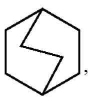, 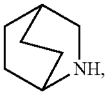

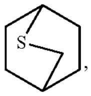, 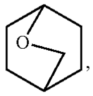, and 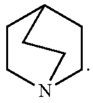.

"Fused ring" refers a ring system with two or more rings having at least one bond and two atoms in common. A "fused aryl" and a "fused heteroaryl" refer to ring systems having at least one aryl and heteroaryl, respectively, that share at least one bond and two atoms in common with another ring.

"Carbonyl" refers to —C(O)—. The carbonyl group may be further substituted with a variety of substituents to form different carbonyl groups including acids, acid halides, aldehydes, amides, esters, and ketones. For example, an —C(O)R', wherein R' is an alkyl is referred to as an alkylcarbonyl. In some embodiments, R' is selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Halogen" or "halo" refers to fluorine, chlorine, bromine and iodine.

"Haloalkyl" refers to an alkyl substituted with 1 or more halogen atoms. Preferably, the alkyl is substituted with 1 to 3 halogen atoms.

"Hydroxy" refers to —OH.

"Oxy" refers to group —O—, which may have various substituents to form different oxy groups, including ethers and esters. In some embodiments, the oxy group is an —OR', wherein R' is selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Acyl" refers to —C(O)R', where R is hydrogen, or an optionally substituted alkyl, heteroalkyl, cycloalkyl, heterocycloalkyl, heterocycloalkylalkyl, aryl, arylalkyl, heteroaryl, or heteroarylalkyl as defined herein. Exemplary acyl groups include, but are not limited to, formyl, acetyl, cyclohexylcarbonyl, cyclohexylmethylcarbonyl, benzoyl, benzylcarbonyl, and the like.

"Alkyloxy" or "alkoxy" refers to —OR', wherein R' is an optionally substituted alkyl.

"Aryloxy" refers to —OR', wherein R' is an optionally substituted aryl.

"Carboxy" refers to $—COO^-$ or COOM, wherein H or a $M^+$ counterion.

"Carbamoyl" refers to —C(O)NR'R', wherein each R' is independently selected from H or an optionally substituted alkyl, cycloalkyl, cycloalkylalkyl, heterocycloalkyl, heterocylcoalkylalkyl, aryl, arylalkyl, heteroaryl, or heteroarylalkyl.

"Cyano" refers to —CN.

"Ester" refers to a group such as —C(═O)OR', alternatively illustrated as —C(O)OR', wherein R' is selected from an optionally substituted: alkyl, cycloalkyl, cycloalkylalkyl, heterocycloalkyl, heterocyclolalkylalkyl, aryl, arylalkyl, heteroaryl, and heteroarylalkyl.

"Silyl" refers to Si, which may have various substituents, for example —SiR'R'R', where R' is as defined in the specification. For example, each R' is independently selected from alkyl, cycloalkyl, cycloalkylalkyl, heterocyloalkyl, heterocycloalkylalkyl, aryl, arylalkyl, heteroaryl, and heteroarylalkyl. As defined herein, any heterocyloalkyl or heteroaryl group present in a silyl group has from 1 to 3 heteroatoms selected independently from O, N, and S.

"Thiol" refers to —SH.

"Sulfanyl" refers to —SR', wherein R' is selected from an optionally substituted: alkyl, cycloalkyl, cycloalkylalkyl, heterocyloalkyl, heterocycloalkylalkyl, aryl, arylalkyl, heteroaryl, and heteroarylalkyl. For example, —SR, wherein R is an alkyl is an alkylsulfanyl.

"Sulfonyl" refers to $—S(O)_2—$, which may have various substituents to form different sulfonyl groups including sulfonic acids, sulfonamides, sulfonate esters, and sulfones. For example, $—S(O)_2R'$, wherein R' is an alkyl refers to an alkylsulfonyl. In some embodiments of $—S(O)_2R'$, R' is selected from an optionally substituted: alkyl, cycloalkyl, cycloalkylalkyl, heterocyloalkyl, heterocycloalkylalkyl, aryl, arylalkyl, heteroaryl, and heteroarylalkyl.

"Amino" or "amine" refers to the group —NR'R' or —NR'R'R', wherein each R' is independently selected from H and an optionally substituted: alkyl, cycloalkyl, heterocycloalkyl, alkyloxy, aryl, heteroaryl, heteroarylalkyl, acyl, alkyloxycarbonyl, sulfanyl, sulfinyl, sulfonyl, and the like. Exemplary amino groups include, but are not limited to, dimethylamino, diethylamino, trimethylammonium, triethylammonium, methylsulfonylamino, furanyl-oxy-sulfamino, and the like.

"Amide" refers to a group such as, —C(═O)NR'R', wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Spiroalkyl" as used herein refers to a monospiro compound having two alicyclic rings attached together through a single common carbon atom. In some embodiments, the spiro compounds have 5 to 12 total ring atoms (e.g., $C_5$-$C_{12}$ or $C_{5-12}$). In some embodiments, one or more of the carbon atoms can be replaced with a heteroatom, such as oxygen, nitrogen or sulfur. Exemplary spiroalkyl compounds include, among others, spiro[3,3]heptyl, spiro[3.4]octyl, and spiro[3,5]decyl.

"Adamantyl" refers to a compound of structural formula:

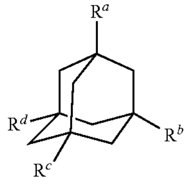

where optional substitutions can be present on one or more of $R^a$, $R^b$, $R^c$, and $R^d$. Adamantyl includes substituted adamantyl, e.g., 1- or 2-adamantyl, substituted by one or more substituents, including alkyl, halo, OH, $NH_2$, and alkoxy. Exemplary derivatives include methyladamatane, haloadamantane, hydroxyadamantane, and aminoadamantane (e.g., amantadine).

"N-protecting group" as used herein refers to those groups intended to protect a nitrogen atom against undesirable reactions during synthetic procedures. Exemplary N-protecting groups include, but is not limited to, acyl groups such acetyl and t-butylacetyl, pivaloyl, alkoxycarbonyl groups such as methyloxycarbonyl and t-butyloxycarbonyl (Boc), aryloxycarbonyl groups such as benzyloxycarbonyl (Cbz) and fluorenylmethoxycarbonyl (Fmoc and aroyl groups such as benzoyl. N-protecting groups are described in Greene's Protective Groups in Organic Synthesis, 5th Edition, P. G. M. Wuts, ed., Wiley (2014).

"Optional" or "optionally" refers to a described event or circumstance may or may not occur, and that the description includes instances where the event or circumstance occurs and instances where the event or circumstance does not. For example, "optionally substituted alkyl" refers to an alkyl group that may or may not be substituted and that the description encompasses both substituted alkyl group and unsubstituted alkyl group.

"Substituted" as used herein means one or more hydrogen atoms of the group is replaced with a substituent atom or group commonly used in pharmaceutical chemistry. Each substituent can be the same or different. Examples of suitable substituents include, but are not limited to, alkyl, alkenyl, alkynyl, cycloalkyl, aryl, arylalkyl, heterocycloalkyl, heteroaryl, OR' (e.g., hydroxyl, alkyloxy (e.g., methoxy, ethoxy, and propoxy), aryloxy, heteroaryloxy, arylalkyloxy, ether, ester, carbamate, etc.), hydroxyalkyl, alkyloxycarbonyl, alkyloxyalkyloxy, perhaloalkyl, alkyloxyalkyl, SR (e.g., thiol, alkylthio, arylthio, heteroarylthio, arylalkylthio, etc.), $S^+R'_2$, S(O)R', $SO_2R'$, NR'R" (e.g., primary amine (i.e., $NH_2$), secondary amine, tertiary amine, amide, carbamate, urea, etc.), hydrazide, halo, nitrile, nitro, sulfide, sulfoxide, sulfone, sulfonamide, thiol, carboxy, aldehyde, keto, carboxylic acid, ester, amide, imine, and imide, including seleno and thio derivatives thereof, wherein each of the substituents can be optionally further substituted. In embodiments in which a functional group with an aromatic carbon ring is substituted, such substitutions will typically number less than about 10 substitutions, more preferably about 1 to 5, with about 1 or 2 substitutions being preferred.

"Stereoisomer" refers to a compound made up of the same atoms bonded by the same bonds but having different three-dimensional structures, which are not interchangeable. Thus, "stereoisomer thereof" with respect to a compound includes any stereoisomer of the compound and mixtures of stereoisomers, and includes "enantiomers," which refers to two stereoisomers whose molecules are nonsuperimposable mirror images of one another. A compound may have more than one chiral center such that the compound may exist as either an individual diastereomer or as a mixture of diastereomers.

"Tautomer" refers to a proton shift from one atom of a molecule to another atom of the same molecule. Thus, "tautomers thereof" with respect to a compound includes any tautomers of the compound.

"Prodrug" refers to a derivative of an active compound (e.g., drug) that requires a transformation under the conditions of use, such as within the body or appropriate in vitro conditions, to release the active drug. Prodrugs are frequently, but not necessarily, pharmacologically inactive until converted into the active drug. Prodrugs can be obtained by masking a functional group in the drug believed to be in part required for activity with a progroup to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

Various progroups, as well as the resultant promoieties, suitable for masking functional groups in the active drugs to yield prodrugs can be used. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed, e.g., in vivo or under appropriate in vitro conditions, to provide the amino group. A carboxyl group may be masked as an ester (including silyl esters and thioesters), amide or hydrazide promoiety, which may be hydrolyzed in vivo to provide the carboxyl group. Included within the scope of prodrugs are, among others, "biohydrolyzable carbonate", "biohydrolyzable ureide", "biohydrolyzable carbamate", "biohydrolyzable ester", "biohydrolyzable amide", and "biohydrolyzable phosphate" groups.

"Solvate" refers to a complex of variable stoichiometry formed by a solute, such as a PKC activator compound, and a solvent. Such solvents are selected to minimally interfere with the biological activity of the solute. Solvents may be, by way of example and not limitation, water, ethanol, or acetic acid.

"Hydrate" refers to a combination of water with a solute, such as a PKC activator compound, wherein the water retains its molecular state as water and is either absorbed, adsorbed or contained within a crystal lattice of the solute (e.g., PKC activating compound).

"Pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure may contain both basic and acidic functionalities that allow the compounds to be converted into either base or acid addition salts. Lists of suitable salts are found in Remington's Pharmaceutical Sciences, 17th Ed., Mack Publishing Company, Easton, Pa., (1985) and Journal of Pharmaceutical Science, 66:2 (1977), each of which is incorporated herein by reference in its entirety.

"Pharmaceutically acceptable carrier" or "pharmaceutically acceptable excipient" refers to an excipient, carrier or adjuvant that can be administered to a subject, together with at least one therapeutic agent, and which does not destroy the pharmacological activity thereof and is generally safe, nontoxic and neither biologically nor otherwise undesirable when administered in doses sufficient to deliver a therapeutic amount of the agent.

"K-RAS" refers to Kirsten rat sarcoma viral oncogene homolog, a small GTPase and a member of the RAS family of proteins involved in signal transduction. Exemplary human K-RAS nucleic acid and protein sequences are provided in GenBank Nos. M54968.1 and AAB414942.1, respectively. "K-RAS" as used herein encompasses variants, including orthologs and interspecies homologs, of the human K-RAS protein.

"Mutant K-RAS polypeptide", "mutant K-RAS protein" and "mutant K-RAS" are used interchangeably and refer to a K-RAS polypeptide comprising at least one K-RAS mutation as compared to the corresponding wild-type K-RAS sequence. Certain exemplary mutant K-RAS polypeptides include, but are not limited to, allelic variants, splice variants, derivative variants, substitution variants, deletion variants, insertion variants, and fusion polypeptides.

"N-RAS" refers to Neuroblastoma RAS Viral (V-RAS) oncogene homolog, a small GTPase and a member of the RAS family of proteins involved in signal transduction. Exemplary human N-RAS nucleic acid and protein sequences are provided in NCBI Accession No. NP_002515 and GenBank Accession No. X02751, respectively. "N-RAS" as used herein encompasses variants, including orthologs and interspecies homologs of the human N-RAS protein.

"Mutant N-RAS polypeptide", "mutant N-RAS protein" and "mutant N-RAS" are used interchangeably and refer to an N-RAS polypeptide comprising at least one N-RAS mutation as compared to the corresponding wild-type N-RAS sequence. Certain exemplary mutant N-RAS polypeptides include, but are not limited to, allelic variants, splice variants, derivative variants, substitution variants, deletion variants, insertion variants, and fusion polypeptides.

"H-RAS" refers to Harvey Rat Sarcoma viral oncogene homolog, a small GTPase and a member of the RAS family of proteins involved in signal transduction. Exemplary human H-RAS nucleic acid and protein sequences are provided in NCBI Accession No. P01112 and GenBank Accession No. NM_176795, respectively. "H-RAS" as used herein encompasses variants, including orthologs and interspecies homologs of the human H-RAS protein.

"Mutant H-RAS polypeptide", "mutant H-RAS protein" and "mutant H-RAS" are used interchangeably and refer to an H-RAS polypeptide comprising at least one H-RAS mutation as compared to the corresponding wild-type H-RAS sequence. Certain exemplary mutant H-RAS polypeptides include, but are not limited to, allelic variants, splice variants, derivative variants, substitution variants, deletion variants, insertion variants, and fusion polypeptides.

"Activating K-RAS" refers to a form of K-RAS that has increased activity compared to wild-type K-RAS. The activation of K-RAS activity can result from a mutation or in some embodiments, overexpression of the K-RAS protein.

"Activating N-RAS" refers to a form of N-RAS that has increased activity compared to wild-type N-RAS. The activation of N-RAS activity can result from a mutation, or in some embodiments, overexpression of the N-RAS protein.

Activating H-RAS" refers to a form of H-RAS that has increased activity compared to wild-type H-RAS. The activation of H-RAS activity can result from a mutation, or in some embodiments, overexpression of the H-RAS protein.

"Mutation" or "mutant" refers to an amino acid or polynucleotide sequence which has been altered by substitution, insertion, and/or deletion. In some embodiments, a mutant or variant sequence can have increased, decreased, or substantially similar activities or properties in comparison to the parental sequence.

"Identified" or "determined" refers to analyzing for, detection of, or carrying out a process for the presence or absence of one or more specified characteristics.

"Wild-type" or "naturally occurring" refers to the form found in nature. For example, a naturally occurring or wild-type polypeptide or polynucleotide sequence is a sequence present in an organism that can be isolated from a source in nature and which has not been intentionally modified by human manipulation.

"Control" or "control sample" or "control group" refers to a sample or group that is compared to another sample or group, where generally the control sample or group are the same as a comparison group except for one or more factors being compared.

"Selecting" refers to the process of determining that a subject will receive an agent to treat the occurrence of a condition. Selecting can be based on an individual susceptibility to a particular disease or condition due to, for example, presence of an identifying cellular, physiological or environment factor or factors. In some embodiments, selecting can be based on determining or identifying whether that subject will be responsive to an agent, for example as assessed by identifying the presence of a biomarker and/or drug target marker that makes the subject sensitive, insensitive, responsive, or unresponsive to an agent or treatment.

"Biological sample" refers to any sample including a biomolecule, such as a protein, a peptide, a nucleic acid, a lipid, a carbohydrate or a combination thereof, that is obtained from an organism, particularly a mammal. Examples of mammals include humans; veterinary animals like cats, dogs, horses, cattle, and swine; and laboratory animals like mice, rats and primates. In some embodiments, a human subject in the clinical setting is referred to as a patient. Biological samples include tissue samples (such as tissue sections and needle biopsies of tissue), cell samples (for example, cytological smears such as Pap or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, milk, vaginal fluid, saliva, swabs (such as buccal swabs), or any material containing biomolecules that is derived from a first biological sample. In particular embodiments, the biological sample is a "cell free sample", such as cell free or extracellular polynucleotides, and cell free or extracellular proteins. In some embodiments, cell free DNA or cfDNA refers to extracellular DNA obtained from blood, particularly the serum.

"Subject" as used herein refers to a mammal, for example a dog, a cat, a horse, or a rabbit. In some embodiments, the subject is a non-human primate, for example a monkey, chimpanzee, or gorilla. In some embodiments, the subject is a human, sometimes referred to herein as a patient.

"Treating" or "treatment" of a disease, disorder, or syndrome, as used herein, includes (i) preventing the disease, disorder, or syndrome from occurring in a subject, i.e., causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art, particularly in view of the guidance provided in the present disclosure.

"Therapeutically effective amount" refers to that amount which, when administered to an animal for treating a disease, is sufficient to effect such treatment for the disease, disorder, or condition.

5.2. Compounds

The present disclosure provides protein kinase C (PKC) modulating compounds. In particular, the compounds are diterpenoid PKC modulating compounds displaying potent PKC modulating activity, as well as enhanced solubility and pharmacokinetic profiles. The diterpenoid PKC modulating compounds show potent activity against tumor cells, and can be applied to treatment of cancer. In one aspect, the present disclosure provides a compound of formula (I):

(I)

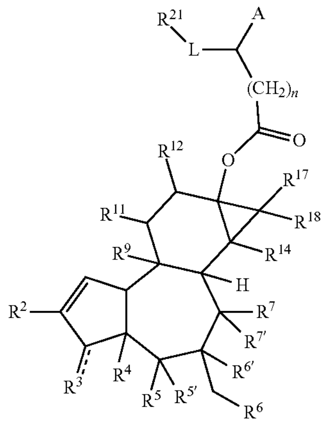

or a pharmaceutically acceptable salt, tautomer, or stereoisomer thereof;

wherein

A is —OH, —C(O)OR$^1$, or —NR$^{13}$R$^{13'}$;

R$^1$ is H or a M+ counterion;

R$^2$ is a $C_1$-$C_4$alkyl;

R$^3$ is O double bonded to the ring carbon when ( - - - ) is a bond, or —OR$^a$; wherein R$^a$ is H or —C(O)R$^{a1}$, wherein R$^{a1}$ is $C_1$-$C_6$alkyl, $C_2$-$C_6$alkenyl, $C_0$-$C_6$alkylaryl, or $C_0$-$C_6$alkylheteroaryl;

R$^4$ and R$^5$ are each independently H or —OR$^b$, wherein R$^b$ is H, $C_1$-$C_6$alkyl, $C_2$-$C_6$alkenyl, $C_0$-$C_6$alkylaryl, or $C_0$-$C_6$alkylheteroaryl;

R$^{5'}$ and R$^{6'}$ are H, or R$^{5'}$ and R$^{6'}$ form a bond or are bonded to a common O atom to form an epoxide ring as permitted by valency;

R$^6$ is OH, halo, or —OC(O)R$^c$, wherein R$^c$ is —$C_1$-$C_6$alkyl, —$C_1$-$C_6$alkyl-(NR$^{c1}$)$_2$ or —$C_1$-$C_6$alkylC(O)OR$^k$, R$^{c1}$ is H, $C_1$-$C_6$alkyl, or two R$^{c1}$ together with the N atom form a 5 to 7 membered heterocyclyl containing 1 to 3 heteroatoms selected from N, O, and S; or R$^6$ is

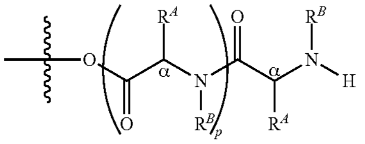

wherein, each occurrence of R$^A$ is independently selected from a side chain of a natural or non-natural amino acid, wherein each occurrence of R$^A$ is same or different;

each occurrence of R$^B$ is independently H, or R$^B$ together with the adjacent R$^A$ and the N atom to which it is attached form a heterocyclic ring of a natural or non-natural amino acid, wherein each occurrence of R$^B$ is same or different; and p is 0, 1, or 2;

R$^{6'}$ and R$^{7'}$ are H, or R$^{6'}$ and R$^{7'}$ form a bond or are bonded to a common O atom to form an epoxide ring, as permitted by valency;

R$^7$ is H or OH;

R$^9$ is OR$^e$, wherein R$^e$ is H, $C_1$-$C_6$alkyl, or aryl;

R$^{11}$ is $C_1$-$C_4$alkyl;

R$^{12}$ is H, —OH, —OC(O)R$^f$, wherein R$^f$ is $C_1$-$C_{12}$alkyl, $C_2$-$C_{12}$alkenyl, —$C_0$-$C_6$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

R$^{13}$ and R$^{13'}$ are each independently H or $C_1$-$C_4$alkyl;

R$^{14}$ is H or OR$^g$; wherein R$^g$ is H or $C_1$-$C_6$alkyl;

R$^{17}$ and R$^{18}$ are each independently $C_1$-$C_4$alkyl or $C_1$-$C_4$alkyl-OR$^h$, wherein R$^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

R$^{21}$ is H, —S(O)$_2$R$^j$, —SR$^j$, —N(R$^j$)$_2$, —Si(R$^j$)$_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)OR$^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of J$^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each R$^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments of the compound of formula (I), the carbon atom marked with "*"

(I)

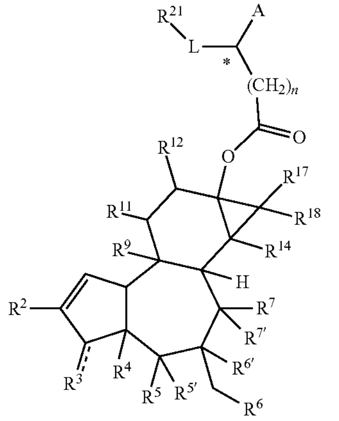

is chiral and thus can be present in S or R stereochemical configuration. In some embodiments, the stereochemical configuration is S isomer. In some embodiments, the stereochemical configuration is R isomer.

In some embodiments, A is —OH. In some embodiments, A is —C(O)OR$^1$, wherein $R^1$ is H or a $M^+$ counterion. In some embodiments, A is —NR$^{13}$R$^{13'}$, wherein $R^{13}$ and $R^{13'}$ are each independently H or $C_1$-$C_4$alkyl.

In the embodiments herein, $M^+$ is a metal cation, an ammonium group, or a suitable organic cation. In some embodiments, $M^+$ is a cation of an alkaline or alkaline earth metal, for example, $K^+$, $Na^+$, $Li^+$, or $Ca^{+2}$. In some embodiments, $M^+$ is an ammonium ion $NH_4^+$, or an organic cation derived from an amine.

In some embodiments, the compound has the structure of formula (Ia):

(Ia)

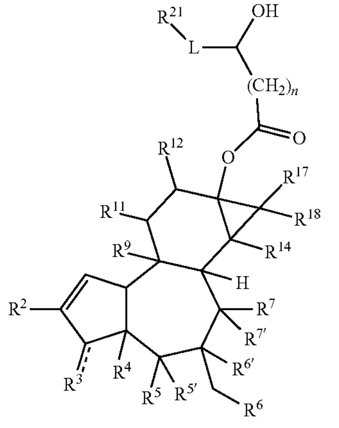

or a pharmaceutically acceptable salt, tautomer, or stereoisomer thereof;

wherein

A is —OH;

$R^2$ is a $C_1$-$C_4$alkyl;

$R^3$ is O double bonded to the ring carbon when ( - - - ) is a bond, or —OR$^a$; wherein $R^a$ is H or —C(O)R$^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —OR$^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^{5'}$ and $R^{6'}$ are H, or $R^{5'}$ and $R^{6'}$ form a bond or are bonded to a common O atom to form an epoxide ring as permitted by valency;

$R^6$ is OH, halo, or —OC(O)R$^c$, wherein $R^c$ is —$C_1$-$C_6$alkyl, —$C_1$-$C_6$alkyl-(NR$^{c1}$)$_2$ or —$C_1$-$C_6$alkylC(O)OR$^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

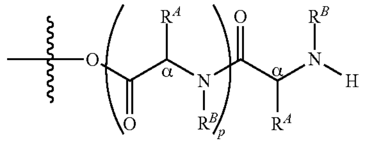

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{6'}$ and $R^{7'}$ are H, or $R^{6'}$ and $R^{7'}$ form a bond or are bonded to a common O atom to form an epoxide ring, as permitted by valency;

$R^7$ is H or OH;

$R^9$ is OR$^e$, wherein $R^e$ is H, $C_1$-$C_6$alkyl, or aryl;

$R^{11}$ is $C_1$-$C_4$alkyl;

$R^{12}$ is H, —OH, —OC(O)R$^f$, wherein $R^f$ is $C_1$-$C_2$alkyl, $C_2$-$C_{12}$alkenyl, —$C_0$-$C_2$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{13}$ and $R^{13'}$ are each independently H or $C_1$-$C_4$alkyl;

$R^{14}$ is H or OR$^g$; wherein $R^g$ is H or $C_1$-$C_6$alkyl;

$R^{17}$ and $R^{18}$ are each independently $C_1$-$C_4$alkyl or $C_1$-$C_4$alkyl-OR$^h$, wherein $R^h$ is H or $C_1$-$C_6$alkyl;

L is absent, $C_1$-$C_{12}$alkylene, or $C_2$-$C_{12}$alkenylene, wherein the $C_1$-$C_2$alkylene or $C_2$-$C_2$alkenylene is optionally substituted with $C_1$-$C_4$alkyl;

$R^{21}$ is H, —S(O)$_2$R$^j$, —SR$^j$, —N(R$^j$)$_2$, —Si(R$^j$)$_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)OR$^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments of the compound of formula (Ia), the carbon atom marked with "*"

(Ia)

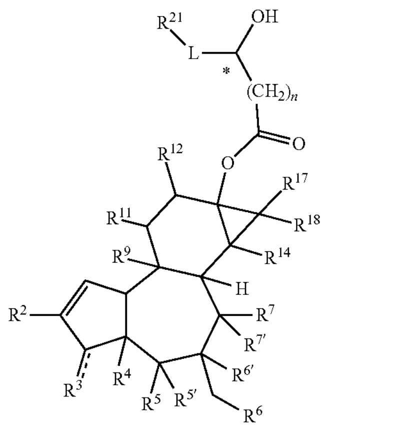

is chiral and thus can be present in S or R stereochemical configuration. In some embodiments, the stereochemical configuration is S isomer. In some embodiments, the stereochemical configuration is R isomer.

In some embodiments, the compound has the structure of formula (Ib):

(Ib)

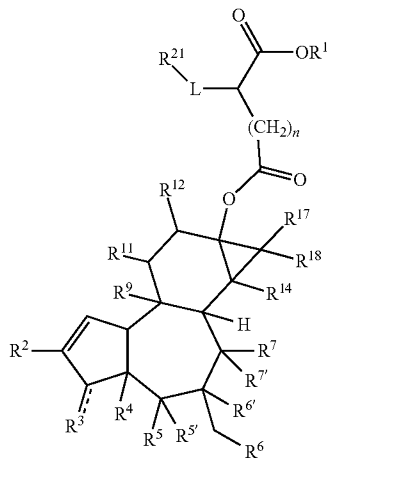

or a pharmaceutically acceptable salt, tautomer, or stereoisomer thereof;

wherein

A is —C(O)$OR^1$;

$R^1$ is H or a M+ counterion;

$R^2$ is a $C_1$-$C_4$alkyl;

$R^3$ is O double bonded to the ring carbon when ( - - - ) is a bond, or —$OR^a$; wherein $R^a$ is H or —C(O)$R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^{5'}$ and $R^{6'}$ are H, or $R^{5'}$ and $R^{6'}$ form a bond or are bonded to a common O atom to form an epoxide ring as permitted by valency;

$R^6$ is OH, halo, or —OC(O)$R^c$, wherein $R^c$ is —$C_1$-$C_6$alkyl, —$C_1$-$C_6$alkyl-($NR^{c1}$)$_2$ or —$C_1$-$C_6$alkylC(O)$OR^k$, $R^{c1}$ is H, $C_1$-$C_6$alkyl, or two $R^c$ together with the N atom form a 5 to 7 membered heterocyclyl containing 1 to 3 heteroatoms selected from N, O, and S; or $R^6$ is

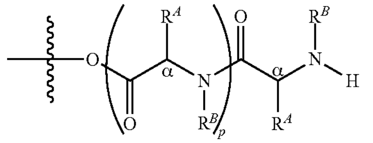

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{6'}$ and $R^{7'}$ are H, or $R^{6'}$ and $R^{7'}$ form a bond or are bonded to a common O atom to form an epoxide ring, as permitted by valency;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —OC(O)$R^f$, wherein $R^f$ is $C_1$-$C_{12}$alkyl, $C_2$-$C_{12}$alkenyl, —$C_0$-$C_{12}$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_6$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)$OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, of the compound of formula (Ib), the carbon atom marked with (Ia)

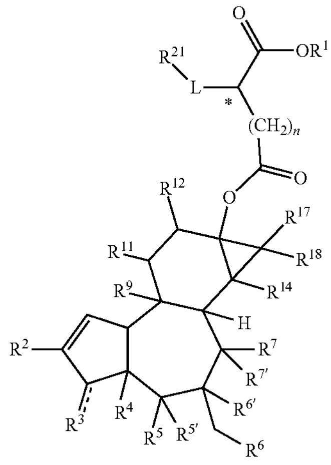

is chiral and thus can be present in S or R stereochemical configuration. In some embodiments, the stereochemical configuration is S isomer. In some embodiments, the stereochemical configuration is R isomer.

In some embodiments, the present disclosure provides a compound of formula (II):

(II)

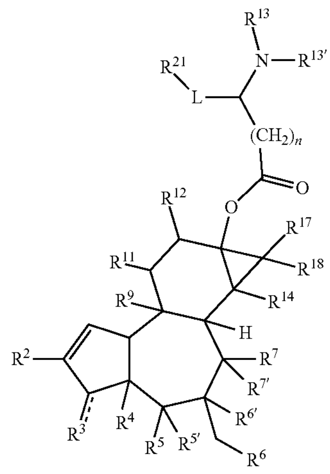

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^{5'}$ and $R^{6'}$ are H, or $R^{5'}$ and $R^{6'}$ form a bond or are bonded to a common O atom to form an epoxide ring as permitted by valency;

$R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

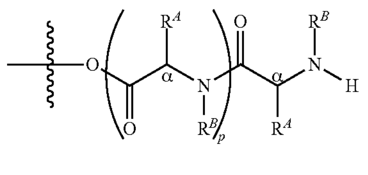

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{6'}$ and $R^{7'}$ are H, or $R^{6'}$ and $R^{7'}$ form a bond or are bonded to a common O atom to form an epoxide ring, as permitted by valency;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —$OC(O)R^f$, wherein $R^f$ is $C_1$-$C_{12}$alkyl, $C_2$-$C_{12}$alkenyl, —$C_0$-$C_6$aliphatic-$C_3$-$C_7$cycloalkyl, —$C_0$-$C_1$aliphatic-heterocycloalkyl, —$C_0$-$C_{12}$aliphatic-aryl, or —$C_0$-$C_{12}$aliphatic-heteroaryl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments of the compound of formula (II), the carbon atom marked with "*"

(II)

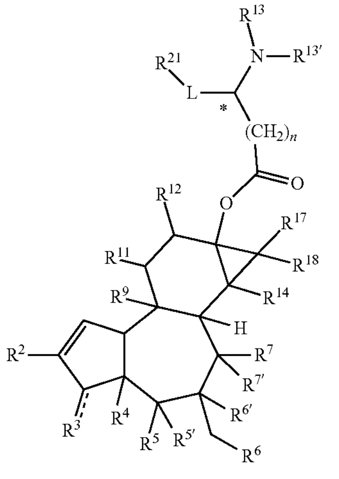

is chiral and thus compound may be present in S or R stereochemical configuration. In some embodiments, the stereochemical configuration is S isomer. In some embodiments, the stereochemical configuration is R isomer. In some embodiments, the compound of formula (II) has the structure of formula (II'):

(II')

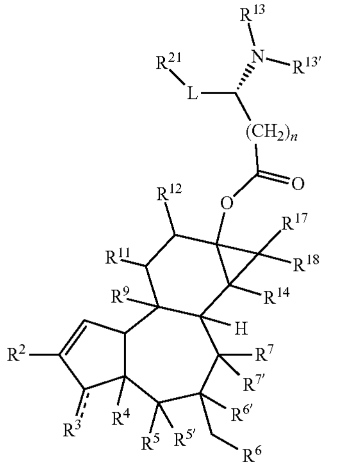

or a pharmaceutically acceptable salt, tautomer, or stereoisomer thereof, wherein $R^2$, $R^3$, $R^4$, $R^5$, $R^{5'}$, $R^6$, $R^{6'}$, $R^7$, $R^{7'}$, $R^9$, $R^{11}$, $R^{12}$, $R^{13}$, $R^{13'}$, $R^{14}$, $R^{17}$, $R^{18}$, L and $R^{21}$ are as defined for formula (II).

In some embodiments, the compound of formula (II) has the structure of formula (II"):

(II")

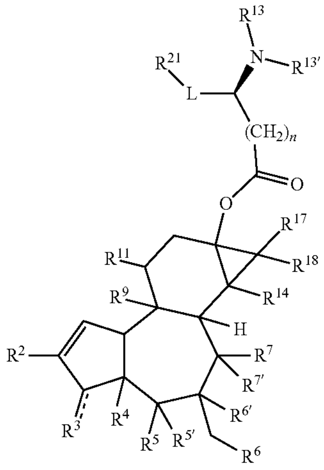

or a pharmaceutically acceptable salt, tautomer, or stereoisomer thereof, wherein $R^2$, $R^3$, $R^4$, $R^5$, $R^{5'}$, $R^6$, $R^{6'}$, $R^7$, $R^{7'}$, $R^9$, $R^{11}$, $R^{12}$, $R^{13}$, $R^{13'}$, $R^{14}$, $R^{17}$, $R^{18}$, L and $R^{21}$ are as defined for formula (II).

In some embodiments, the compound has the structure of formula (IIa):

(IIa)

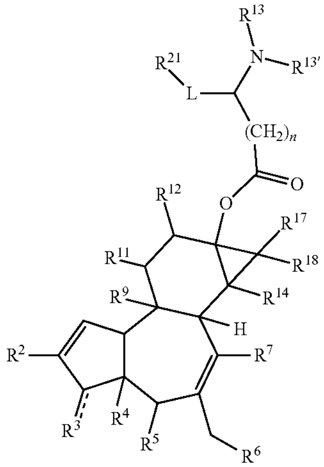

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —OR, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —$OC(O)R^c$, wherein $R^c$ is —$C_1$-$C_6$alkyl, —$C_1$-$C_6$alkyl-$(NR^c)_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

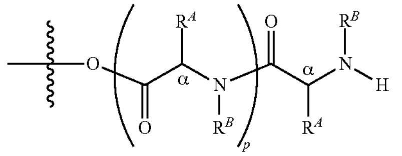

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —OC(O)$R^f$, wherein $R^f$ is $C_1$-$C_{12}$alkyl, $C_2$-$C_{12}$alkenyl, —$C_0$-$C_2$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_2$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)$OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, the compound of formula (IIa) has the structure for formula (IIa'):

(IIa')

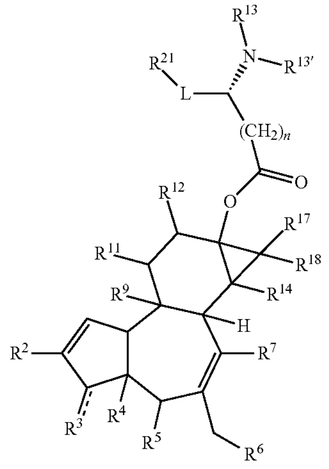

or a pharmaceutically acceptable salt, tautomer, or stereoisomer thereof, wherein $R^2$, $R^3$, $R^4$, $R^5$, $R^6$, $R^7$, $R^9$, $R^{11}$, $R^{12}$, $R^{13}$, $R^{13'}$, $R^{14}$, $R^{17}$, $R^{18}$, L and $R^{21}$ are as defined for formula (II).

In some embodiments, the compound of formula (IIa) has the structure for formula (IIa"):

(IIa")

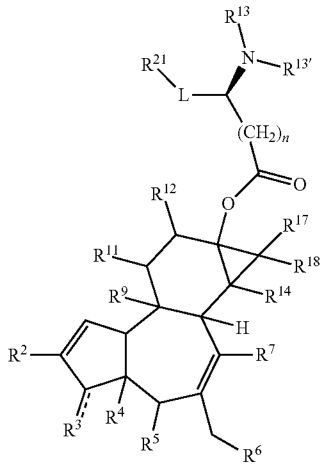

or a pharmaceutically acceptable salt, tautomer, or stereoisomer thereof, wherein $R^2$, $R^{3'}$ $R^4$, $R^5$, $R^6$, $R^7$, $R^9$, $R^{11}$, $R^{12}$, $R^{13}$, $R^{13'}$, $R^{14}$, $R^{17}$, $R^{18}$, L and $R^{21}$ are as defined for formula (II).

In some embodiments, the compound has the structure of formula (IIb):

(IIb)

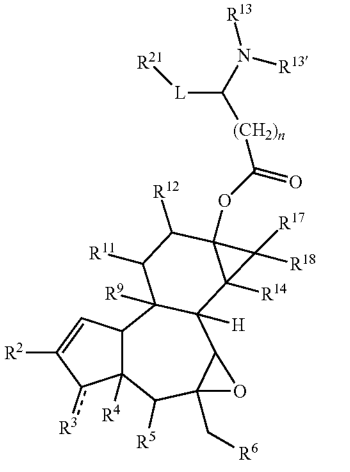

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —OR, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

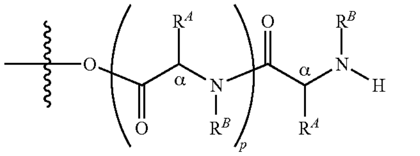

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —$OC(O)R^f$, wherein $R^f$ is $C_1$-$C_{12}$alkyl, $C_2$-$C_{12}$alkenyl, —$C_0$-$C_2$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_2$alkylene, or $C_2$-$C_{12}$alkenylene, wherein the $C_1$-$C_2$alkylene or $C_2$-$C_{12}$alkenylene is optionally substituted with $C_1$-$C_4$alkyl;

$R^{21}$ is H, —$S(O)_2R^j$, —SR, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_2$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, the compound has the structure of formula (IIb'):

(IIb')

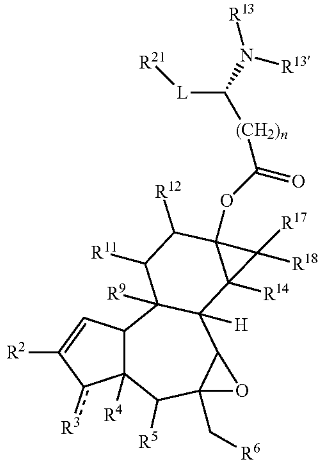

or a pharmaceutically acceptable salt, tautomer, or stereoisomer thereof, wherein $R^2$, $R^3$, $R^4$, $R^5$, $R^6$, $R^9$, $R^{11}$, $R^{12}$, $R^{13}$, $R^{13'}$, $R^{14}$, $R^{17}$, $R^{18}$, L and $R^{21}$ are as defined for formula (II).

In some embodiments, the compound has the structure of formula (IIb"):

(IIb")

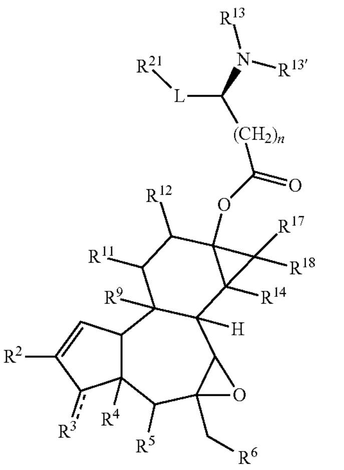

or a pharmaceutically acceptable salt, tautomer, or stereoisomer thereof, wherein $R^2$, $R^3$, $R^4$, $R^5$, $R^6$, $R^9$, $R^{11}$, $R^{12}$, $R^{13}$, $R^{13'}$, $R^{14}$, $R^{17}$, $R^{18}$, L and $R^{21}$ are as defined for formula (II).

In some embodiments of the compound of formula (I), (Ia), (Ib), (II), (II'), (II"), (IIa), (IIa'), (IIa"), (IIb), (IIb'), and (IIb"), $R^3$ is —$OR^a$; wherein $R^a$ is H or —C(O)$R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl. In some embodiments, the aryl of $C_0$-$C_6$alkylaryl is phenyl. In some embodiments, the aryl of $C_0$-$C_6$alkylaryl is optionally substituted with 1 to 3 of OH, CN, halo, $C_1$-$C_4$alkyl, and halo$C_1$-$C_4$alkyl. In some embodiments, $R^{a1}$ is selected from:

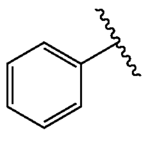

and

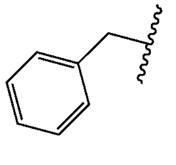

In some embodiments, $R^{a1}$ is selected from:

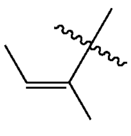

and

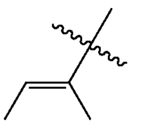

In some embodiments of the compound of formula (I), (Ia), (Ib), (II), (II'), (II"), (IIa), (IIa'), (IIa"), (IIb), (IIb'), and (IIb"), $R^3$ is O double bonded to the carbon atom.

In some embodiments of the compound of formula (I), (Ia), (Ib), (II), (II'), (II"), (IIa), (IIa'), (IIa"), (IIb), (IIb'), and (IIb"), one or more of R, $R^{11}$, $R^{17}$, and $R^{18}$ are —$CH_3$. In some embodiments, each of $R^2$, $R^{11}$, $R^7$, and $R^{18}$ is —$CH_3$.

In some embodiments of the compound of formula (I), (Ia), (Ib), (II), (II'), (II"), (IIa), (IIa'), (IIa"), (IIb), (IIb'), and (IIb"), $R^4$ and $R^5$ are each independently H or —OH.

In some embodiments of the compound of formula (I), (Ia), (Ib), (II), (II'), (II"), (IIa), (IIa'), (IIa"), (IIb), (IIb'), and (IIb"), $R^2$, $R^{11}$, $R^{17}$, and $R^{18}$ are —$CH_3$;

$R^3$ is O double bonded to the carbon atom; and $R^4$ and $R^5$ are each independently H or —OH.

In some embodiments, the compound has the structure of formula (IIc):

(IIc)

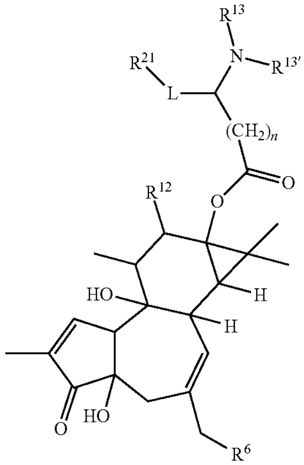

or a pharmaceutically acceptable salt, tautomer, or stereoisomer thereof;

wherein $R^6$ is OH, halo, or —OC(O)$R^c$, wherein $R^c$ is —$C_1$-$C_6$alkyl, —$C_1$-$C_6$alkyl-($NR^{c1}$)$_2$ or —$C_1$-$C_6$alkylC(O)$OR^k$, $R^c$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

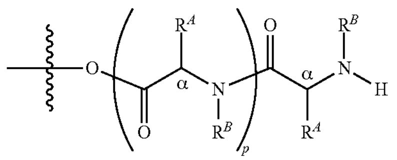

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{12}$ is H, —OH, —OC(O)$R^f$, wherein $R^f$ is $C_1$-$C_2$alkyl, $C_2$-$C_{12}$alkenyl, —$C_0$-$C_{12}$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{13}$ and $R^{13'}$ are each independently H or $C_1$-$C_4$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)$OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, the compound has the structure of formula (IIc'):

(IIc')

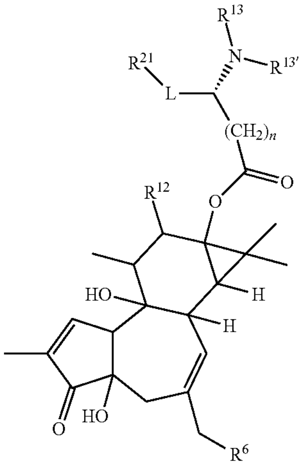

or a pharmaceutically acceptable salt, tautomer, or stereoisomer thereof, wherein $R^6$, $R^{12}$, $R^{13}$, $R^{13'}$, L and $R^{21}$ are as defined for formula (IIc).

In some embodiments, the compound has the structure of formula (IIc"):

(IIc")

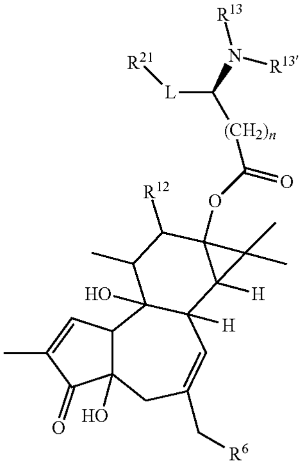

or a pharmaceutically acceptable salt, tautomer, or stereoisomer thereof, wherein $R^6$, $R^{12}$, $R^{13}$, $R^{13'}$, L and $R^{21}$ are as defined for formula (IIc).

In some embodiments, the compound has the structure of formula (IId):

(IId)

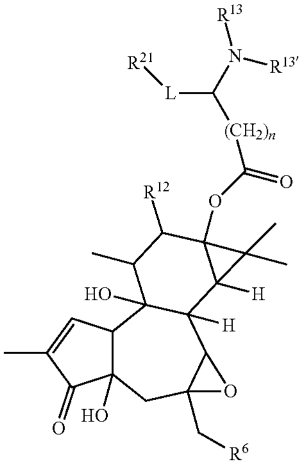

or a pharmaceutically acceptable salt, tautomer, or stereoisomer thereof;

wherein $R^6$ is OH, halo, or —OC(O)$R^c$, wherein $R^c$ is —$C_1$-$C_6$alkyl, —$C_1$-$C_6$alkyl-$(NR^{c1})_2$ or —$C_1$-$C_6$alkylC(O)O$R^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

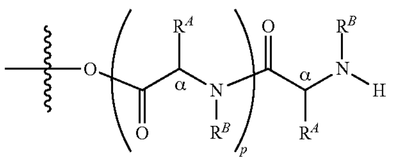

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{12}$ is H, —OH, —OC(O)$R^f$, wherein $R^f$ is $C_1$-$C_{12}$alkyl, $C_2$-$C_{12}$alkenyl, —$C_0$-$C_{12}$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{13}$ and $R^{13'}$ are each independently H or $C_1$-$C_4$alkyl;

L is absent, $C_1$-$C_2$alkylene, or $C_2$-$C_{12}$alkenylene, wherein the $C_1$-$C_2$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)O$R^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, the compound has the structure of formula (IId'):

(IId')

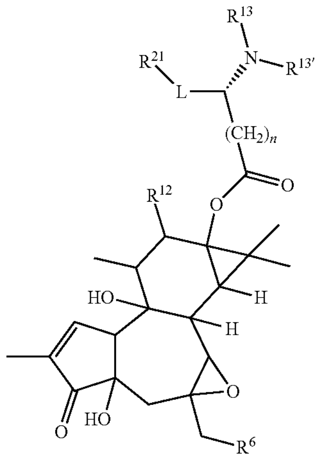

or a pharmaceutically acceptable salt, tautomer, or stereoisomer thereof, wherein $R^6$, $R^{12}$, $R^{13}$, $R^{13'}$, L and $R^{21}$ are as defined for formula (IId).

In some embodiments, the compound has the structure of formula (IId"):

(IId")

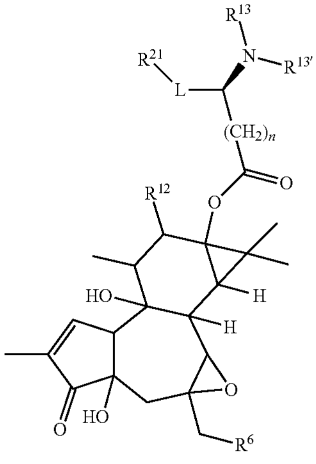

or a pharmaceutically acceptable salt, tautomer, or stereoisomer thereof, wherein $R^6$, $R^{12}$, $R^{13}$, $R^{13'}$, L and $R^{21}$ are as defined for formula (IId).

In some embodiments of the compound of formula (I), (Ia), (Ib), (II), (II'), (II"), (IIa), (IIa'), (IIa"), (IIb), (IIb'), (IIb"), (IIc), (IIc"), (IId), (IId') and (IId"), $R^{12}$ is —OC(O)$R^f$, wherein $R^f$ is $C_1$-$C_{12}$alkyl, $C_2$-$C_{12}$alkenyl, —$C_0$-$C_{12}$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl. In some some embodiments, $R^f$ is selected from

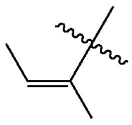

and

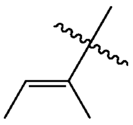

In some some embodiments, $R^f$ is selected from:

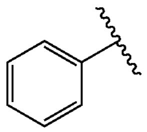

and

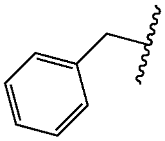

In some embodiments, the compound has the structure of formula (III):

(III)

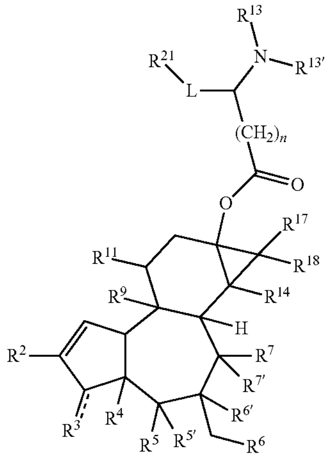

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —O$R^a$; wherein $R^a$ is H or —C(O)$R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —O$R^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^{5'}$ and $R^{6'}$ are H, or $R^{5'}$ and $R^{6'}$ form a bond or are bonded to a common O atom to form an epoxide ring as permitted by valency;

$R^6$ is OH, halo, or —OC(O)$R^c$, wherein $R^c$ is —$C_1$-$C_6$alkyl, —$C_1$-$C_6$alkyl-$(NR^{c1})_2$ or —$C_1$-$C_6$alkylC(O)

$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

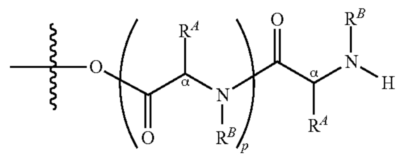

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{6'}$ and $R^{7'}$ are H, or $R^{6'}$ and $R^{7'}$ form a bond or are bonded to a common O atom to form an epoxide ring, as permitted by valency;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —SR, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, the compound has the structure of formula (III'):

(III')

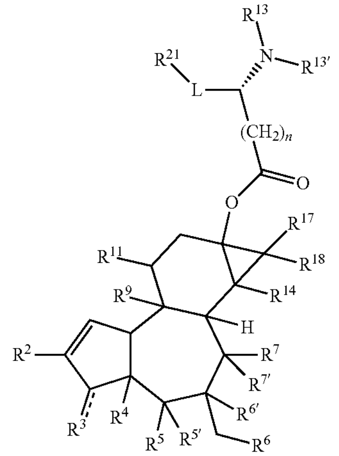

or a pharmaceutically acceptable salt, tautomer, or stereoisomer thereof, wherein $R^2$, $R^3$, $R^4$, $R^5$, $R^{5'}$, $R^{6'}$, $R^6$, $R^{6'}$, $R^{7'}$, $R^7$, $R^9$, $R^{11}$, $R^{13}$, $R^{13'}$, $R^{14}$, $R^{17}$, $R^{18}$, L and $R^{21}$ are as defined for formula (III).

In some embodiments, the compound has the structure of formula (III"):

(III")

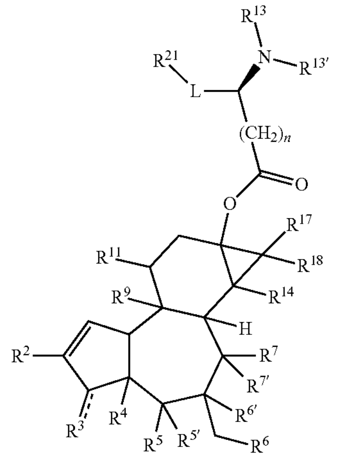

or a pharmaceutically acceptable salt, tautomer, or stereoisomer thereof, wherein $R^2$, $R^3$, $R^4$, $R^5$, $R^{5'}$, $R^{6'}$, $R^6$, $R^{6'}$, $R^{7'}$, $R^7$, $R^9$, $R^{11}$, $R^{13}$, $R^{13'}$, $R^{14}$, $R^{17}$, $R^{18}$, L and $R^{21}$ are as defined for formula (III).

In some embodiments, the compound has the structure of formula (IIIa):

(IIIa)

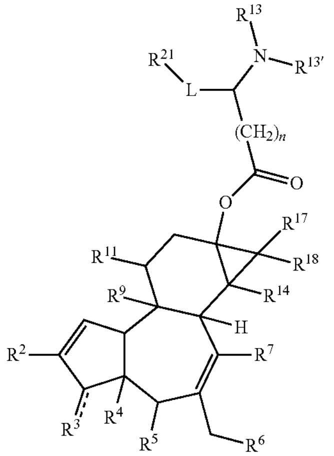

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —OR, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

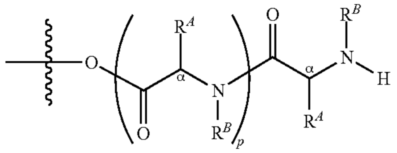

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^7$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_2$alkylene, or $C_2$-$C_{12}$alkenylene, wherein the $C_1$-$C_2$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_2$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, the compound has the structure of formula (IIIa'):

(IIIa')

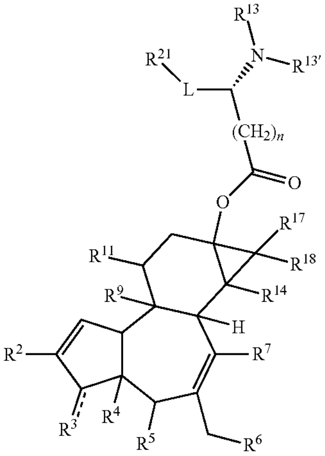

or a pharmaceutically acceptable salt, tautomer, or stereoisomer thereof, wherein $R^2$, $R^3$, $R^4$, $R^5$, $R^6$, $R^7$, $R^9$, $R^{11}$, $R^{12}$, $R^{13}$, $R^{13'}$, $R^{14}$, $R^{17}$, $R^{18}$, L and $R^{21}$ are as defined for formula (III).

In some embodiments, the compound has the structure of formula (IIIa''):

(IIIa″)

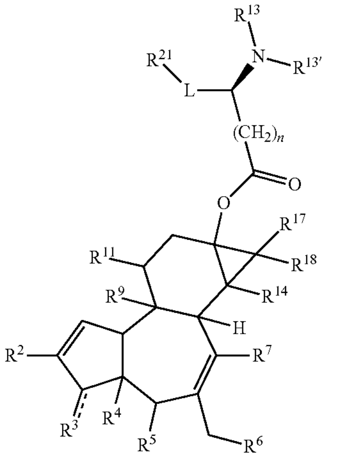

or a pharmaceutically acceptable salt, tautomer, or stereoisomer thereof, wherein $R^2$, $R^3$, $R^4$, $R^5$, $R^6$, $R^7$, $R^9$, $R^{11}$, $R^{12}$, $R^{13}$, $R^{13'}$, $R^{14}$, $R^{17}$, $R^{18}$, L and $R^{21}$ are as defined for formula (III).

In some embodiments, the compound has the structure of formula (IIIb):

(IIIb)

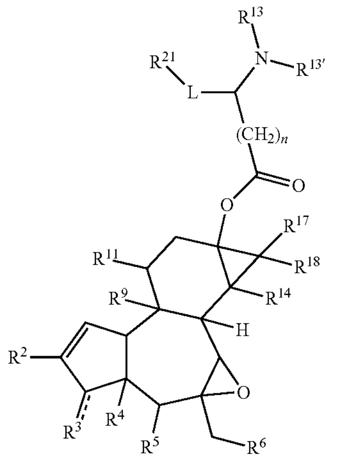

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —OR, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

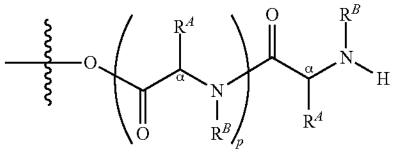

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^9$ is $OR^e$, wherein $R^e$ is H, $C_1$-$C_6$alkyl, or aryl;

$R^{11}$ is $C_1$-$C_4$alkyl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —SR, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, the compound has the structure of formula (IIIb'):

(IIIb')

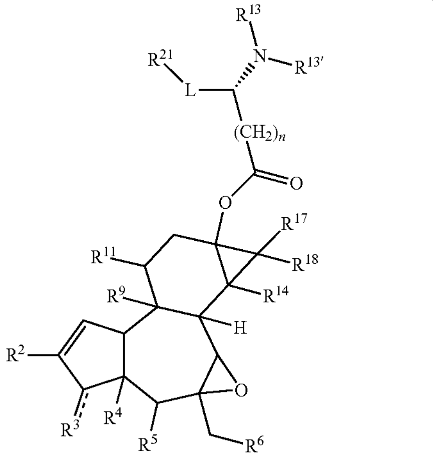

or a pharmaceutically acceptable salt, tautomer, or stereoisomer thereof, wherein $R^2$, $R^3$, $R^4$, $R^5$, $R^6$, $R^9$, $R^{11}$, $R^{13}$, $R^{13'}$, $R^{14}$, $R^{17}$, $R^{18}$, L and $R^{21}$ are as defined for formula (III).

In some embodiments, the compound has the structure of formula (IIIb"):

(IIIb")

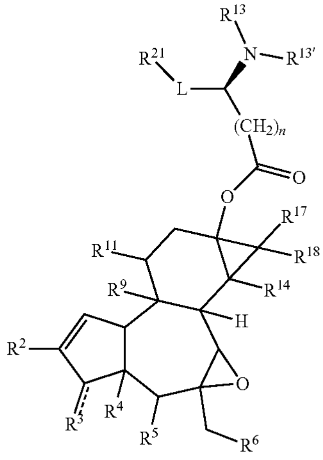

or a pharmaceutically acceptable salt, tautomer, or stereoisomer thereof, wherein $R^2$, $R^3$, $R^4$, $R^5$, $R^6$, $R^9$, $R^{11}$, $R^{13}$, $R^{13'}$, $R^{14}$, $R^{17}$, $R^{18}$, L and $R^{21}$ are as defined for formula (III).

In some embodiments of the compound of formula (III), (III'), (III"), (IIIa), (IIIa'), (IIIa"), (IIIb), (IIIb') and (IIIb"), $R^3$ is —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl. In some embodiments, the aryl of $C_0$-$C_6$alkylaryl is phenyl. In some embodiments, the aryl of $C_0$-$C_6$alkylaryl is optionally substituted with 1 to 3 of OH, CN, halo, $C_1$-$C_4$alkyl, and halo$C_1$-$C_4$alkyl. In some embodiments, $R^{a1}$ is selected from:

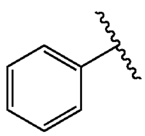

and

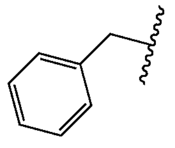

In some embodiments, $R^{a1}$ is selected from:

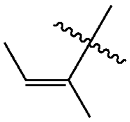

and

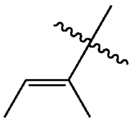

In some embodiments of the compound of formula (III), (III'), (III"), (IIIa), (IIIa'), (IIIa"), (IIIb), (IIIb') and (IIIb"), $R^3$ is O double bonded to the carbon atom.

In some embodiments of the compound of formula (III), (III'), (III"), (IIIa), (IIIa'), (IIIa"), (IIIb), (IIIb') and (IIIb"), one or more of $R^2$, $R^{11}$, $R^{17}$, and $R^{18}$ are —$CH_3$. In some embodiments, each of $R^2$, $R^{11}$, $R^{17}$, and $R^{18}$ is —$CH_3$.

In some embodiments of the compound of formula (III), (III'), (IIIa), (IIIa'), (IIIb), and (IIIb'), $R^4$ and $R^5$ are each independently H or —OH.

In some embodiments of the compound of formula (III), (III'), (IIIa), (IIIa'), (IIIb), and (IIIb'), $R^2$, $R^{11}$, $R^{17}$, and $R^{18}$ are —$CH_3$;

$R^3$ is O double bonded to the carbon atom; and $R^4$ and $R^5$ are each independently H or —OH.

In some embodiments, the compound has the structure of formula (IIIc):

(IIIc)

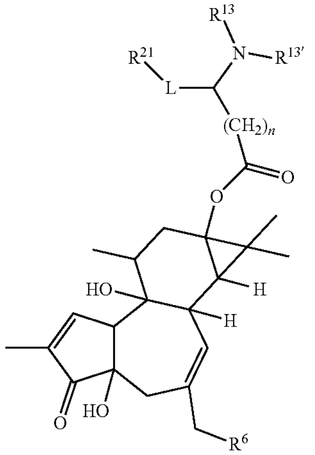

or a pharmaceutically acceptable salt, tautomer, or stereoisomer thereof;

wherein $R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

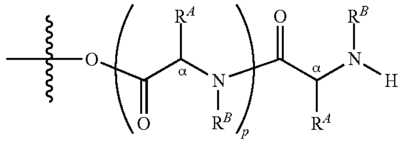

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{13}$ and $R^{13'}$ are each independently H or $C_1$-$C_4$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, the compound has the structure of formula (IIIc'):

(IIIc')

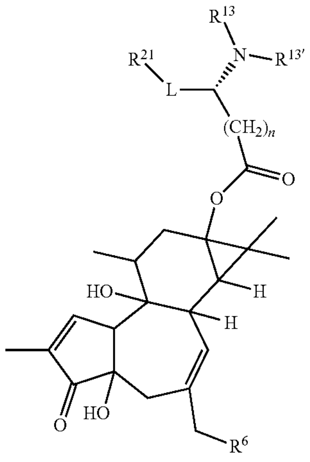

or a pharmaceutically acceptable salt, tautomer, or stereoisomer thereof, wherein $R^6$, $R^{13}$, $R^{13'}$, L and $R^{21}$ are as defined for formula (IIIc).

In some embodiments, the compound has the structure of formula (IIIc"):

(IIIc")

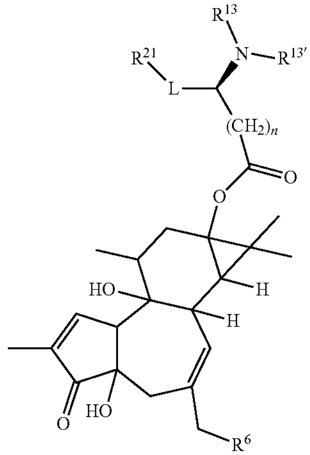

or a pharmaceutically acceptable salt, tautomer, or stereoisomer thereof, wherein $R^6$, $R^{13}$, $R^{13'}$, L and $R^{21}$ are as defined for formula (IIIc).

In some embodiments, the compound has the structure of formula (IIId):

(IIId)

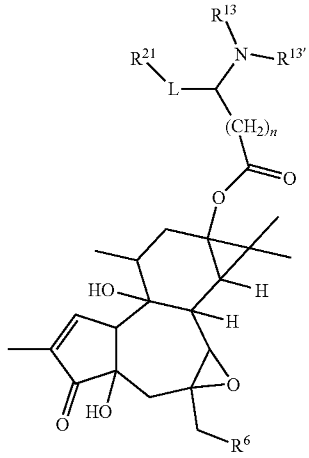

or a pharmaceutically acceptable salt, tautomer, or stereoisomer thereof;

wherein $R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

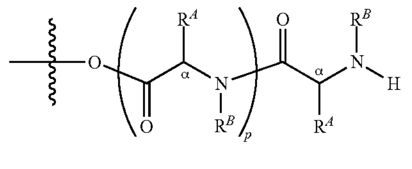

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{13}$ and $R^{13'}$ are each independently H or $C_1$-$C_4$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

In some embodiments, the compound has the structure of formula (IIId'):

(IIId')

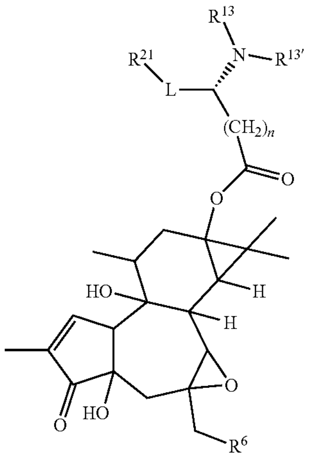

or a pharmaceutically acceptable salt, tautomer, or stereoisomer thereof, wherein $R^6$, $R^{13}$, $R^{13'}$, L and $R^2$ are as defined for formula (IIId).

In some embodiments, the compound has the structure of formula (IIId"):

(IIId")

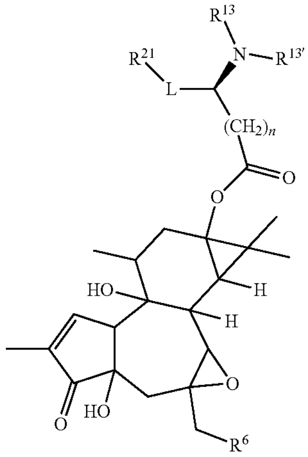

or a pharmaceutically acceptable salt, tautomer, or stereoisomer thereof, wherein $R^6$, $R^{13}$, $R^{13'}$, L and $R^2$ are as defined for formula (IIId).

In some embodiments for the compound of any of the foregoing embodiments, n is 0.

In some embodiments for the compound of any of the foregoing embodiments, each of $R^{13}$ and $R^{13'}$ is H.

In some embodiments, the compound has the structure of formula (IIIe):

(IIIe)

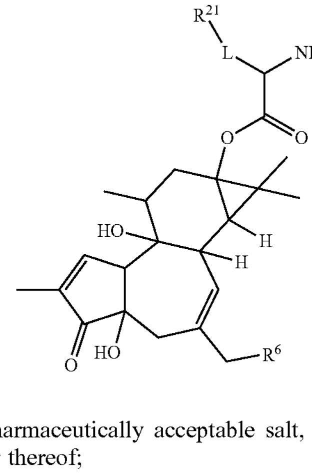

or a pharmaceutically acceptable salt, tautomer, or stereoisomer thereof;

wherein $R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

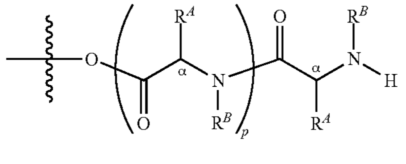

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion; and $J^1$ is selected from OH, CN, halo, $C_1$-$C_4$alkyl, and halo$C_1$-$C_4$alkyl.

In some embodiments, the compound has the structure of formula (IIIe'):

(IIIe')

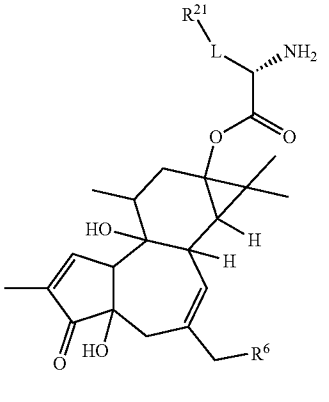

or a pharmaceutically acceptable salt, tautomer, or stereoisomer thereof, wherein $R^6$, L and $R^{21}$ are as defined for formula (IIIe).

In some embodiments, the compound has the structure of formula (IIIe"):

(IIIe")

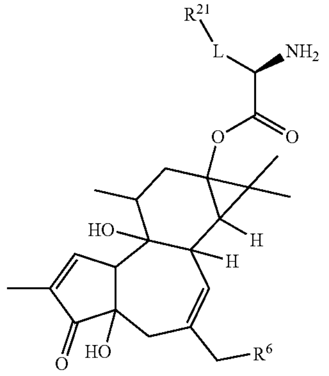

or a pharmaceutically acceptable salt, tautomer, or stereoisomer thereof, wherein $R^6$, L and $R^{21}$ are as defined for formula (IIIe).

In some embodiments, the compound has the structure of formula (IIIf):

(IIIf)

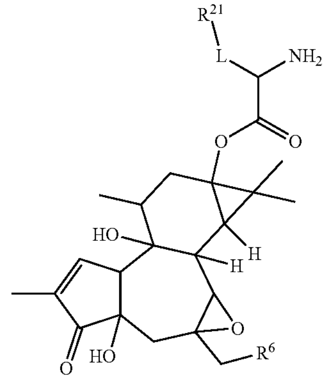

or a pharmaceutically acceptable salt, tautomer, or stereoisomer thereof;

wherein $R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

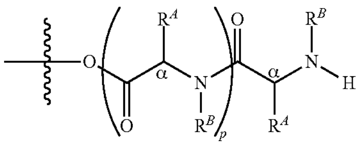

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion; and $J^1$ is selected from OH, CN, halo, $C_1$-$C_4$alkyl, and halo$C_1$-$C_4$alkyl.

In some embodiments, the compound has the structure of formula (IIIf'):

(IIIf')

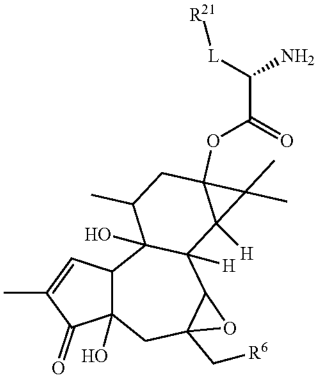

or a pharmaceutically acceptable salt, tautomer, or stereoisomer thereof;

wherein $R^6$, L and $R^{21}$ are as defined for formula (IIIf).

In some embodiments, the compound has the structure of formula (IIIf'):

(IIIf'')

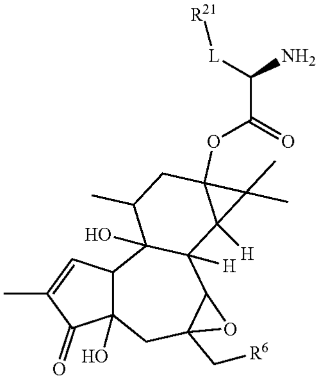

or a pharmaceutically acceptable salt, tautomer, or stereoisomer thereof, wherein $R^6$, L and $R^{21}$ are as defined for formula (IIIf).

In some embodiments of the compounds of (I), (Ia), (Ib), (II), (II'), (II''), (IIa), (IIa'), (IIa''), (IIb), (IIb'), (IIb''), (III), (III'), (III''), (IIIa), (IIIa'), (IIIa''), (IIIb), (IIIb'), (IIIb''), (IIIc), (IIIc'), (IIc''), (IIId), (IIId'), (IIId''), (IIIe), (IIIe'), (IIIe''), (IIIf), (IIIf'), and (IIIf'), $R^{21}$ is $C_3$-$C_7$cycloalkyl, wherein the $C_3$-$C_7$cycloalkyl is optionally substituted with 1 to 3 of J, wherein J is selected from OH, CN, halo, $C_1$-$C_4$alkyl, and halo$C_1$-$C_4$alkyl. In some of the foregoing embodiments, the $C_3$-$C_7$cycloalkyl is selected from the group consisting of cyclobutyl, cyclopentyl, cyclohexyl, and cycloheptyl.

In some embodiments of the compounds of (I), (Ia), (Ib), (II), (II'), (II''), (IIa), (IIa'), (IIa''), (IIb), (IIb'), (IIb''), (III), (III'), (III''), (IIIa), (IIIa'), (IIIa''), (IIIb), (IIIb'), (IIIb''), (IIIc), (IIIc'), (IIIc''), (IIId), (IIId'), (IIId''), (IIIe), (IIIe'), (IIIe''), (IIIf), (IIIf'), and (IIIf'), $R^{21}$ is a heterocyclyl, wherein the heterocyclyl is optionally substituted with 1 to 3 of $J^1$, wherein $J^1$ is selected from OH, CN, halo, $C_1$-$C_4$alkyl, and halo$C_1$-$C_4$alkyl. In some embodiments, the heterocyclyl is selected from oxiranyl, oxetanyl, azetidynyl, oxazolyl, thiazolidinyl, thiazolyl, morpholinyl, pyrrolidinonyl, pyrrolidinyl, piperidinyl, piperazinyl, 2,3-dihydrofuranyl, dihydropyranyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and azapanyl, wherein the heterocyclyl is optionally substituted with 1 to 3 of OH, CN, halo, $C_1$-$C_4$alkyl, and halo$C_1$-$C_4$alkyl.

In some embodiments of the compounds of (I), (Ia), (Ib), (II), (II'), (II''), (IIa), (IIa'), (IIa''), (IIb), (IIb'), (IIb''), (III), (III'), (III''), (IIIa), (IIIa'), (IIIa''), (IIIb), (IIIb'), (IIIb''), (IIIc), (IIIc'), (IIIc''), (IIId), (IIId'), (IIId''), (IIIe), (IIIe'), (IIIe''), (IIIf), (IIIf'), and (IIIf'), $R^{21}$ is aryl, wherein the aryl is optionally substituted with 1 to 3 of $J^1$, wherein $J^1$ is selected from OH, CN, halo, $C_1$-$C_4$alkyl, and halo$C_1$-$C_4$alkyl. In some of the foregoing embodiments, $R^{21}$ is a phenyl or naphthyl, wherein the phenyl or naphthyl is optionally substituted with 1 to 3 of OH, CN, halo, $C_1$-$C_4$alkyl, and halo$C_1$-$C_4$alkyl.

In some embodiments of the compounds of (I), (Ia), (Ib), (II), (II'), (II''), (IIa), (IIa'), (IIa''), (IIb), (IIb'), (IIb''), (III), (III'), (III''), (IIIa), (IIIa'), (IIIa''), (IIIb), (IIIb'), (IIIb''), (IIIc), (IIIc'), (IIIc''), (IIId), (IIId'), (IIId''), (IIIe), (IIIe'), (IIIe''), (IIIf), (IIIf'), and (IIIf'), $R^{21}$ is heteroaryl, wherein the heteroaryl is optionally substituted with 1 to 3 of $J^1$, wherein $J^1$ is selected from OH, CN, halo, $C_1$-$C_4$alkyl, and halo$C_1$-$C_4$alkyl. In some of the foregoing embodiments, the heteroaryl is selected from the group consisting of pyrrolyl, pyrazolyl, imidazolyl, pyrazinyl, oxazolyl, isoxazolyl, thiazolyl, furyl, thienyl, pyridyl, pyrimidyl, benzoxazolyl, benzothiazolyl, purinyl, benzimidazolyl, indolyl, isoquinolyl, quinoxalinyl, and quinolyl, wherein the heteroaryl is optionally substituted with 1 to 3 of OH, CN, halo, $C_1$-$C_4$alkyl, and halo$C_1$-$C_4$alkyl.

In some embodiments of the compounds of (I), (Ia), (Ib), (II), (II'), (II''), (IIa), (IIa'), (IIa''), (IIb), (IIb'), (IIb''), (III), (III'), (III''), (IIIa), (IIIa'), (IIIa''), (IIIb), (IIIb'), (IIIb''), (IIIc), (IIIc'), (IIIc''), (IIId), (IIId'), (IIId''), (IIIe), (IIIe'), (IIIe''), (IIIf), (IIIf'), and (IIIf'), $R^{21}$ is adamantyl, wherein the adamantyl is optionally substituted with $J^1$, wherein $J^1$ is selected from OH, halo, $C_1$-$C_4$alkyl, and halo$C_1$-$C_4$alkyl.

In some embodiments of the compounds of (I), (Ia), (Ib), (II), (II'), (II''), (IIa), (IIa'), (IIa''), (IIb), (IIb'), (IIb''), (III), (III'), (III''), (IIIa), (IIIa'), (IIIa''), (IIIb), (IIIb'), (IIIb''), (IIIc), (IIIc'), (IIIc''), (IIId), (IIId'), (IIId''), (IIIe), (IIIe'), (IIIe''), (IIIf), (IIIf'), and (IIIf'), $R^{21}$ is spiro$C_5$-$C_{12}$ cycloalkyl, wherein the spiro$C_5$-$C_{12}$ cycloalkyl has 0-2 carbon atoms replaced with 0-2 heteroatoms selected from N, O and S, and is optionally substituted with 1 to 3 of $J^1$, wherein $J^1$ is selected from OH, CN, halo, $C_1$-$C_4$alkyl, and halo$C_1$-$C_4$alkyl, or when an N atom is present, is optionally substituted with an N-protecting group.

In some embodiments of the compounds of (I), (Ia), (Ib), (II), (II'), (II"), (IIa), (IIa'), (IIa"), (IIb), (IIb'), (IIb"), (III), (III'), (III"), (IIIa), (IIIa'), (IIIa"), (IIIb), (IIIb'), (IIIb"), (IIIc), (IIIc'), (IIIc"), (IIId), (IIId'), (IIId"), (IIIe), (IIIe'), (IIIe"), (IIIf), (IIIf'), and (IIIf'), $R^{21}$ is 5 to 12 membered bridged bicyclyl, wherein the bridged bicyclyl has 0-2 carbon atoms replaced with 0-2 heteroatoms selected from N, O and S, and is optionally substituted with 1 to 3 of $J^1$, wherein $J^1$ is selected from OH, CN, halo, $C_1$-$C_4$alkyl, and halo$C_1$-$C_4$alkyl, or when an N atom is present, is optionally substituted with an N-protecting group.

In some embodiments of the compounds of formula (I), (Ia), (Ib), (II), (II'), (II"), (IIa), (IIa'), (IIa"), (IIb), (IIb'), (IIb"), (III), (III'), (III"), (IIIa), (IIIa'), (IIIa"), (IIIb), (IIIb'), (IIIb"), (IIIc), (IIIc'), (IIIc"), (IIId), (IIId'), (IIId"), (IIIe), (IIIe'), (IIIe"), (IIIf), (IIIf'), and (IIIf'), $R^{21}$ is selected from the following:

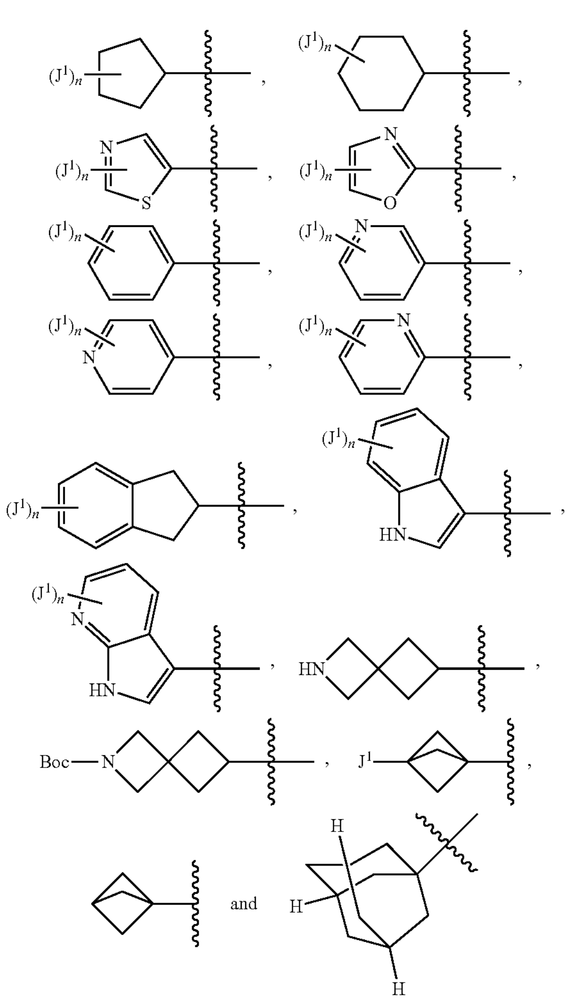

wherein J is OH, CN, halo, $C_1$-$C_4$alkyl, and halo$C_1$-$C_4$alkyl, and n is 0-3. In some embodiments, n is 0. In some embodiments, n is 1. In some embodiments, n is 2. In some embodiments, halo$C_1$-$C_4$alkyl is —$CH_2F$, —$CHF_2$, or —$CF_3$.

In some embodiments, for any of the compounds herein, L is $C_3$-$C_{12}$alkylene. In some embodiments, for any of the compounds herein, L is $C_3$-$C_6$alkylene. In some embodiments, for any of the compounds herein, L is $C_1$-$C_6$alkylene.

In some embodiments, for any of the compounds herein, L is $C_3$-$C_{12}$alkenylene. In some embodiments, for any of the compounds herein, L is $C_3$-$C_6$alkenylene. In some embodiments, for any of the compounds herein, L is $C_1$-$C_6$alkenylene.

In some embodiments, L is $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl; and $R^{21}$ is H.

In some embodiments of the compounds of formula (I), (Ia), (Ib), (II), (II'), (II"), (IIa), (IIa'), (IIa"), (IIb), (IIb'), (IIb"), (III), (III'), (III"), (IIIa), (IIIa'), (IIIa"), (IIIb), (IIIb'), (IIIb"), (IIIc), (IIIc'), (IIIc"), (IId), (IIId'), (IIId"), (IIIe), (IIIe'), (IIIe"), (IIIf), (IIIf'), and (IIIf'), -L-$R^{21}$ is a $C_2$-$C_6$alkenyl selected from:

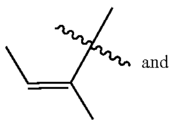

and

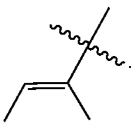

In some embodiments for any of the foregoing compounds, e.g., formula (I), (Ia), (Ib), (II), (II'), (II"), (IIa), (IIa'), (IIa"), (IIb), (IIb'), (IIb"), (III), (III'), (III"), (IIIa), (IIIa'), (IIIa"), (IIIb), (IIIb'), (IIIb"), (IIIc), (IIIc'), (IIIC"), (IIId), (IIId'), (IIId"), (IIIe), (IIIe'), (IIIe"), (IIIf), (IIIf'), and (IIIf'), wherein $R^6$ is

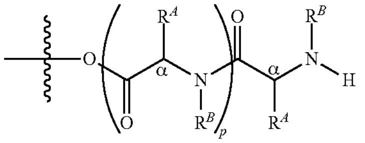

each occurrence of $R^A$ is independently hydrogen (glycine), methyl (alanine), propan-2-yl (valine), propan-1-yl (norvaline), 2-methylpropan-1-yl (leucine), 1-methylpropan-1-yl (isoleucine), butan-1-yl (norleucine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 3-guanidinopropan-1-yl (arginine), or 3-ureido-propan-1-yl (citrulline);

each occurrence of $R^B$ is independently H, or $R^B$ together with the adjacent $R_A$ and the N atom form a prolyl side chain:

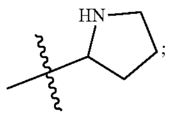

and p is 0, 1 or 2.

In some embodiments for any of the foregoing compounds, e.g., formula (I), (Ia), (Ib), (II), (II'), (II"), (IIa), (IIa'), (IIa"), (IIb), (IIb'), (IIb"), (III), (III'), (III"), (IIIa), (IIIa'), (IIIa"), (IIIb), (IIIb'), (IIIb"), (IIIc), (IIIc'), (IIIc"), (IIId), (IIId'), (IIId"), (IIIe), (IIIe'), (IIIe"), (IIIf), (IIIf'), and (IIIf'), wherein $R^6$ is

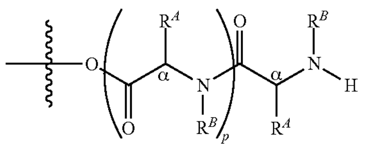

each occurrence of $R^A$ is independently methyl (alanine), propan-2-yl (valine), 2-methylpropan-1-yl (leucine), imidazol-4-ylmethyl (histidine), hydroxymethyl (serine), 1-hydroxyethyl (threonine), carbamoylmethyl (asparagine), 2-carbamoylethyl (glutamine), 4-aminobutan-1-yl (lysine), carboxymethyl (aspartic acid), 3-guanidinopropan-1-yl (arginine), benzyl (phenylalanine), or 4-aminobutan-1-yl (lysine);

$R^B$ is H; and p 0, 1, or 2.

In some embodiments for any of the foregoing compounds, e.g., formula (I), (Ia), (Ib), (II), (II'), (II"), (IIa), (IIa'), (IIa"), (IIb), (IIb'), (IIb"), (III), (III'), (III"), (IIIa), (IIIa'), (IIIa"), (IIIb), (IIIb'), (IIIb"), (IIIc), (IIIc'), (IIIc"), (IIId), (IIId'), (IIId"), (IIIe), (IIIe'), (IIIe"), (IIIf), (IIIf'), and (IIIf'), wherein $R^6$ is

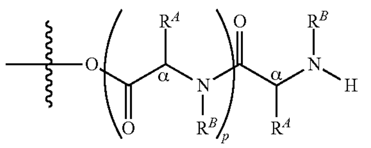

each occurrence of $R^A$ is independently propan-2-yl (valine), 2-methylpropan-1-yl (leucine), carboxymethyl (aspartic acid), benzyl (phenylalanine), or 4-aminobutan-1-yl (lysine);

each $R^B$ is H; and p is 0, 1, or 2.

In some embodiments for any of the foregoing compounds, e.g., formula (I), (Ia), (Ib), (II), (II'), (II"), (IIa), (IIa'), (IIa"), (IIb), (IIb'), (IIb"), (III), (III'), (III"), (IIIa), (IIIa'), (IIIa"), (IIIb), (IIIb'), (IIIb"), (IIIc), (IIIc'), (IIIc"), (IIId), (IIId'), (IIId"), (IIIe), (IIIe'), (IIIe"), (IIIf), (IIIf'), and (IIIf'), p is 0.

In some embodiments for any of the foregoing compounds, e.g., formula (I), (Ia), (Ib), (II), (II'), (II"), (IIa), (IIa'), (IIa"), (IIb), (IIb'), (IIb"), (III), (III'), (III"), (IIIa), (IIIa'), (IIIa"), (IIIb), (IIIb'), (IIIb"), (IIIc), (IIIc'), (IIIc"), (IIId), (IIId'), (IIId"), (IIIe), (IIIe'), (IIIe"), (IIIf), (IIIf'), and (IIIf'), p is 1.

In some embodiments for any of the foregoing compounds, e.g., formula (I), (Ia), (Ib), (II), (II'), (II"), (IIa), (IIa'), (IIa"), (IIb), (IIb'), (IIb"), (III), (III'), (III"), (IIIa), (IIIa'), (IIIa"), (IIIb), (IIIb'), (IIIb"), (IIIc), (IIIc'), (IIIc"), (IIId), (IIId'), (IIId"), (IIIe), (IIIe'), (IIIe"), (IIIf), (IIIf'), and (IIIf'), wherein $R^6$ is

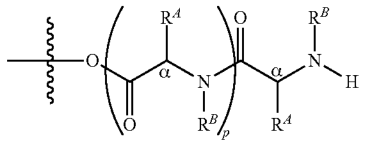

and p is 1;

first of $R^A$ is propan-2-yl (valine) and second of $R^A$ is propan-2-yl (valine); and each of $R^B$ is H (i.e., dipeptide Val-Val); or first of $R^A$ is 2-methylpropan-1-yl (leucine), and second of $R^A$ is 2-methylpropan-1-yl (leucine); and each of $R^B$ is H (i.e., dipeptide Leu-Leu); or first of $R^A$ is methyl (alanine) and second of $R^A$ is methyl (alanine); and each of $R^B$ is H (i.e., dipeptide Ala-Ala); or first of $R^A$ is 4-aminobutan-1-yl (lysine); second of $R^A$ is 4-aminobutan-1-yl (lysine); and each of $R^B$ is H (i.e., dipeptide Lys-Lys); or first of $R^A$ is hydrogen; second of $R^A$ is 4-aminobutan-1-yl, and each of $R^B$ is H (i.e., dipeptide Gly-Lys).

In some embodiments for any of the foregoing compounds, e.g., formula (I), (Ia), (Ib), (II), (II'), (II"), (IIa), (IIa'), (IIa"), (IIb), (IIb'), (IIb"), (III), (III'), (III"), (IIIa), (IIIa'), (IIIa"), (IIIb), (IIIb'), (IIIb"), (IIIc), (IIIc'), (IIIc"), (IIId), (IIId'), (IIId"), (IIIe), (IIIe'), (IIIe"), (IIIf), (IIIf'), and (IIIf'), wherein $R^6$ is

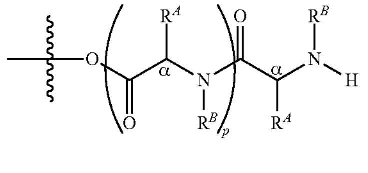

each of the α-carbon of the amino acid other than glycine is in the L or D configuration. In some embodiments, the α-carbon of the amino acid other than glycine is in the L configuration In some embodiments, the compound is selected from the group consisting of the compounds or a pharmaceutical salt thereof in Table 1:

TABLE 1
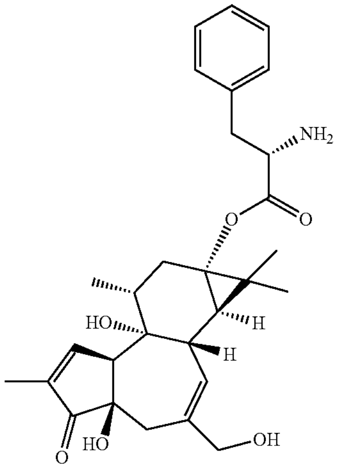
K101-C1303
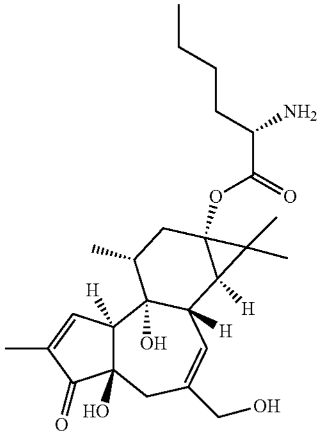
K101-C1317
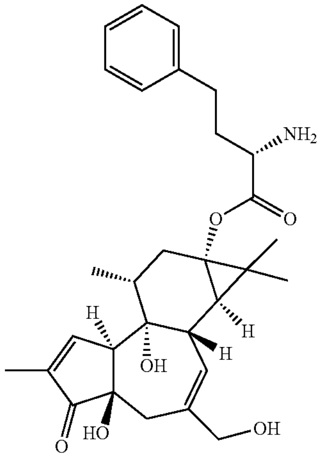
K101-C1318
TABLE 1-continued
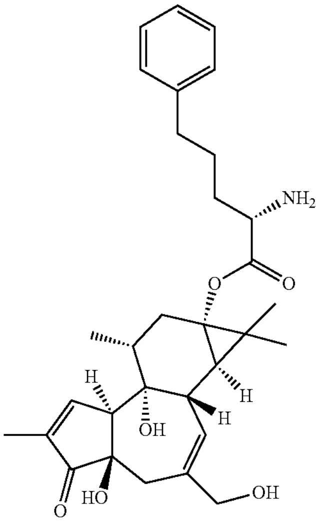
K101-C1319
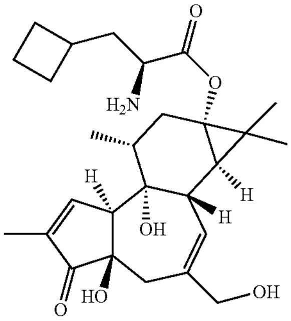
K101-C1325
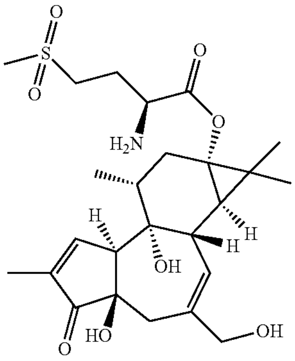
K101-C1326

TABLE 1-continued
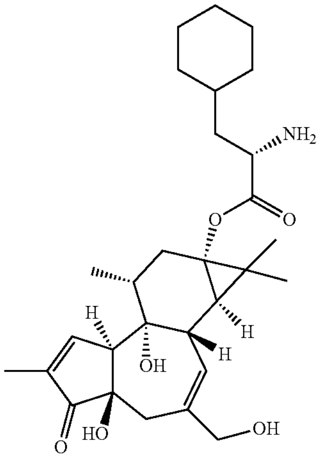
K101-C1327
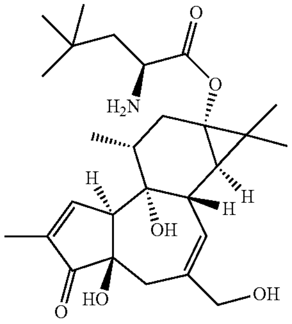
K101-C1328
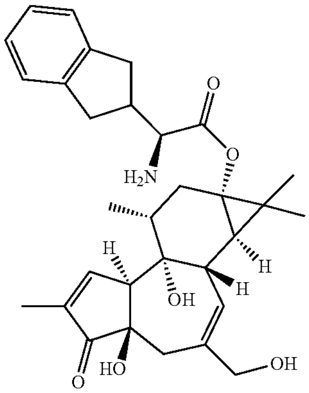
K101-C1329
TABLE 1-continued
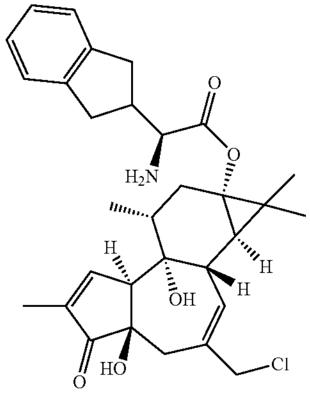
K101-C1329-Cl
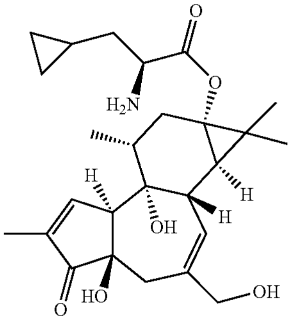
K101-C1330
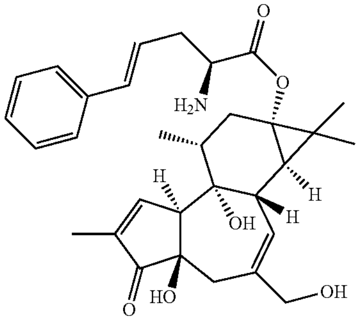
K101-C1331
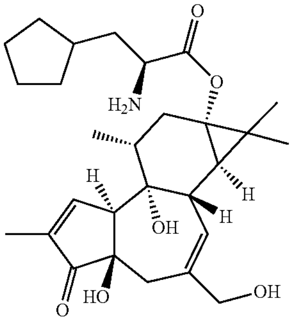
K101-C1332

TABLE 1-continued
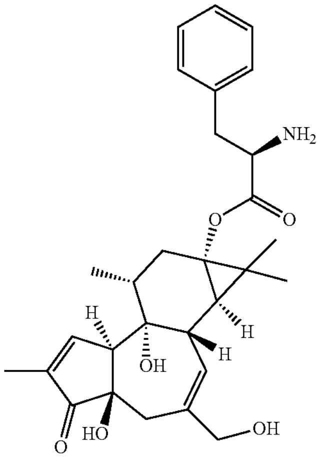
K101-C1336
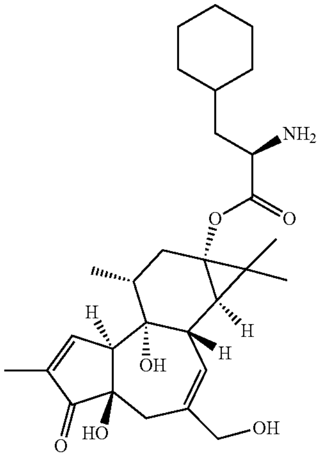
K101-C1337
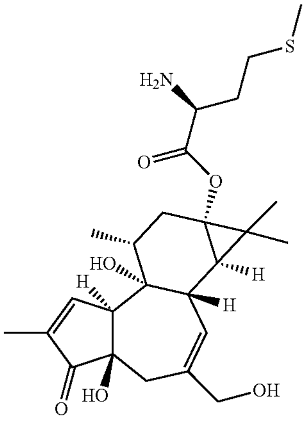
K101-C1338
TABLE 1-continued
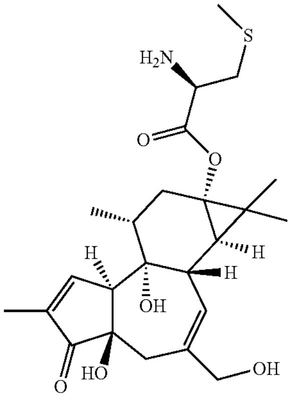
K101-C1339
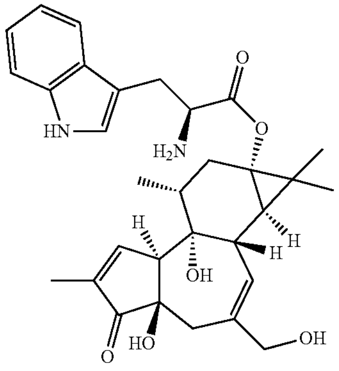
K101-C1340
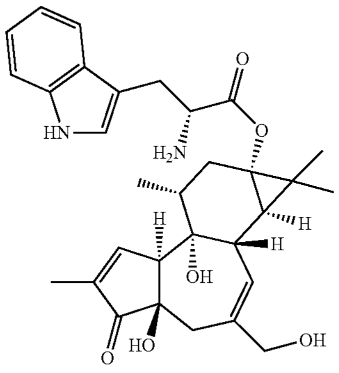
K101-C1341
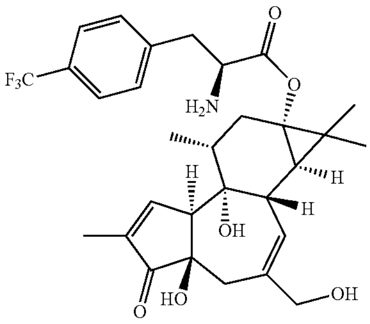
K101-C1342

TABLE 1-continued
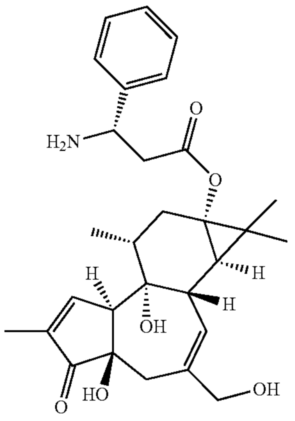
K101-C1343
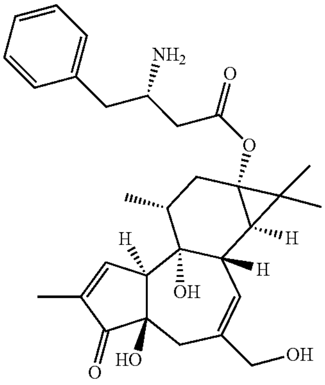
K101-C1344
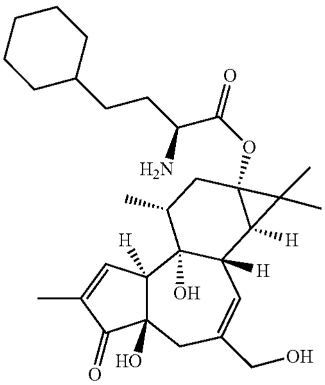
K101-C1345
TABLE 1-continued
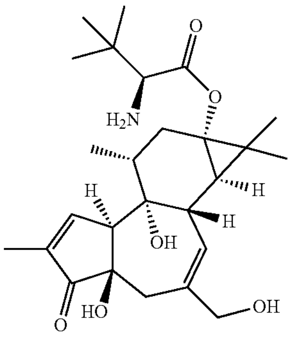
K101-C1346
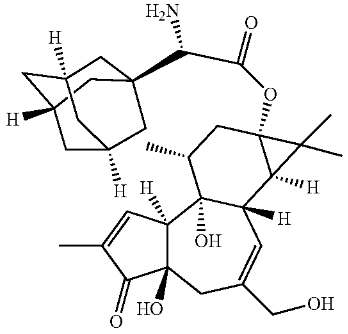
K101-C1347
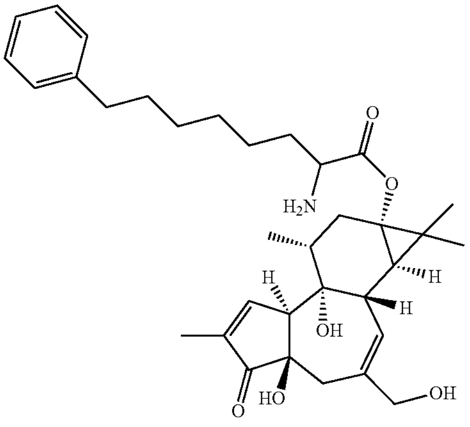
K101-C1348

TABLE 1-continued
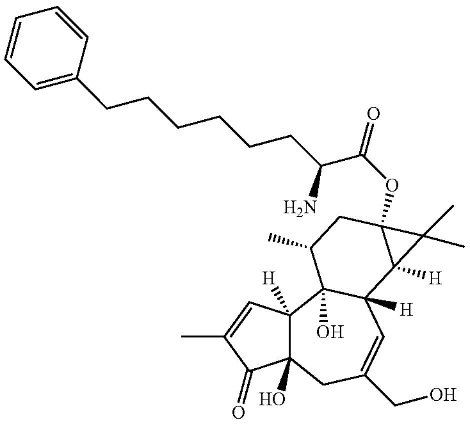
K101-C134802
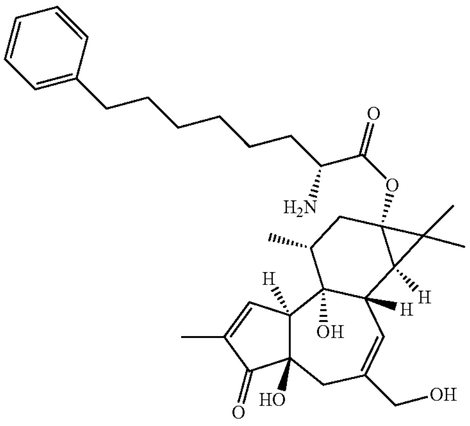
K101-C134801
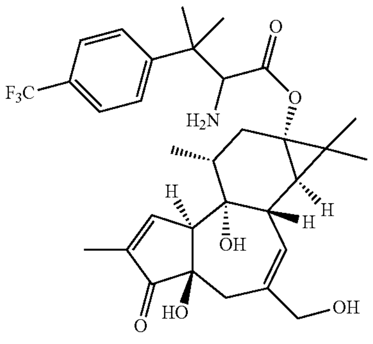
K101-C1349
TABLE 1-continued
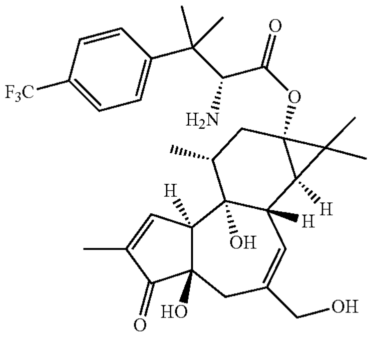
K101-C134901
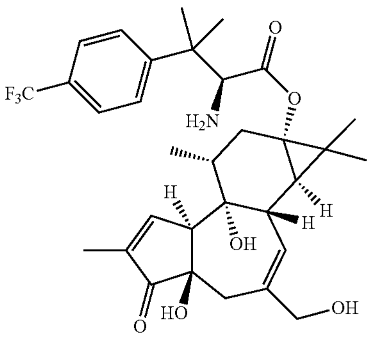
K101-C134902
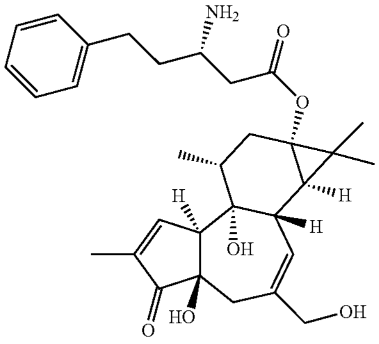
K101-C1350

TABLE 1-continued
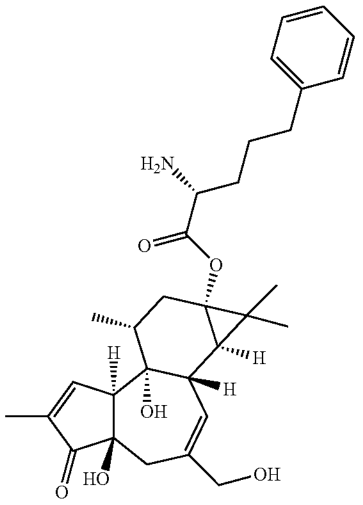
K101-C1351
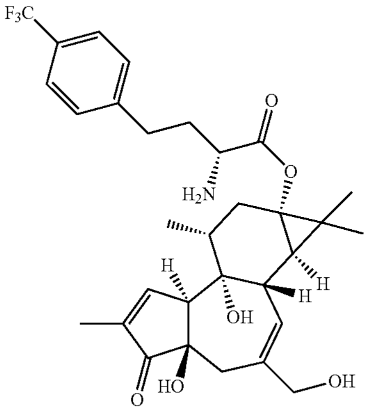
K101-C135601
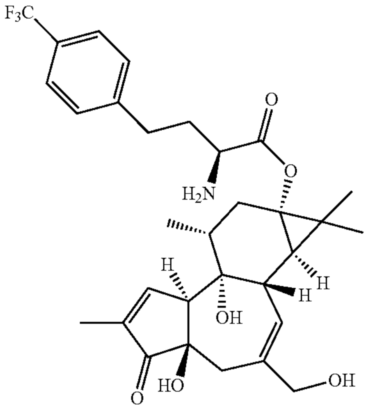
K101-C135002
TABLE 1-continued
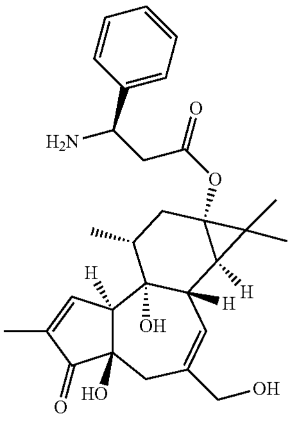
K101-C1357
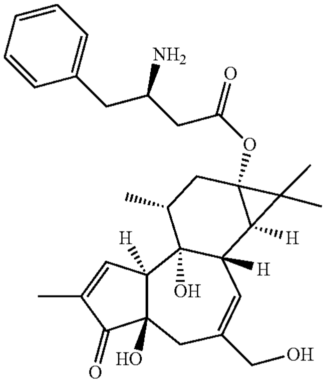
K101-C1358
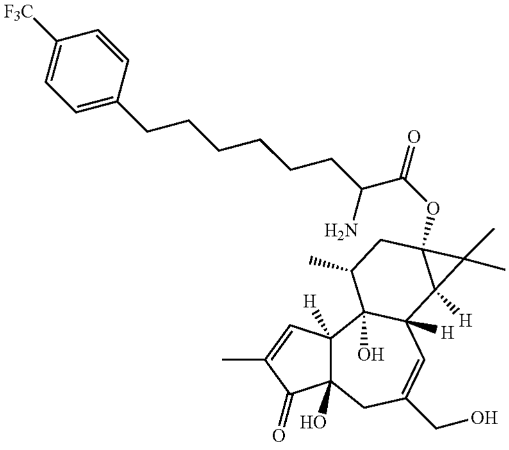
K101-C1359

TABLE 1-continued
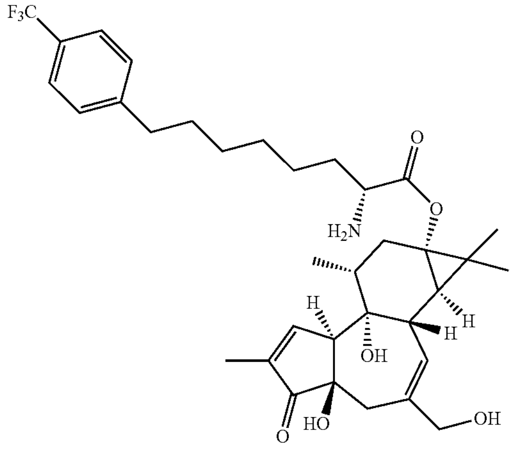
K101-C135901
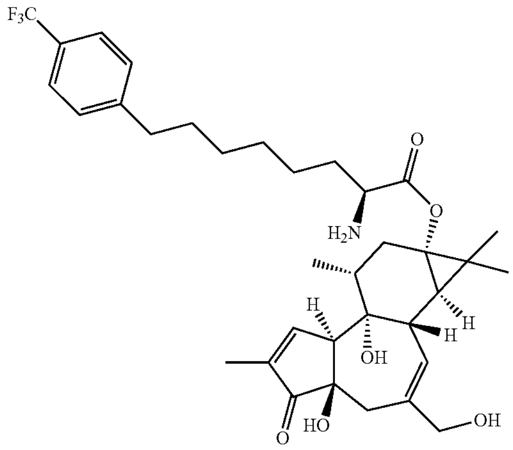
K101-C135902
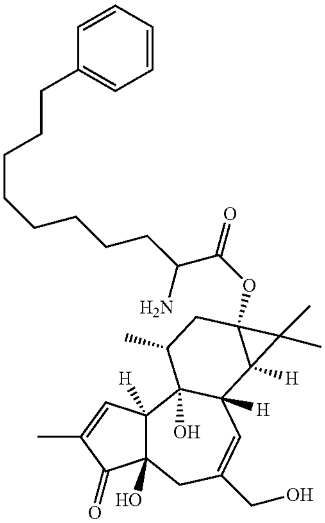
K101-C1361
TABLE 1-continued
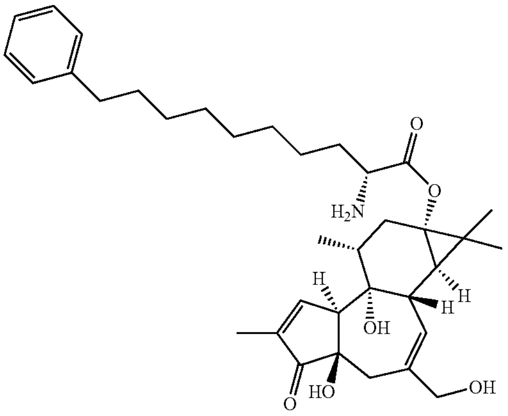
K101-C136101
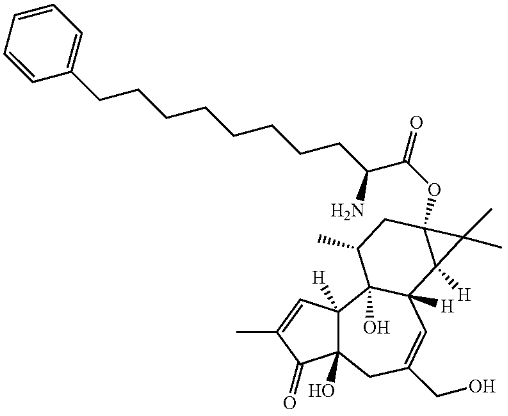
K101-C136102
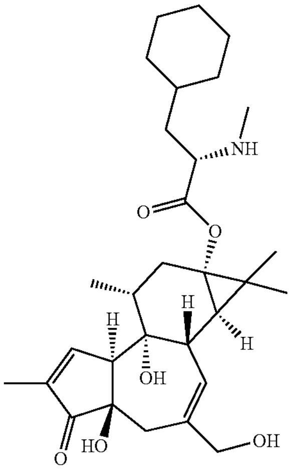
K101-C1364

TABLE 1-continued
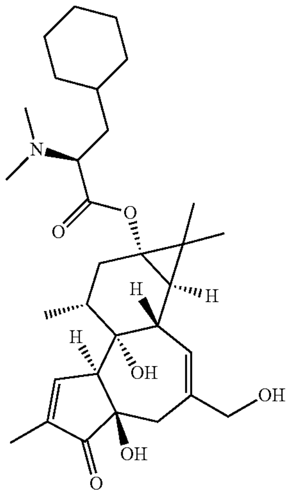
K101-C1365
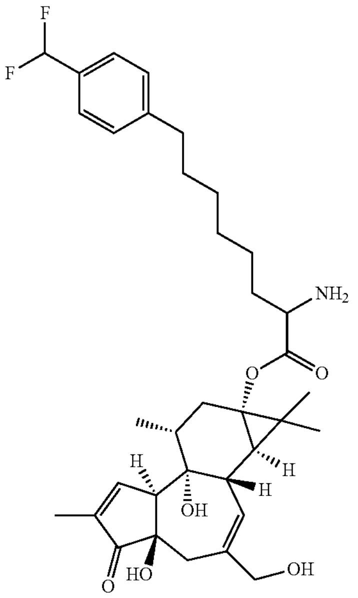
K101-C1370
TABLE 1-continued
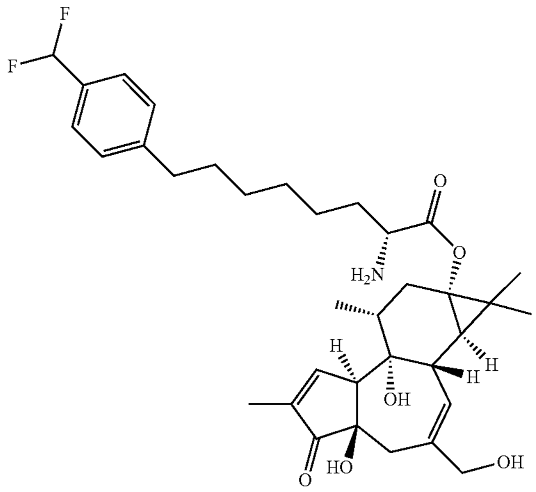
K101-C137001
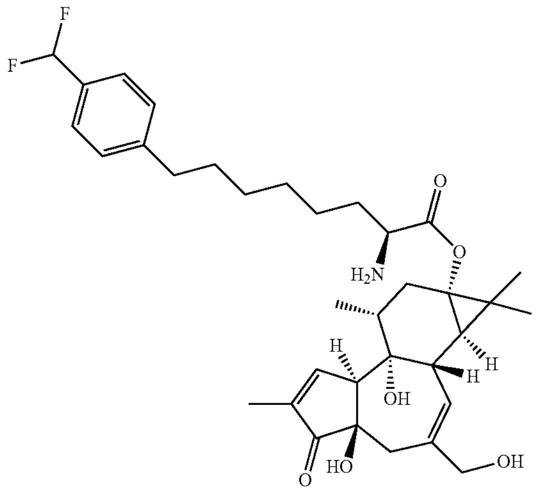
K101-C137002
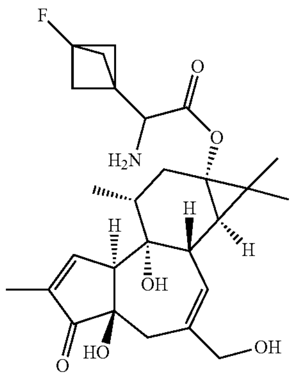
K101-C1373

TABLE 1-continued

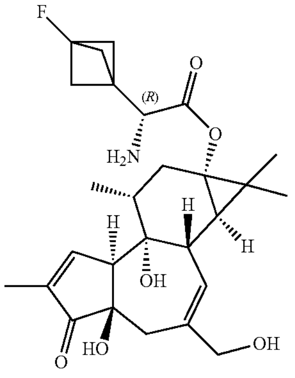

K101-C137301

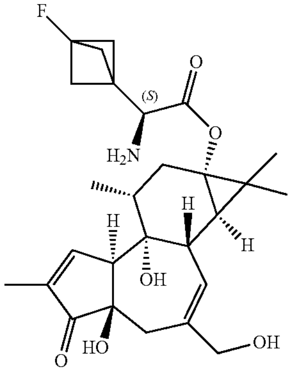

K101-C137302

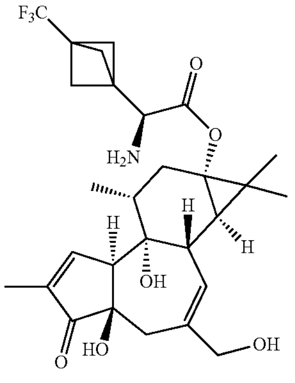

K101-C1375

TABLE 1-continued

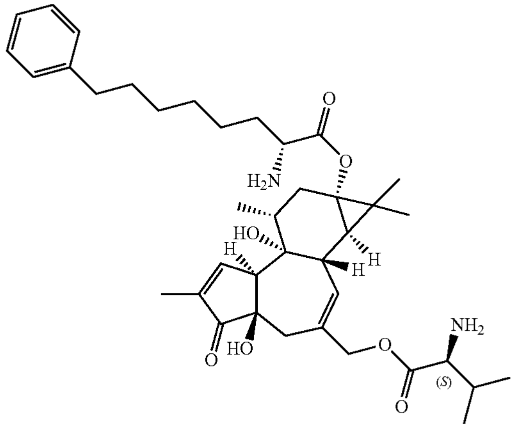

K101-C134801C2003

In some embodiments, for each of the compounds of Table 1, the —OH on the C20 carbon atom, where appropriate, is substituted with

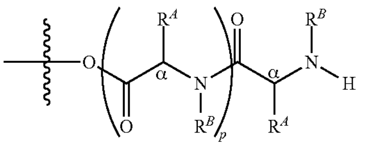

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2;

In some embodiments of the amino acid moiety on the C20 carbon, each occurrence of $R^A$ is independently hydrogen (glycine), methyl (alanine), propan-2-yl (valine), propan-1-yl (norvaline), 2-methylpropan-1-yl (leucine), 1-methylpropan-1-yl (isoleucine), butan-1-yl (norleucine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 3-guanidinopropan-1-yl (arginine), or 3-ureido-propan-1-yl (citrulline);

each occurrence of $R^B$ is independently H, or $R^B$ together with the adjacent $R_A$ and the N atom form a prolyl side chain:

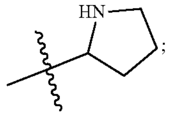 [SMILES: *C1CCCN1]

and p is 0, 1 or 2.

In some embodiments, each occurrence of $R^A$ is independently methyl (alanine), propan-2-yl (valine), 2-methylpropan-1-yl (leucine), imidazol-4-ylmethyl (histidine), hydroxymethyl (serine), 1-hydroxyethyl (threonine), carbamoylmethyl (asparagine), 2-carbamoylethyl (glutamine), 4-aminobutan-1-yl (lysine), carboxymethyl (aspartic acid), 3-guanidinopropan-1-yl (arginine), benzyl (phenylalanine), or 4-aminobutan-1-yl (lysine);

$R^B$ is H; and p 0, 1, or 2.

In some embodiments, each occurrence of $R^A$ is independently propan-2-yl (valine), 2-methylpropan-1-yl (leucine), carboxymethyl (aspartic acid), benzyl (phenylalanine), or 4-aminobutan-1-yl (lysine);

each $R^B$ is H; and p is 0, 1, or 2.

In some embodiments, p is 0.

In some embodiments, p is 1.

In some embodiments, p is 1;

first of $R^A$ is propan-2-yl (valine) and second of $R^A$ is propan-2-yl (valine); and each of $R^B$ is H (i.e., dipeptide Val-Val); or first of $R^A$ is 2-methylpropan-1-yl (leucine), and second of $R^A$ is 2-methylpropan-1-yl (leucine); and each of $R^B$ is H (i.e., dipeptide Leu-Leu); or first of $R^A$ is methyl (alanine) and second of $R^A$ is methyl (alanine); and each of $R^B$ is H (i.e., dipeptide Ala-Ala); or first of $R^A$ is 4-aminobutan-1-yl (lysine); second of $R^A$ is 4-aminobutan-1-yl (lysine); and each of $R^B$ is H (i.e., dipeptide Lys-Lys); or first of $R^A$ is hydrogen; second of $R^A$ is 4-aminobutan-1-yl, and each of $R^B$ is H (i.e., dipeptide Gly-Lys).

In some embodiments, each of the α-carbon of the amino acid other than glycine is in the L or D configuration. In some embodiments, each of the α-carbon of the amino acid other than glycine is in the L configuration.

In another aspect, the present disclosure provides a compound of formula (IV):

(IV)

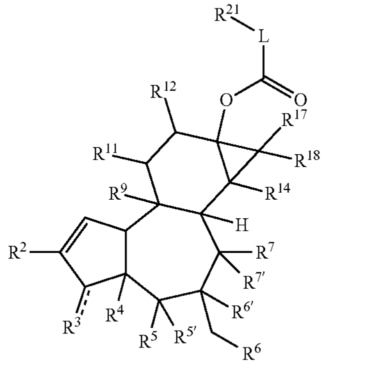

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —OR, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^{5'}$ and $R^{6'}$ are H, or $R^{5'}$ and $R^{6'}$ form a bond or are bonded to a common O atom to form an epoxide ring as permitted by valency;

$R^6$ is OH, halo, or —$OC(O)R^c$, wherein $R^c$ is —$C_1$-$C_6$alkyl, —$C_1$-$C_6$alkyl-$(NR^c)_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

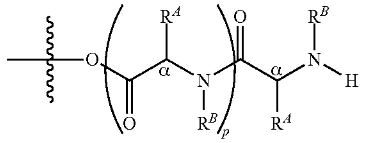

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2;

$R^{6'}$ and $R^{7'}$ are H, or $R^{6'}$ and $R^{7'}$ form a bond or are bonded to a common O atom to form an epoxide ring, as permitted by valency;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —$OC(O)R^f$, wherein $R^f$ is $C_1$-$C_2$alkyl, $C_2$-$C_2$alkenyl, —$C_0$-$C_{12}$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is $C_0$-$C_6$alkylarylene, $C_0$-$C_6$alkylheteroarylene, $C_0$-$C_6$alkyl$C_3$-$C_7$cycloalkylene, $C_1$-$C_{12}$alkylene or $C_2$-$C_{12}$alkenylene, wherein the $C_1$-$C_2$alkylene or $C_2$-$C_{12}$alkenylene is optionally substituted with OH or $C_1$-$C_4$alkyl; and $R^{21}$ is H, —OH, —SH, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$; and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl or, when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$J^1$ is selected from OH, CN, halo, $C_1$-$C_4$alkyl, and halo$C_1$-$C_4$alkyl; and $R^k$ is H or $M^+$ counterion.

In some embodiments, excluded from the compounds of formula (IV) are compounds in which:

-L-$R^{21}$ is

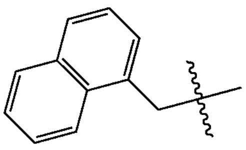
or
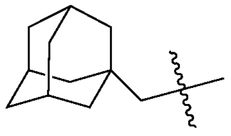

$R^2$ and $R^{11}$ are $CH_3$;

$R^3$ is =O;

$R^4$ is OH;

$R^5$, $R^{5'}$, $R^7$ and $R^{14}$ are H;

$R^{6'}$ and $R^{7'}$ together form a bond;

$R^9$ is OH;

$R^{12}$ is H;

$R^7$ and $R^{18}$ are —$CH_3$;

$R^A$ is propan-2-yl (valine);

$R^B$ is H; and p is 0.

In some embodiments, the compound has the structure of formula (IVa):

(IVa)

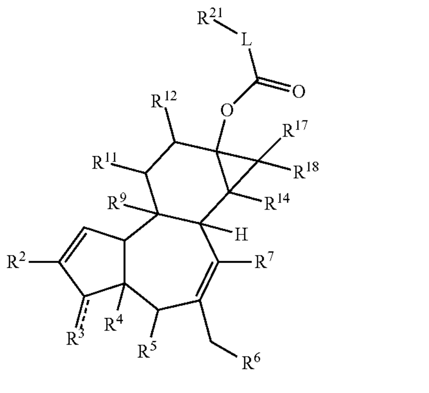

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —C(O)$R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —OC(O)$R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

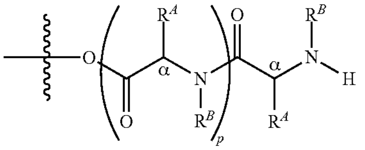

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —OC(O)$R^f$, wherein $R^f$ is $C_1$-$C_{12}$alkyl, $C_2$-$C_{12}$alkenyl, —$C_0$-$C_2$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is $C_0$-$C_6$alkylarylene, $C_0$-$C_6$alkylheteroarylene, $C_0$-$C_6$alkyl$C_3$-$C_7$cycloalkylene, $C_1$-$C_{12}$alkylene or $C_2$-$C_{12}$alkenylene, wherein the $C_1$-$C_{12}$alkylene or $C_2$-$C_{12}$alkenylene is optionally substituted with OH or $C_1$-$C_4$alkyl; and $R^{21}$ is H, —OH, —SH, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)$OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$; and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl or, when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$J^1$ is selected from OH, CN, halo, $C_1$-$C_4$alkyl, and halo$C_1$-$C_4$alkyl; and $R^k$ is H or $M^+$ counterion.

In some embodiments, excluded from the compounds of formula (IVa) are compounds in which:

-L-$R^{21}$ is

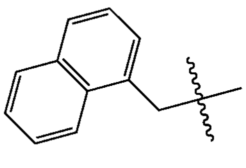
or
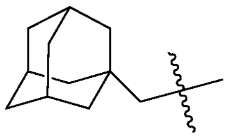

$R^2$ and $R^{11}$ are $CH_3$;
$R^3$ is =O;
$R^4$ is OH;
$R^5$, $R^7$ and $R^{14}$ are H;
$R^9$ is OH;
$R^{12}$ is H;
$R^{17}$ and $R^{18}$ are —$CH_3$;
$R^A$ is propan-2-yl (valine);
$R^B$ is H; and
p is 0.

In some embodiments, the compound has the structure of formula (IVb)

(IVb)

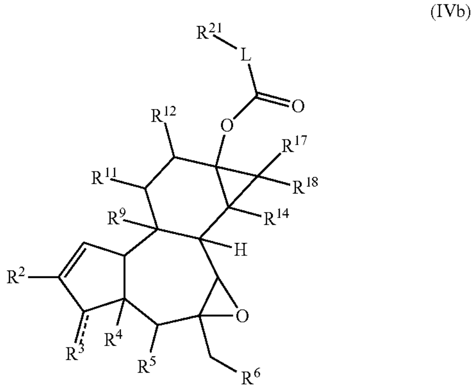

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —OR, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

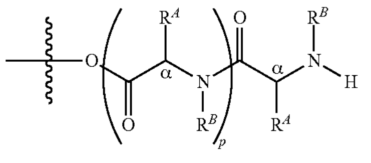

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —$OC(O)R^f$, wherein $R^f$ is $C_1$-$C_2$alkyl, $C_2$-$C_{12}$alkenyl, —$C_0$-$C_2$aliphatic-$C_3$-$C_7$cycloalkyl, —$C_0$-$C_{12}$aliphatic-heterocycloalkyl, —$C_0$-$C_{12}$aliphatic-aryl, or —$C_0$-$C_{12}$aliphatic-heteroaryl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is $C_0$-$C_6$alkylarylene, $C_0$-$C_6$alkylheteroarylene, $C_0$-$C_6$alkyl$C_3$-$C_7$cycloalkylene, $C_1$-$C_2$alkylene or $C_2$-$C_{12}$alkenylene, wherein the $C_1$-$C_{12}$alkylene or $C_2$-$C_{12}$alkenylene is optionally substituted with OH or $C_1$-$C_4$alkyl; and $R^{21}$ is H, —OH, —SH, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$; and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl or, when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$J^1$ is selected from OH, CN, halo, $C_1$-$C_4$alkyl, and halo$C_1$-$C_4$alkyl; and $R^k$ is H or $M^+$ counterion.

In some embodiments of the compound of formula (IV), (IVa), and (IVb), the $C_2$-$C_6$alkenyl of $R^{a1}$ is independently selected from:

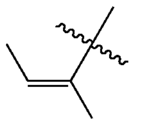

and

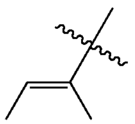

In some embodiments, $R^{a1}$ is independently selected from:

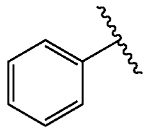

and

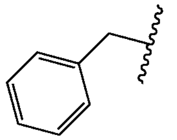

In some embodiments, $R^3$ is —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl. In some embodiments, the aryl of $C_0$-$C_6$alkylaryl is phenyl. In some embodiments, the aryl of $C_0$-$C_6$alkylaryl is optionally substituted with 1 to 3 of OH, CN, halo, $C_1$-$C_4$alkyl, and halo$C_1$-$C_4$alkyl.

In some embodiments of the compound of formula (IV), (IVa), and (IVb), $R^3$ is O double bonded to the carbon atom.

In some embodiments of the compound of formula (IV), (IVa), and (IVb), the $C_2$-$C_{12}$alkenyl of $R^f$ is independently selected from:

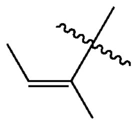

and

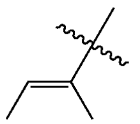

In some embodiments, $R^f$ is independently selected from:

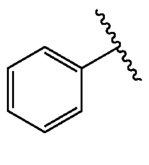

and

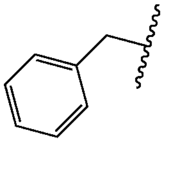

In some embodiments of the compound of formula (IV), (IVa), and (IVb), one or more of $R^2$, $R^{11}$, $R^{17}$, and $R^{18}$ are —$CH_3$. In some embodiments, each of $R^2$, $R^{11}$, $R^{17}$, and $R^{18}$ is —$CH_3$.

In some embodiments of the compound of formula (IV), (IVa), and (IVb), $R^4$ and $R^5$ are each independently H or —OH.

In some embodiments of the compound of formula (IV), (IVa), and (IVb), $R^2$, $R^{11}$, $R^{17}$, and $R^{18}$ are —$CH_3$;

$R^3$ is O double bonded to the carbon atom; and $R^4$ and $R^5$ are each independently H or —OH.

In some embodiments, the compound has the structure of formula (V):

(V)

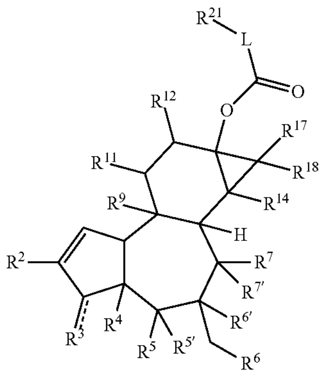

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^{5'}$ and $R^{6'}$ are H, or $R^{5'}$ and $R^{6'}$ form a bond or are bonded to a common O atom to form an epoxide ring as permitted by valency;

$R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

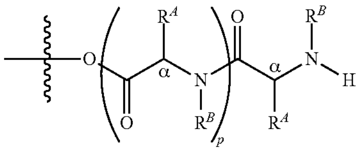

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2;

$R^{6'}$ and $R^{7'}$ are H, or $R^{6'}$ and $R^{7'}$ form a bond or are bonded to a common O atom to form an epoxide ring, as permitted by valency;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is $C_0$-$C_6$alkylarylene, $C_0$-$C_6$alkylheteroarylene, $C_0$-$C_6$alkyl$C_3$-$C_7$cycloalkylene, $C_1$-$C_{12}$alkylene or $C_2$-$C_{12}$alkenylene, wherein the $C_1$-$C_1$alkylene or $C_2$-$C_{12}$alkenylene is optionally substituted with OH or $C_1$-$C_4$alkyl; and $R^{21}$ is H, —OH, —SH, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$; and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl or, when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$J^1$ is selected from OH, CN, halo, $C_1$-$C_4$alkyl, and halo$C_1$-$C_4$alkyl; and $R^k$ is H or $M^+$ counterion.

In some embodiments, excluded from the compounds of formula (V) are compounds in which:

-L-$R^{21}$ is

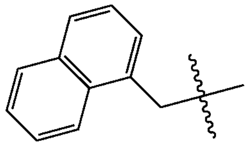

or

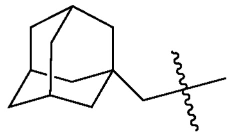

$R^2$ and $R^{11}$ are $CH_3$;
$R^3$ is =O;
$R^4$ is OH;
$R^5$, $R^{5'}$, $R^7$ and $R^{14}$ are H;
$R^{6'}$ and $R^{7'}$ together form a bond;
$R^9$ is OH;
$R^{17}$ and $R^{18}$ are —$CH_3$;
$R^A$ is propan-2-yl (valine);
$R^B$ is H; and
p is 0.

In some embodiments, the compound has the structure of formula (Va):

(Va)

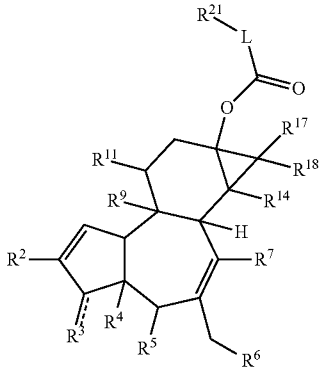

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —C(O)$R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —OC(O)$R^c$, wherein $R^1$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

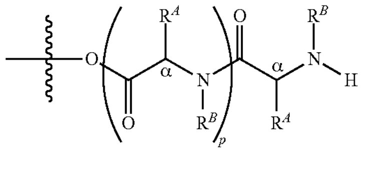

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is $C_0$-$C_6$alkylarylene, $C_0$-$C_6$alkylheteroarylene, $C_0$-$C_6$alkyl$C_3$-$C_7$cycloalkylene, $C_1$-$C_{12}$alkylene or $C_2$-$C_{12}$alkenylene, wherein the $C_1$-$C_2$alkylene or $C_2$-$C_{12}$alkenylene is optionally substituted with OH or $C_1$-$C_4$alkyl; and $R^{21}$ is H, —OH, —SH, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)$OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$; and wherein optionally 1 to 2 carbon atoms of the spiro$C_5$-$C_2$cycloalkyl or bridged bicyclyl is replaced with a heteroatom selected from N, O and S, and optionally substituted with $C_1$-$C_4$alkyl or, when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$J^1$ is selected from OH, CN, halo, $C_1$-$C_4$alkyl, and halo$C_1$-$C_4$alkyl; and $R^k$ is H or $M^+$ counterion.

In some embodiments, excluded from the compounds of formula (V) are compounds in which:

-L-$R^{21}$ is

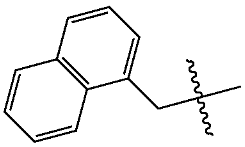

or

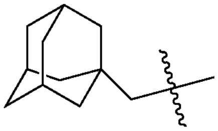

$R^2$ and $R^{11}$ are $CH_3$;
$R^3$ is =O;
$R^4$ is OH;
$R^5$, $R^7$ and $R^{14}$ are H;
$R^9$ is OH;
$R^{17}$ and $R^{18}$ are —$CH_3$;
$R^A$ is propan-2-yl (valine);
$R^B$ is H; and
p is 0.

In some embodiments, the compound has the structure of formula (Vb):

(Vb)

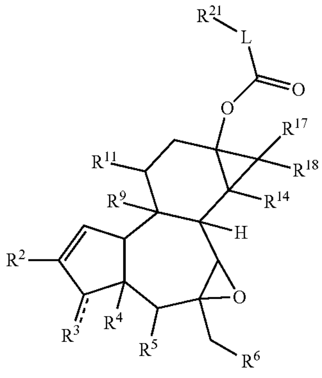

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

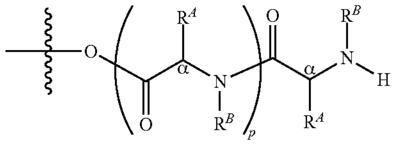

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2;

$R^9$ is $OR^e$, wherein $R^e$ is H, $C_1$-$C_6$alkyl, or aryl;

$R^{11}$ is $C_1$-$C_4$alkyl;

$R^{14}$ is H or $OR^g$; wherein R is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is $C_0$-$C_6$alkylarylene, $C_0$-$C_6$alkylheteroarylene, $C_0$-$C_6$alkyl$C_3$-$C_7$cycloalkylene, $C_1$-$C_{12}$alkylene or $C_2$-$C_{12}$alkenylene, wherein the $C_1$-$C_{12}$alkylene or $C_2$-$C_{12}$alkenylene is optionally substituted with OH or $C_1$-$C_4$alkyl; and $R^{21}$ is H, —OH, —SH, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$; and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl or, when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$J^1$ is selected from OH, CN, halo, $C_1$-$C_4$alkyl, and halo$C_1$-$C_4$alkyl; and $R^k$ is H or $M^+$ counterion.

In some embodiments of the compound of formula (V), (Va), and (Vb), $R^3$ is —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl. In some embodiments, the aryl of $C_0$-$C_6$alkylaryl is phenyl. In some embodiments, the aryl of $C_0$-$C_6$alkylaryl is optionally substituted with 1 to 3 of OH, CN, halo, $C_1$-$C_4$alkyl, and halo$C_1$-$C_4$alkyl. In some embodiments, $R^{a1}$ is selected from:

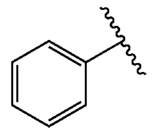

and

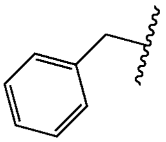

In some embodiments, $R^{a1}$ is selected from:

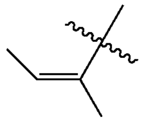

and

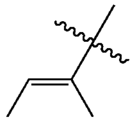

In some embodiments of the compound of formula (V), (Va), and (Vb), $R^3$ is O double bonded to the carbon atom.

In some embodiments of the compound of formula (V), (Va), and (Vb), one or more of $R^2$, $R^{11}$, $R^{17}$, and $R^{18}$ are —$CH_3$. In some embodiments, each of $R^2$, $R^{11}$, $R^{17}$, and $R^{18}$ is —$CH_3$.

In some embodiments of the compound of formula (V), (Va), and (Vb), $R^4$ and R are each independently H or —OH.

In some embodiments of the compound of formula (V), (Va), and (Vb), $R^2$, $R^{11}$, $R^{17}$, and $R^{18}$ are —$CH_3$;

$R^3$ is O double bonded to the carbon atom; and $R^4$ and $R^5$ are each independently H or —OH.

In some embodiments, the compound has the structure of formula (Vc):

(Vc)

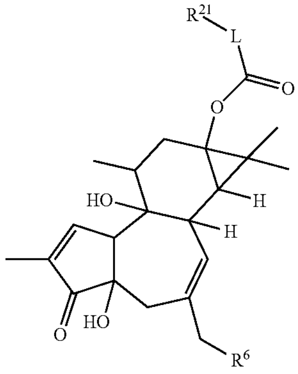

or a pharmaceutically acceptable salt, tautomer, or stereoisomer thereof;

wherein $R^6$ is OH, halo, or —OC(O)$R^c$, wherein $R^c$ is —$C_1$-$C_6$alkyl, —$C_1$-$C_6$alkyl-($NR^{c1}$)$_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

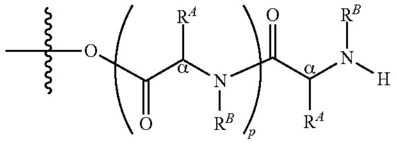

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2;

L is $C_0$-$C_6$alkylarylene, $C_0$-$C_6$alkylheteroarylene, $C_0$-$C_6$alkyl$C_3$-$C_7$cycloalkylene, $C_1$-$C_2$alkylene or $C_2$-$C_2$alkenylene, wherein the $C_1$-$C_{12}$alkylene or $C_2$-$C_2$alkenylene is optionally substituted with OH or $C_1$-$C_4$alkyl; and $R^{21}$ is H, —OH, —SH, —S(O)$_2R^j$, —$SR^j$, —N($R^j$)$_2$, —Si($R^j$)$_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)$OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$; and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl or, when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$J^1$ is selected from OH, CN, halo, $C_1$-$C_4$alkyl, and halo$C_1$-$C_4$alkyl; and $R^k$ is H or $M^+$ counterion.

In some embodiments, excluded from the compounds of formula (Vc) are compounds in which:

-L-$R^{21}$ is

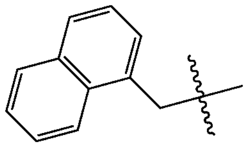

or

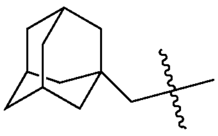

$R^A$ is propan-2-yl (valine);

$R^B$ is H; and p is 0.

In some embodiments, specifically excluded from the compounds of formula (IV), (IVa), (V), (Va) and (Vc) are compounds of the following structure:

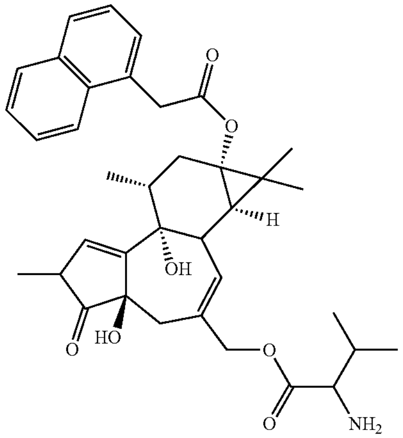

and

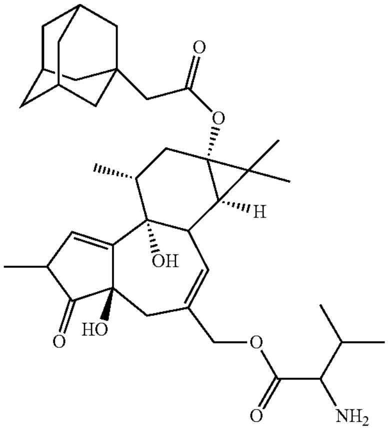

In some embodiments, the compound has the structure of formula (Vd):

(Vd)

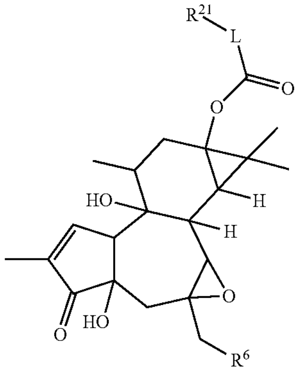

or a pharmaceutically acceptable salt, tautomer, or stereoisomer thereof;

wherein $R^6$ is OH, halo, or —OC(O)$R^c$, wherein $R^c$ is —$C_1$-$C_6$alkyl, —$C_1$-$C_6$alkyl-($NR^{c1}$)$_2$ or —$C_1$-$C_6$alkylC(O)O$R^k$, $R^{c1}$ is H, $C_1$-$C_6$alkyl, or two $R^c$ together with the N atom form a 5 to 7 membered heterocyclyl containing 1 to 3 heteroatoms selected from N, O, and S; or $R^6$ is

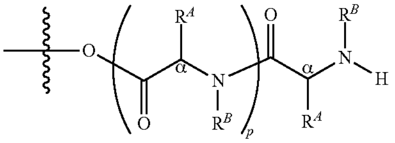

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2;

L is $C_0$-$C_6$alkylarylene, $C_0$-$C_6$alkylheteroarylene, $C_0$-$C_6$alkyl$C_3$-$C_7$cycloalkylene, $C_1$-$C_{12}$alkylene or $C_2$-$C_{12}$alkenylene, wherein the $C_1$-$C_{12}$alkylene or $C_2$-$C_{12}$alkenylene is optionally substituted with OH or $C_1$-$C_4$alkyl; and $R^{21}$ is H, —OH, —SH, —S(O)$_2R^j$, —S$R^j$, —N($R^j$)$_2$, —Si($R^j$)$_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)O$R^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$; and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl or, when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$J^1$ is selected from OH, CN, halo, $C_1$-$C_4$alkyl, and halo$C_1$-$C_4$alkyl; and $R^k$ is H or $M^+$ counterion.

In some embodiments of the compounds of (IV), (IVa), (IVb), (V), (Va), (Vb), (Vc) and (Vd), $R^{21}$ is $C_3$-$C_7$cycloalkyl, wherein the $C_3$-$C_7$cycloalkyl is optionally substituted with 1 to 3 of $J^1$. In some of the foregoing embodiments, the $C_3$-$C_7$cycloalkyl is selected from the group consisting of cyclobutyl, cyclopentyl, cyclohexyl, and cycloheptyl.

In some embodiments of the compounds of (IV), (IVa), (IVb), (V), (Va), (Vb), (Vc) and (Vd), $R^{21}$ is a heterocyclyl, wherein the heterocyclyl is optionally substituted with 1 to 3 of $J^1$. In some embodiments, the heterocycloalkyl is selected from oxiranyl, oxetanyl, azetidynyl, oxazolyl, thiazolidinyl, thiazolyl, morpholinyl, pyrrolidinonyl, pyrrolidinyl, piperidinyl, piperazinyl, 2,3-dihydrofuranyl, dihydropyranyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and azapanyl.

In some embodiments of the compounds of (IV), (IVa), (IVb), (V), (Va), (Vb), (Vc), and (Vd), $R^{21}$ is aryl, wherein the aryl is optionally substituted with 1 to 3 of $J^1$. In some of the foregoing embodiments, $R^{21}$ is a phenyl, wherein the phenyl is optionally substituted with 1 to 3 of OH, CN, halo, $C_1$-$C_4$alkyl, and halo$C_1$-$C_4$alkyl.

In some embodiments of the compounds of (IV), (IVa), (IVb), (V), (Va), (Vb), (Vc), and (Vd), $R^{21}$ is heteroaryl, wherein the heteroaryl is optionally substituted with 1 to 3 of $J^1$. In some of the foregoing embodiments, the heteroaryl is selected from the group consisting of pyrrolyl, pyrazolyl, imidazolyl, pyrazinyl, oxazolyl, isoxazolyl, thiazolyl, furyl, thienyl, pyridyl, pyrimidyl, benzoxazolyl, benzothiazolyl, purinyl, benzimidazolyl, indolyl, isoquinolyl, quinoxalinyl, and quinolyl, wherein the heteroaryl is optionally substituted with 1 to 3 of OH, CN, halo, $C_1$-$C_4$alkyl, and halo$C_1$-$C_4$alkyl.

In some embodiments of the compounds of (IV), (IVa), (IVb), (V), (Va), (Vb), (Vc), and (Vd), $R^{21}$ is adamantyl, wherein the adamantyl is optionally substituted with OH, halo, or $C_1$-$C_4$alkyl.

In some embodiments of the compounds of (IV), (IVa), (IVb), (V), (Va), (Vb), (Vc), and (Vd), $R^{21}$ is spiro$C_5$-$C_{12}$ cycloalkyl, wherein the spiro$C_5$-$C_{12}$ cycloalkyl has 0-2 carbon atoms replaced with 0-2 heteroatoms selected from N, O and S, and is optionally substituted with 1 to 3 of OH, CN, halo, $C_1$-$C_4$alkyl, and halo$C_1$-$C_4$alkyl, or when an N atom is present an N-protecting group.

In some embodiments of the compounds of (IV), (IVa), (IVb), (V), (Va), (Vb), (Vc) and (Vd), $R^{21}$ is 5 to 12 membered bridged bicyclyl, wherein the bridged bicyclyl has 0-2 carbon atoms replaced with 0-2 heteroatoms selected from N, O and S, and is optionally substituted with 1 to 3 of OH, CN, halo, $C_1$-$C_4$alkyl, and halo$C_1$-$C_4$alkyl, or when an N atom is present an N-protecting group.

In some embodiments of the compounds of formula (IV), (IVa), (IVb), (V), (Va), (Vb), (Vc) and (Vd), $R^{21}$ is selected from the following:

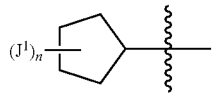,

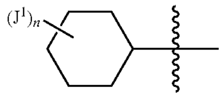,

-continued

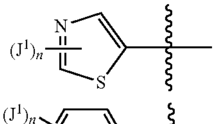 , 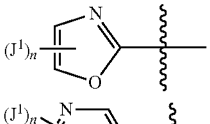 ,

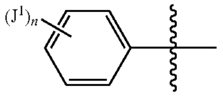 , 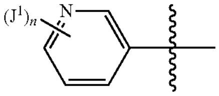 ,

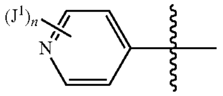 , 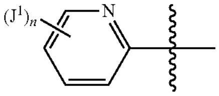 ,

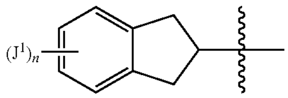 , 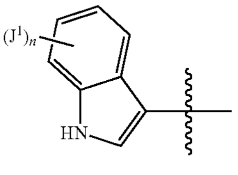 ,

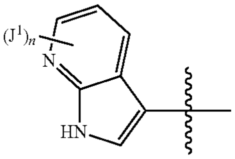 , 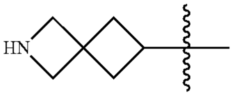 ,

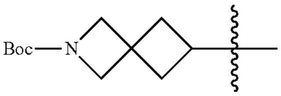 , 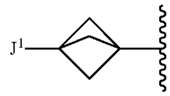 ,

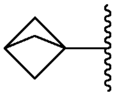 and 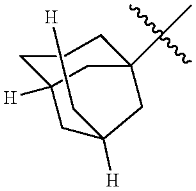

wherein J is OH, CN, halo, $C_1$-$C_4$alkyl, and halo$C_1$-$C_4$alkyl, and n is 0-3. In some embodiments, n is 0. In some embodiments, n is 1. In some embodiments, n is 2. In some embodiments, halo$C_1$-$C_4$alkyl is —$CH_2F$, —$CHF_2$, or —$CF_3$.

In some embodiments, for any of the compounds herein, L is $C_3$-$C_{12}$alkylene. In some embodiments, for any of the compounds herein, L is $C_3$-$C_6$alkylene. In some embodiments, for any of the compounds herein, L is $C_1$-$C_6$alkylene.

In some embodiments, for any of the compounds herein, L is $C_3$-$C_{12}$alkenylene. In some embodiments, for any of the compounds herein, L is $C_3$-$C_6$alkenylene. In some embodiments, for any of the compounds herein, L is $C_1$-$C_6$alkenylene.

In some embodiments of the compounds of formula (IV), (IVa), (IVb), (V), (Va), (Vb), (Vc) and (Vd), -L-$R^{21}$ is a $C_2$-$C_6$alkenyl selected from:

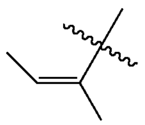 and 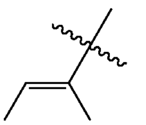 .

In some embodiments for any of the foregoing compounds, e.g., formula (IV), (IVa), (IVb), (V), (Va), (Vb), (Vc) and (Vd), wherein $R^6$ is

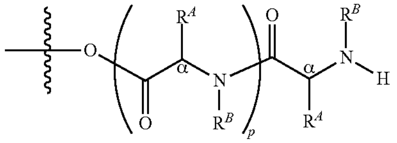

each occurrence of $R^A$ is independently hydrogen (glycine), methyl (alanine), propan-2-yl (valine), propan-1-yl (norvaline), 2-methylpropan-1-yl (leucine), 1-methylpropan-1-yl (isoleucine), butan-1-yl (norleucine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 3-guanidinopropan-1-yl (arginine), or 3-ureido-propan-1-yl (citrulline);

each occurrence of $R^B$ is H, or $R^B$ together with the adjacent $R_A$ and the N atom form a prolyl side chain:

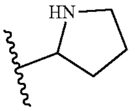 ;

and p is 0, 1 or 2.

In some embodiments for any of the foregoing compounds, e.g., formula (IV), (IVa), (IVb), (V), (Va), (Vb), (Vc) and (Vd), each $R^A$ is independently methyl (alanine), propan-2-yl (valine), 2-methylpropan-1-yl (leucine), imidazol-4-ylmethyl (histidine), hydroxymethyl (serine), 1-hydroxyethyl (threonine), carbamoylmethyl (asparagine), 2-carbamoylethyl (glutamine), 4-aminobutan-1-yl (lysine), carboxymethyl (aspartic acid), 3-guanidinopropan-1-yl (arginine), benzyl (phenylalanine), or 4-aminobutan-1-yl (lysine);

$R^B$ is H; and p 0, 1, or 2.

In some embodiments for any of the foregoing compounds, e.g., formula (IV), (IVa), (IVb), (V), (Va), (Vb), (Vc) and (Vd), wherein $R^6$ is

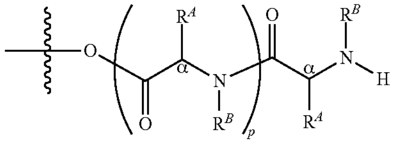

each occurrence of $R^A$ is independently propan-2-yl (valine), 2-methylpropan-1-yl (leucine), carboxymethyl (aspartic acid), benzyl (phenylalanine), or 4-aminobutan-1-yl (lysine);

each $R^B$ is H; and p is 0, 1, or 2.

In some embodiments for any of the foregoing compounds, e.g., formula (IV), (IVa), (IVb), (V), (Va), (Vb), (Vc) and (Vd), p is 0.

In some embodiments for any of the foregoing compounds, e.g., formula (IV), (IVa), (IVb), (V), (Va), (Vb), (Vc) and (Vd), p is 1.

In some embodiments for any of the foregoing compounds, e.g., formula (IV), (IVa), (IVb), (V), (Va), (Vb), (Vc) and (Vd), wherein $R^6$ is

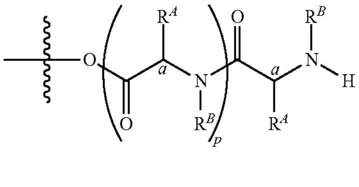

and p is 1;

first of $R^A$ is propan-2-yl (valine) and second of $R^A$ is propan-2-yl (valine); and each of $R^B$ is H (i.e., dipeptide Val-Val); or first of $R^A$ is 2-methylpropan-1-yl (leucine), and second of $R^A$ is 2-methylpropan-1-yl (leucine); and each of $R^B$ is H (i.e., dipeptide Leu-Leu); or first of $R^A$ is methyl (alanine) and second of $R^A$ is methyl (alanine); and each of $R^B$ is H (i.e., dipeptide Ala-Ala); or first of $R^A$ is 4-aminobutan-1-yl (lysine); second of $R^A$ is 4-aminobutan-1-yl (lysine); and each of $R^B$ is H (i.e., dipeptide Lys-Lys); or first of $R^A$ is hydrogen; second of $R^A$ is 4-aminobutan-1-yl, and each of $R^B$ is H (i.e., dipeptide Gly-Lys).

In some embodiments for any of the foregoing compounds, e.g., formula (IV), (IVa), (IVb), (V), (Va), (Vb), (Vc) and (Vd), wherein $R^6$ is

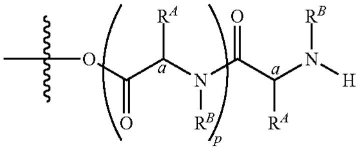

each of the α-carbon of the amino acid other than glycine is in the L or D configuration. In some embodiments, each of the α-carbon of the amino acid other than glycine is in the L configuration.

In some embodiments, the compound is selected from the group consisting of the compounds or a pharmaceutical salt thereof, in Table 2.

TABLE 2

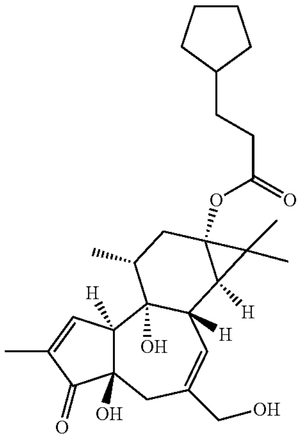

K101-C1301

TABLE 2-continued
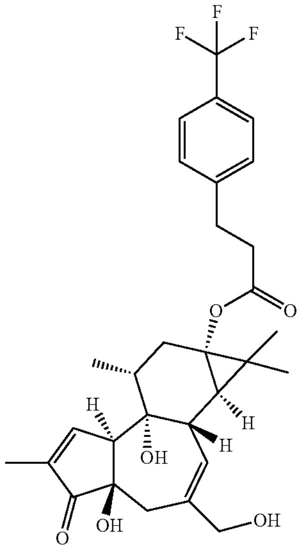
K101-C1302
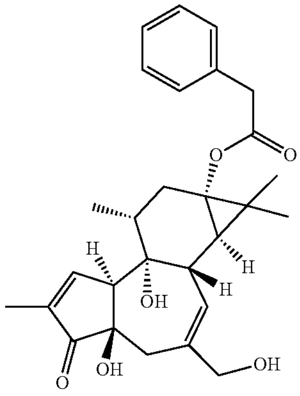
K101-C1304
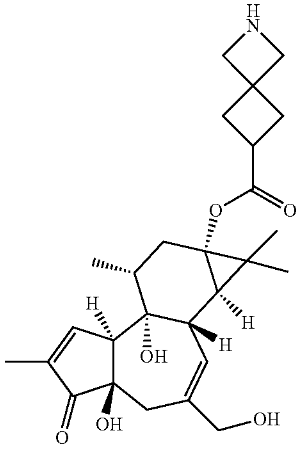
K101-C1305

TABLE 2-continued
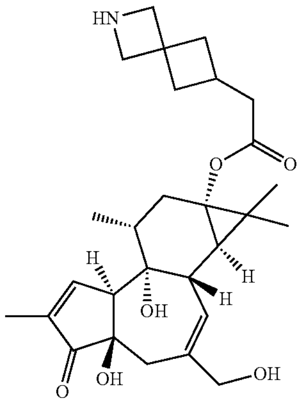
K101-C1306
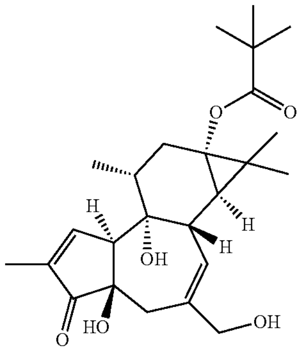
K101-C1308
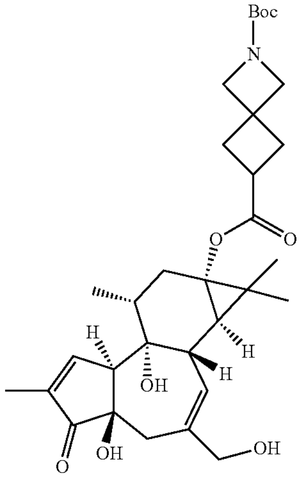
K101-C1311

TABLE 2-continued
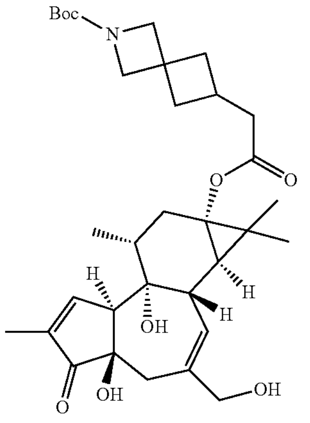
K101-C1312
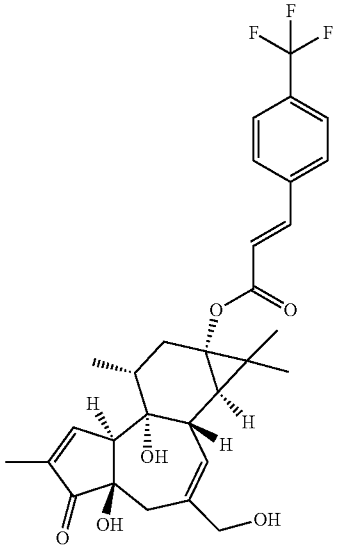
K101-C1313
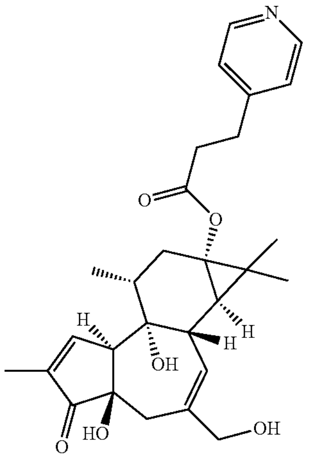
K101-C1315

TABLE 2-continued
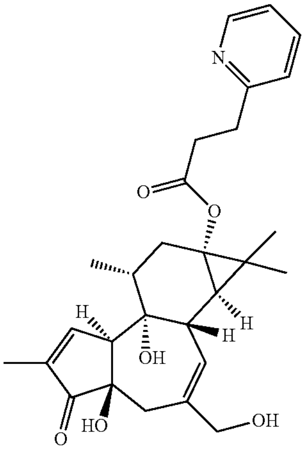
K101-C1316
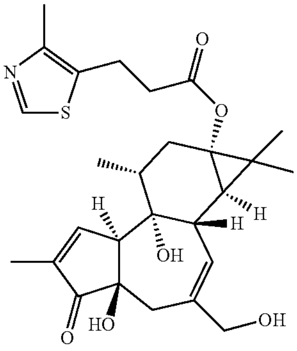
K101-C1320
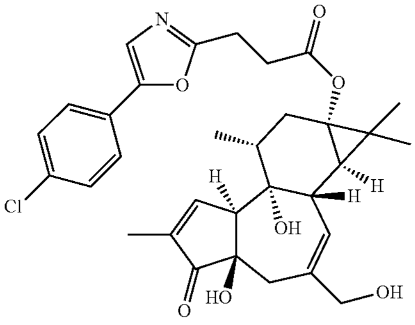
K101-C1321
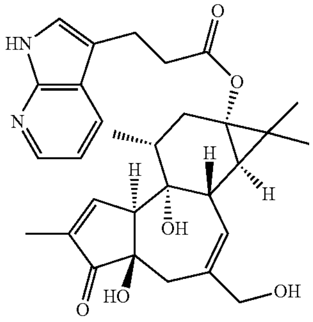
K101-C1322

TABLE 2-continued
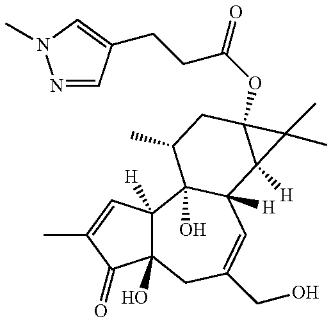
K101-C1323
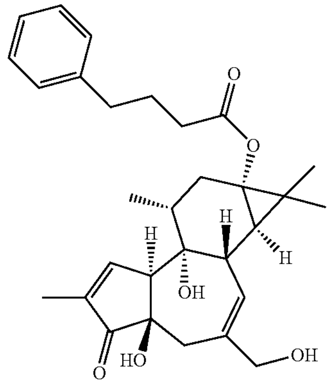
K101-C1324
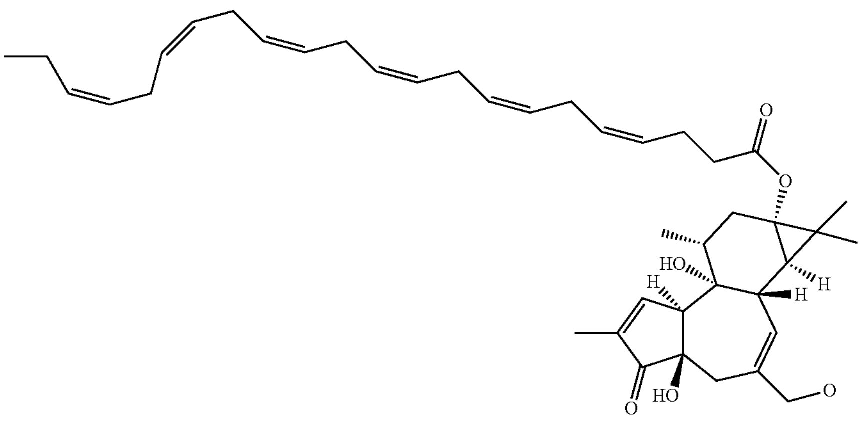
K101-C1333

TABLE 2-continued
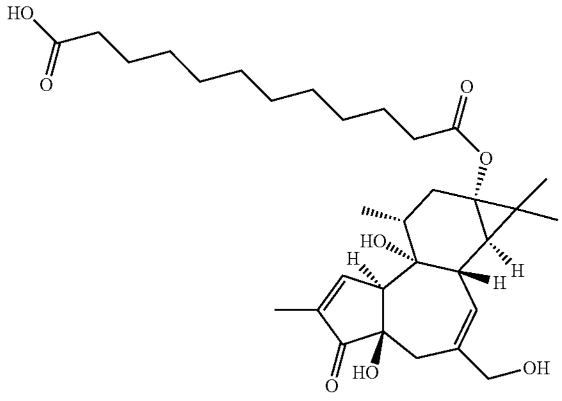
K101-C1334
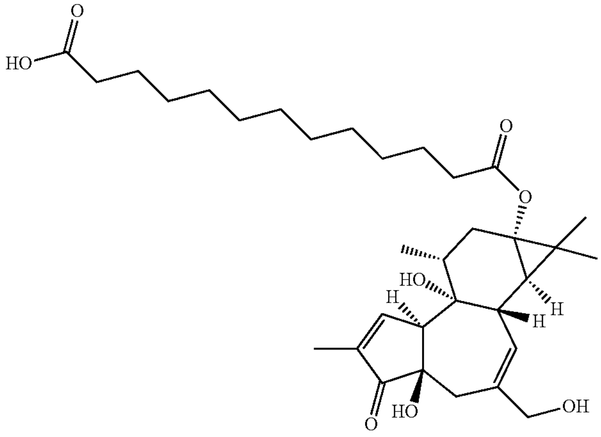
K101-C1335
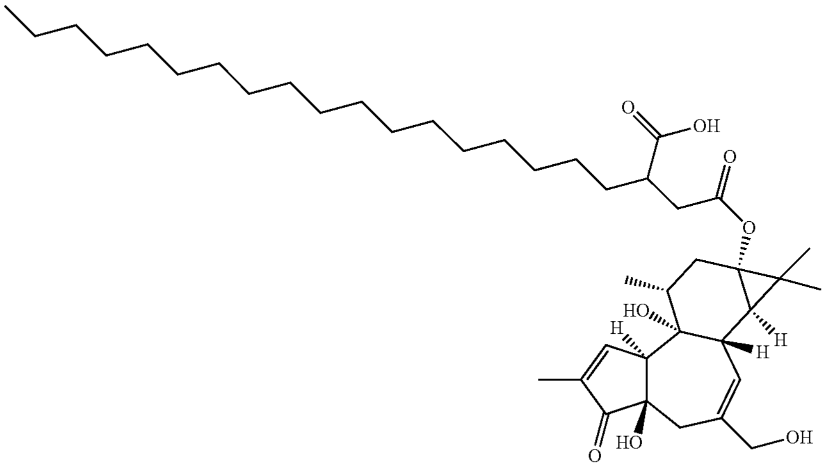
K101-C1352

TABLE 2-continued

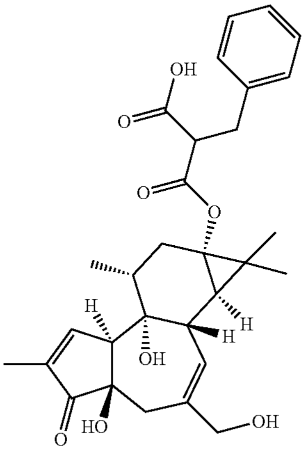

K101-C1353

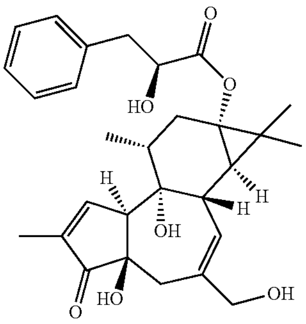

K101-C1354

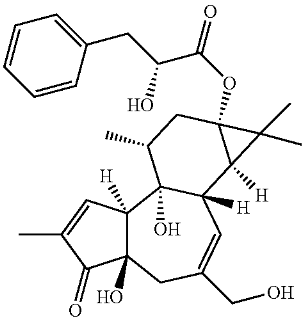

K101-C1355 or a pharmaceutically acceptable salt, tautomer, or stereoisomer thereof.

In some embodiments, for each of the compounds of Table 2, the —OH on the C20 carbon atom is substituted with

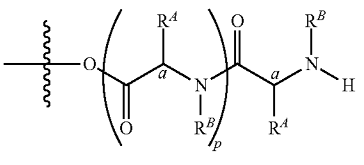

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2.

In some embodiments of the amino acid moiety on the C20 carbon, each occurrence of $R^A$ is independently hydrogen (glycine), methyl (alanine), propan-2-yl (valine), propan-1-yl (norvaline), 2-methylpropan-1-yl (leucine), 1-methylpropan-1-yl (isoleucine), butan-1-yl (norleucine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 3-guanidinopropan-1-yl (arginine), or 3-ureido-propan-1-yl (citrulline);

each occurrence of $R^B$ is independently H, or $R^B$ together with the adjacent $R_A$ and the N atom form a prolyl side chain:

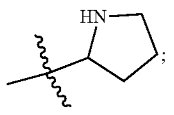 [SMILES: *C1CCCN1]

;

and p is 0, 1 or 2.

In some embodiments, each occurrence of $R^A$ is independently methyl (alanine), propan-2-yl (valine), 2-methylpropan-1-yl (leucine), imidazol-4-ylmethyl (histidine), hydroxymethyl (serine), 1-hydroxyethyl (threonine), carbamoylmethyl (asparagine), 2-carbamoylethyl (glutamine), 4-aminobutan-1-yl (lysine), carboxymethyl (aspartic acid), 3-guanidinopropan-1-yl (arginine), benzyl (phenylalanine), or 4-aminobutan-1-yl (lysine);

$R^B$ is H; and p 0, 1, or 2.

In some embodiments, each occurrence of $R^A$ is independently propan-2-yl (valine), 2-methylpropan-1-yl (leucine), carboxymethyl (aspartic acid), benzyl (phenylalanine), or 4-aminobutan-1-yl (lysine);

each $R^B$ is H; and p is 0, 1, or 2.

In some embodiments, p is 0.

In some embodiments, p is 1.

In some embodiments, p is 1;

first of $R^A$ is propan-2-yl (valine) and second of $R^A$ is propan-2-yl (valine); and each of $R^B$ is H (dipeptide Val-Val); or first of $R^A$ is 2-methylpropan-1-yl (leucine), and second of $R^A$ is 2-methylpropan-1-yl (leucine); and each of $R^B$ is H (dipeptide Leu-Leu); or first of $R^A$ is methyl (alanine) and second of $R^A$ is methyl (alanine); and each of $R^B$ is H (dipeptide Ala-Ala); or first of $R^A$ is 4-aminobutan-1-yl (lysine); second of $R^A$ is 4-aminobutan-1-yl (lysine); and each of $R^B$ is H (dipeptide Lys-Lys); or first of $R^A$ is hydrogen; second of $R^A$ is 4-aminobutan-1-yl, and each of $R^B$ is H (dipeptide Gly-Lys).

In some embodiments, each of the α-carbon of the amino acid other than glycine is in the L or D configuration.

In some embodiments, compounds disclosed herein can be synthesized according to the general schemes shown outlined below in Scheme 1 and Scheme 2, where suitable reagents can be purchased form commercial sources or synthesized via known methods or methods adapted from the example procedures provided herein:

Scheme 1

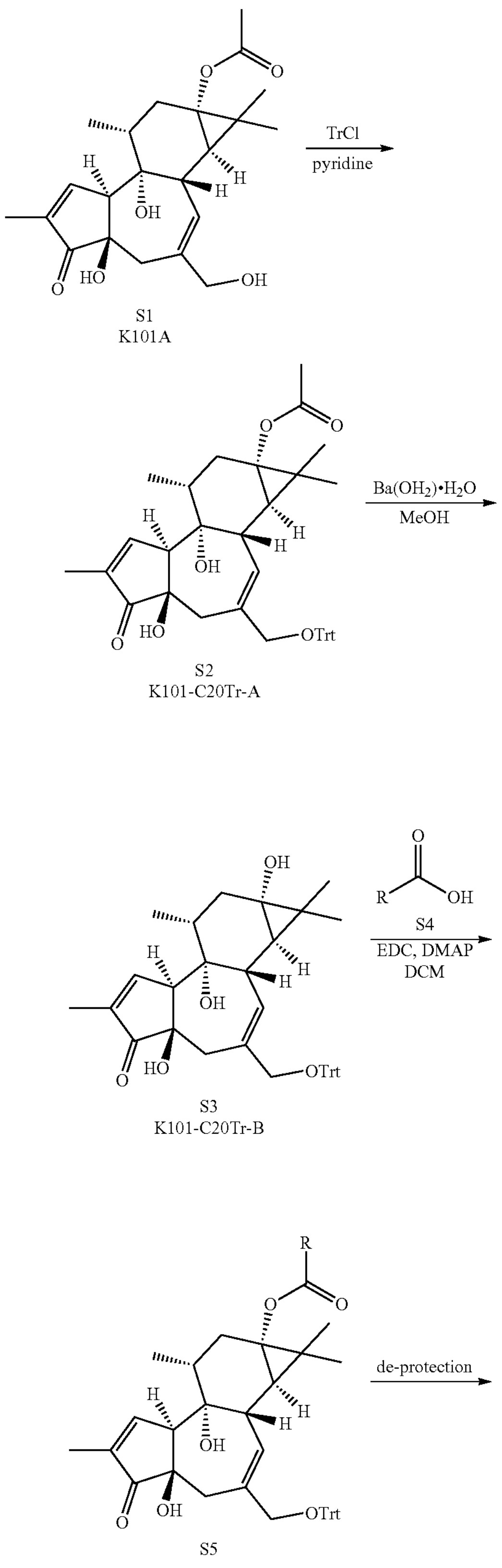

-continued

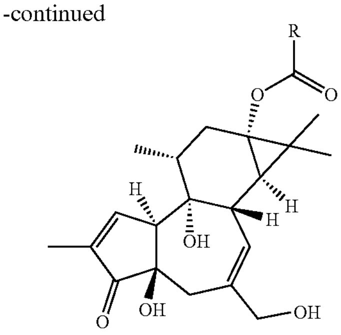

S6

Scheme 2

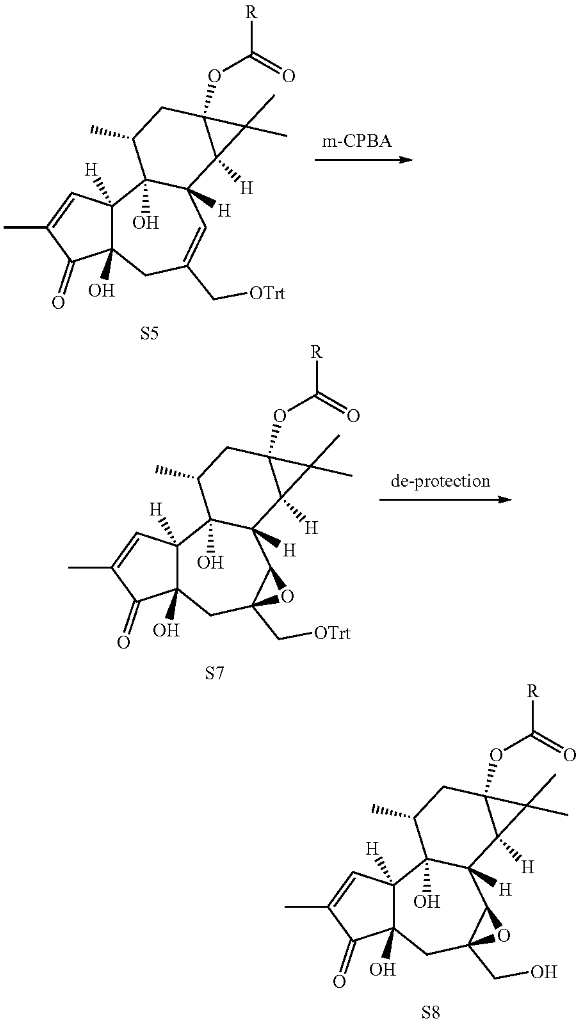

S5

S7

S8

In Scheme 1, protection of S1 (K101A shown as example) with trityl chloride (or triphenylmethyl chloride) provides S2 (K101-C20Tr-A shown as example). Hydrolysis of S2 (K101-C20Tr-A shown as example) provides S3 (K101-C20Tr-B, shown as example), which can then be coupled with compound S4 under esterification conditions using 1-ethyl-3-(3-dimethylaminopropyl)carbodiimide (EDC, or EDCI) as the carboxyl activating agent and 4-dimethylaminopyridine (DMAP) as the catalyst to provide S5. Deprotection of S5 followed by further separation and purification provides S6.

In Scheme 2, S7 is prepared by epoxidation of S5 with a peroxycarboxylic acid such as meta-chloroperoxybenzoic acid (m-CPBA). Further separation and purification of S7 provides S8.

Appropriate starting materials and reagents for use in Scheme 1 and Scheme 2 can be purchased or prepared by methods known to one of skill in the art.

In some embodiments of the methods of Scheme 1 and Scheme 2, the various substituents on the starting compounds (e.g., compounds S1 and S3) are as defined for Formula I. However, it should also be appreciated that chemical derivatization and/or functional group interconversion, can be used to further modify of any of the compounds of Scheme 1 and Scheme 2 in order to provide the various compounds of Formula I.

In some embodiments, synthesis of the prodrugs are prepared by reacting protected amino acids (e.g., N-protected amino acids) with relevant compounds, e.g., compounds having an —OH group at the $R^6$ position. Guidance is provided in Examples 63 and 64 illustrating synthesis of amino acid prodrugs as well as knowledge of general procedures available in the art for producing such prodrugs (see, e.g., Vale et al., 2018, Molecules. 23(9):2318; Beauchamp et al., 1992, Antiviral Chemistry & Chemotherapy 3(3):157-164; incorporated herein by reference).

Other compounds of the disclosure can be synthesized using the synthetic routes above and adapting chemical synthetic procedures available to the skilled in the art. Exemplary methods of synthesis are provided in the Examples. It is to be understood that each of the procedures describing synthesis of exemplary compounds are part of the specification, and thus incorporated herein into the Detailed Description of this disclosure.

5.3. Pharmaceutically Acceptable Salts

In some embodiments, the PKC modulating compounds are in free form or where appropriate as pharmaceutically acceptable salt. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

Pharmaceutically acceptable salts of the compounds of this invention include those derived from suitable inorganic and organic acids and bases. In some embodiments, pharmaceutically acceptable salt of the compounds herein can be prepared during final isolation and purification of the compounds. For example, a pharmaceutically acceptable salt of the compounds herein can be prepared by (1) reacting the compound in free base form with a suitable organic or inorganic acid, and (2) isolating the salt thus formed. Examples of pharmaceutically acceptable, nontoxic acid addition salts are salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Base addition salts can be prepared by (1) reacting the compound, such as the purified compound, in its acid form with a suitable organic or inorganic base, and (2) isolating the salt thus formed. Salts derived from appropriate bases include alkali metal, alkaline earth metal, ammonium and $N^{+}(C_1\text{-}C_4alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

5.4. Methods of Use

In another aspect, the compounds described herein are used in a method of treating cancer. In some embodiments, the method of treating cancer comprises administering to a subject in need thereof a therapeutically effective amount any of the compounds described herein.

In some embodiments, the compounds can be used as monotherapy, or as further provided below, in a combination therapy with one or more therapeutic treatments, particularly in combination with one or more chemotherapeutic agents. In some embodiments, the compounds are used in combination with a second therapeutic agent, where the compounds are used at levels that sensitizes the cancer or cancer cell to the second therapeutic agent, for example at levels of the compound that do not cause significant cell death. In some embodiments, the compounds can be used in combination with radiation therapy, either to sensitize the cells to radiation therapy or as an adjunct to radiation therapy (e.g., at doses sufficient to activate cell death pathway).

In some embodiments, the cancer for treatment with the compound can be selected from, among others, adrenocortical cancer, anal cancer, biliary cancer, bladder cancer, bone cancer (e.g., osteosarcoma), brain cancer (e.g., gliomas, astrocytoma, neuroblastoma, etc.), breast cancer, cervical cancer, colon cancer, endometrial cancer, esophageal cancer, head and neck cancer, hematologic cancer (e.g., leukemia and lymphoma), intestinal cancer (small intestine), liver cancer, lung cancer (e.g., bronchial cancer, small cell lung cancer, non-small cell lung cancer, etc.), oral cancer, ovarian cancer, pancreatic cancer, renal cancer, prostate cancer, salivary gland cancer, skin cancer (e.g., basal cell carcinoma, melanoma), stomach cancer, testicular cancer, throat cancer, thyroid cancer, uterine cancer, vaginal cancer, sarcoma, and soft tissue carcinomas.

In some embodiments, the cancer for treatment with the compound is pancreatic cancer. In some embodiments, the pancreatic cancer for treatment with the compounds is pancreatic adenocarcinoma or metastatic pancreatic cancer. In some embodiments, the cancer for treatment with the compounds is stage I, stage II, stage III, or stage IV pancreatic adenocarcinoma.

In some embodiments, the cancer for treatment with the compounds is lung cancer. In some embodiments, the lung cancer for treatment with the compounds is small cell lung cancer or non-small cell lung cancer. In some embodiments, the non-small cell lung cancer for treatment with the compounds is an adenocarcinoma, squamous cell carcinoma, or large cell carcinoma. In some embodiments, the lung cancer for treatment with the compounds is metastatic lung cancer.

In some embodiments, the cancer for treatment with the compounds is a hematologic cancer. In some embodiments, the hematologic cancer is selected from acute lymphoblastic leukemia (ALL), acute myeloid leukemia (AML), lymphoma (e.g., Hodgkin's lymphoma, Non-Hodgkin's lymphoma, Burkitt's lymphoma), chronic lymphocytic leukemia (CLL), chronic myelogenous leukemia (CML), Hairy Cell chronic myelogenous leukemia (CML), and multiple myeloma.

In some embodiments, the cancer for treatment with the compounds is a leukemia selected from acute lymphoblastic leukemia (ALL), acute myeloid leukemia (AML), chronic lymphocytic leukemia (CLL), chronic myelogenous leukemia (CML), Hairy Cell chronic myelogenous leukemia (CML), and multiple myeloma.

In some embodiments, the cancer for treatment with the compound is a lymphoma selected from Hodgkin's lymphoma, Non-Hodgkin's lymphoma, and Burkitt's lymphoma).

In some embodiments, the cancer for treatment with the compound is a cancer characterized by mesenchymal features or mesenchymal phenotype. In some cancers, gain of mesenchymal features is associated with migratory (e.g., intravasation) and invasiveness of cancers. Mesenchymal features can include, among others, enhanced migratory capacity, invasiveness, elevated resistance to apoptosis, and increased production of extracellular matrix (ECM) components. In addition to these physiological characteristics, the mesenchymal features can include expression of certain biomarkers, including among others, E-cadherin, N-cadherin, integrins, FSP-1, α-SMA, vimentin, P-catenin, collagen I, collagen II, collagen III, collagen IV, fibronectin, laminin 5, SNAIL-1, SNAIL-2, Twist-1, Twist-2, and Lef-1. In some embodiments, the cancer selected for treatment with the compounds herein include, among others, breast cancer, lung cancer, head and neck cancer, prostate cancer, and colon cancer. In some embodiments, the mesenchymal features can be inherent to the cancer type or induced by or selected for by treatment of cancers with chemotherapy and/or radiation therapy.

In some embodiments, the cancer for treatment with the compound is identified as having or determined to have an activating or oncogenic RAS activity. In some embodiments, the RAS is K-RAS, H-RAS or N-RAS. In some embodiments, the activating or oncogenic RAS is an activating or oncogenic RAS mutation.

In some embodiments, the cancer for treatment is identified as having or determined to have an activating or oncogenic K-RAS mutation. In some embodiments, the cancer selected for treatment is identified as having or determined to have an activating or oncogenic mutation in human K-RAS at one or more of codon 5, codon 9, codon 12, codon 13, codon 14, codon 18, codon 19, codon 22, codon 23, codon 24, codon 26, codon 33, codon 36, codon 57, codon 59, codon 61, codon 62, codon 63, codon 64, codon 68, codon 74, codon 84, codon 92, codon 35, codon 97, codon 110, codon 115, codon 117, codon 118, codon 119, codon 135, codon 138, codon 140, codon 146, codon 147, codon 153, codon 156, codon 160, codon 164, codon 171, codon 176, codon 185, and codon 188.

In some embodiments, the activating or oncogenic K-RAS mutation can be a mutation in which: codon 5 is K5E; codon 9 is V91; codon 12 is G12A, G12C, G12D, G12F, G12R, G12S, G12V, or G12Y; codon 13 is G13C, G13D, or G13V; codon 14 is V14I or V14L; codon 18 is A18D; codon 19 is L19F; codon 22 is Q22K; codon 23 is L23R; codon 24 is I24N; codon 26 is N26K; codon 33 is D33E; codon 36 is I36L or I36M; codon 57 is D57N; codon 59 is A59E, A59G, or A59T; codon 61 is Q61H, Q61K, Q61L, or Q61R; codon 62 is E62G or E62K; codon 63 is E63K; codon 64 is Y64D, Y64H, or Y64N; codon 68 is R68S; codon 74 is T74P; codon 84 is I84T; codon 92 is D92Y; codon 97 is R97I; codon 110 is P110H or P110S; codon 115 is G15E; codon 117 is K117N; codon 118 is C118S; codon 119 is D119N; codon 135 is R135T; codon 138 is G138V; codon 140 is P140H; codon 146 is A146T or A146V; codon 147 is K147N; codon 153 is D153N; codon 156 is F156L; codon 160 is V160A; codon 164 is R164Q; codon 171 is I117M; codon 176 is K176Q; codon 185 is C185R or C185S; and codon 188 is M188V.

In particular, the cancer for treatment is identified as having or determined to have an oncogenic or activating K-RAS mutations at codon 12, codon 13 and/or codon 61. In some embodiments, the oncogenic or activating K-RAS mutation at codon 12 is G12A, G12C, G12D, G12F, G12R, G12S, G12V, or G12Y; at codon 13 is G13C, G13D, or G13V; and at codon 61 is Q61H, Q61K, Q61L, or Q61R. In some embodiments, the oncogenic or activating K-RAS mutation is a combination of oncogenic or activating K-RAS mutations at codon 12 and codon 13; codon 12 and codon 61; codon 13 and 61; or codon 12, codon 13 and codon 61.

In some embodiments, the cancer for treatment is identified as having or determined to have an activating or oncogenic N-RAS mutation. In some embodiments, the cancer is identified as having or determined to have an activating or oncogenic mutation in human N-RAS at one or more of codon 12, codon 13 and codon 61. In some embodiments, the activating or oncogenic N-RAS mutation at codon 12 is G12A, G12C, G12D, G12R, G12S, or G12V. In some embodiments, the activating or oncogenic N-RAS mutation at codon 13 is G13A, G13C, G13D, G13R, G13S, or G13V. In some embodiments, the activating or oncogenic N-RAS mutation at codon 61 is Q61E, Q61H, Q61K, Q61L, Q61P, or Q61R. In some embodiments, the oncogenic or activating N-RAS mutation is a combination of activating or oncogenic N-RAS mutations at codon 12 and codon 13; codon 12 and codon 61; codon 13 and 61; or codon 12, codon 13 and codon 61.

In some embodiments, the cancer for treatment is identified as having or determined to have an activating or oncogenic H-RAS mutation. In some embodiments, the cancer selected for treatment is identified as having an activating or oncogenic mutation in human H-RAS at one or more of codon 12, codon 13 and codon 61. In some embodiments, the activating or oncogenic H-RAS mutation at codon 12 is G12A, G12C, G12D, G12R, G12S, or G12V. In some embodiments, the activating or oncogenic H-RAS mutation at codon 13 is G13A, G13C, G13D, G13R, G13S, or G13V. In some embodiments, the activating or oncogenic H-RAS mutation at codon 61 is Q61E, Q61H, Q61K, Q61L, Q61P, or Q61R. In some embodiments, the oncogenic or activating H-RAS mutation is a combination of activating or oncogenic H-RAS mutations at codon 12 and codon 13; codon 12 and codon 61; codon 13 and 61; or codon 12, codon 13 and codon 61.

In some embodiments, the cancer for treatment can be a cancer having prevalence (e.g., at least about 10% or more, or about 15% or more of the cancers), of an activating or oncogenic RAS mutation, such as cancer of the biliary tract, cervix, endometrium, pancreas, lung, colon, head and neck, stomach (gastric), biliary tract, endometrium, hematologic (e.g., leukemia, lymphomas, etc.), large intestine, lung, ovary, pancreas, prostate, salivary gland, skin, small intestine, stomach thyroid, aerodigestive tract, urinary tract, and ovary, small intestine, and urinary tract.

Biological sample for the method herein include any samples are amenable to analysis herein, such as tissue or biopsy samples containing cancer cells, or any biological fluids that contain the material of interests (e.g., DNA), such as blood, plasma, saliva, tissue swabs, and intestinal fluids. In some embodiments, exosomes extruded by cancer cells and obtained from blood or other body fluids can be used to detect nucleic acids and proteins produced by the cancer cells.

General biological, biochemical, immunological and molecular biological methods applicable to the present disclosure are described in Sambrook et al., Molecular Cloning: A Laboratory Manual $2^{nd}$ Ed. (1989) Cold Spring Harbor Laboratory Press, Cold Spring Harbor, N.Y.; Current Protocols in Molecular Biology, Ausubel et al., ed., John Wiley & Sons (2015); Current Protocols in Immunology, Coligan, J E ed., John Wiley & Sons (2015); and Methods in Enzymology, Vol. 200, Abelson et al., ed., Academic Press (1991). All publications are incorporated herein by reference.

5.5. Combination Treatments

In some embodiments, the diterpenoid PKC modulating compounds are used in combination with one or more second therapeutic agents. In some embodiments, the second therapeutic agent is selected from a platinating agent, alkylating agent, antibiotic agent, antimetabolic agent (e.g., folate antagonists, purine analogs, pyrimidine analogs, etc.), topoisomerase inhibiting agent, antimicrotubule agent (e.g., taxanes, *vinca* alkaloids), hormonal agent (e.g., aromatase inhibitors), plant-derived agent and synthetic derivatives thereof, anti- angiogenic agent, differentiation inducing agent, cell growth arrest inducing agent, apoptosis inducing agent, cytotoxic agent, agent affecting cell bioenergetics, i.e., affecting cellular ATP levels and molecules/activities regulating these levels, anti-cancer biologic agent (e.g., monoclonal antibodies), kinase inhibitors and inhibitors of growth factors and their receptors.

In some embodiments, the second chemotherapeutic agent is selected from afatinib, afuresertib, alectinib, alisertib, alvocidib, amsacrine, amonafide, amuvatinib, axitinib, azacitidine, azathioprine, bafetinib, barasertib, bendamustine, bleomycin, bosutinib, bortezomib, busulfan, cabozantinib, camptothecin, canertinib, capecitabine, cabazitaxel, carboplatin, carmustine, cenisertib, ceritinib, chlorambucil, cisplatin, cladribine, clofarabine, crenolanib, crizotinib, cyclophosphamide, cytarabine, dabrafenib, dacarbazine, dacomitinib, dactinomycin, danusertib, dasatinib, daunorubicin, decitabine, dinaciclib, docetaxel, dovitinib, doxorubicin, epirubicin, epitinib, eribulin mesylate, errlotinib, etirinotecan, etoposide, everolimus, exemestane, floxuridine, fludarabine, fluorouracil, gefitinib, gemcitabine, hydroxyurea, ibrutinib, icotinib, idarubicin, idelalisib, ifosfamide, imatinib, imetelstat, ipatasertib, irinotecan, ixabepilone, lapatinib, lenalidomide, lestaurtinib, lomustine, lucitanib, masitinib, mechlorethamine, melphalan, mercaptopurine, methotrexate, midostaurin, mitomycin, mitoxantrone, mubritinib, nelarabine, neratinib, nilotinib, nintedanib, omacetaxine mepesuccinate, olaparib, orantinib, oxaliplatin, paclitaxel, palbociclib, palifosfamide tris, pazopanib, pelitinib, pemetrexed, pentostatin, plicamycin, ponatinib, poziotinib, pralatrexate, procarbazine, quizartinib, raltitrexed, regorafenib, ruxolitinib, seliciclib, sorafenib, streptozocin, sulfatinib, sunitinib, tamoxifen, tandutinib, temozolomide, temsirolimus, teniposide, theliatinib, thioguanine, thiotepa, topotecan, uramustine, valrubicin, vandetanib, vemurafenib (Zelborae), vincristine, vinblastine, vinorelbine, vindesine, and the like.

In some embodiments, the second therapeutic agent is selected from the group consisting of a phosphoinositol-3 kinase (PI3K) inhibitor, AKT inhibitor, mammalian target of rapamycin (mTOR) inhibitor, poly ADP ribose polymerase (PARP) inhibitor, platinum-based anti-cancer compound (PBAC), CBP/P-catenin inhibitor, Tankyrase (TNKS) inhibitor, probable protein-cysteine N-palmitoyltransferase (PORCN) inhibitor, scr kinase/bcr-abl kinase inhibitor, Smoothened (SMO) inhibitor, anti-cancer nucleoside analog or anti-metabolite, histone deacetylase (HDAC) inhibitor, Bromodomain and Extra-Terminal motif (BET) inhibitor, all-trans-retinoic acid (ATRA), Bruton's tyrosine kinase (BTK) inhibitor, EGFR receptor inhibitor, and combinations thereof.

In some embodiments, the second therapeutic agent is selected from the group consisting of idelalisib, pictilisib, duvelisib, pilaralisib, alpelisib, copanlisib, voxtalisib, dactolisib, gedatolisib, apitolisib, perifosine, miltefosine, ipatasertib, sirolimus, everolimus, temsirolimus, tacrolimus, ridaforolimus, ridaforolimus, dactolisib, olaparib, veliparib, rucaparib, talazoparib, niraparib, cisplatin, carboplatin, oxaliplatin, dicycloplatin, nedaplatin, lobaplatin, heptaplatin, phenathriplatin, phosphaplatin, LA-12, ICG-001, PRI-724, XAV-939, G007-LK, LGK-974, ETC-159, staurosporine, nilotinib, imatinib, ponatinib, saracatinib, dasatinib, bosutinib, saracatinib, cyclopamine, vismodegib, glasdegib, SANT-1, sonidegib, saridegib, taladegib, GSK1210151A, GSK525762, CPI-0610, RVX-208, vorinostat (SAHA), entinostat, panobinostat, mocetinostat, belinostat, romidepsin, rocilinostat, abexinostat, resminostat, givinostat, quisinostat, pracinostat, kevetrin, CC-292, CNX-774, LFM-A13, CGI1746, trastuzumab, pertuzumab, ado-trastuzumab emtansine, cetuximab, panitumumab, nimotuzuma, mAb806, rrindopepimut, lapatinib, erlotinib, gefitinib, afatinib, neratinib, osimertinib, rociletinib, canertinib, and dacomitinib.

5.6. Formulations and Administration

In some embodiments, the pharmaceutical compositions of the therapeutic agents can be formulated by standard techniques using one or more physiologically acceptable carriers or excipients. Suitable pharmaceutical carriers are described herein and in Remington: The Science and Practice of Pharmacy, $21^{st}$ Ed. (2005). The therapeutic compounds and their physiologically acceptable salts, hydrates and solvates can be formulated for administration by any suitable route, including, among others, topically, nasally, orally, parenterally, rectally or by inhalation. In some embodiments, the compounds and pharmaceutical compositions thereof are administered by intradermal, subdermal, intravenous, intramuscular, intranasal, intracerebral, intratracheal, intraarterial, intraperitoneal, intravesical, intrapleural, intracoronary or intratumoral injection, such as with a syringe or other devices. Transdermal administration is also contemplated, as are inhalation or aerosol administration. Tablets, capsules, and solutions can be administered orally, rectally or vaginally.

For oral administration, a pharmaceutical composition can take the form of, for example, a tablet or a capsule prepared by conventional means with a pharmaceutically acceptable excipient. Tablets and capsules comprising the active ingredient can be prepared together with excipients such as: (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; (c) binders, e.g., magnesium aluminum silicate, starch paste, gelatin, tragacanth, methylcellulose, sodium carboxymethylcellulose, polyvinylpyrrolidone and/or hydroxypropyl methylcellulose; (d) disintegrants, e.g., starches (including potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners. The compositions are prepared according to conventional mixing, granulating or coating methods.

Tablets may be either film coated or enteric coated according to methods known in the art. Liquid preparations for oral administration can take the form of, for example, solutions, syrups, or suspensions, or they can be presented as a dry product for reconstitution with water or other suitable vehicle before use. Such liquid preparations can be prepared by conventional means with pharmaceutically acceptable carriers and additives, for example, suspending agents, e.g., sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

The therapeutic agents can be formulated for parenteral administration, for example by bolus injection or continuous infusion. Formulations for injection can be presented in unit dosage form, for example, in ampoules or in multi-dose containers, with an optionally added preservative. Injectable compositions can be aqueous isotonic solutions or suspensions. In some embodiments for parenteral administration, the therapeutic agents can be prepared with a surfactant, such as Cremaphor, or lipophilic solvents, such as triglycerides or liposomes. The compositions may be sterilized and/or contain adjuvants, such as preserving, stabilizing, wetting or emulsifying agents, solution promoters, salts for regulating the osmotic pressure and/or buffers. Alternatively, the therapeutic agent can be in powder form for reconstitution with a suitable vehicle, for example, sterile pyrogen-free water, before use. In addition, they may also contain other therapeutically effective substances.

In some embodiments, the therapeutic agent, e.g., the diterpenoid PKC modulating compounds, are administered intratumorally. In some embodiments, the therapeutic agent is administered directly into the tumor, allowing for high local concentration of the therapeutic agent and in some embodiments, increased bioavailability of the therapeutic agent at the site of the tumor. Any formulation of the therapeutic agent suitable for intratumoral administration can be used in the embodiments herein. Intratumoral administration can be by injection of the therapeutic agent into the tumor (see, e.g., Celikoglu et al., 2008, Cancer Therapy, 6:545-552) or by intravenous administration to blood vessels feeding to the tumor. In some embodiments, the injection device has a porous delivery channel (e.g., needle) for wider distribution or infusion of the therapeutic agent for treating tumors with large volume.

For administration by inhalation, the therapeutic agent may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a therapeutic agent with a carrier. Preferred carriers include absorbable pharmacologically acceptable solvents to assist passage through the skin of the subject. For example, transdermal devices are in the form of a bandage or patch comprising a backing member, a reservoir containing the therapeutic agent optionally with carriers, optionally a rate controlling barrier to deliver the compound to the skin of the host at a controlled and predetermined rate over a prolonged period of time, and a means to secure the device to the skin. Matrix transdermal formulations may also be used.

Suitable formulations for topical application, e.g., to the skin and eyes, are preferably aqueous solutions, ointments, creams or gels well-known in the art. The formulations may contain solubilizers, stabilizers, tonicity enhancing agents, buffers and preservatives.

In some embodiments, the therapeutic agent can also be formulated as a rectal composition, for example, suppositories or retention enemas, for example, containing conventional suppository bases, for example, cocoa butter or other glycerides, or gel forming agents, such as carbomers.

In some embodiments, the therapeutic agent can be formulated as a depot preparation. Such long-acting formulations can be administered by implantation (for example, subcutaneously or intramuscularly) or by intramuscular injection. The therapeutic agent can be formulated with suitable polymeric or hydrophobic materials (for example as an emulsion in an acceptable oil), ion exchange resins, biodegradable polymers, or as sparingly soluble derivatives, for example, as a sparingly soluble salt.

In some embodiments, the carrier is a cyclodextrins, such as to enhance solubility and/or bioavailability of the compounds herein. In some embodiments, the cyclodextrin for use in the pharmaceutical compositions can be selected from α-cyclodextrin, β-cyclodextrin, γ-cyclodextrin, derivatives thereof, and combinations thereof. In particular, the cyclodextrin is selected from β-cyclodextrin, γ-cyclodextrin, derivatives thereof, and combinations thereof.

In some embodiments, the compounds can be formulated with a cyclodextrin or derivative thereof selected from carboxyalkyl cyclodextrin, hydroxyalkyl cyclodextrin, sulfoalkylether cyclodextrin, and an alkyl cyclodextrin. In various embodiments, the alkyl group in the cyclodextrin is methyl, ethyl, propyl, butyl, or pentyl.

In some embodiments, the cyclodextrin is α-cyclodextrin or a derivative thereof. In some embodiments, the α-cyclodextrin or derivative thereof is selected from carboxyalkyl-α-cyclodextrin, hydroxyalkyl-α-cyclodextrin, sulfoalkylether-α-cyclodextrin, alkyl-α-cyclodextrin, and combinations thereof. In some embodiments, the alkyl group in the α-cyclodextrin derivative is methyl, ethyl, propyl, butyl, or pentyl.

In some embodiments, the cyclodextrin is β-cyclodextrin or a derivative thereof. In some embodiments, the β-cyclodextrin or derivative thereof is selected from carboxyalkyl-β- cyclodextrin, hydroxyalkyl-β-cyclodextrin, sulfoalkylether-β-cyclodextrin, alkyl-β-cyclodextrin, and combinations thereof. In some embodiments, the alkyl group in the β-cyclodextrin derivative is methyl, ethyl, propyl, butyl, or pentyl.

In some embodiments, the β-cyclodextrin or a derivative thereof is hydroxyalkyl-β-cyclodextrin or sulfoalkylether-β-cyclodextrin. In some embodiments, the hydroxyalkyl-β-cyclodextrin is hydroxypropyl-β-cyclodextrin. In some embodiments, the sulfoalkylether-β-cyclodextrin is sulfobutylether-β-cyclodextrin. In some embodiments, β-cyclodextrin or a derivative thereof is alkyl-β-cyclodextrin, in particular methyl-β-cyclodextrin. In some embodiments using methyl-β-cyclodextrin, the β-cyclodextrin is randomly methylated β-cyclodextrin.

In some embodiments, the cyclodextrin is γ-cyclodextrin or a derivative thereof. In some embodiments, the γ-cyclodextrin or derivative thereof is selected from carboxyalkyl-γ-cyclodextrin, hydroxyalkyl-γ-cyclodextrin, sulfoalkylether-γ-cyclodextrin, and alkyl-γ-cyclodextrin. In some embodiments, the alkyl group in the γ-cyclodextrin derivative is methyl, ethyl, propyl, butyl, or pentyl. In some embodiments, the γ-cyclodextrin or derivative thereof is hydroxyalkyl-γ-cyclodextrin or sulfoalkylether-γ-cyclodextrin. In some embodiments, the hydroxyalkyl-γ-cyclodextrin is hydroxypropyl-γ-cyclodextrin.

When used in a formulation with the compound of the present disclosure, the cyclodextrin can be present at about 0.1 w/v to about 30% w/v, about 0.1 w/v to about 20% w/v, about 0.5% w/v to about 10% w/v, or about 1% w/v to about 5% w/v. In some embodiments, the cyclodextrin is present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v or more.

The pharmaceutical compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

5.7. Effective Amount and Dosing

In some embodiments, a pharmaceutical composition of the therapeutic agent is administered to a subject, preferably a human, at a therapeutically effective dose to prevent, treat, or control a condition or disease as described herein. The pharmaceutical composition is administered to a subject in an amount sufficient to elicit an effective therapeutic response in the subject. An effective therapeutic response is a response that at least partially arrests or slows the symptoms or complications of the condition or disease. An amount adequate to accomplish this is defined as "therapeutically effective dose" or "therapeutically effective amount."

The dosage of therapeutic agents can take into consideration, among others, the species of warm-blooded animal (mammal), the body weight, age, condition being treated, the severity of the condition being treated, the form of administration, route of administration. The size of the dose also will be determined by the existence, nature, and extent of any adverse effects that accompany the administration of a particular therapeutic compound in a particular subject.

In some embodiments, the diterpenoid PKC activating compound, the compound can be administered in a dose in the range from about 0.001 mg per kg of subject weight (0.001 mg/kg) to about 1000 mg/kg. In some embodiments, the dose is in the range of about 0.001 mg/kg to about 500 mg/kg. In some embodiments, the dose is in the range of about 1 mg/kg to about 500 mg/kg. In some embodiments, the dose is about 2 mg/kg to about 250 mg/kg. In another embodiment, the dose is about 5 mg/kg to about 100 mg/kg. In another embodiment, the dose is about 5 mg/kg to about 100 mg/kg. In some embodiments, the dose is about 0.001 mg/kg, 0.01 mg/kg, 0.05 mg/kg, 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/kg, 10 mg/kg, 20 mg/kg, 40 mg/kg, 50 mg/kg, 100 mg/kg, 200 mg/kg or 500 mg/kg. In some embodiments, the dose can be administered once per day or divided into subdoses and administered in multiple doses, e.g., twice, three times, or four times per day.

In some embodiments, the diterpenoid PKC activator can be administered with one or more of the second therapeutic agent sequentially or concurrently, either by the same route or by different routes of administration. When administered sequentially, the time between administrations is selected to benefit, among others, the therapeutic efficacy and/or safety of the combination treatment. In some embodiments, the diterpenoid PKC activator can be administered first followed by a second therapeutic agent, or alternatively, the second therapeutic agent administered first followed by the diterpenoid PKC activator. By way of example and not limitation, the time between administrations is about 1 hr, about 2 hr, about 4 hr, about 6 hr, about 12 hr, about 16 hr or about 20 hr. In some embodiments, the time between administrations is about 1, about 2, about 3, about 4, about 5, about 6, or about 7 more days. In some embodiments, the time between administrations is about 1 week, 2 weeks, 3 weeks, or 4 weeks or more. In some embodiments, the time between administrations is about 1 month or 2 months or more.

When administered concurrently, the diterpenoid PKC modulator can be administered separately at the same time as the second therapeutic agent, by the same or different routes, or administered in a single composition by the same route.

In some embodiments, the amount and frequency of administration of the second therapeutic agent can used standard dosages and standard administration frequencies used for the particular therapeutic agent. See, e.g., Physicians' Desk Reference, $70^{th}$ Ed., PDR Network, 2015; incorporated herein by reference.

In some embodiments, where administration of the therapeutic agent is to a localized site, for example, intratumoral injection, the dosages can be the dosages used for systemic administration, such as dosages used for intravenous, intramuscular, and intraperitoneal administration. In some embodiments, the dose for localized administration, e.g., intratumoral administration, is higher than those used for systemic administration. In some embodiments, the administered dose is sufficient for the intended effect, for example killing or necrotization of tumor tissue. In some embodiments, intratumoral administration is done once, twice, three times, four times, five time or up to six times or more, where each administration is separated in time, for example, until the desired outcome is achieved.

It to be understood that optimum dosages, toxicity, and therapeutic efficacy of such therapeutic agents may vary depending on the relative potency of individual therapeutic agent and can be determined by pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Therapeutic agents or combinations thereof that exhibit large therapeutic indices are preferred. While certain agents that exhibit toxic side effects can be used, care should be used to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such small molecule compounds lies preferably within a range of circulating concentrations that include the $ED_{50}$ with little or no toxicity. The dosage can vary within this range depending upon the dosage form employed and the route of administration. For any compounds used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

The following examples are provided to further illustrate the methods of the present disclosure, and the compounds and compositions for use in the methods. The examples described are illustrative only and are not intended to limit the scope of the invention in any way.

6. EXAMPLES

Example 1: Synthesis Scheme of K101-Epoxide and K101-DI-OH

The scheme for synthesis of compounds K101-Epoxide and K101-DI-OH are illustrated below.

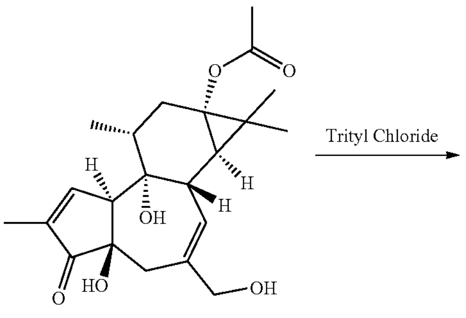

K101A (prostratin)

-continued

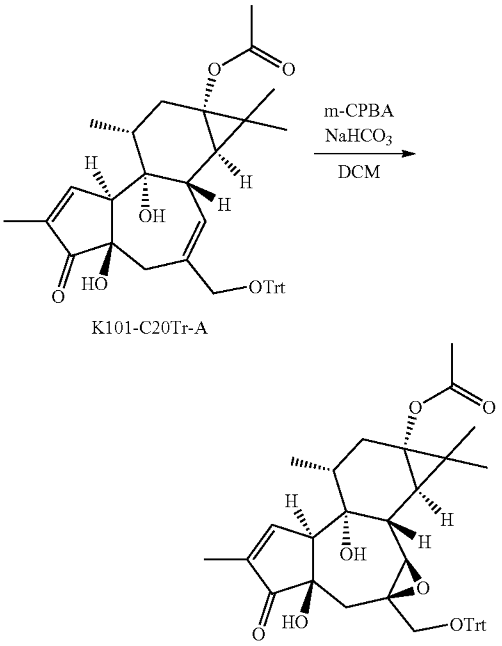

K101-C20Tr-A

Epoxide-Trt

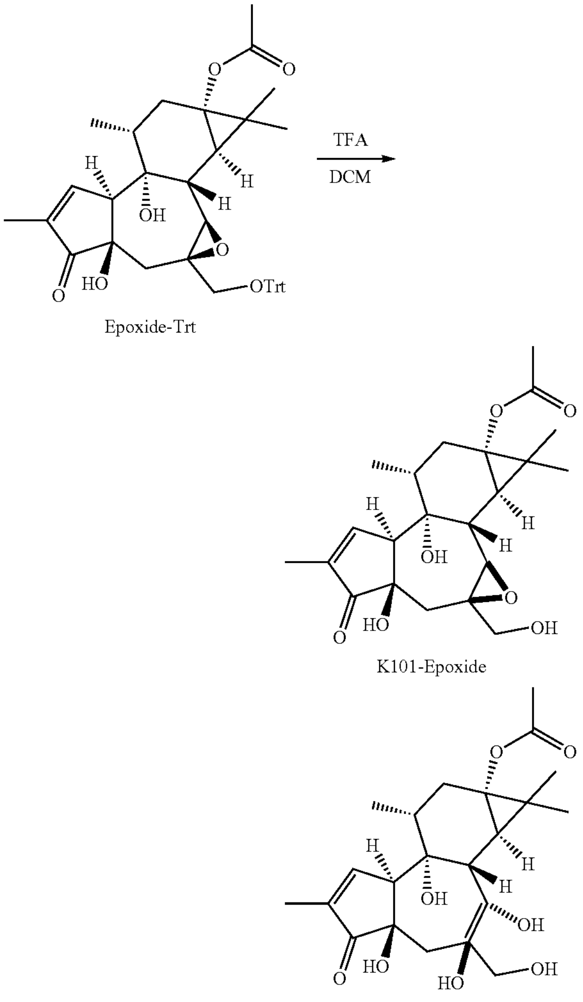

Epoxide-Trt

K101-Epoxide

K101-DI-OH

Preparation of Compound K101-C20Tr-A. To a solution of K101A (1 g, 2.56 mmol, 1 eq) in pyridine (40 mL) was added Trityl chloride (2.14 g, 7.68 mmol, 3.00 eq). The mixture was stirred at 40° C. for 14 hours (hr) to give a yellow solution. LC-MS showed desired mass was found, and K101A was remained. The mixture was stirred at 40° C. for 12 hr again. LC-MS and TLC (eluting with: PE/EtOAc=2/1) showed the reaction was complete. The reaction mixture was concentrated by drumming $N_2$ to give the crude product. The crude product was purified by flash column (eluting with: petroleum ether (PE)/ethyl acetate=100% PE to 20%) to give K101-C20Tr-A (1.6 g, 2.53 mmol, 98.73% yield) as a white solid.

$^1$H NMR (400 MHz, $CDCl_3$) δ 7.59 (s, 1H), 7.44-7.42 (m, 6H), 7.31-7.29 (m, 6H), 7.24-7.21 (m, 3H), 5.63 (brs, 1H), 3.51 (s, 2H), 3.28 (s, 1H), 2.93 (s, 1H), 2.49-2.41 (m, 2H), 2.09-2.06 (m, 5H), 2.09-2.03 (m, 7H), 1.99-1.94 (m, 1H), 1.78 (s, 3H), 1.20 (s, 3H), 1.07 (s, 3H), 0.89-0.81 (m, 4H).

Preparation of Compound Epoxide-Trt. To a solution of K101-C20Tr-A (30.00 mg, 47.41 μmol, 1.00 equivalent (hereafter as eq)) in dichloromethane (hereafter as DCM) (2.00 mL) was added $NaHCO_3$ (11.95 mg, 142.23 μmol, 5.53 uL, 3.00 eq), meta-chloroperoxybenzoic acid (m-CPBA) (14.44 mg, 71.11 μmol, 1.5 eq, 85% purity), and the reaction mixture was stirred at 20° C. for 2 hours (h) to give a suspension. LC-MS showed the reaction was complete, and the desired MS value was observed. Thin-layer chromatography (TLC) (petroleum ether/ethyl acetate mixture ration 2:1 (PE/EtOAc=2/1), $SiO_2$) analysis showed no new spots. The reaction mixture was mixed with DCM (5 mL) and brine (2 mL), and the organic layer was separated and concentrated under reduced pressure to give 35.5 mg of crude product as a colorless gum. The product was purified by preparative (prep)-TLC (PE/EtOAc=2/1, $SiO_2$) to give Epoxide-Trt (20.10 mg, 65.34% yield) as a colorless gum.

$^1$H NMR (400 MHz, $CDCl_3$) δ 7.63 (s, 1H), 7.37-7.30 (m, 6H), 7.30-7.18 (m, 11H), 5.54 (brs, 1H), 3.96-3.89 (m, 1H), 3.17 (d, J=9.3 Hz, 1H), 3.08 (d, J=8.5 Hz, 1H), 2.85-2.74 (m, 2H), 2.09 (s, 3H), 2.07-2.03 (m, 1H), 2.02 (s, 1H), 1.98 (s, 1H), 1.96-1.87 (m, 1H), 1.86-1.81 (m, 1H), 1.80-1.74 (m, 3H), 1.66-1.59 (m, 1H), 1.21 (s, 3H), 1.04 (s, 3H), 0.97 (d, J=4.3 Hz, 1H), 0.89 (d, J=6.5 Hz, 3H).

Preparation of Compound K101-Epoxide and K101-DI-OH. To a solution of Epoxide-Trt (10.00 mg, 15.41 μmol, 1.00 eq) in DCM (500.00 uL) was added trifluoroacetic acid (hereafter as TFA) (100.00 μL), and the reaction solution stirred at 0° C. for 1 h. TLC (PE/EtOAc=2/1, $SiO_2$) showed the reaction was complete. The reaction was quenched by saturated aqueous $NaHCO_3$ (2 mL) at 0° C., then extracted with DCM (5 mL×2), dried over $Na_2SO_4$, filtered, and concentrated under reduced pressure to give a colorless gum. The residue was combined with a second preparation of crude product and purified by prep-HPLC (column: Waters Xbridge 150×25×5 mm; mobile phase: A [A: water (0.05% ammonia hydroxide v/v)]; B [acetonitrile (ACN)]; gradient B %: 25%-55% in 10 min to give K101-Epoxide (1.51 mg, 3.71 μmol, 24.11% yield, 100% purity) and K101-DI-OH (1.20 mg, 2.60 μmol, 16.90% yield, 92.1% purity), both as white solid after lyophilization.

K101-Epoxide: LC-MS (m/z): 429.2 $[M+Na]^+$

K101-Epoxide: $^1$H NMR (400 MHz, CD3OD) δ 7.53 (s, 1H), 3.48 (d, J=11.9 Hz, 1H), 3.44-3.39 (m, 1H), 3.36 (s, 1H), 3.16 (d, J=8.6 Hz, 1H), 2.66 (d, J=16.8 Hz, 1H), 2.14-2.06 (m, 4H), 2.04-1.89 (m, 3H), 1.77-1.74 (m, 3H), 1.59 (dd, J=11.2, 14.3 Hz, 1H), 1.22 (s, 3H), 1.06 (s, 3H), 1.02 (d, J=4.9 Hz, 1H), 0.89 (d, J=6.6 Hz, 3H).

K101-DI-OH: LC-MS (m/z): 447.1 $[M+Na]^+$

K101-DI-OH: $^{1}$H NMR (400 MHz, CD3OD) δ 7.70 (s, 1H), 3.89 (s, 1H), 3.72-3.68 (m, 1H), 3.53 (d, J=2.6 Hz, 2H), 2.45 (d, J=7.9 Hz, 1H), 2.21-2.07 (m, 2H), 2.03 (s, 3H), 1.85-1.79 (m, 1H), 1.79-1.74 (m, 3H), 1.60-1.48 (m, 2H), 1.14 (s, 3H), 1.08 (s, 4H), 0.92 (d, J=6.8 Hz, 3H).

Example 2: Synthesis Scheme of K101-C13OH

The scheme for synthesis of compound K101-C13OH is illustrated below.

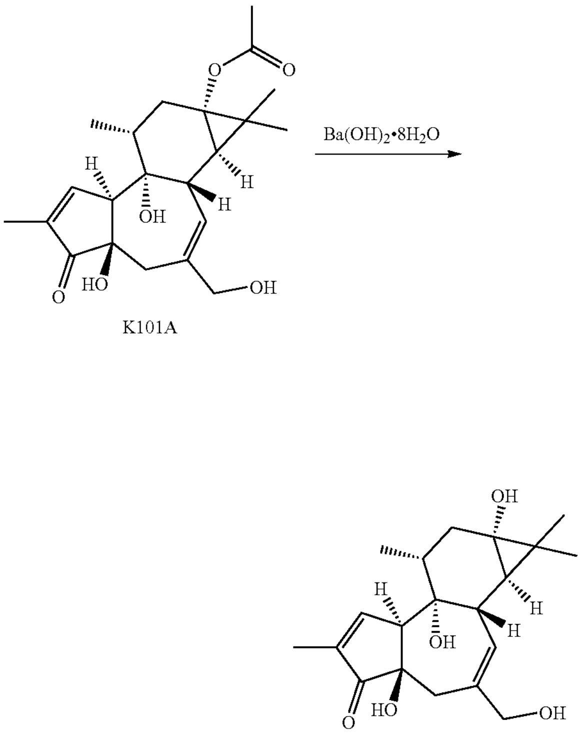

K101A

K101-C13OH

Preparation of Compound K101-C13OH. To a solution of K101A (40.00 mg, 102.44 μmol, 1.00 eq) in MeOH (20.00 mL) was added $Ba(OH)_2.8H_2O$ (322.69 mg, 1.02 mmol, 10.00 eq). The mixture was stirred at 20° C. for 4 hours to give a yellow suspension. LC-MS and TLC (eluting with: EtOAc=100%) showed the reaction was complete. The reaction mixture was quenched with saturated $NH_4Cl$ (10 mL) and extracted with dichloromethane (DCM) (100 mL×3). The organic layers were dried over $Na_2SO_4$ and concentrated to give the crude product. The crude product was purified by prep-TLC (eluting with: EtOAc=2/1) to give K101-C13OH (9.30 mg, 26.69 μmol, 26.05% yield, 100% purity) as a white solid.

LC-MS (m/z): 371.2 $[M+Na]^+$ $^{1}$H NMR (400 MHz, $CD_3OD$) δ 7.29 (s, 1H), 5.18 (s, 1H), 4.58 (s, 2H), 3.81-3.75 (m, 1H), 3.50-3.46 (m, 1H), 3.20-3.11 (m, 3H), 2.16-2.11 (m, 1H), 1.76-1.63 (m, 5H), 1.27 (m, 1H), 1.17 (m, 3H), 1.74-1.53 (m, 8H), 1.17 (s, 3H), 1.05 (s, 3H), 1.06-0.88 (m, 6H).

Example 3: Synthesis Scheme of K101-C1301

The scheme for synthesis of compound K101-C1301 is illustrated below.

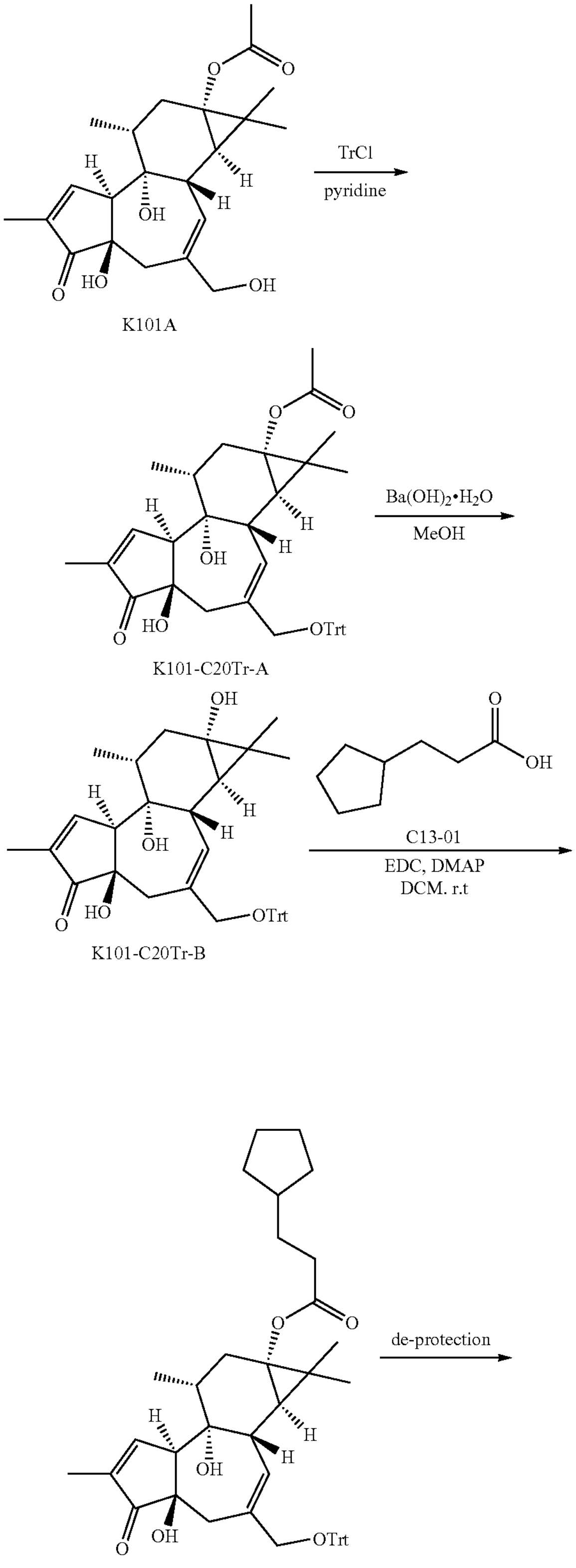

K101A

K101-C20Tr-A

K101-C20Tr-B

K101-C1301-A

-continued

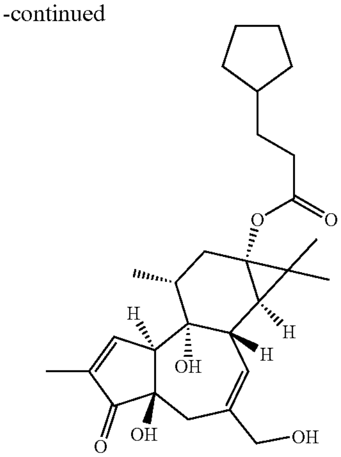

K101-C1301

Preparation of Compound K101-C20Tr-A. To a solution of K101A (500.00 mg, 1.28 mmol, 1.00 eq) in pyridine (10.00 mL) was added trityl chloride (TrtCl) (1.07 g, 3.84 mmol, 3.00 eq). The mixture was stirred at 20° C. for 14 hours to give a yellow solution. LC-MS and TLC (eluting with: PE/EtOAc=2/1) showed the reaction was complete. The reaction mixture was concentrated by $N_2$ to give the crude product. The product was purified by flash column (eluting with: EtOAc in PE 1% to 50%) to give K101-C20Tr-A (790.00 mg, 1.02 mmol, 79.78% yield, 81.795% purity) as a white solid.

Preparation of Compound K101-C20Tr-B. To a solution of K101-C20Tr-A (290.00 mg, 458.30 μmol, 1.00 eq) in MeOH (76.00 mL) was added $Ba(OH)_2.8H_2O$ (1.44 g, 4.58 mmol, 10.00 eq) at 0° C. The mixture was stirred at 20° C. for 3 hours to give yellow suspension. LC-MS showed the reaction was complete. The reaction mixture was quenched with saturated aqueous $NH_4Cl$ (50 mL) and extracted with dicholoromethane (DCM) (300 mLx3). The organic layers were dried over $Na_2SO_4$. The organic layers was filtered on silica gel and washed with EtOAc (50 mL). The organic layer was concentrated to give K101-C20Tr-B (260.00 mg, 425.57 μmol, 92.86% yield, 96.694% purity) as a white solid.

Preparation of Compound K101-C1301-A. To solution of K101-C1301-B (35.00 mg, 59.25 mol, 1.00 eq) in DCM (500.00 uL) were added 3-cyclopentylpropanoic acid (10.11 mg, 71.10 μmol, 10.11 uL, 1.20 eq), N-(3-Dimethylamino-propyl)-N'-ethylcarbodiimide hydrochlorideEDC (EDC) (22.72 mg, 118.49 μmol, 2.00 eq) and 4-Dimethylamino-pyridine (DMAP) (14.48 mg, 118.50 μmol, 2.00 eq). The mixture was stirred at 20° C. for 14 hours to give a yellow solution. LC-MS and TLC (eluting with: PE/EtOAc=4/1) showed the reaction was complete. The reaction mixture was combined with a second preparation of the compound, quenched with $H_2O$ (10 mL) and extracted with DCM (15 mLx3). The combined organic layers were dried over $Na_2SO_4$ and concentrated to give the crude product. The product was purified by prep-TLC (eluting with: PE/EtOAc=4/1) to give K101-C1301-A (32.00 mg, 44.76 μmol, 65.12% yield, 100% purity) as a white solid.

Preparation of Compound K101-C1301. To a solution of K101-C1301-A (32.00 mg, 44.76 μmol, 1.00 eq) in DCM (1.00 mL) was added TFA (385.00 mg, 3.38 mmol, 250.00 uL, 75.44 eq). The mixture was stirred at 20° C. for 1 hour to give a yellow solution. LC-MS and TLC (eluting with: PE/EtOAc=1/1) showed the reaction was complete. The solvent was removed by $N_2$ to give a crude product. The product was purified by prep-TLC (eluting with: PE/EtOAc=1/1) to give K101-C1301 (8.10 mg, 17.14 μmol, 38.29% yield, 100% purity) as a white solid.

LC-MS (m/z): 495.3 $[M+Na]^+$ $^1H$ NMR (400 MHz, $CD_3OD$) δ 7.53 (s, 1H), 5.59 (s, 1H), 4.54-4.49 (m, 2H), 3.95-3.88 (m, 2H), 3.14 (s, 1H), 3.04 (s, 1H), 2.53-2.43 (m, 2H), 2.35-2.31 (m, 2H), 2.10-1.90 (m, 2H), 1.77-1.72 (m, 6H), 1.62-1.52 (m, 7H), 1.15 (s, 3H), 1.05 (s, 3H), 0.89-0.83 (m, 4H).

Example 4: Synthesis Scheme of K101-C1302

The scheme for synthesis of compound K101-C1302 is illustrated below.

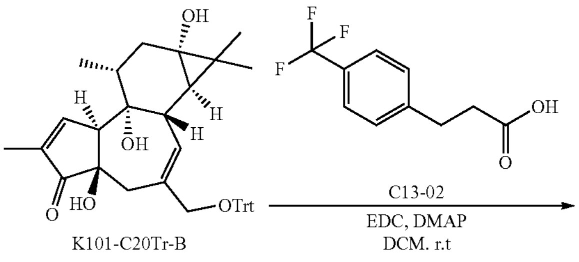

K101-C20Tr-B

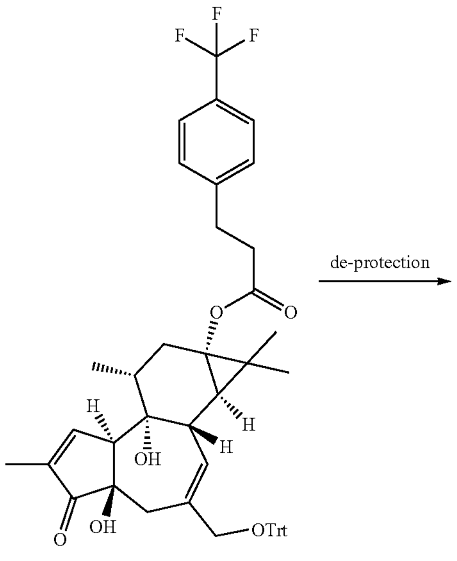

K101-C1302-A

-continued

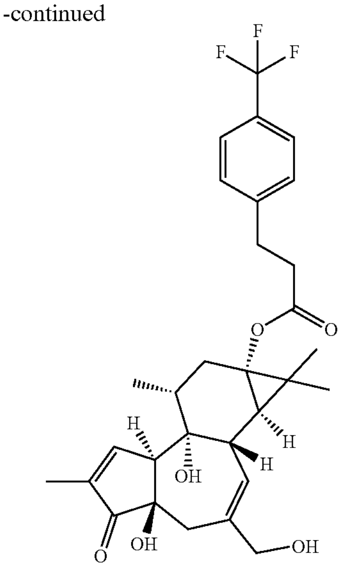

K101-C1302

Preparation of Compound K101-C1302-A. To a solution of K101-C20Tr-B (40.00 mg, 67.71 mol, 1.00 eq) in DCM (1.00 mL) were added 3-[4-(trifluoromethyl)phenyl]propanoic acid (C13-02) (17.73 mg, 81.25 μmol, 1.20 eq), DMAP (16.54 mg, 135.42 μmol, 2.00 eq) and EDC (25.96 mg, 135.42 μmol, 2.00 eq). The mixture was stirred at 20° C. for 2 hours to give a yellow solution.

LC-MS and TLC (eluting with: PE/EtOAc=2/1) showed the reaction was complete. The mixture was combined with a second preparation of the compound, quenched with saturated $NaHCO_3$ (5 mL) and extracted with DCM (10 mL×3). The organic layers were washed with $H_2O$ (5 mL), dried over $Na_2SO_4$ and then concentrated to give the crude product. The product was purified by prep-TLC (eluting with: PE/EtOAc=2/1) to give K101-C1302-A (34.00 mg, 42.45 μmol, 53.72% yield, 98.736% purity) as a white solid.

Preparation of compound K101-C1302. To a solution of K101-C1302-A (28.00 mg, 35.40 μmol, 1.00 eq) in MeOH (1.00 mL) was added $HClO_4$ (464.95 mg, 4.63 mmol, 280.09 uL, 130.73 eq). The mixture was stirred at 0° C. for 0.5 hour to give a yellow solution. LC-MS showed the reaction was complete. The reaction mixture was combined with a second preparation of the compound and purified by prep-HPLC (column: Waters XSELECT C18 150×30 mm×5 um; mobile phase: [A: water (0.1% TFA)-B: B: ACN]; B %: 33%-63%, 10 min) to give K101-C1302 (10.60 mg, 18.56 μmol, 52.42% yield, 96.032% purity) as a white solid.

LC-MS (m/z): 571.3 $[M+Na]^+$ $^1H$ NMR (400 MHz, $CD_3OD$) δ 7.58-7.52 (m, 2H), 7.43-7.41 (m, 2H), 5.55 (s, 1H), 3.95-3.87 (m, 2H), 3.29-2.99 (m, 4H), 2.72-2.68 (m, 2H), 2.47-2.37 (m, 2H), 2.05-1.96 (m, 2H), 1.72 (s, 3H), 1.43-1.40 (m, 1H), 1.01 (s, 6H), 0.85-0.83 (m, 3H), 0.75-0.73 (m, 3H).

Example 5: Synthesis Scheme of K101-C1303

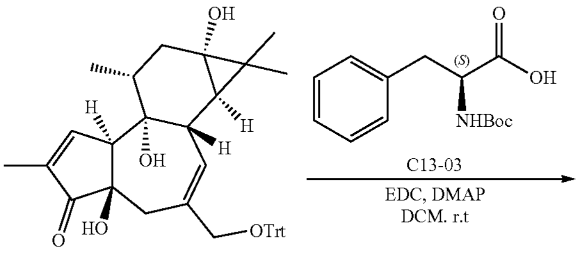

K101-C20Tr-B

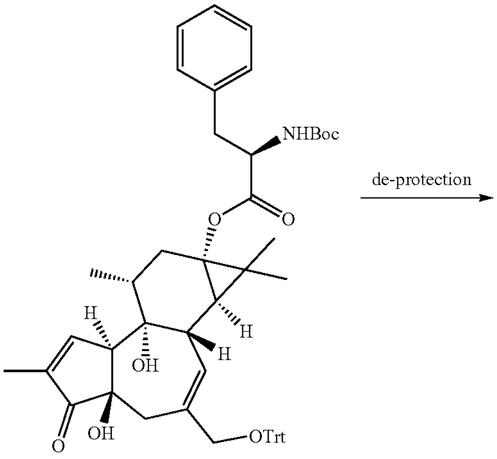

K101-C1303-A

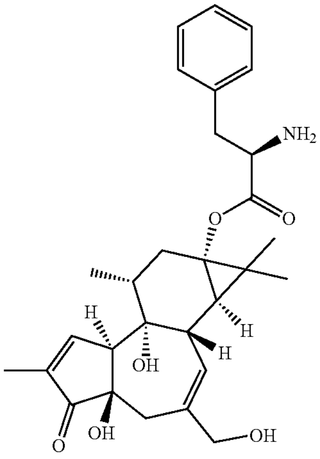

K101-C1303

Preparation of Compound K101-C1303-A: To a solution of K101-C20Tr-B (30.00 mg, 50.78 μmol, 1.00 eq) in DCM (2.00 mL) were added (2S)-2-(tert-butoxycarbonylamino)-3-phenyl-propanoic acid (C13-03) (26.95 mg, 101.57 μmol, 2.00 eq), DMAP (24.82 mg, 203.13 μmol, 4.00 eq) and EDC (19.47 mg, 101.57 μmol, 2.00 eq). The mixture was stirred at 20° C. for 48 hours to give a yellow solution. LC-MS and TLC (eluting with: PE/EtOAc=2/1) showed the reaction was complete.

The reaction mixture was quenched with saturated $NaHCO_3$ (5 mL) and extracted with DCM (10 mL*3). The organic layers were dried over $Na_2SO_4$ and concentrated to give the crude product. The crude product was purified by prep-TLC (eluting with: PE/EtOAc=2/1) to give K101-C1303-A (30.00 mg, 34.85 μmol, 68.63% yield, 97.349% purity) as a white solid.

$^1$H NMR (400 MHz, $CDCl_3$) δ 7.50 (s, 1H), 7.37-7.35 (m, 5H), 7.24-7.22 (m, 8H), 7.17-7.12 (m, 7H), 5.54 (s, 1H), 5.04 (m, 1H), 4.87-4.85 (m, 1H), 4.49 (m, 1H), 3.18 (s, 1H), 3.02 (m, 1H), 2.83 (m, 1H), 2.46-2.41 (m, 1H), 2.32-2.28 (m, 1H), 1.98-1.93 (m, 2H), 1.70 (m, 3H), 1.35 (s, 9H), 1.19 (s, 3H), 0.99-0.98 (m, 3H), 0.78-0.77 (m, 3H), 0.70-0.69 (m, 1H).

Preparation of Compound K101-C1303: To a solution of K101-C20Tr-B (30.00 mg, 35.80 μmol, 1.00 eq) in DCM (1.00 mL) was added TFA (154.00 mg, 1.35 mmol, 100.00 uL, 37.73 eq) at 0° C. The mixture was stirred at 0° C. for 2 hr to give a red-brown solution. The mixture was stirred at 20° C. for 14 hours to give a red-brown solution again. The reaction mixture was quenched with $H_2O$ (5 mL) and the organic layer was separated. The water layer was lyophilized. The organic layer was dissolved in MeOH (3.00 mL) and added $HClO_4$ (83.00 mg, 826.20 μmol, 50.00 uL, 23.08 eq) at 0° C. The mixture was stirred at 0° C. for 2 hours to give a yellow solution. LC-MS showed the reaction was complete. The reaction mixture was purified by prep-HPLC (column: Phenomenex Gemini 150*25 mm*10 um; mobile phase: [A: water (0.1% TFA)-B: B: ACN]; B %: 18%-48%, 10 min) to give K101-C1303 (4.50 mg, 6.90 μmol, 19.27% yield, 93.438% purity, TFA salt) as a white solid.

LC-MS (m/z): 519.3 $[M+H]^+$ $^1$H NMR (400 MHz, $CD_3OD$) δ 7.45 (s, 1H), 7.31-7.21 (m, 5H), 5.51 (s, 1H), 4.27-4.21 (m, 1H), 3.84 (s, 2H), 3.25 (m, 1H), 3.06-3.00 (m, 3H), 2.40-2.33 (m, 1H), 2.33-2.28 (m, 1H), 2.08 (m, 1H), 2.04 (m, 1H), 1.65 (s, 3H), 1.44-1.40 (m, 1H), 1.03 (s, 3H), 0.97 (s, 3H), 0.87-0.81 (m, 4H).

Example 6: Synthesis Scheme of K101-C1304

The scheme for synthesis of compound K101-C1304 is illustrated below.

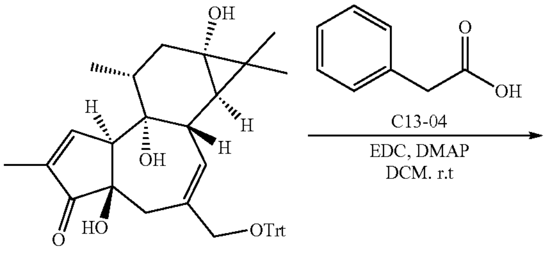

K101-C20Tr-B

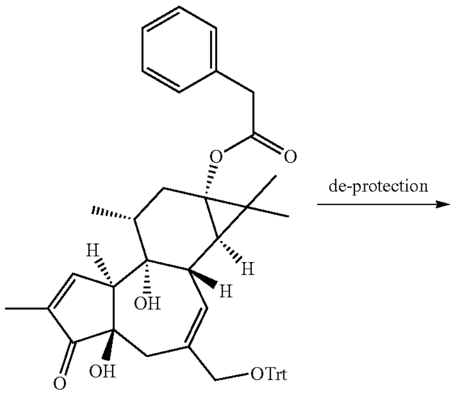

K101-C1304-A

-continued

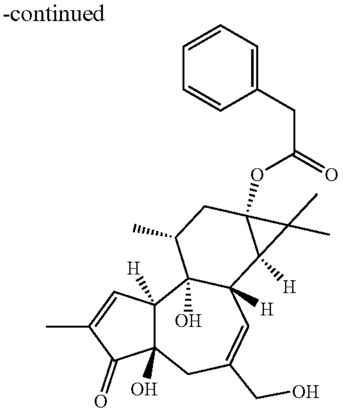

K101-C1304

Preparation of Compound K101-C1304-A. To a solution of K101-C20Tr-B (40.00 mg, 67.71 μmol, 1.00 eq) in DCM (2.00 mL) were added 2-phenylacetic acid (C13-04) (11.06 mg, 81.25 mol, 10.24 uL, 1.20 eq), DMAP (33.09 mg, 270.84 μmol, 4.00 eq) and EDC (25.96 mg, 135.42 μmol, 2.00 eq). The mixture was stirred at 20° C. for 12 hours to give a yellow solution. LC-MS and TLC (eluting with: PE/EtOAc=2/1) showed the reaction was complete. The reaction mixture was combined with a second preparation of the compound, quenched with $H_2O$ (5 mL) and extracted with DCM (15 mL×3). The organic layers were dried over $Na_2SO_4$ and concentrated to give the crude product. The product was purified by prep-TLC (eluting with: PE/EtOAc=2/1) to give K101-C1304-A (40.00 mg, 56.43 μmol, 65.78% yield) as a white solid.

Preparation of Compound K101-C1304. To a solution of K101-C1304-A (40.00 mg, 56.43 μmol, 1.00 eq) in MeOH (3.00 mL) was added $HClO_4$ (83.00 mg, 826.14 μmol, 50.00 uL, 14.64 eq) at 0° C. The mixture was stirred at 0° C. for 0.5 hr to give a yellow solution. LC-MS showed the reaction was complete. The mixture was purified by prep-HPLC (column: Waters XSELECT C18 150×30 mm×5 um; mobile phase: [A: water (0.1% TFA)-B: B: ACN]; B %: 33%-63%, 10 min) to give K101-C1304 (16.30 mg, 34.94 μmol, 61.91% yield) as a white solid.

LC-MS (m/z): 489.3 $[M+Na]^+$ $^1$H NMR (400 MHz, $CD_3OD$) δ 7.53 (s, 1H), 7.33-7.28 (m, 5H), 5.57 (s, 1H), 3.95-3.88 (m, 2H), 3.64 (s, 2H), 3.14-3.03 (m, 2H), 2.48-2.39 (m, 2H), 2.12-2.02 (m, 2H), 1.73 (s, 3H), 1.56-1.50 (m, 1H), 1.03-1.01 (m, 6H), 0.88-0.78 (m, 4H).

Example 7: Synthesis Scheme of K101-C1305

The scheme for synthesis of compound K101-C1305 is illustrated below.

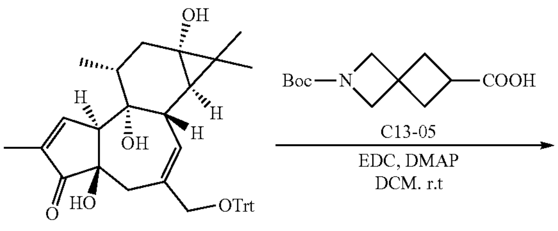

K101-C20Tr-B

-continued

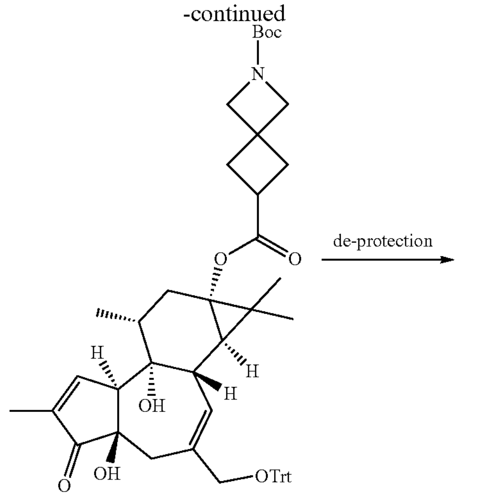

K101-C1305-A

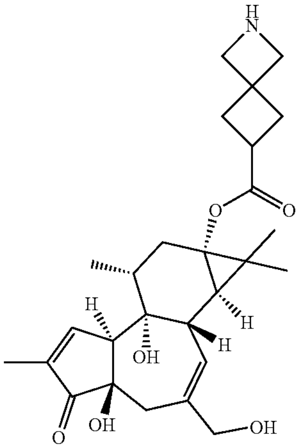

K101-C1305

Preparation of Compound K101-C1305-A. To a solution of K101-C20Tr-B (45.00 mg, 76.17 μmol, 1.00 eq) in DCM (2.00 mL) were added 2-tert-butoxycarbonyl-2-azaspiro [3.3] heptane-6-carboxylic acid (C13-05) (27.57 mg, 114.26 μmol, 1.50 eq), DMAP (37.22 mg, 304.68 μmol, 4.00 eq), N,N-diisopropylethylamine (DIEA) (19.69 mg, 152.34 μmol, 26.61 uL, 2.00 eq) and EDC (29.21 mg, 152.34 μmol, 2.00 eq). The mixture was stirred at 20° C. for 48 hours to give a yellow solution. LC-MS and TLC (eluting with: PE/EtOAc=2/1) showed the reaction was complete. The reaction mixture was combined with a second preparation of the compound, quenched with saturated $NaHCO_3$ (5 mL) and extracted with DCM (10 mL×3). The organic layers were dried over $Na_2SO_4$ and concentrated to give the crude product. The product was purified by prep-TLC (eluting with: PE/EtOAc=2/1) to give K101-C13050-A (70.00 mg, crude) as a white solid.

Preparation of Compound K101-C1305. To a solution of K101-C1305-A (70.00 mg, 85.99 μmol, 1.00 eq) in DCM (1.00 mL) was added TFA (154.00 mg, 1.35 mmol, 100.00 uL, 15.71 eq) at 0° C. The mixture was stirred at 0° C. for 2 hr give a red-brown solution. The mixture was stirred at 20° C. for 16 hours (hr). LC-MS showed that the desired product was no present. The reaction mixture was quenched with $H_2O$ (5 mL) and the organic layer was separated. LC-MS The organic layer was dissolved in MeOH (3.00 mL) followed by addition of $HClO_4$ (83.00 mg, 826.20

μmol, 50.00 uL, 9.61 eq) at 0° C. The mixture was stirred at 0° C. for 2 hr to give a yellow solution. LC-MS showed the reaction was complete complete. The mixture was purified by prep-HPLC (column: Phenomenex Gemini 150×25 mm×10 um; mobile phase: [A: water (0.1% TFA)-B: ACN]; B %: 10%-40%, 10 min) to give K101-C1305 (11.80 mg, 20.15 μmol, 23.43% yield, TFA) as a yellow solid.

LC-MS (m/z): 494.2 $[M+Na]^+$ $^1H$ NMR (400 MHz, $CD_3OD$) δ 7.56 (s, 1H), 5.63 (s, 1H), 4.11-4.09 (m, 4H), 4.00-3.96 (m, 2H), 3.19-3.07 (m, 3H), 2.60-2.46 (m, 6H), 2.16-2.12 (m, 2H), 1.77 (s, 3H), 1.76-1.53 (m, 1H), 1.17 (s, 3H), 1.09 (s, 3H), 0.93-0.89 (m, 4H).

Example 8: Synthesis Scheme of K101-C1306

The scheme for synthesis of compound K101-C1306 is illustrated below.

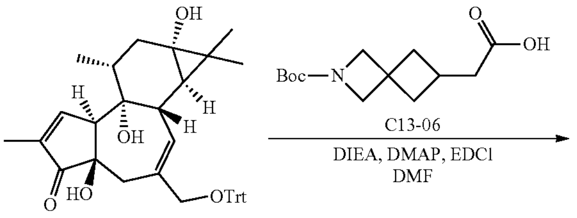

K101-C20Tr-B

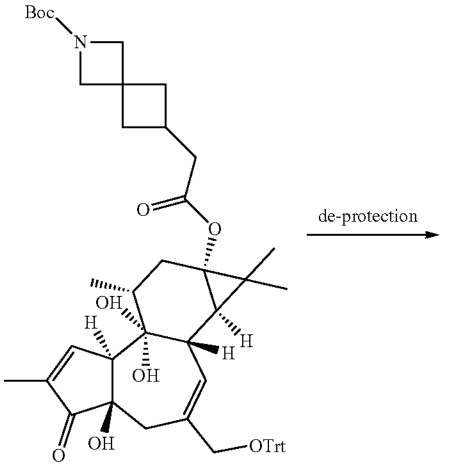

K101-C1306-A

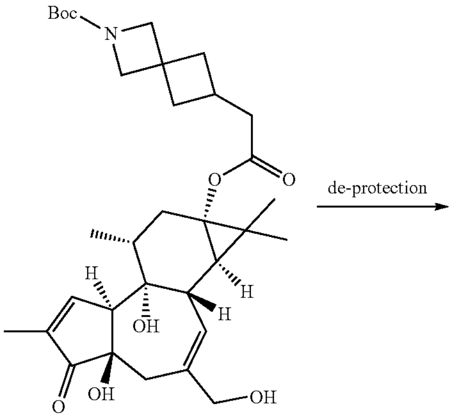

K101-C1312

-continued

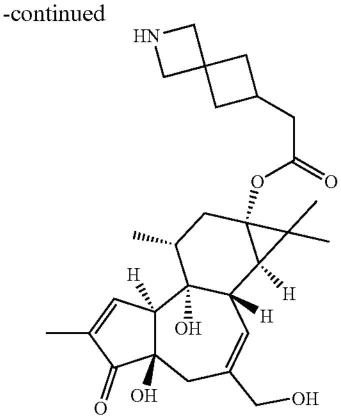

K101-C1306

Preparation of Compound K101-C1306-A. To a solution of K101-C20Tr-B (40.00 mg, 67.71 mol, 1.00 eq) in DCM (2.00 mL) were added 2-(2-tert-butoxycarbonyl-2-azaspiro [3.3]heptan-6-yl)acetic acid (25.93 mg, 101.56 μmol, 1.50 eq), DMAP (33.09 mg, 270.84 μmol, 4.00 eq), DIEA (26.25 mg, 203.13 mol, 35.47 uL, 3.00 eq) and EDC (25.96 mg, 135.42 mol, 2.00 eq). The mixture was stirred at 20° C. for 16 hr to give a yellow solution. LC-MS and TLC (eluting with: PE/EtOAc=2/1) showed the reaction was complete complete. The mixture was combined with a second preparation of the compound, quenched with Saturated $NaHCO_3$ (5 mL) and extracted with DCM (10 mLx3). The organic layers were dried over $Na_2SO_4$ and concentrated to give the crude product. The product was purified by prep-TLC (eluting with: PE/EtOAc=2/1) to give K101-C1306-A (40.00 mg, 47.90 μmol, 70.74% yield, 99.157% purity) as a white solid.

Preparation of compound K101-C1312. To a solution of K101-C1306-A (10.00 mg, 12.08 μmol, 1.00 eq) in MeOH (3.00 mL) was added $HClO_4$ (83.00 mg, 826.20 μmol, 50.00 uL, 68.39 eq) at 0° C., and the mixture stirred at 0° C. for 0.5 hr. The mixture was stirred at 20° C. for an additional 15.5 hr. LC-MS showed the reaction was complete complete. The mixture was purified by prep-HPLC (column: Waters Xbridge Prep OBD C18 150x30x5 um; mobile phase: [A: water (0.05% ammonia hydroxide v/v)-B: ACN]; B %: 45%-75%, 10 min) to give K101-C1306-A (3.80 mg, 6.49 μmol, 53.71% yield) as a white solid.

LC-MS (m/z): 608.2 $[M+Na]^+$ $^1H$ NMR (400 MHz, $CD_3OD$) δ 7.56 (s, 1H), 5.62 (s, 1H), 4.60-4.58 (m, 3H), 3.99-0.96 (m, 4H), 3.92-3.82 (m, 2H), 3.19-3.18 (m, 2H), 2.52-2.37 (m, 7H), 2.10-1.94 (m, 4H), 1.77 (s, 3H), 1.76-1.46 (m, 1H), 1.44 (s, 9H), 1.18 (s, 3H), 1.08 (s, 3H), 0.93-0.86 (m, 4H).

Preparation of compound K101-C1306. To a solution of K101-C1312 (15.00 mg, 25.61 mol, 1.00 eq) in THF (500.00 uL) was added TFA (288.72 mg, 2.53 mmol, 187.48 uL, 98.88 eq), and the mixture stirred at 20° C. for 4 hr to give a colorless solution. LC-MS showed the reaction was complete complete, but mass of P2 was found. The reaction mixture was concentrated by $N_2$, and the resultant product dissolved in MeOH (500.00 uL)/$H_2O$ (50.00 uL). The mixture was stirred at 20° C. for 14 hr to give a colorless solution. LC-MS showed the reaction was complete complete. The mixture was combined with a second preparation of the compound and concentrated by $N_2$ to give the desired product. The product was lyophilized to give K101-C1306 (4.20 mg, 7.00 μmol, 25.80% yield, TFA) as a yellow gum. The product (13.4 mg) was purified by prep- HPLC (column: Phenomenex Gemini 150x25 mmx10 um; mobile phase: [water (0.1% TFA)-ACN]; B %: 20%-50%, 10 min) to give K101-C1306 (4.20 mg, 7.00 μmol, 25.80% yield, TFA) as a white solid.

LC-MS (m/z): 508.2 $[M+Na]^+$ $^1H$ NMR (400 MHz, $CD_3OD$) δ 7.55 (s, 1H), 5.62-5.60 (m, 1H), 4.14 (s, 2H), 4.00 (s, 2H). 3.95 (s, 2H), 3.18 (s, 1H), 3.07 (s, 1H), 2.52-2.46 (m, 7H), 2.10-2.02 (m, 4H), 1.77 (s, 3H), 1.54-1.52 (m, 1H), 1.18 (s, 3H), 1.08 (s, 3H), 0.93-0.86 (m, 4H).

Example 9: Synthesis Scheme of K101-C1311

The scheme for synthesis of compound K101-C1311 is illustrated below.

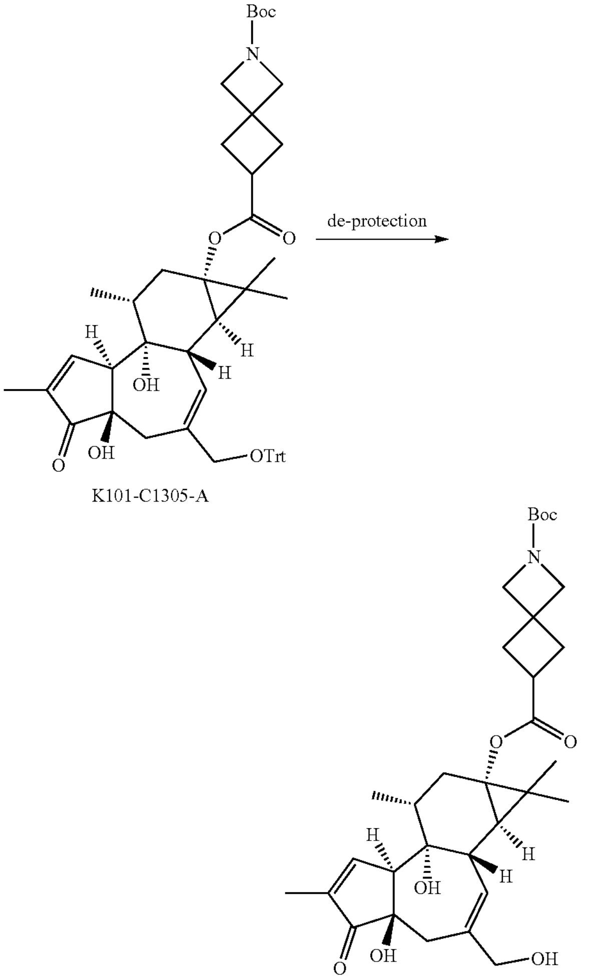

K101-C1305-A

K101-C1311

Preparation of Compound K101-C1311. To a solution of K101-C1305-A (22.00 mg, 27.03 μmol, 1.00 eq) in MeOH (3.00 mL) was added $HClO_4$ (26.09 mg, 259.73 μmol, 15.72 uL, 9.61 eq) at 0° C., and the mixture stirred at 0° C. for 1 hr. LC-MS showed the reaction was complete. The mixture was purified by prep-HPLC (column: Waters Xbridge 150x 25x5u; mobile phase: [A: water (0.05% ammonia hydroxide v/v)-B: ACN]; B %: 40%-70%, 10 min) to give K101-C1311 (3.30 mg, 5.77 μmol, 21.36% yield, 100% purity) as a yellow solid.

LC-MS (m/z): 594.3 $[M+Na]^+$ $^1H$ NMR (400 MHz, $CD_3OD$) δ 7.57 (s, 1H), 5.63 (s, 1H), 3.99-0.89 (m, 5H), 3.18-3.05 (m, 3H), 2.56-2.42 (m, 5H), 2.15-2.04 (m, 2H), 1.76 (m, 3H), 1.44 (s, 9H), 1.36-1.31 (m, 3H), 1.17 (s, 3H), 1.09 (s, 3H), 0.93-0.88 (m, 4H).

Example 10: Synthesis Scheme of K101-C1312

The scheme for synthesis of compound K101-C1312 is illustrated below.

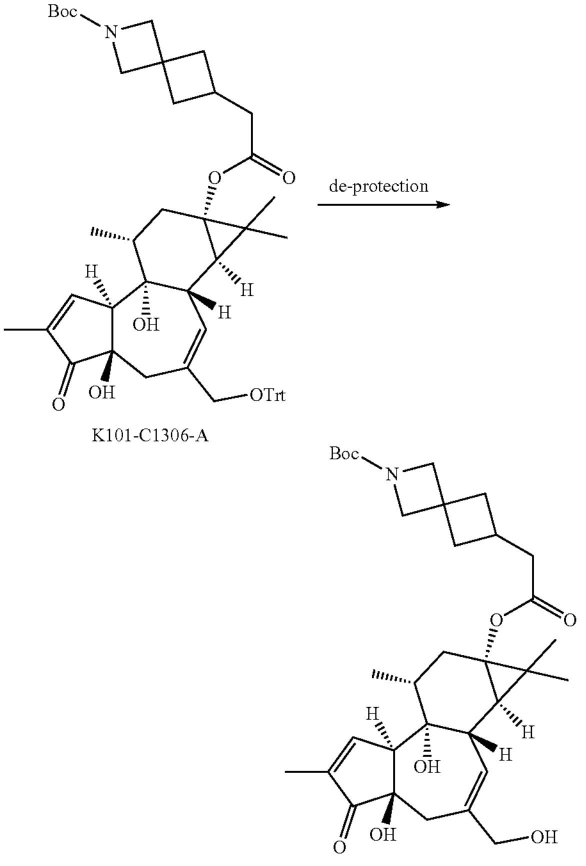

K101-C1306-A

K101-C1312

Preparation of compound K101-C1312. To a solution of K101-C1306-A (10.00 mg, 12.08 μmol, 1.00 eq) in MeOH (3.00 mL) was added $HClO_4$ (83.00 mg, 826.20 μmol, 50.00 uL, 68.39 eq) at 0° C., and the mixture stirred at 0° C. for 0.5 hr. The mixture was stirred at 20° C. for an additional 15.5 hr to give a yellow solution. LC-MS showed the reaction was complete. The mixture was purified by prep-HPLC (column: Waters Xbridge Prep OBD C18 150×30×5u; mobile phase: [A: water (0.05% ammonia hydroxide v/v)-B: ACN]; B %: 45%-75%, 10 min) to give K101-C1306-A (3.80 mg, 6.49 μmol, 53.71% yield) as a white solid.

LC-MS (m/z): 608.2 $[M+Na]^+$ $^1H$ NMR (400 MHz, $CD_3OD$) δ 7.56 (s, 1H), 5.62 (s, 1H), 4.60-4.58 (m, 3H), 3.99-0.96 (m, 4H), 3.92-3.82 (m, 2H), 3.19-3.18 (m, 2H), 2.52-2.37 (m, 7H), 2.10-1.94 (m, 4H), 1.77 (s, 3H), 1.76-1.46 (m, 1H), 1.44 (s, 9H), 1.18 (s, 3H), 1.08 (s, 3H), 0.93-0.86 (m, 4H).

Example 11: Synthesis Scheme of K101-C1313

The scheme for synthesis of compound K101-C1313 is illustrated below.

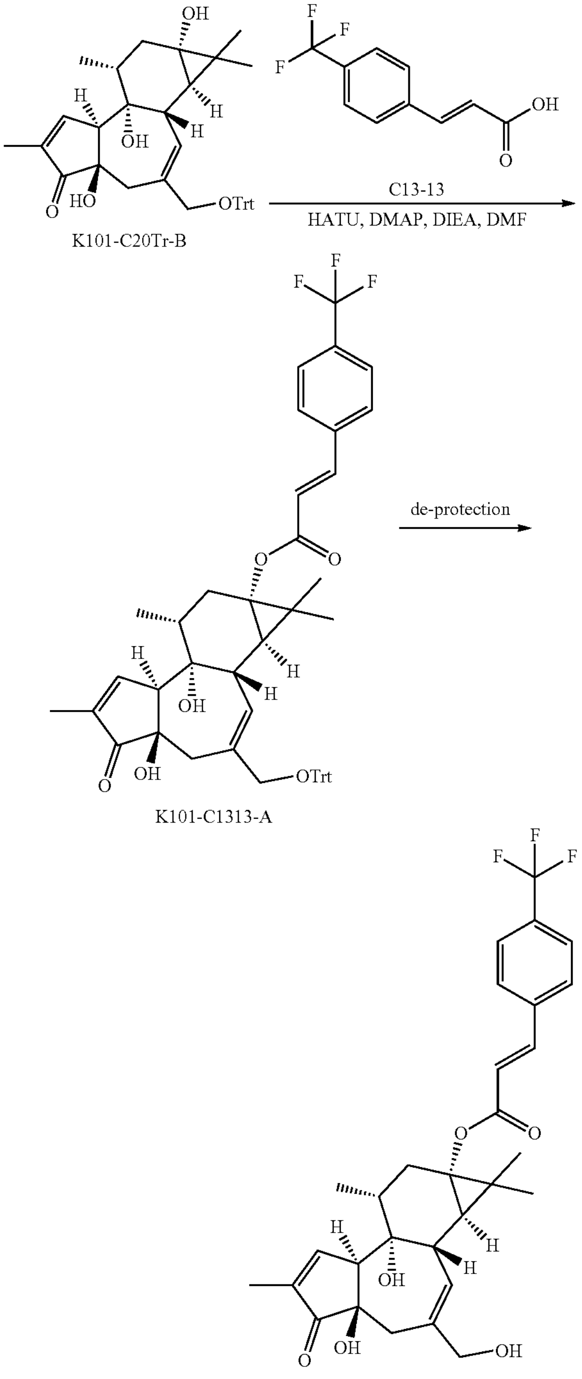

K101-C20Tr-B

K101-C1313-A

K101-C1313

Preparation of Compound K101-C1313-A. To a solution of K101-C20Tr-B (30.00 mg, 50.78 μmol, 1.00 eq) in DMF (2.00 mL) were added (E)-3-[4-(trifluoromethyl)phenyl] prop-2-enoic acid (C13-13) (21.95 mg, 101.56 μmol, 2.00 eq), DIEA (19.69 mg, 152.34 μmol, 26.61 uL, 3.00 eq), DMAP (24.82 mg, 203.12 μmol, 4.00 eq) and Hexafluorophosphate Azabenzotriazole Tetramethyl Uronium (HATU)

(38.62 mg, 101.56 μmol, 2.00 eq). The mixture was stirred at 20° C. for 14 hr to give a yellow solution. LC-MS and TLC (eluting with: PE/EtOAc=2/1) showed the reaction was complete. The mixture was quenched with saturated $NaHCO_3$ (5 mL) and extracted with methyl-tert-butyl ether (MTBE) (15 mL×3). The organic layers were washed with ($H_2O$), dried over $Na_2SO_4$ and then concentrated to give the crude product. The product was purified by prep-TLC (eluting with: PE/EtOAc=2/1) to give K101-C1313-A (21.00 mg, 26.62 μmol, 45.19% yield) as a white solid.

Preparation of compound K101-C1313. To a solution of K101-C1313-A (21.00 mg, 26.62 μmol, 1.00 eq) in MeOH (3.00 mL) was added $HClO_4$ (83.00 mg, 826.28 μmol, 50.00 uL, 31.04 eq) at 0° C. The mixture was stirred at 0° C. for 1 hr to give a yellow solution. LC-MS showed the reaction was complete. The mixture was purified by prep-HPLC (column: Phenomenex Gemini 150×25 mm×10 um; mobile phase: [A: water (0.1% TFA)-B: ACN]; B %: 55%-85%, 10 min) to give K101-C1313 (4.40 mg, 6.10 μmol, 22.90% yield, 91.518% purity, TFA) as a yellow solid.

LC-MS (m/z): 569.1 $[M+Na]^+$ $^1H$ NMR (400 MHz, $CD_3OD$) δ 7.74-7.68 (m, 3H), 7.63-7.58 (m, 2H), 7.48-7.16 (m, 1H), 6.60-6.56 (m, 1H), 5.60-5.50 (m, 1H), 3.89-3.82 (m, 2H), 3.12-3.08 (m, 1H), 3.07-2.90 (m, 1H), 2.42-2.33 (m, 2H), 2.13-2.11 (m, 1H), 2.07-1.99 (m, 1H), 1.66 (s, 3H), 1.58-1.51 (m, 1H), 1.14 (s, 3H), 1.02 (s, 3H), 0.88-0.83 (m, 4H).

Example 12: Synthesis Scheme of K101-C1315

The scheme for synthesis of compound K101-C1315 is illustrated below.

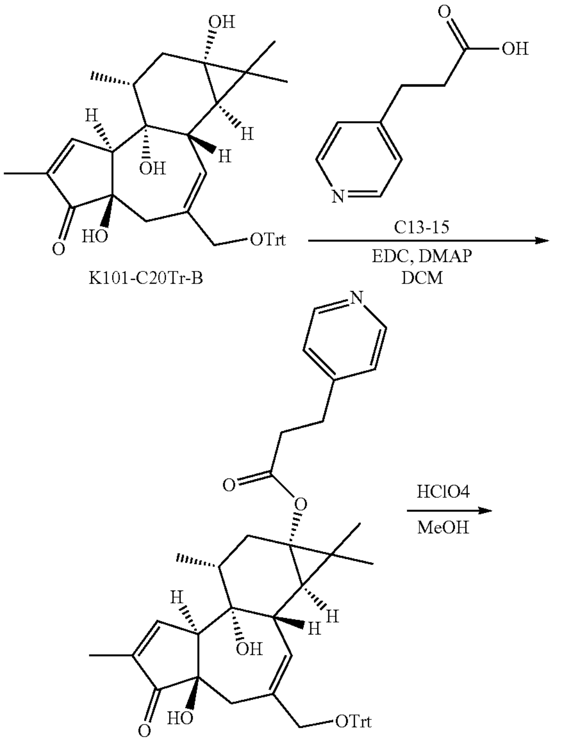

K101-C20Tr-B

K101-C1315-A

-continued

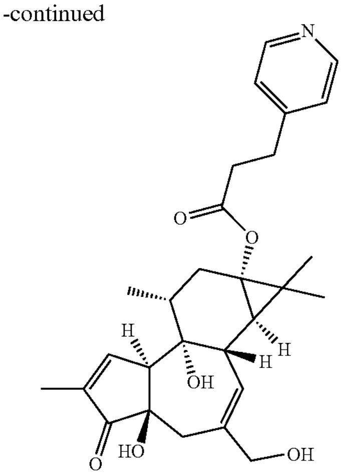

K101-C1315

Preparation of Compound K101-C1315-A. To a solution of K101-C20Tr-B (20.00 mg, 33.86 μmol, 1.00 eq) and C13-15 (15.35 mg, 101.58 μmol, 3.00 eq) in DCM (1.00 mL) was added EDC (19.47 mg, 101.58 μmol, 3.00 eq) and DMAP (20.68 mg, 169.30 μmol, 5.00 eq). The reaction solution was stirred at 25° C. for 3 hours to give a brown solution. LC-MS showed the reaction was complete. The reaction solution was diluted with DCM (5 mL), washed with brine (2 mL), dried over anhydrous $Na_2SO_4$, filtered, and the concentrated under reduced pressure to give K101-C1315-A (28.70 mg, crude) as a brown gum, which was used directly in the next step without further purification.

Preparation of compound K101-C1315. To a solution of K101-C1315-A (25.00 mg, crude) in MeOH (1.00 mL) was added $HClO_4$ (30.00 uL) at 25° C. The reaction solution was stirred at 25° C. for 0.5 hour to give a brown solution. LC-MS showed the reaction was complete. The reaction solution was quenched by adding $K_2CO_3$ (34 mg) in water (1 mL) dropwise at 0° C. to adjust the pH to 9. The mixture was filtered and the filtrate purified by prep-HPLC (column: Phenomenex Gemini 150×25 mm×10 um; mobile phase: [A: water (0.1% TFA)-B: ACN]; B %: 15%-45%, 10 min) to give K101-C1315 (3.60 mg, 97% purity, TFA salt) as a white solid after lyophilization.

LC-MS (m/z): 504.2 $[M+Na]^+$ $^1H$ NMR (400 MHz, $CD_3OD$) δ=8.72 (d, J=6.5 Hz, 2H), 7.95 (d, J=6.5 Hz, 2H), 7.53 (s, 1H), 5.61-5.55 (m, 1H), 3.99-3.89 (m, 2H), 3.24 (t, J=7.3 Hz, 2H), 3.17-3.11 (m, 1H), 3.06-3.01 (s, 1H), 2.90 (t, J=7.2 Hz, 2H), 2.57-2.47 (m, 1H), 2.45-2.37 (m, 1H), 2.15-1.95 (m, 2H), 1.77-1.72 (m, 3H), 1.48 (dd, J=10.5, 14.3 Hz, 1H), 1.10 (s, 3H), 1.05 (s, 3H), 0.92-0.83 (m, 4H).

Example 13: Synthesis Scheme of K101-C1316

The scheme for synthesis of compound K101-C1316 is illustrated below.

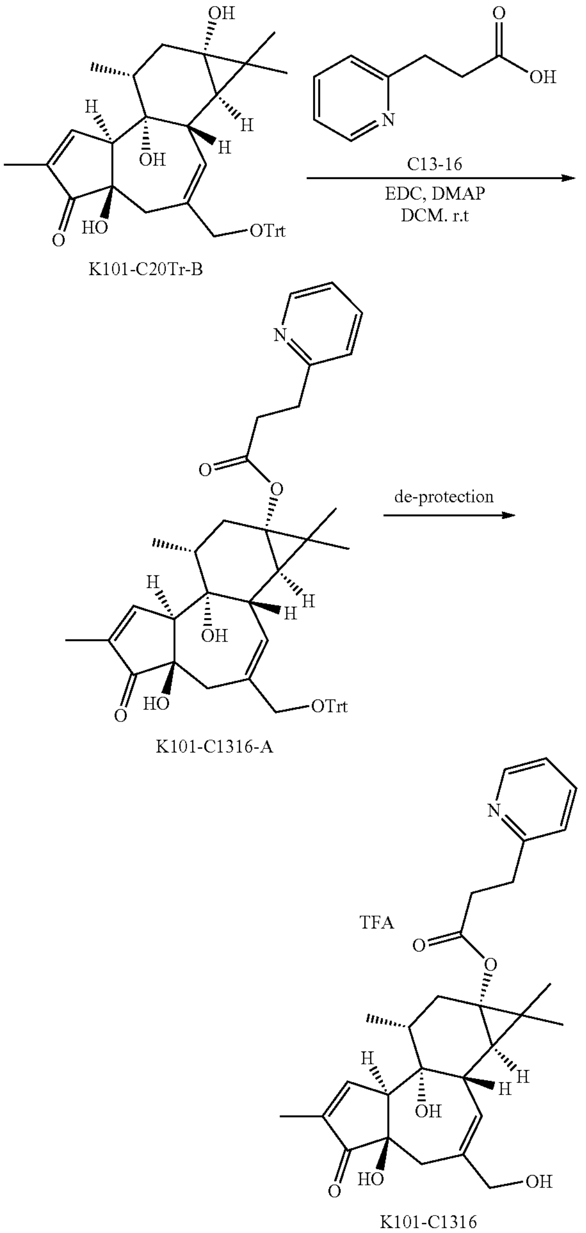

K101-C20Tr-B
K101-C1316-A
K101-C1316

Preparation of Compound K101-C1316-A. To a solution of K101-C20Tr-B (40.00 mg, 67.71 μmol, 1.00 eq) in DCM (2.00 mL) were added C13-16 (51.18 mg, 338.55 μmol, 5.00 eq), DMAP (33.09 mg, 270.84 μmol, 4.00 eq), hydroxybenzotriazole (HOBt) (18.30 mg, 135.42 mol, 2.00 eq) and EDC (25.96 mg, 135.42 μmol, 2.00 eq). The mixture was stirred at 20° C. for 12 h to give a black solution. LC-MS showed 43.779% of the desired mass, with 16.864% of reactant remaining. The mixture was quenched with saturated $NaHCO_3$ (10 mL) and extracted with DCM (15 mL×3). The organic layers were dried over $Na_2SO_4$ and concentrated to give the crude product. The product was purified by prep-TLC (eluting with: PE/EtOAc=2/1) to give K101-C1316-A (27.00 mg, 37.30 μmol, 48.97% yield) as a white solid.

Preparation of Compound K101-C1316. To a solution of K101-C1316-A (27.00 mg, 37.30 μmol, 1.00 eq) in MeOH (2.00 mL) was added $HClO_4$ (83.00 mg, 826.20 μmol, 50.00 uL, 22.15 eq) at 0° C. The mixture was stirred at 0° C. for 0.5 hr to give a yellow solution. LC-MS showed the reaction was complete. The mixture was purified by prep-HPLC (column: Phenomenex Gemini 150×25 mm×10 um; mobile phase: [A: water (0.1% TFA)-B: ACN]; B %: 20%-50%, 10 min) to give K101-C1316 (11.40 mg, 18.81 μmol, 50.43% yield, 98.3% purity, TFA salt) as a white solid.

LC-MS (m/z): 504.2 $[M+Na]^+$ $^1H$ NMR (400 MHz, $CD_3OD$) δ 8.72-8.71 (d, J=5.2 Hz, 1H), 8.45-8.41 (t, J=8.0 Hz, 1H), 7.95-7.93 (d, J=8.0 Hz, 1H), 7.86-7.83 (t, J=6.8 Hz, 1H), 7.55 (s, 1H), 5.60-5.59 (m, 1H), 3.99-3.95 (m, 2H), 3.31-3.29 (m, 2H), 3.16 (s, 1H), 3.05 (s, 1H), 3.00-2.96 (m, 2H), 2.51-2.40 (m, 2H), 2.15-2.03 (m, 2H), 1.76-1.75 (m, 3H), 1.51-1.47 (m, 3H), 1.10 (s, 3H), 1.06 (s, 3H), 0.90-0.86 (m, 4H).

Example 14: Synthesis Scheme of K101-C1317

The scheme for synthesis of compound K101-C1317 is illustrated below.

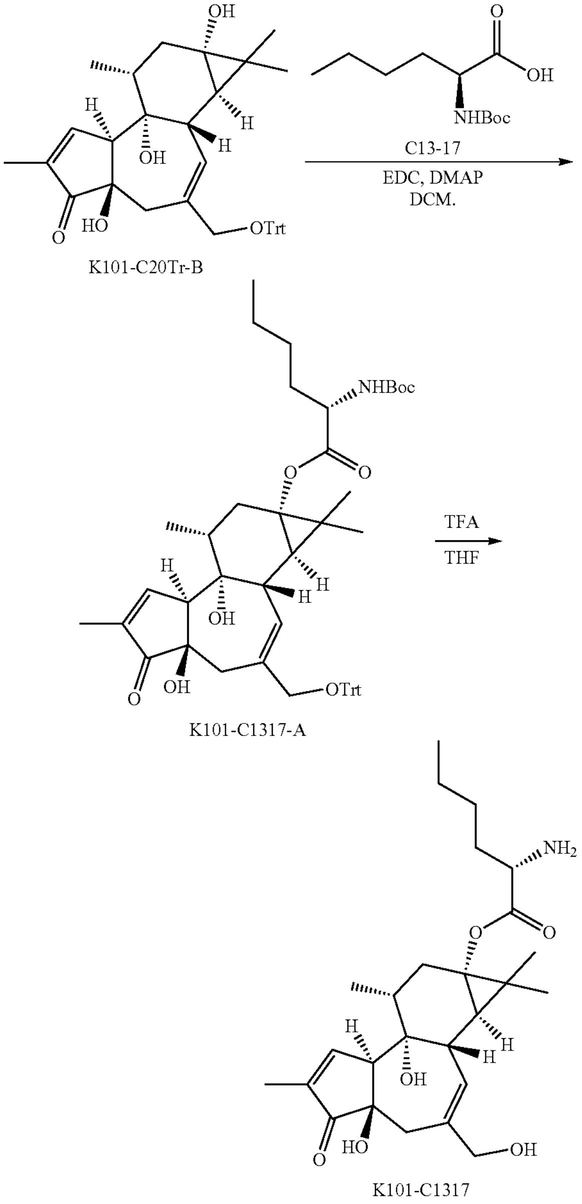

K101-C20Tr-B
K101-C1317-A
K101-C1317

Preparation of Compound K101-C1317-A. To a solution of K101-C20Tr-B (30.00 mg, 50.78 μmol, 1.00 eq) in DCM (1.00 mL) were added (2S)-2-(tert-butoxycarbonylamino) hexanoic acid (C13-17) (23.49 mg, 101.57 μmol, 2.00 eq), DMAP (24.82 mg, 203.13 μmol, 4.00 eq) and EDC (19.47 mg, 101.57 μmol, 2.00 eq). The mixture was stirred at 20° C. for 5 h to give a colorless solution. LC-MS and TLC showed the reaction was complete. The mixture was quenched with $H_2O$ (15 mL) and extracted with DCM (15 mL×5). The organic layers were dried over $Na_2SO_4$ and concentrated to give a yellow solid. The product was purified by prep-TLC (eluting with Petroleum ether: Ethyl acetate=5/1) to give K101-C1317-A (35.00 mg, 43.53 μmol, 85.73% yield) as a white solid.

Preparation of Compound K101-C1317. To a solution of K101-C1317-A (46.00 mg, 57.21 mol, 1.00 eq) in THF (2.00 mL) were added TFA (6.52 mg, 57.21 μmol, 4.23 uL, 1.00 eq) and $Et_3SiH$ (6.65 mg, 57.21 μmol, 9.11 uL, 1.00 eq). The mixture was stirred at 20° C. for 2 h to give a colorless solution, which was concentrated to give yellow oil. TFA (1 mL) was added to the yellow oil in DCM (2 mL), and the mixture stirred at 20° C. for 0.5 h. LC-MS showed the reaction was complete. The reaction mixture was concentrated, dissolved with MeOH (20 mL), and stirred at 20° C. for 14 h to give a yellow liquid. The product was concentrated to give a yellow solid, which was then purified by prep-HPLC (column: Phenomenex Gemini 150×25 mm×10 um; mobile phase: [A: water (0.1% TFA)-B: ACN]; B %: 30%-60%, 8 min). The separated layers were lyophilized to give K101-C1317 (7.00 mg, 12.16 μmol, 21.26% yield, 100% purity, TFA) as a white solid.

LC-MS (m/z): 584.2 $[M+Na]^+$ $^1H$ NMR (400 MHz, MeOD) δ 7.57 (s, 1H), 5.64 (d, J=4.5 Hz, 1H), 4.04 (t, J=6.4 Hz, 1H), 4.00-3.94 (m, 2H), 3.20-3.15 (m, 1H), 3.10-3.05 (m, 1H), 2.59-2.39 (m, 2H), 2.27 (dd, J=7.0, 14.8 Hz, 1H), 2.13-1.93 (m, 2H), 1.90-1.80 (m, 1H), 1.80-1.70 (d, J=1.5 Hz, 3H), 1.60-1.50 (dd, J=10.4, 14.9 Hz, 1H), 1.53-1.37 (m, 4H), 1.20 (s, 3H), 1.11 (s, 3H), 1.05-0.91 (m, 7H).

Example 15: Synthesis Scheme of K101-C1318

The scheme for synthesis of compound K101-C1318 is illustrated below.

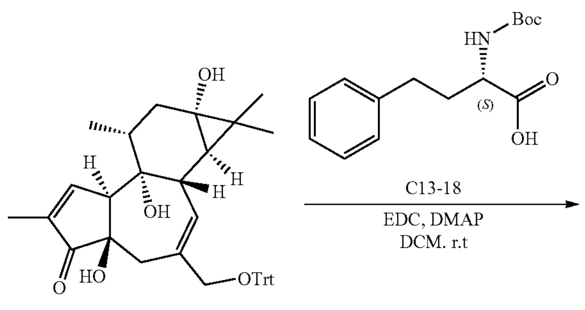

K101-C20Tr-B

-continued

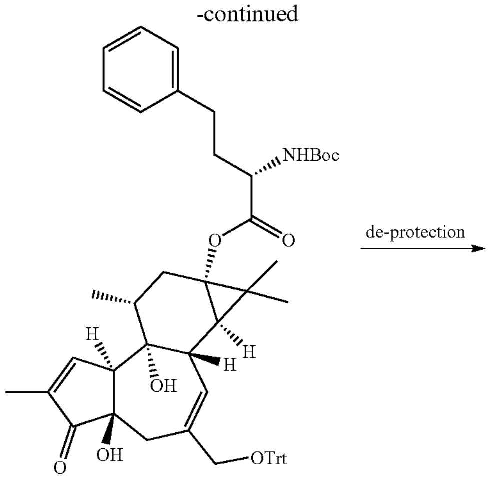

K101-C1318-A

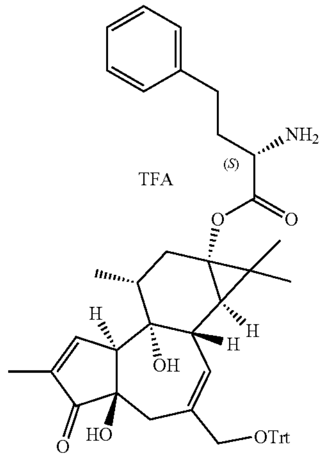

K101-C1318

Preparation of Compound K101-C1318-A. To a solution of K101-C20Tr-B (30.00 mg, 50.78 μmol, 1.00 eq) in DCM (2.00 mL) were added (2S)-2-(tert-butoxycarbonylamino)-4-phenyl-butanoic acid (C13-18) (28.37 mg, 101.56 μmol, 2.00 eq), DMAP (24.82 mg, 203.12 μmol, 4.00 eq) and EDC (19.47 mg, 101.56 μmol, 2.00 eq). The mixture was stirred at 20° C. for 12 hr to give a yellow solution. LC-MS and TLC (eluting with: PE/EtOAc=2/1) showed the reaction was complete.

The reaction mixture combined a second preparation of the compound, the mixture quenched with $H_2O$ (10 mL) and then extracted with DCM (15 mL×3). The organic layers were dried over $Na_2SO_4$ and concentrated to give the crude product. The product was purified by prep-TLC (eluting with: PE/EtOAc=2/1) to give K101-C1318-A (32.00 mg, 37.56 μmol, 63.38% yield) as a white solid.

Preparation of Compound K101-C1318. To a solution of K101-C1318-A (30.00 mg, 35.21 mol, 1.00 eq) in THF (2.00 mL) were added TFA (308.00 mg, 2.70 mmol, 200.00 uL, 76.72 eq) and $Et_3SiH$ (4.91 mg, 42.25 μmol, 6.73 uL, 1.20 eq). The mixture was stirred at 20° C. for 4 hr to give a yellow solution. LC-MS showed the reaction was complete. The reaction mixture was concentrated by $N_2$, and the resultant residue dissolved in MeOH (20 mL). The mixture was stirred at 20° C. for 12 hr. LC-MS showed the reaction was complete. The mixture was concentrated to give the crude product. The product was purified by prep-HPLC (column: Phenomenex Gemini 150×25 mm×10 um; mobile phase: [A: water (0.1% TFA)-B: ACN]; B %: 23%-53%, 10 min) to give K101-C1318 (10.80 mg, 17.24 μmol, 48.98% yield, 99.58% purity, TFA) as a white solid.

LC-MS (m/z): 532.1 $[M+Na]^+$ $^1H$ NMR (400 MHz, $CD_3OD$) δ 7.58 (s, 1H), 7.36-7.33 (m, 2H), 7.27-7.23 (m, 3H), 5.65 (s, 1H), 4.07-4.03 (m, 1H), 3.97 (s, 2H), 3.18 (s, 1H), 3.08 (m, 1H), 2.83-2.81 (m, 2H), 2.53-2.41 (m, 2H), 2.10-2.09 (m, 2H), 1.77 (s, 3H), 1.64-1.61 (m, 1H), 1.21 (s, 3H), 1.12 (s, 3H), 1.05-1.04 (m, 1H), 0.97-0.95 (m, 3H).

Example 16: Synthesis Scheme of K101-C1319

The scheme for synthesis of compound K101-C1319 is illustrated below.

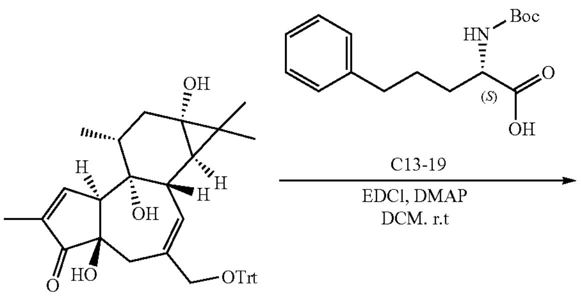

K101-C20Tr-B

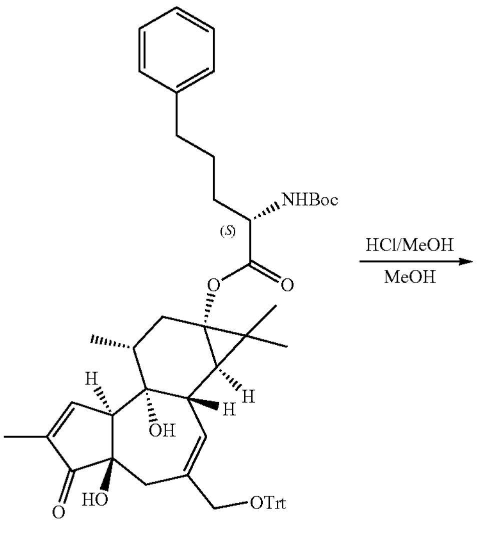

K101-C1319-A

-continued

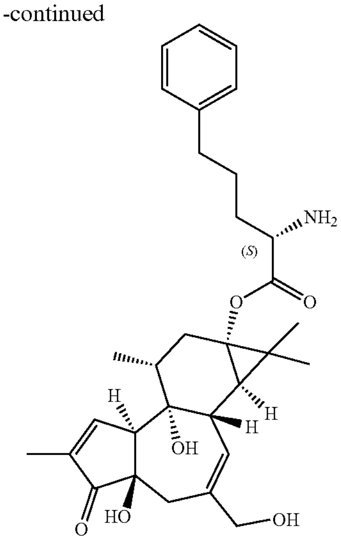

K101-C1319

Preparation of compound K101-C1319-A. To a solution of K101-C20Tr-B (200.00 mg, 338.55 μmol, 1.00 eq) and C13-19 (119.18 mg, 406.26 μmol, 1.20 eq) in anhydrous DCM (2.00 mL) were added EDC (194.70 mg, 1.02 mmol, 3.00 eq) and DMAP (124.08 mg, 1.02 mmol, 3.00 eq). The reaction solution was stirred at 20° C. for 16 hours to give a light brown solution. LC-MS showed the reaction was complete. The reaction solution was concentrated under reduced pressure to give the crude product, and the product purified by silica gel column chromatography (PE/EtOAc=3/1) to give K101-C1319-A (273.50 mg, 315.79 μmol, 93.28% yield) as a colorless gum.

Preparation of compound K101-C1319. To a solution of K101-C1319-A (273.00 mg, 315.21 μmol, 1.00 eq) in MeOH (5.00 mL) was added HCl/MeOH (4 M, 5.00 mL, 63.45 eq) at 0° C. The reaction solution was stirred at 0° C. for 3.5 h to give a clear solution. LC-MS showed the reaction was not complete, and thus the reaction solution was stirred at 20° C. for 1.5 h. LC-MS showed the reaction was complete. The reaction solution was bubbled with $N_2$ for 0.5 hour to remove HCl, and the residual solution cooled to 0° C. and the solution adjusted to pH 7 with saturated aqueous $NaHCO_3$. The mixture was extracted with DCM (10 mL×2), and the combined extract dried over $Na_2SO_4$ and concentrated under reduced pressure to give the crude product as a brown gum. The product was purified by prep-TLC (DCM/MeOH=10/1, $SiO_2$) to give K101-$C_{1319}$ (78.70 mg, 140.52 μmol, 44.58% yield, 93.5% purity) as a colorless gum. The product was lyophilized to give a white solid.

MS (m/z): 546.2 $[M+Na]^+$ $^1H$ NMR (400 MHz, $CD_3OD$) δ 7.55 (s, 1H), 7.29-7.23 (m, 2H), 7.21-7.13 (m, 3H), 5.60 (d, J=5.0 Hz, 1H), 4.00-3.88 (m, 2H), 3.47 (t, J=5.8 Hz, 1H), 3.19-3.14 (m, 1H), 3.10-3.03 (m, 1H), 2.65 (t, J=7.0 Hz, 2H), 2.57-2.48 (m, 1H), 2.48-2.38 (m, 1H), 2.17-1.99 (m, 2H), 1.80-1.62 (m, 7H), 1.51 (dd, J=10.5, 14.3 Hz, 1H), 1.15 (s, 3H), 1.07 (s, 3H), 0.90 (d, J=6.3 Hz, 4H).

Example 17: Synthesis Scheme of K101-C1320

The scheme for synthesis of compound K101-C1320 is illustrated below.

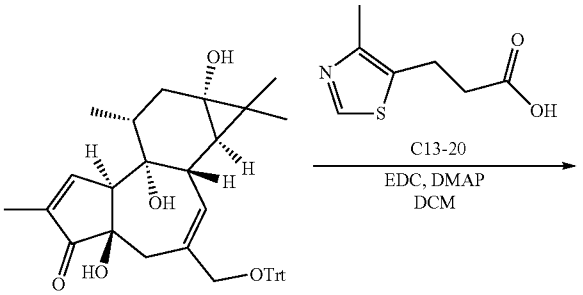

K101-C20Tr-B

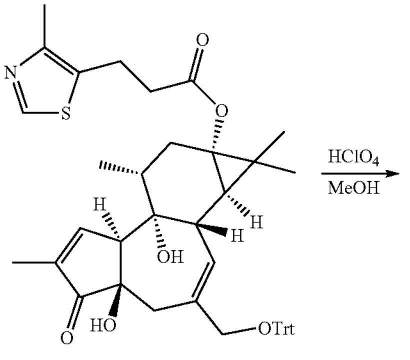

K101-C1320-A

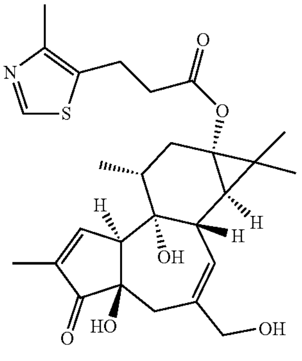

K101-C1320

Preparation of Compound K101-C1320-A. To a solution of K101-C20Tr-B (30.00 mg, 50.78 μmol, 1.00 eq) and C13-20 (26.09 mg, 152.34 μmol, 3.00 eq) in DCM (2.00 mL) were added EDC (58.41 mg, 304.68 μmol, 6.00 eq) and DMAP (37.22 mg, 304.68 μmol, 6.00 eq). The reaction solution was stirred at 25° C. for 16 hours to give a brown solution. TLC (PE/EtOAc=2/1, $SiO_2$) showed the reaction was complete. The reaction solutions were combined 5 mg of K101-C20Tr-B, diluted with DCM (5 mL), and washed with brine (2 mL). The extracted layers were dried over anhydrous $Na_2SO_4$, filtered, and then concentrated under reduced pressure to give the crude product as a brown gum. The product was purified by prep-TLC (PE/EtOAc=2/1) to give K101-C1320-A (27.30 mg, 72.26% yield) as a colorless gum.

Preparation of Compound K101-C1320. To a solution of K101-C1320-A (25.00 mg, 33.60 μmol, 1.00 eq) in MeOH (1.00 mL) was added $HClO_4$ (30.00 uL). The reaction solution was stirred at 25° C. for 0.5 hour to give a clear solution. LC-MS showed the reaction was complete. The product was purified by prep-HPLC (column: Phenomenex Gemini 150×25 mm×10 um; mobile phase: [A: water (0.1% TFA)-B: ACN]; B %: 25%-55%, 10 min) to give K101-C1320 (9.50 mg, 18.46 μmol, 54.95% yield, 97.5% purity) as a white powder after lyophilization.

LC-MS (m/z): 524.1 $[M+Na]^+$ $^1H$ NMR (400 MHz, METHANOL-$d_4$) δ=9.04 (s, 1H), 7.56-7.51 (m, 1H), 5.58 (d, J=4.3 Hz, 1H), 3.99-3.89 (m, 2H), 3.19-3.13 (m, 3H), 3.04 (t, J=5.4 Hz, 1H), 2.72 (dt, J=1.6, 7.0 Hz, 2H), 2.56-2.47 (m, 1H), 2.46-2.39 (m, 4H), 2.13-1.98 (m, 2H), 1.74 (dd, J=1.3, 3.0 Hz, 3H), 1.47 (dd, J=10.4, 14.2 Hz, 1H), 1.06 (d, J=10.5 Hz, 6H), 0.88 (d, J=6.3 Hz, 3H), 0.82 (d, J=5.8 Hz, 1H).

Example 18: Synthesis Scheme of K101-C1321

The scheme for synthesis of compound K101-C1321 is illustrated below.

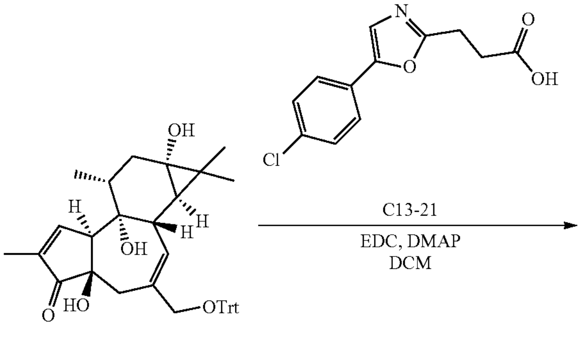

K101-C20Tr-B

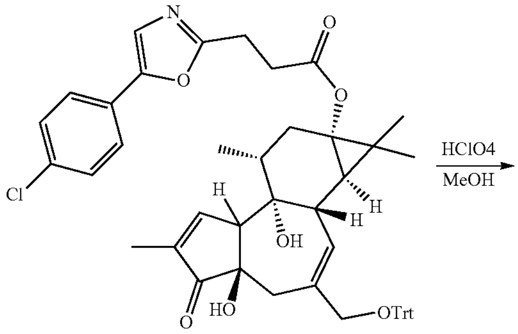

K101-C1321-A

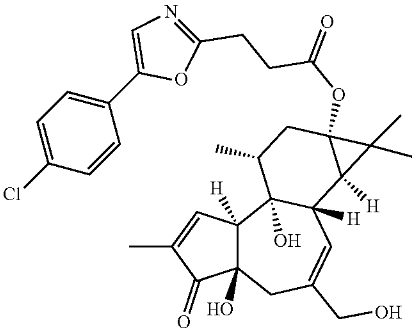

K101-C1321

Preparation of Compound K101-C1321-A. To a solution of K101-C20Tr-B (30.00 mg, 50.78 μmol, 1.00 eq) and C13-21 (76.68 mg, 304.68 μmol, 6.00 eq) in DCM (1.00 mL) were added EDC (58.41 mg, 304.68 μmol, 6.00 eq) and DMAP (37.22 mg, 304.68 μmol, 6.00 eq). The reaction solution was stirred at 25° C. for 2 hours to give a light brown solution. LC-MS shows improved conversion to product. The reaction solution was combined with a second preparation of the compound, and the mixture partitioned between water (2 mL) and DCM (2 mL). The organic layer was dried over anhydrous $Na_2SO_4$, filtered, and then concentrated under reduced pressure to give the crude product as a brown gum. The product was purified by prep-TLC (PE/EtOAc=3/2) to give K101-C1321-A (32.70 mg, 39.67 μmol, 78.11% yield) as a colorless gum.

Preparation of Compound K101-C1321. To a solution of K101-C1321-A (32.70 mg, 39.67 μmol, 1.00 eq) in MeOH (1.00 mL) was added $HClO_4$ (30.00 uL) at 25° C. The reaction solution was stirred at 25° C. for 0.5 hour to give a brown solution. LC-MS showed the reaction was complete. The reaction solution was purified by prep-HPLC (column: Phenomenex Gemini 150×25 mm×10 um; mobile phase: [A: water (0.1% TFA)-B: ACN]; B %: 50%-80%, 10 min) to give K101-C1321 (12.50 mg, 52.08% yield, 96.2% purity) as a white solid after lyophilization.

LC-MS (m/z): 604.1 $[M+Na]^+$ $^1H$ NMR (400 MHz, $CD_3OD$) δ 7.69-7.65 (m, 2H), 7.54-7.50 (m, 1H), 7.48-7.41 (m, 3H), 5.56-5.52 (m, 1H), 3.95-3.87 (m, 2H), 3.20-3.12 (m, 3H), 3.06-3.01 (m, 1H), 2.94-2.89 (m, 2H), 2.55-2.47 (m, 1H), 2.45-2.38 (m, 1H), 2.13-1.98 (m, 2H), 1.73 (dd, J=1.3, 3.0 Hz, 3H), 1.60-1.52 (m, 1H), 1.12 (s, 3H), 1.04 (s, 3H), 0.89-0.83 (m, 4H).

Example 19: Synthesis Scheme of K101-C1322

The scheme for synthesis of compound K101-C1322 is illustrated below.

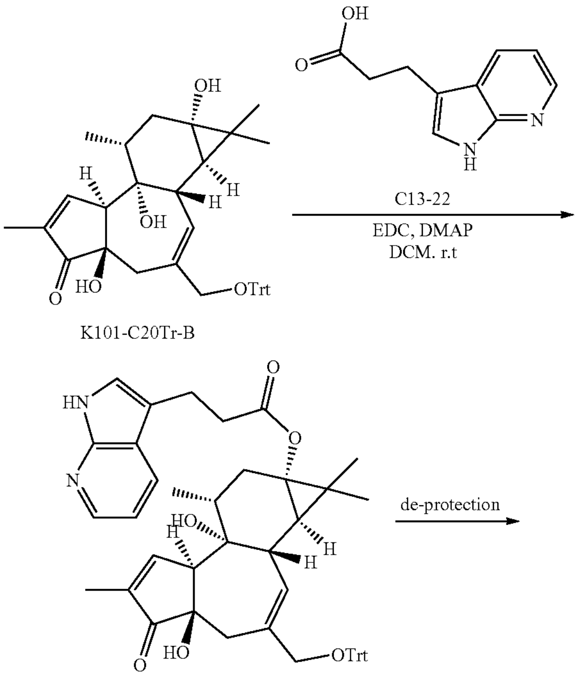

-continued

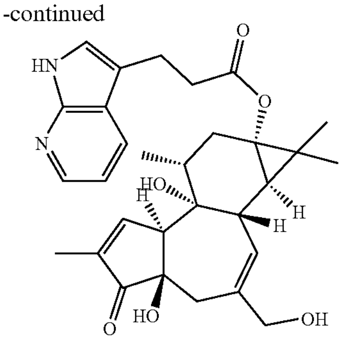

K101-C1322

Preparation of Compound K101-C1322-A. To a solution of K101-C20Tr-B (30.00 mg, 50.78 μmol, 1.00 eq) in DCM (2.00 mL) were added 3-(1H-pyrrolo [2,3-b] pyridin-3-yl) propanoic acid (C13-22) (19.32 mg, 101.56 μmol, 2.00 eq), DMAP (24.82 mg, 203.12 μmol, 4.00 eq), HOBt (13.72 mg, 101.56 μmol, 2.00 eq) and EDC (19.47 mg, 101.56 μmol, 2.00 eq). The mixture was stirred at 20° C. for 12 h to give a yellow solution. LC-MS and TLC (eluting with: PE/EtOAc=1/1) showed the reaction was complete. The mixture was quenched with $H_2O$ (5 mL) and extracted with DCM (15 mL×3). The organic layers were dried over $Na_2SO_4$ and concentrated to give the crude product. The product was purified by prep-TLC (eluting with: PE/EtOAc=1/1) to give K101-C1322-A (30.00 mg, 39.32 μmol, 58.22% yield) as a white solid.

Preparation of Compound K101-C1322. To a solution of K101-C1322-A (30.00 mg, 39.32 μmol, 1.00 eq) in MeOH (2.00 mL) was added $HClO_4$ (83.00 mg, 826.11 μmol, 50.00 uL, 21.01 eq) at 0° C. The mixture was stirred at 0° C. for 0.5 h to give a yellow solution. LC-MS showed the reaction was complete. The product was purified by prep-HPLC (column: Phenomenex Gemini 150×25 mm×10 um; mobile phase: [A: water (0.1% TFA)-B: ACN]; B %: 22%-52%, 10 min) to give K101-C1322 (17.40 mg, 27.42 μmol, 69.73% yield, TFA salt) as a yellow solid.

LC-MS (m/z): 543.1 $[M+Na]^+$ $^1H$ NMR (400 MHz, $CD_3OD$) δ 8.19-8.18 (m, 1H), 8.06-8.04 (m, 1H), 7.55 (s, 1H), 7.24 (s, 1H), 7.15-7.12 (m, 1H), 5.55-5.54 (m, 1H), 3.99-3.95 (m, 2H), 3.16-3.10 (m, 3H), 3.01 (s, 1H), 2.78-2.73 (m, 2H), 2.50-2.46 (m, 2H), 2.01-2.96 (m, 2H), 1.42-1.41 (m, 1H), 1.00 (s, 3H), 0.91 (s, 3H), 0.86-0.85 (m, 1H), 0.63-0.62 (m, 3H).

Example 20: Synthesis Scheme of K101-C1323

The scheme for synthesis of compound K101-C1323 is illustrated below.

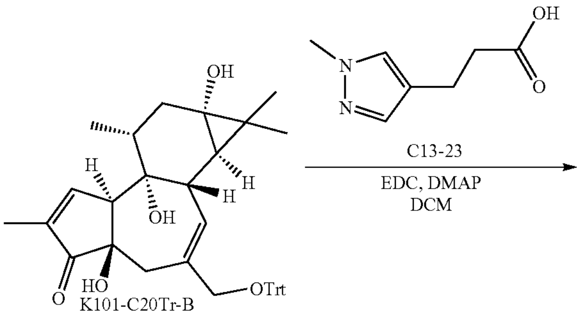

-continued

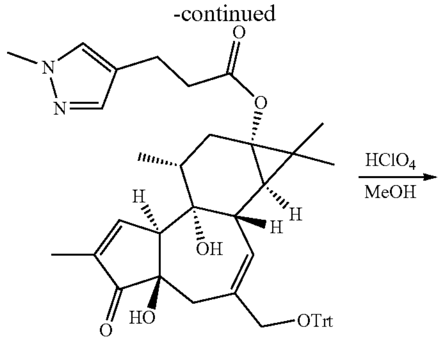

K101-C1323-A

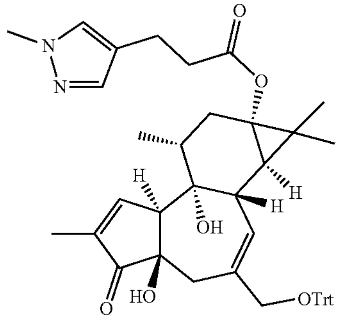

K101-C1323

Preparation of compound K101-C1323-A. To a solution of K101-C20Tr-B (30.00 mg, 50.78 mol, 1.00 eq) and C13-23 (23.49 mg, 152.34 μmol, 3.00 eq) in DCM (1.00 mL) were added EDC (58.41 mg, 304.68 μmol, 6.00 eq) and DMAP (37.22 mg, 304.68 μmol, 6.00 eq). The reaction solution was stirred at 25° C. for 2 h to give a brown solution. TLC (PE/EtOAc=1/1, $SiO_2$) showed the reaction was complete. The reaction solution was combined with a second preparation of the compound, diluted with DCM (2 mL), washed with water (1 mL), brine (1 mL), and dried over anhydrous $Na_2SO_4$. The mixture was filtered and then concentrated under reduced pressure to give the crude product as a brown gum. The product was purified by prep-TLC (PE/EtOAc=1/1) to give 32.5 mg of K101-C1323-A as a colorless gum.

Preparation of Compound K101-C1323. To a solution of K101-C1323-A (32.00 mg, 44.02 μmol, 1.00 eq) in MeOH (1.00 mL) was added $HClO_4$ (30.00 uL) at 25° C. The reaction solution was stirred at 25° C. for 0.5 hour to give a clear solution. LC-MS showed the reaction was complete. The reaction solution was directly purified by prep-HPLC (column: Phenomenex Gemini 150×25 mm×10 um; mobile phase: [A: water (0.1% TFA)-B: ACN]; B %: 25%-55%, 10 min) to give K101-C1323 (9.10 mg, 40.48% yield, 94.9% purity) as a white solid.

LC-MS (m/z): 507.2 $[M+Na]^+$ $^1H$ NMR (400 MHz, $CD_3OD$) δ 7.56-7.53 (m, 1H), 7.46 (s, 1H), 7.36 (s, 1H), 5.61-5.57 (m, 1H), 3.98-3.90 (m, 2H), 3.84 (s, 3H), 3.18-3.14 (m, 1H), 3.07-3.01 (m, 1H), 2.81-2.76 (m, 2H), 2.63-2.57 (m, 2H), 2.55-2.47 (m, 1H), 2.46-2.39 (m, 1H), 2.12-1.98 (m, 2H), 1.74 (dd, J=1.3, 2.8 Hz, 3H), 1.47 (dd, J=10.4, 14.2 Hz, 1H), 1.08 (s, 3H), 1.05 (s, 3H), 0.89 (d, J=6.3 Hz, 3H), 0.79 (d, J=5.8 Hz, 1H).

Example 21: Synthesis Scheme of K101-C1324

The scheme for synthesis of compound K101-C1324 is illustrated below.

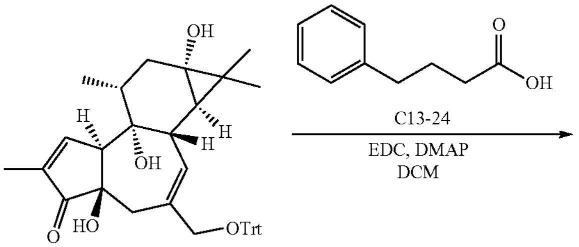

K101-C20Tr-B

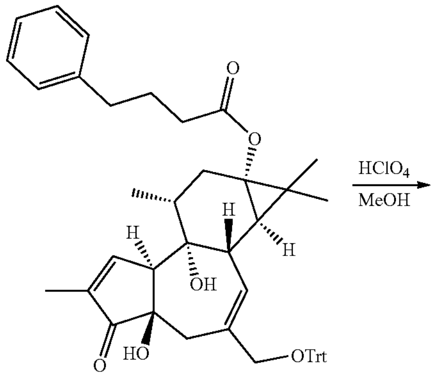

K101-C1324-A

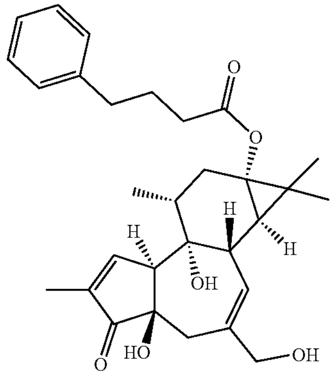

K101-C1324

Preparation of Compound K101-C1324-A. To a solution of K101-C20Tr-B (30.00 mg, 50.78 μmol, 1.00 eq) and C13-24 (25.01 mg, 152.34 μmol, 3.00 eq) in DCM (1.00 mL) were added EDC (58.41 mg, 304.68 μmol, 6.00 eq) and DMAP (37.22 mg, 304.68 μmol, 6.00 eq). The reaction solution was stirred at 25° C. for 2 h to give a brown solution. TLC (PE/EtOAc=2/1, $SiO_2$) showed the reaction was complete. The reaction solution was diluted with DCM (2 mL), washed with water (1 mL), brine (1 mL), and dried over anhydrous $Na_2SO_4$. The mixture was filtered and then concentrated under reduced pressure to give the crude product as a brown gum. The product was purified by silica gel column chromatography (eluting with PE/EtOAc=5/1) to give K101-C1324-A (37.20 mg, 99.41% yield) as a colorless gum.

Preparation of Compound K101-C1324. To a solution of K101-C1324-A (37.20 mg, 50.48 μmol, 1.00 eq) in MeOH (1.00 mL) was added $HClO_4$ (30.00 uL), and the reaction solution stirred at 25° C. for 1 hour to give a clear solution. LC-MS showed the reaction was complete. The product was purified by prep-HPLC (column: Phenomenex Gemini 150×25 mm×10 um; mobile phase: [A: water (0.1% TFA)-B:

ACN]; B %: 55%-85%, 10 min) to give K101-C1324 (7.80 mg, 30.40% yield, 97.3% purity) as a white solid after lyophilization.

LC-MS (m/z): 517.2 $[M+Na]^+$ $^1H$ NMR (400 MHz, $CD_3OD$) δ 7.55 (s, 1H), 7.30-7.24 (m, 2H), 7.21-7.14 (m, 3H), 5.63-5.58 (m, 1H), 4.00-3.89 (m, 2H), 3.19-3.15 (m, 1H), 3.09-3.03 (m, 1H), 2.65 (t, J=7.7 Hz, 2H), 2.57-2.48 (m, 1H), 2.47-2.39 (m, 1H), 2.34 (t, J=7.3 Hz, 2H), 2.15-2.07 (m, 1H), 2.07-1.98 (m, 1H), 1.97-1.88 (m, 2H), 1.74 (dd, J=1.3, 2.8 Hz, 3H), 1.53 (dd, J=10.5, 14.3 Hz, 1H), 1.16 (s, 3H), 1.07 (s, 3H), 0.91 (d, J=6.3 Hz, 3H), 0.85 (d, J=5.5 Hz, 1H).

Example 22: Synthesis Scheme of K101-C1325

The scheme for synthesis of compound K101-C1325 is illustrated below.

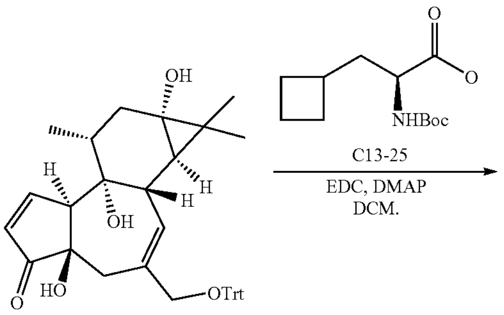

K101-C20Tr-B

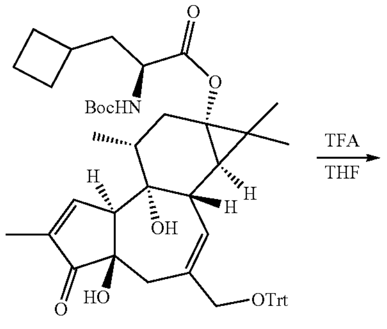

K101-C1325-A

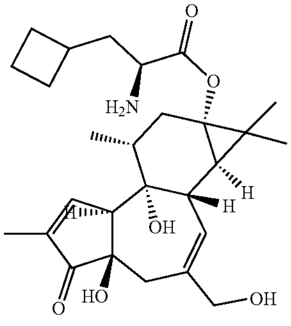

K101-C1325

Preparation of Compound K101-C1325-A. To a solution of K101-C20Tr-B (30.00 mg, 50.78 μmol, 1.00 eq) in DCM (5.00 mL) were added (2S)-2-(tert-butoxycarbonylamino)-3-cyclobutyl-propanoic acid (C13-25) (24.71 mg, 101.56 μmol, 2.00 eq), DMAP (24.82 mg, 203.12 mol, 4.00 eq), HOBT (13.72 mg, 101.56 μmol, 2.00 eq) and EDC (19.47 mg, 101.56 μmol, 2.00 eq). The mixture was stirred at 20° C. for 14 h to give a yellow solution. LC-MS and TLC showed the reaction was complete. The reaction mixture was quenched with $H_2O$ (15 mL) and extracted with DCM (15 mL×5). The organic layers were dried over $Na_2SO_4$ and concentrated to give a yellow solid. The product was purified by prep-TLC (eluting with Petroleum ether: Ethyl acetate=7/2) to give K101-C1325-A (33.50 mg, 41.05 μmol, 69.09% yield) as a white solid.

Preparation of Compound K101-C1325. To a solution of K101-C1325-A (33.50 mg, 41.05 mol, 1.00 eq) in DMF (20.00 mL) in THF (2.00 mL) were added TFA (1.54 g, 13.51 mmol, 1.00 mL, 329.02 eq) and $Et_3SiH$ (4.77 mg, 41.05 μmol, 6.53 uL, 1.00 eq). The mixture was stirred at 20° C. for 5 h to give a colorless solution, which was concentrated to give a yellow oil. The oil was dissolved with DCM (2 mL) followed by addition of TFA (0.5 mL). The mixture was stirred at 20° C. for 1 h to give a yellow solution. LC-MS showed the reaction was complete. The reaction mixture was concentrated to give a yellow oil, which was then purified by prep-HPLC (column: Phenomenex Gemini 150×25 mm×10 um; mobile phase: [A: water (0.1% TFA)-B: ACN]; B %: 20%-50%, 10 min). The separated products were lyophilized to give K101-C1325 (10.00 mg, 17.02 μmol, 41.46% yield, 94.5% purity, TFA) as a white solid.

LC-MS (m/z): 596.2 $[M+Na]^+$ $^1H$ NMR (400 MHz, MeOH) δ=7.54 (s, 1H), 5.60 (d, J=4.0 Hz, 1H), 3.99-3.83 (m, 3H), 3.14 (s, 1H), 3.07-2.98 (m, 1H), 2.57-2.33 (m, 3H), 2.26-1.84 (m, 8H), 1.79-1.65 (s, 5H), 1.58 (dd, J=10.4, 14.8 Hz, 1H), 1.17 (s, 3H), 1.07 (s, 3H), 0.99-0.95 (m, 1H), 0.97 (d, J=6.0 Hz, 1H), 0.92 (d, J=6.6 Hz, 3H)

Example 23: Synthesis Scheme of K101-C1326

The scheme for synthesis of compound K101-C1326 is illustrated below.

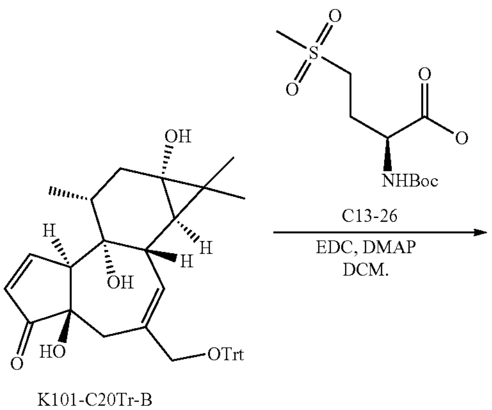

K101-C20Tr-B

-continued

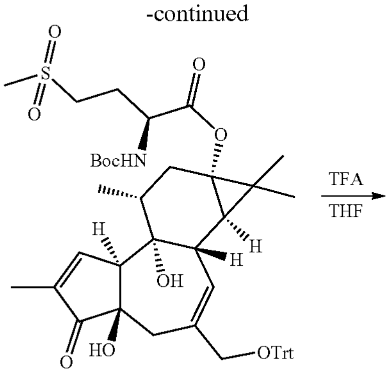

K101-C1326-A

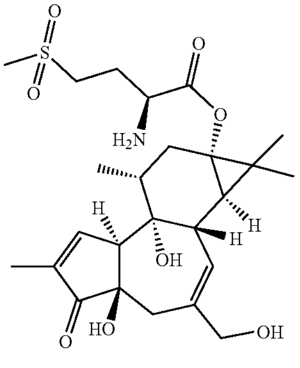

K101-C1326

Preparation of Compound K101-C1326-A. To a solution of K101-C20Tr-B (30.00 mg, 50.78 μmol, 1.00 eq) in DCM (5.00 mL) were added (2S)-2-(tert-butoxycarbonylamino)-4-methylsulfonyl-butanoic acid (C13-26) (30.00 mg, 106.64 μmol, 2.10 eq), DMAP (30.00 mg, 245.78 mol, 4.84 eq), EDC (19.96 mg, 104.10 μmol, 2.05 eq), and HOBt (14.00 mg, 103.59 μmol, 2.04 eq). The mixture was stirred at 20° C. for 19 h to give a colorless solution. LC-MS and TLC showed the reaction was complete. The reaction mixture was quenched with $H_2O$ (15 mL) and extracted with DCM (15 mL×5). The organic layers were dried over $Na_2SO_4$ and concentrated to give a yellow oil. The product was purified by prep-TLC (eluting with Petroleum ether: Ethyl acetate=3/2) to give K101-C1326-A (23.00 mg, 26.93 mol, 53.03% yield, crude product) as a colorless solid.

Preparation of compound K101-C1326. To a solution of K101-C1326-A (25.00 mg, 29.27 mol, 1.00 eq) in THF (2.00 mL) were added TFA (3.34 mg, 29.27 mol, 2.17 uL, 1.00 eq) and $Et_3SiH$ (3.40 mg, 29.27 mol, 4.66 uL, 1.00 eq). The mixture was stirred at 20° C. for 3 h to give a colorless solution. LC-MS showed some of the K101-C1326-A remained. Accordingly, the reaction mixture was concentrated to give a yellow oil, which was then dissolved with DCM (2 mL) followed by the addition of TFA (2 mL). The mixture was stirred at 20° C. for 2 h to give a colorless solution. LC-MS showed the reaction was complete. The reaction mixture was concentrated to give a yellow oil, which was then purified by prep-HPLC (column: Phenomenex Gemini 150×25 mm×10 um; mobile phase: [A: water (0.1% TFA)-B: ACN]; B %: 10%-40%, 10 min). The separated layers were lyophilized to give K101-C1326 (4.20 mg, 6.04 μmol, 20.64% yield, 90% purity, TFA) as a yellow solid.

LC-MS (m/z): 534.1 $[M+Na]^+$ $^1H$ NMR (400 MHz, MeOD) δ=7.58 (s, 1H), 5.66 (s, 1H), 4.62 (s, 1H), 4.16 (s, 1H), 3.97 (s, 2H), 3.23-3.11 (m, 1H), 3.06 (s, 4H), 2.61-2.35 (m, 3H), 2.27 (dd, J=7.2, 14.7 Hz, 2H), 2.06 (s, 1H), 1.77 (d, J=1.5 Hz, 3H), 1.62 (dd, J=10.8, 14.8 Hz, 1H), 1.40-1.28 (m, 2H), 1.21 (s, 3H), 1.12 (s, 3H), 1.05 (d, J=6.0 Hz, 1H), 0.96 (d, J=6.5 Hz, 3H).

Example 24: Synthesis Scheme of K101-C1327

The scheme for synthesis of compound K101-C1327 is illustrated below.

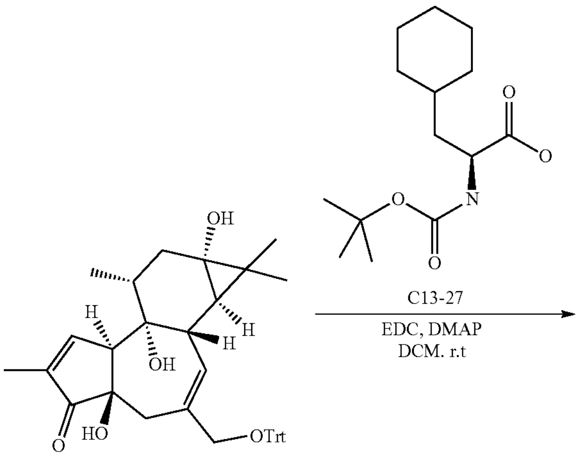

K101-C20Tr-B

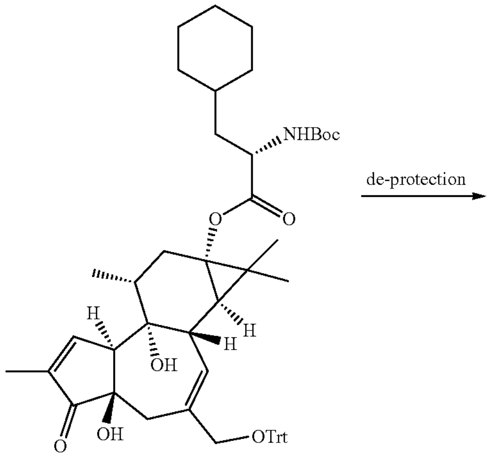

K101-C1327-A

-continued

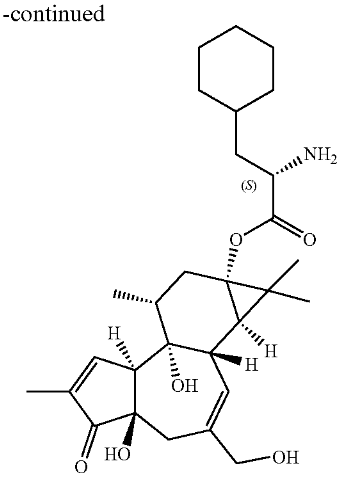

K101-C1327

Preparation of Compound K101-C1327-A. To a solution of K101-C20Tr-B (200.00 mg, 338.55 μmol, 1.00 eq) in DCM (2.00 mL) were added C13-27 (367.46 mg, 1.35 mmol, 4.00 eq), DMAP (330.89 mg, 2.71 mmol, 8.00 eq), HOBt (91.49 mg, 677.11 μmol, 2.00 eq) and EDC (259.60 mg, 1.35 mmol, 4.00 eq). The mixture was stirred at 20° C. for 12 h to give a yellow solution. LC-MS and TLC (eluting with: PE/EtOAc=2/1) showed the reaction was complete. The mixture was quenched with $H_2O$ (15 mL) and extracted with DCM (30 mL×3). The organic layers were dried over $Na_2SO_4$ and concentrated to give the crude product. The product was purified by prep-TLC (eluting with: PE/EtOAc=2/1) to give K101-C1327-A (180.00 mg, 213.25 μmol, 62.99% yield) as a white solid.

Preparation of Compound K101-C1327. To a solution of K101-C1327-A (180.00 mg, 213.25 μmol, 1.00 eq) in THF (3.00 mL) were added TFA (3.08 g, 27.01 mmol, 2.00 mL, 126.67 eq) and $Et_3SiH$ (49.59 mg, 426.50 μmol, 67.93 uL, 2.00 eq). The mixture was stirred at 20° C. for 24 h to give a yellow solution. LC-MS showed the reaction was complete. The reaction mixture was concentrated by $N_2$, and the resultant residue dissolved in MeOH (20 mL) and then stirred at 20° C. for 70 h. LC-MS showed the reaction was complete. The mixture was concentrated to give the crude product. The crude product was triturated with PE (30 mL×3) to give the desired product. The product was dissolved in saturated $NaHCO_3$ (20 mL) and extracted with DCM (30 mL×3). The organic layers were dried over $Na_2SO_4$ and concentrated to give the free desired product, which was then lyophilized to give K101-C1327 (70.00 mg, 136.05 μmol, 63.80% yield, 97.5% purity) as a white solid.

LC-MS (m/z): 524.2 $[M+Na]^+$ $^1H$ NMR (400 MHz, $CD_3OD$) δ 7.57 (s, 1H), 5.64-5.63 (m, 1H), 4.00-3.93 (m, 2H), 3.53-3.49 (m, 1H), 3.19 (s, 1H), 3.09 (s, 1H), 2.57-2.47 (m, 2H), 2.19-2.17 (m, 2H), 1.80-1.77 (m, 8H), 1.73-1.60 (m, 2H), 1.48-1.47 (m, 2H), 1.29-1.26 (m, 3H), 1.21 (s, 3H), 1.10 (s, 3H), 1.02-1.01 (m, 2H), 0.95-0.92 (m, 3H).

Second Procedure for Preparation of Compound K101-C1327-A. To a solution of K101-C20Tr-B (30.00 mg, 50.78 μmol, 1.00 eq) in DCM (2.00 mL) were added (2S)-2-(tert-butoxycarbonylamino)-3-cyclohexyl-propanoic acid (C13-27) (27.56 mg, 101.56 μmol, 2.00 eq), DMAP (24.82 mg, 203.12 μmol, 4.00 eq) and EDC (19.47 mg, 101.56 μmol, 2.00 eq). The mixture was stirred at 20° C. for 12 hr to give a yellow solution. LC-MS and TLC (eluting with: PE/EtOAc=2/1) showed the reaction was complete. The mixture was quenched with $H_2O$ (10 mL) and extracted with DCM (15 mL×3). The organic layers were dried over $Na_2SO_4$ and concentrated to give the crude product. The product was purified by prep-TLC (eluting with: PE/EtOAc=2/1) to give K101-C1327-A (24.00 mg, 28.43 μmol, 47.97% yield) as a white solid.

Second Procedure for Preparation of Compound K101-C1327. To a solution of K101-C1327-A (24.00 mg, 28.43 μmol, 1.00 eq) in THF (2.00 mL) were added TFA (308.00 mg, 2.70 mmol, 200.00 uL, 95.02 eq) and $Et_3SiH$ (3.97 mg, 34.12 μmol, 5.43 uL, 1.20 eq). The mixture was stirred at 20° C. for 4 hr to give a yellow solution. LC-MS showed the reaction was complete. The reaction mixture was concentrated by $N_2$, and the resultant residue dissolved in MeOH (20 mL). The mixture was stirred at 20° C. for 12 hr. LC-MS showed the reaction was complete. The mixture was concentrated to give the crude product. The product was purified by prep-HPLC (column: Phenomenex Gemini 150×25 mm×10 um; mobile phase: [A: water (0.1% TFA)-B: ACN]; B %: 25%-55%, 10 min) to give K101-C1327 (5.10 mg, 7.95 μmol, 27.97% yield, 95.99% purity, TFA) as a white solid.

LC-MS (m/z): 524.2 $[M+Na]^+$ $^1H$ NMR (400 MHz, $CD_3OD$) δ 7.57 (s, 1H), 5.64 (s, 1H), 4.10-4.07 (m, 1H), 4.00-3.93 (s, 2H), 3.18 (s, 1H), 3.08 (s, 1H), 2.53-2.45 (m, 1H), 2.45-2.41 (m, 1H), 2.29-2.27 (m, 1H), 2.05 (m, 1H), 1.84-1.29 (m, 16H), 1.19 (s, 3H), 1.11 (s, 3H), 1.02-1.01 (m, 2H), 0.96-0.94 (m, 3H).

Example 25: Synthesis Scheme of K101-C1328

The scheme for synthesis of compound K101-C1328 is illustrated below.

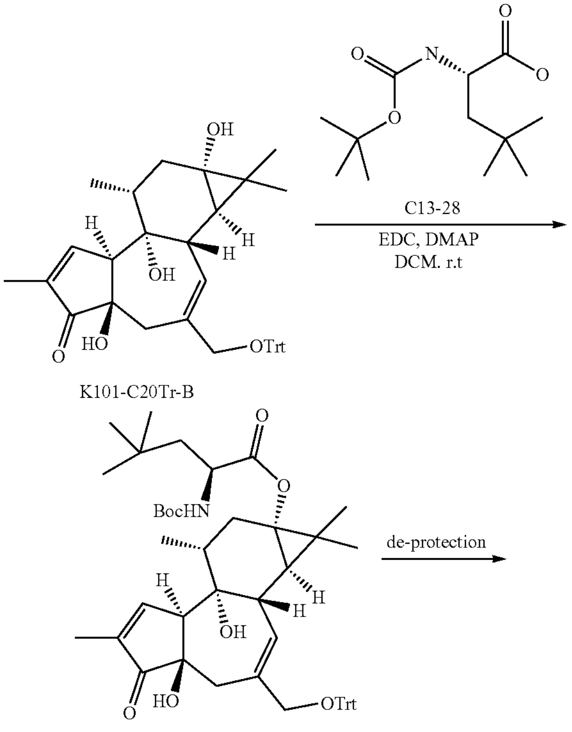

K101-C20Tr-B

K101-C1328-A

-continued

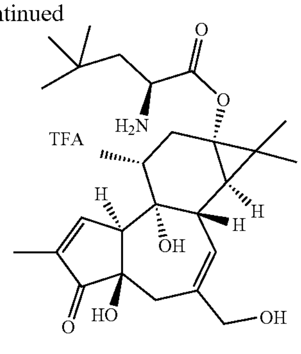

K101-C1328

Preparation of Compound K101-C1328-A. To a solution of K101-C20Tr-B (30.00 mg, 50.78 μmol, 1.00 eq) in DCM (2.00 mL) were added (2S)-2-(tert-butoxycarbonylamino)-4,4-dimethyl-pentanoic acid (C13-28) (24.92 mg, 101.56 μmol, 2.00 eq), DMAP (24.82 mg, 203.12 μmol, 4.00 eq), HOBt (13.72 mg, 101.56 μmol, 2.00 eq) and EDC (19.47 mg, 101.56 μmol, 2.00 eq). The mixture was stirred at 20° C. for 12 h to give a yellow solution. LC-MS and TLC (eluting with: PE/EtOAc=2/1) showed the reaction was complete. The mixture was quenched with $H_2O$ (10 mL) and extracted with DCM (15 mL×3). The organic layers were dried over $Na_2SO_4$ and concentrated to give the crude product. The product was purified by prep-TLC (eluting with: PE/EtOAc=2/1) to give K101-C1328-A (28.00 mg, 34.23 μmol, 67.40% yield) as a white solid.

Preparation of Compound K101-C1328. To a solution of K101-C1328-A (28.00 mg, 34.23 mol, 1.00 eq) in THF (2.00 mL) were added TFA (770.00 mg, 6.75 mmol, 500.00 uL, 197.29 eq) and $Et_3SiH$ (7.96 mg, 68.46 μmol, 10.90 uL, 2.00 eq). The mixture was stirred at 20° C. for 12 h to give a yellow solution. LC-MS showed the reaction was complete. The reaction mixture was concentrated by $N_2$ and the resultant product purified by prep-HPLC (column: Phenomenex Gemini 150×25 mm×10 um; mobile phase: [A: water (0.1% TFA)-B: ACN]; B %: 30%-70%, 10 min) to give K101-C1328 (9.50 mg, 15.88 μmol, 46.38% yield, 98.54% purity, TFA) as a white solid.

LC-MS (m/z): 498.2 $[M+Na]^+$ $^1H$ NMR (400 MHz, $CD_3OD$) δ 7.57 (s, 1H), 5.64-5.63 (m, 1H), 4.07-4.00 (m, 1H), 3.97-3.93 (m, 2H), 3.18 (s, 1H), 3.09 (s, 1H), 2.52-2.45 (m, 1H), 2.45-2.38 (m, 1H), 2.27-2.23 (m, 1H), 2.05-2.00 (m, 2H), 1.77 (s, 3H), 1.64-1.61 (m, 2H), 1.21 (s, 3H), 1.12 (s, 3H), 1.05 (s, 9H), 1.03-1.01 (m, 1H), 0.96-0.94 (m, 3H).

Example 26: Synthesis Scheme of K101-C1329

The scheme for synthesis of compound K101-C1329 is illustrated below.

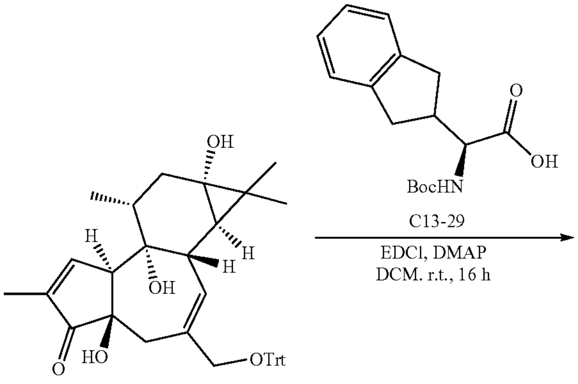

K101-C20Tr-B

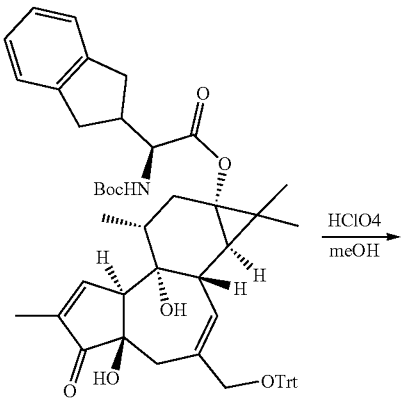

K101-C1329-A

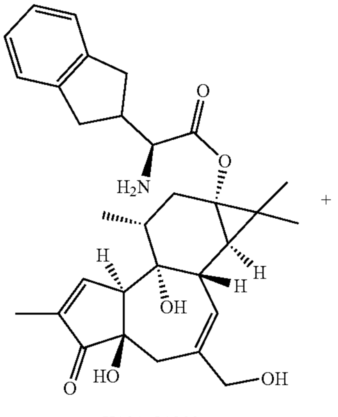

K101-C1329

-continued

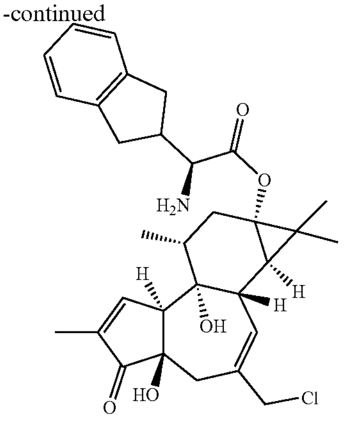

K101-C1329-Cl

Preparation of Compound K101-C1329-A. To a solution of K101-C20Tr-B (20.00 mg, 33.86 μmol, 1.00 eq) and C13-29 (14.80 mg, 50.79 μmol, 1.50 eq) in DCM (2.00 mL) were added EDC (38.95 mg, 203.16 μmol, 6.00 eq) and DMAP (24.82 mg, 203.16 μmol, 6.00 eq). The reaction solution was stirred at 25° C. for 16 hours to give a brown solution. LC-MS showed the reaction was complete. The reaction solution was diluted with DCM (10 mL), then washed with water (3 mL), 0.5 M HCl (2 mL), brine (2 mL), and dried over anhydrous $Na_2SO_4$. The product was filtered and then concentrated under reduced pressure to give crude K101-C1329-A. The crude K101-C1329-A was purified by prep-TLC (PE/EtOAc=3/1, $SiO_2$) to give 15.7 mg of K101-C1329-A as a colorless gum.

Preparation of Compound K101-C1329. To a solution of K101-C1329-A (15.70 mg, 18.17 mol, 1.00 eq) in dioxane (400.00 μL) was added HCl/dioxane (4 M, 200.46 μL, 44.13 eq). The reaction mixture was stirred at 25° C. for 2 hours to give a light brown solution. LC-MS showed the reaction was not complete so the reaction solution was stirred at 25° C. for an additional 1 hour and then for an additional 16 hours. LC-MS showed the reaction was complete. A byproduct was also detected by the LC-MS analysis. The reaction solution was diluted with $CH_3CN$ (1 mL) and the solution adjusted with $K_2CO_3$ (55 mg) in water (0.5 mL) to basic conditions. The product was purified by prep-HPLC (column: Phenomenex Gemini 150×25 mm×10 um; mobile phase: [A: water (0.1% TFA)-B: ACN]; B %: 30%-60%, 10 min) to give K101-C1329 (2.00 mg, 3.62 μmol, 19.92% yield, 94.4% purity) and K101-C1329-Cl (2.70 mg, 4.47 μmol, 24.60% yield, 92.4% purity), both as white solids after lyophilization.

K101-C1329 MS (m/z): 544.1 $[M+Na]^+$

K101-C1329 $^1H$ NMR (400 MHz, $CD_3OD$) δ 7.53 (s, 1H), 7.26-7.20 (m, 2H), 7.20-7.14 (m, 2H), 5.63-5.57 (m, 1H), 4.22 (d, J=6.0 Hz, 1H), 3.99-3.89 (m, 2H), 3.23-3.13 (m, 3H), 3.10-2.97 (m, 4H), 2.57-2.47 (m, 1H), 2.45-2.36 (m, 1H), 2.05-1.93 (m, 2H), 1.75 (dd, J=1.3, 2.8 Hz, 3H), 1.34-1.23 (m, 1H), 1.18 (s, 3H), 1.06 (s, 3H), 0.95 (d, J=6.0 Hz, 1H), 0.86 (d, J=6.0 Hz, 3H).

K101-C1329-Cl LC-MS (m/z): 562.1 $[M+Na]^+$

K101-C1329-Cl $^1H$ NMR (400 MHz, $CD_3OD$) δ 7.52 (s, 1H), 7.26-7.20 (m, 2H), 7.19-7.14 (m, 2H), 5.81-5.76 (m, 1H), 4.22 (d, J=5.8 Hz, 1H), 4.17-4.02 (m, 2H), 3.22-3.11 (m, 3H), 3.08-2.97 (m, 4H), 2.68-2.41 (m, 2H), 2.04-1.93 (m, 2H), 1.78-1.73 (m, 3H), 1.30-1.22 (m, 1H), 1.22-1.18 (m, 3H), 1.10-1.04 (m, 3H), 0.98-0.93 (m, 1H), 0.85 (d, J=6.3 Hz, 3H).

Example 27: Synthesis Scheme of K101-C1330

The scheme for synthesis of compound K101-C1330 is illustrated below.

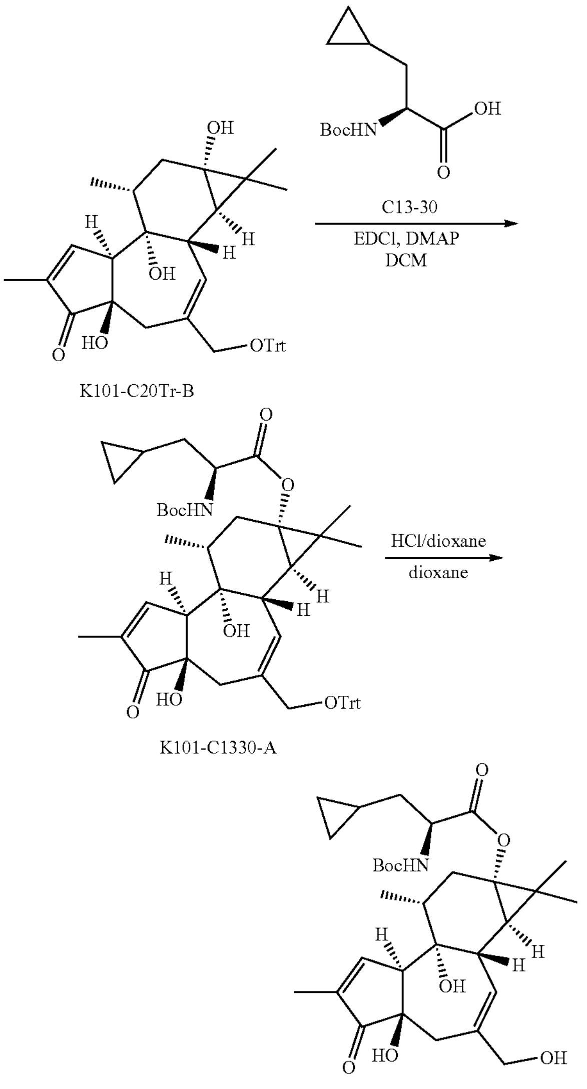

K101-C20Tr-B

K101-C1330-A

K101-C1330

Preparation of Compound K101-C1330-A. To a solution of K101-C20Tr-B (20.00 mg, 33.86 μmol, 1.00 eq) and C13-30 (46.57 mg, 203.16 μmol, 6.00 eq) in DCM (2.00 mL) were added EDC (38.94 mg, 203.16 μmol, 6.00 eq) and DMAP (24.82 mg, 203.16 μmol, 6.00 eq). The reaction solution was stirred at 25° C. for 16 hours to give a brown solution. LC-MS showed the reaction was complete. The reaction solution was diluted with DCM (10 mL), then washed with water (3 mL), 0.5 M HCl (2 mL), brine (2 mL), and dried over anhydrous $Na_2SO_4$. The product was filtered and concentrated under reduced pressure to give the crude product. The product was purified by prep-TLC (PE/EtOAc=3/1, $SiO_2$) to give 16.2 mg of K101-C1330-A as a colorless gum.

Preparation of Compound K101-C1330. To a solution of K101-C1330-A (10.00 mg, 12.47 mol, 1.00 eq) in dioxane (400.00 uL) was added HCl/dioxane (4 M, 200.17 uL, 64.21 eq). The reaction mixture was stirred at 25° C. for 2 hours to give a light brown solution. LC-MS showed the reaction was not complete so 0.2 mL of HCl/dioxane (4 M) was added and the reaction solution stirred at 25° C. for an additional 1 hour. LC-MS showed the reaction was almost complete. The reaction solution was combined with another preparation of K101-C1330-A and concentrated under reduced pressure. The residue was diluted with $CH_3CN$ (1 mL) and water (1 mL) and the solution adjusted to pH 8 with addition of solid $K_2CO_3$ (5 mg). The product was purified by prep-HPLC (column: Phenomenex Gemini 150×25 mm×10 um; mobile phase: [A: water (0.1% TFA)-B: ACN]; B %: 25%-55%, 10 min) to give K101-C1330 (4.70 mg, 65.05% yield, 99.0% purity, TFA salt) as a white powder after lyophilization.

MS (m/z): 482.1 $[M+Na]^+$ $^1H$ NMR (400 MHz, $CD_3OD$) δ 7.55 (s, 1H), 5.64-5.59 (m, 1H), 4.12 (dd, J=5.3, 7.8 Hz, 1H), 4.00-3.90 (m, 2H), 3.19-3.14 (m, 1H), 3.09-3.03 (m, 1H), 2.58-2.48 (m, 1H), 2.45-2.37 (m, 1H), 2.25 (dd, J=6.8, 14.6 Hz, 1H), 2.12-2.01 (m, 1H), 1.95-1.85 (m, 1H), 1.80-1.70 (m, 4H), 1.61 (dd, J=10.4, 14.7 Hz, 1H), 1.18 (s, 3H), 1.09 (s, 3H), 1.02-0.97 (m, 1H), 0.93 (d, J=6.8 Hz, 3H), 0.8-0.76 (m, 1H), 0.66-0.59 (m, 2H), 0.27-0.17 (m, 2H).

Example 28: Synthesis Scheme of K101-C1331

The scheme for synthesis of compound K101-C1331 is illustrated below.

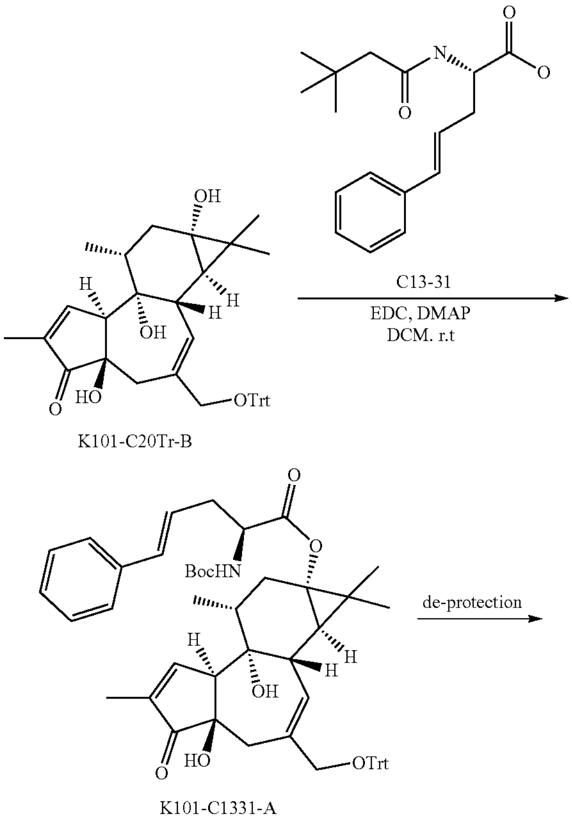

K101-C20Tr-B

K101-C1331-A

-continued

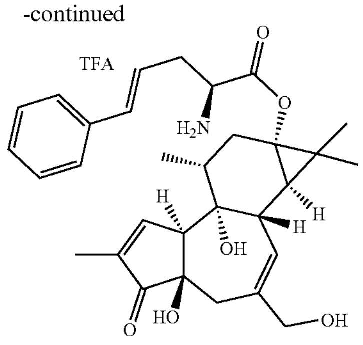

K101-C1331

Preparation of Compound K101-C1331-A. To a solution of K101-C20Tr-B (30.00 mg, 50.78 μmol, 1.00 eq) in DCM (2.00 mL) were added (E,2S)-2-(tert-butoxycarbonylamino)-5-phenyl-pent-4-enoic acid (C13-31) (29.59 mg, 101.56 μmol, 2.00 eq), DMAP (24.82 mg, 203.12 μmol, 4.00 eq), HOBt (13.72 mg, 101.56 μmol, 2.00 eq) and EDC (19.47 mg, 101.56 μmol, 2.00 eq). The mixture was stirred at 20° C. for 12 h to give a yellow solution. LC-MS and TLC (eluting with: PE/EtOAc=2/1) showed the reaction was complete. The mixture was combined with a second preparation of K101-C1331-A and the mixture quenched with $H_2O$ (10 mL) and then extracted with DCM (15 mL×3). The organic layers were dried over $Na_2SO_4$ and concentrated to give the crude product. The product was purified by prep-TLC (eluting with: PE/EtOAc=2/1) to give K101-C1331-A (32.00 mg, 37.03 μmol, 62.49% yield) as a white solid.

Preparation of Compound K101-C1331. To a solution of K101-C1331-A (32.00 mg, 37.03 mol, 1.00 eq) in THF (2.00 mL) were added TFA (770.00 mg, 6.75 mmol, 500.00 uL, 182.37 eq) and $Et_3SiH$ (8.61 mg, 74.06 μmol, 11.79 uL, 2.00 eq). The mixture was stirred at 20° C. for 12 h to give a yellow solution. LC-MS showed the reaction was complete. The reaction mixture was concentrated by $N_2$, and the product purified by prep-HPLC (column: Phenomenex Gemini 150×25 mm×10 um; mobile phase: [A: water (0.1% TFA)-B: ACN]; B %: 27%-57%, 10 min) to give K101-C1331 (10.00 mg, 15.73 μmol, 42.48% yield, 100% purity, TFA salt) as a white solid.

LC-MS (m/z): 524.2 $[M+Na]^+$ $^1H$ NMR (400 MHz, $CD_3OD$) δ 7.57 (s, 1H), 5.64 (s, 1H), 4.10-4.07 (m, 1H), 4.00-3.93 (s, 2H), 3.18 (s, 1H), 3.08 (s, 1H), 2.53-2.45 (m, 1H), 2.45-2.41 (m, 1H), 2.29-2.27 (m, 1H), 2.05 (m, 1H), 1.84-1.29 (m, 16H), 1.19 (s, 3H), 1.11 (s, 3H), 1.02-1.01 (m, 2H), 0.96-0.94 (m, 3H).

Example 29: Synthesis Scheme of K101-C1332

The scheme for synthesis of compound K101-C1332 is illustrated below.

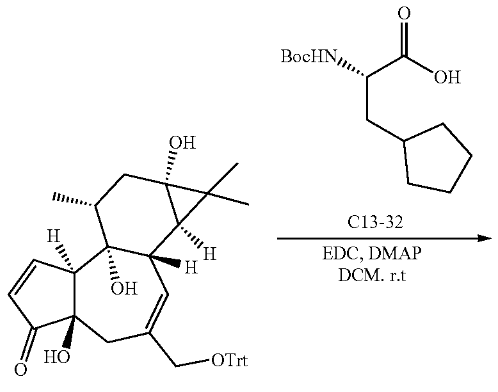

K101-C20Tr-B

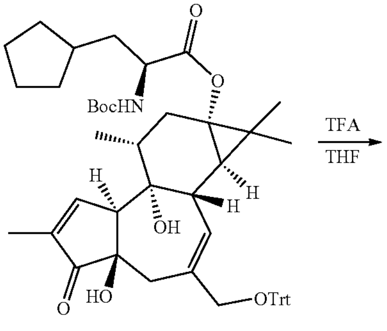

K101-C1332-A

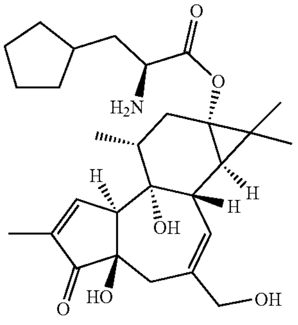

K101-C1322

Preparation of Compound K101-C1332-A. To a solution of K101-C20Tr-B (30.00 mg, 50.78 μmol, 1.00 eq) in DCM (5.00 mL) were added (2S)-2-(tert-butoxycarbonylamino)-3-cyclopentyl-propanoic acid (C13-32) (26.14 mg, 101.56 μmol, 2.00 eq), DMAP (24.82 mg, 203.12 mol, 4.00 eq) and EDC (19.47 mg, 101.56 μmol, 2.00 eq). The mixture was stirred at 20° C. for 5 h to give a yellow solution. LC-MS showed the reaction was incomplete. Additional EDC (10 mg) was added, and mixture stirred at 20° C. for 14 hr. LC-MS showed some of the K101-C20Tr-B still remained. A further amount of EDC (11 mg) was added, and the mixture stirred at 20° C. for another 5 hr. LC-MS and TLC showed the reaction was complete. The reaction mixture was quenched with $H_2O$ (15 mL) and extracted with DCM (15 mL×5). The organic layers were dried over $Na_2SO_4$ and concentrated to give a yellow solid. The product was purified by prep-TLC (eluting with Petroleum ether: Ethyl acetate=7/2) to give K101-C1332-A (23.00 mg, 27.71 μmol, 54.57% yield) as a colorless solid.

Preparation of Compound K101-C1332. To a solution of K101-C1332-A (23.00 mg, 27.71 mol, 1.00 eq) in THF (2.00 mL) were added $Et_3SiH$ (3.22 mg, 27.71 μmol, 4.41 uL, 1.00 eq) and TFA (770.00 mg, 6.75 mmol, 500.00 uL, 243.71 eq). The mixture was stirred at 20° C. for 1.5 h to give a colorless solution. The reaction mixture was concentrated to give a yellow oil, which was dissolved in DCM (2 mL) followed by addition of TFA (0.5 mL). The mixture was stirred at 20° C. for 1 hr and concentrated to give a yellow oil. LC-MS showed the reaction was complete. The reaction mixture was concentrated, and the product purified by prep-HPLC (column: Phenomenex Gemini 150×25 mm×10 um; mobile phase: [A: water (0.1% TFA)-B: ACN]; B %: 30%-60%, 10 min). The separated layers were lyophilized to give K101-C1332 (8.00 mg, 13.03 μmol, 47.03% yield, 98% purity, TFA salt) as a white solid.

LC-MS (m/z): 510.2 $[M+Na]^+$ $^1H$ NMR (400 MHz, $CDCl_3$) δ=7.57 (s, 1H), 5.64 (d, J=4.5 Hz, 1H), 4.02-3.99 (m, 1H), 3.97 (s, 2H), 3.18 (s, 1H), 3.15-3.02 (m, 1H), 2.60-2.36 (m, 2H), 2.26 (dd, J=6.9, 14.7 Hz, 1H), 2.05 (dd, J=6.9, 13.2 Hz, 1H), 2.02-1.97 (m, 1H), 1.94-1.83 (m, 2H), 1.83 (t, J=7.8 Hz, 1H), 1.77 (d, J=1.5 Hz, 4H), 1.74-1.54 (m, 5H), 1.35-1.14 (m, 6H), 1.11 (s, 3H), 1.02 (d, J=6.0 Hz, 1H), 0.95 (d, J=6.5 Hz, 3H)

Example 30: Synthesis Scheme of K101-C1333

The scheme for synthesis of compound K101-C1333 is illustrated below.

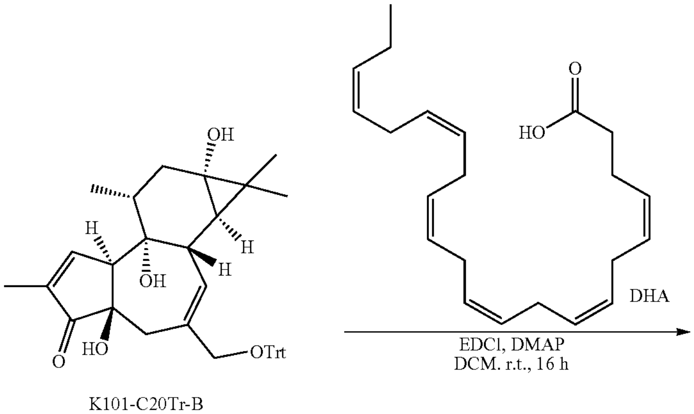

K101-C20Tr-B

-continued

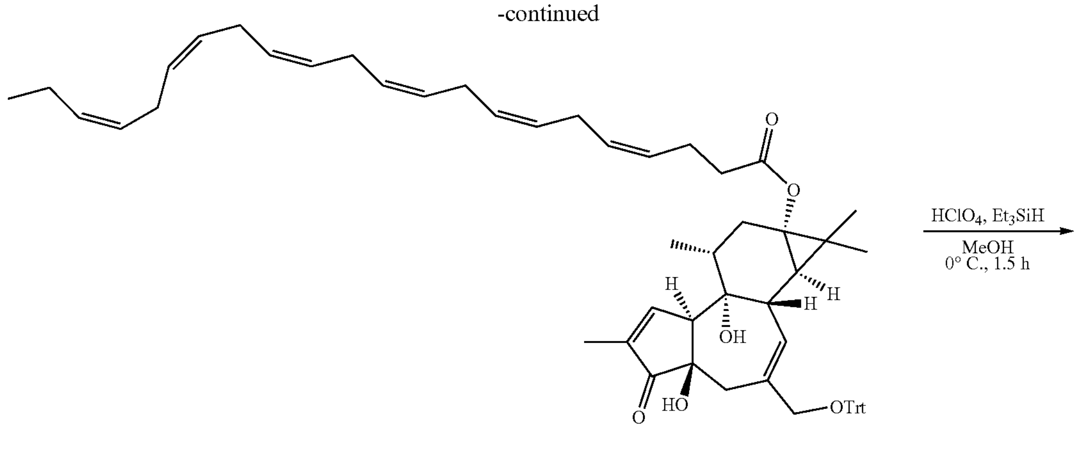

K101-C1333-A

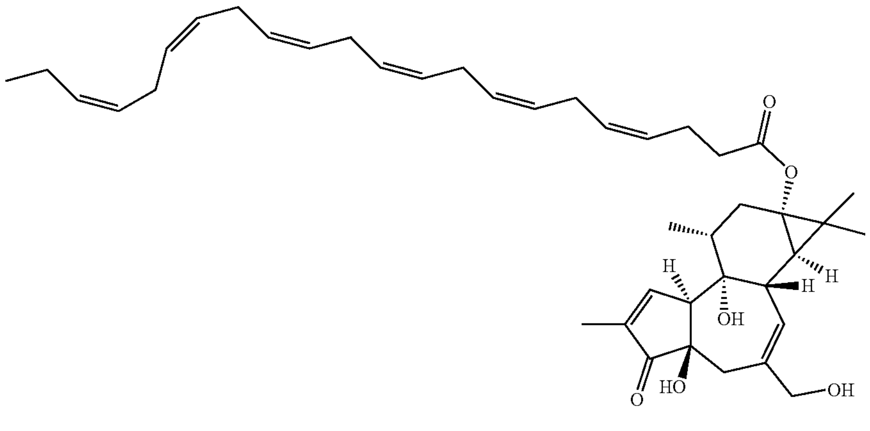

K101-C1333

Preparation of Compound K101-C1333-A: To a solution of K101-C20Tr-B (22.00 mg, 37.24 μmol, 1.17 eq) and DHA (10.50 mg, 31.96 μmol, 1.00 eq) in DCM (500.00 uL) was added EDCI (36.77 mg, 191.79 μmol, 6.00 eq) and DMAP (23.43 mg, 191.79 μmol, 6.00 eq). The reaction solution was stirred at 20° C. for 16 hours to give a brown solution. LCMS showed the desired MS value. The reaction mixture was combined with reaction mixture of ES5329-184 (5 mg of K101-C20Tr-B was used in this batch) and concentrated under reduced pressure. The residue was purified by prep-TLC (PE/EtOAc=5/1) to give K101-C1333-A (7.00 mg, 7.77 μmol, 24.30% yield) as a colorless oil.

$^1$H NMR (400 MHz, $CDCl_3$) δ 7.58 (s, 1H), 7.46-7.38 (m, 6H), 7.31-7.26 (m, 6H), 7.24-7.18 (m, 3H), 5.60 (d, J=3.5 Hz, 1H), 5.42-5.27 (m, 12H), 3.51 (s, 2H), 3.31-3.25 (m, 1H), 2.96-2.90 (m, 1H), 2.90-2.67 (m, 10H), 2.57-2.47 (m, 1H), 2.44-2.30 (m, 5H), 2.13-1.91 (m, 7H), 1.77 (dd, J=1.1, 2.9 Hz, 3H), 1.59-1.51 (m, 1H), 1.19 (s, 3H), 1.07 (s, 3H), 0.97 (t, J=7.5 Hz, 3H), 0.87 (d, J=6.3 Hz, 3H), 0.79 (d, J=5.3 Hz, 1H).

Preparation of Compound K101-C1333: To a solution of K101-C1333-A (6.00 mg, 6.66 mol, 1.00 eq) in MeOH (200.00 uL) was added $HClO_4$ (9.96 mg, 99.17 μmol, 6.00 uL, 14.89 eq) and $Et_3SiH$ (774.15 ug, 6.66 μmol, 1.06 uL, 1.00 eq). Then the reaction mixture was stirred at 0° C. for 1.5 hour to give a white suspension. TLC (DCM/MeOH=20/1, $SiO_2$) showed no starting material remained and a new spot was observed. The reaction mixture was concentrated under reduced pressure. The residue was purified by prep-TLC (PE/EtOAc=1/1) to give K101-C1333 (3.65 mg, 79.85% yield, 96.0% purity) as a white solid after lyophilization.

MS (m/z): 681.3 [M+Na]$^+$ $^1$H NMR (400 MHz, $CD_3OD$) δ 7.56-7.53 (m, 1H), 5.62-5.58 (m, 1H), 5.51-5.20 (m, 12H), 3.99-3.88 (m, 2H), 3.20-3.14 (m, 1H), 3.09-3.03 (m, 1H), 2.92-2.80 (m, 10H), 2.56-2.48 (m, 1H), 2.47-2.38 (m, 5H), 2.15-2.06 (m, 3H), 2.06-1.99 (m, 1H), 1.74 (dd, J=1.3, 2.9 Hz, 3H), 1.55 (dd, J=10.7, 14.4 Hz, 1H), 1.18 (s, 3H), 1.07 (s, 3H), 0.97 (t, J=7.5 Hz, 3H), 0.90 (d, J=6.4 Hz, 4H), 0.86 (d, J=5.5 Hz, 1H).

Example 31: Synthesis Scheme of K101-C1334

The scheme for synthesis of compound K101-C1334 is illustrated below.

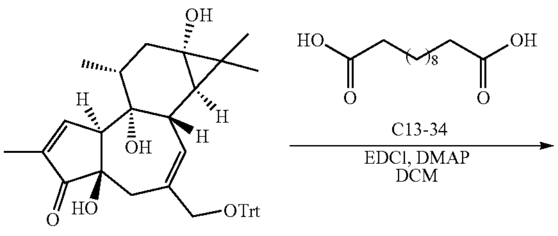

K101-C20Tr-B

-continued

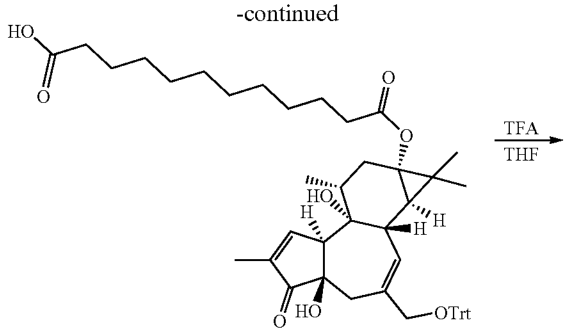

K101-C1334-A

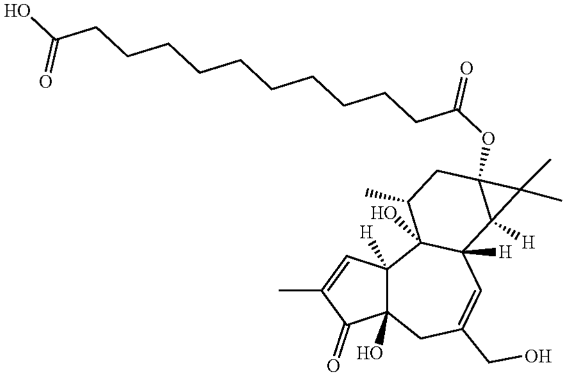

K101-C1334

Preparation of Compound K101-C1334-A: To a solution of K101-C20Tr-B (35.00 mg, 59.25 μmol, 1.00 eq) and C13-34 (136.45 mg, 592.47 μmol, 10.00 eq) in DCM (1.00 mL) was added EDCI (34.07 mg, 177.74 μmol, 3.00 eq) and DMAP (21.71 mg, 177.74 μmol, 3.00 eq), then the mixture was stirred at 20° C. for 14 hours to give colorless solution. The reaction was complete detected by LCMS (ES6477-17-P1B). The reaction solution was diluted with $H_2O$ (10 ml), extracted with DCM:MeOH=10:1 (10 ml*5). The combined organic layers were dried over anhydrous $Na_2SO_4$, filtered, concentrated under reduced pressure to give crude product. The crude product purified by prep-TLC ($SiO_2$, PE:EA=2:1) to give K101-C1334-A (26.40 mg, 32.88 μmol, 55.49% yield) as a white solid.

K101-C1334-A $^1$H NMR (400 MHz, $CDCl_3$) δ 7.59 (s, 1H), 7.44-7.39 (m, 6H), 7.31-7.27 (m, 5H), 7.24-7.18 (m, 3H), 5.61 (s, 1H), 5.30 (s, 1H), 3.50 (s, 2H), 3.27 (s, 1H), 2.97-2.86 (m, 3H), 2.58-2.47 (m, 1H), 2.38 (d, J=18.8 Hz, 3H), 2.28 (t, J=7.4 Hz, 4H), 2.08-1.90 (m, 3H), 1.76 (s, 3H), 1.60-1.49 (m, 3H), 1.25 (s, 16H), 1.20-1.16 (m, 1H), 1.18 (s, 3H), 1.06 (s, 3H), 0.92-0.75 (m, 5H).

Preparation of Compound K101-C1334: To a solution of K101-C1334-A (26.00 mg, 32.38 mol, 1.00 eq) in THF (3.00 mL) was added TFA (770.00 mg, 6.75 mmol, 500.00 uL, 208.56 eq). Then the solution was stirred at 0° C. for 18 hours to give colorless solution. The reaction was complete detected by LCMS (ES6477-18-P1B). The reaction was concentrated under ordinary pressure to give yellow oil. The residue was purified by prep-HPLC (column: Phenomenex Gemini 150*25 mm*10 um; mobile phase: [water (0.1% TFA)-ACN]; B %: 50%-80%, 10 min). The separated layers were lyophilized to give K101-C1334 (3.00 mg, 5.35 mol, 16.52% yield, 97.28% purity, Free) as a white solid.

K101-C1334: LC-MS (m/z): 583.1 [M+Na]$^+$ $^1$H NMR (400 MHz, MeOD) δ 7.56 (s, 1H), 5.63-5.58 (m, 1H), 3.99-3.89 (m, 2H), 3.20-3.15 (m, 1H), 3.09-3.04 (m, 1H), 2.56-2.49 (m, 1H), 2.47-2.40 (m, 1H), 2.37-2.26 (m, 4H), 2.22-2.10 (m, 1H), 2.10-1.99 (m, 2H), 1.77-1.73 (m, 3H), 1.66-1.51 (m, 5H), 1.32 (s, 12H), 1.18 (s, 3H), 1.07 (s, 3H), 0.91 (d, J=6.3 Hz, 3H), 0.86 (d, J=5.5 Hz, 1H).

Example 32: Synthesis Scheme of K101-C1335

The scheme for synthesis of compound K101-C1335 is illustrated below.

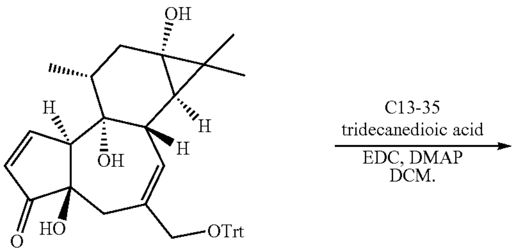

K101-C20Tr-B

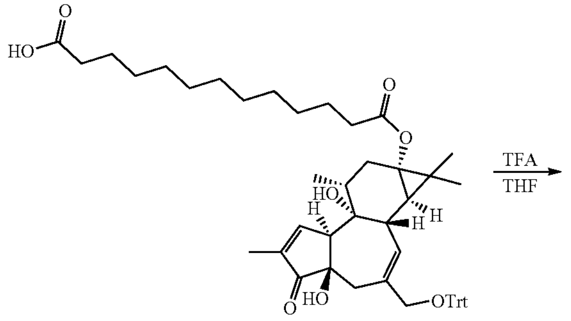

K101-C1335-A

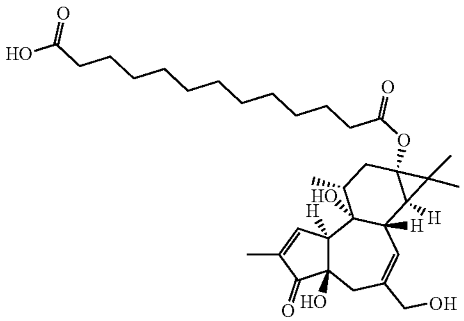

K101-C1335

Preparation of Compound K101-C1335-A: To a solution of K101-C20Tr-B (30.00 mg, 50.78 μmol, 1.00 eq) in DCM (2.00 mL) were added tridecanedioic acid (62.04 mg, 253.90 μmol, 5.00 eq), DMAP (37.22 mg, 304.68 μmol, 6.00 eq) and EDCI (58.41 mg, 304.68 μmol, 6.00 eq). The mixture was stirred at 20° C. for 14 hr to give a colorless solution. The mixture was stirred at 20° C. for 5 hr to give a colorless solution. LCMS and TLC showed the reaction was completed. The reaction mixture was quenched with $H_2O$ (15 mL) and extracted with DCM (15 mL*5). The organic layers were dried over $Na_2SO_4$ and concentrated to give a yellow solid. The yellow solid was purified by prep-TLC (eluting with Petroleum ether: Ethyl acetate=3/1) to give K101-C1335-A (24.00 mg, 29.37 μmol, 57.84% yield) as a white solid.

$^1H$ NMR (400 MHz, $CDCl_3$) δ=7.65-7.55 (s, 1H), 7.45-7.35 (m, 6H), 7.32-7.27 (m, 6H), 7.25-7.19 (m, 3H), 5.65-5.55 (m, 1H), 3.55-3.45 (m, 2H), 3.30-3.25 (m, 1H), 3.00-2.90 (m, 1H), 2.59-2.22 (m, 6H), 2.20 (s, 3H), 2.13-1.90 (m, 4H), 1.80-1.72 (m, 3H), 1.45-1.20 (m, 14H), 1.19 (s, 3H), 1.07 (s, 3H), 0.88 (d, J=6.3 Hz, 3H), 0.79 (d, J=5.3 Hz, 1H).

Preparation of Compound K101-C1335: To a solution of K101-C1335-A (24.00 mg, 29.37 mol, 1.00 eq) in THF (10.00 mL) was added TFA (770.00 mg, 6.75 mmol, 500.00 uL, 229.94 eq). The mixture was stirred at 0° C. for 14 hr to give a yellow solution. LCMS showed K101-C1335-A was remained, then added TFA (0.1 mL). The mixture was stirred at 0° C. for 14 hr to give a colorless solution. LCMS showed the reaction was completed. The reaction mixture was concentrated to give yellow oil. The yellow oil was purified by prep-HPLC (column: Phenomenex Gemini 150*25 mm*10 um; mobile phase: [water (0.1% TFA)-ACN]; B %: 70%-70%, 10 min). The separated layers were lyophilized to give K101-C1335 (5.40 mg, 9.15 μmol, 31.16% yield, 97.4% purity, Free) as a white solid.

LC-MS (m/z): 597.3 $[M+Na]^+$ $^1H$ NMR (400 MHz, MeOD) δ=7.60-7.50 (m, 1H), 5.62 (m, 1H), 4.03-3.84 (m, 2H), 3.25-3.14 (m, 1H), 3.12-3.01 (m, 1H), 2.61-2.41 (m, 2H), 2.41-2.23 (m, 4H), 2.19-1.99 (m, 2H), 1.83-1.71 (m, 3H), 1.71-1.48 (m, 5H), 1.45-1.35 (m, 14H), 1.19 (s, 3H), 1.09 (s, 3H), 0.93 (d, J=6.3 Hz, 3H), 0.87 (d, J=5.8 Hz, 1H)

Example 33: Synthesis Scheme of K101-C1336

The scheme for synthesis of compound K101-C1336 is illustrated below.

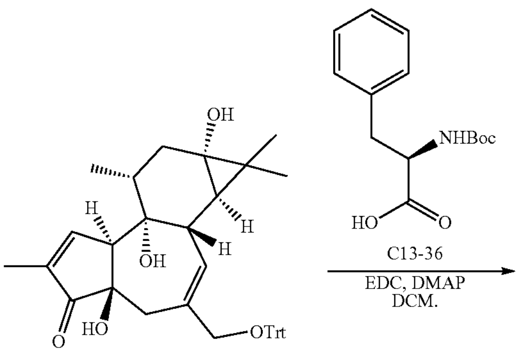

K101-C20Tr-B

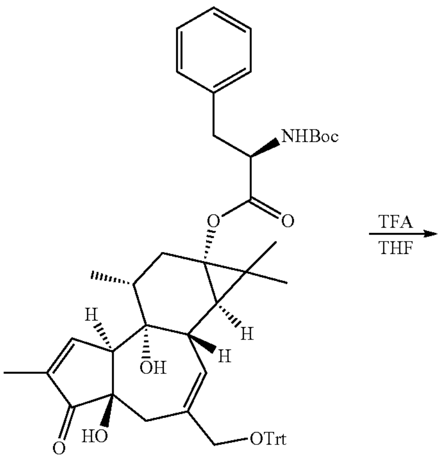

K101-C1336-A

-continued

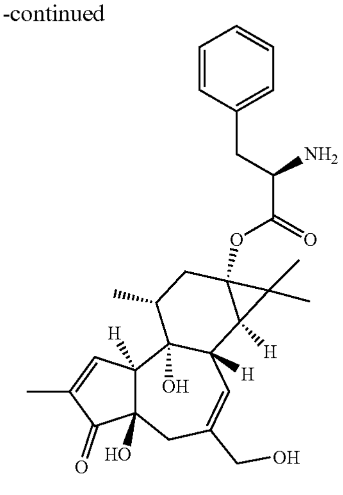

K101-C1336

Preparation of Compound K101-C1336-A. To a solution of K101-C20Tr-B (30.00 mg, 50.78 μmol, 1.00 eq) in DCM (5.00 mL) were added (2R)-2-(tert-butoxycarbonylamino)-3-phenyl-propanoic acid (C13-36) (26.95 mg, 101.56 μmol, 2.00 eq), DMAP (30.00 mg, 245.78 μmol, 4.84 eq) and EDC (19.96 mg, 104.10 μmol, 2.05 eq). The mixture was stirred at 20° C. for 19 h to give a colorless solution. LC-MS and TLC showed the reaction was complete. The reaction mixture was quenched with $H_2O$ (15 mL) and extracted with DCM (15 mL×5). The organic layers were dried over $Na_2SO_4$ and concentrated to give a yellow solid. The product was purified by prep-TLC (eluting with Petroleum ether: Ethyl acetate=3/1) to give K101-C1336-A (16.00 mg, 19.09 μmol, 37.60% yield) as a colorless solid.

Preparation of Compound K101-C1336. To a solution of K101-C1336-A 16.00 mg, 19.09 mol, 1.00 eq) in DCM (2.00 mL) were added TFA (770.00 mg, 6.75 mmol, 500.00 uL, 353.76 eq) and $Et_3SiH$ (2.22 mg, 19.09 μmol, 3.04 uL, 1.00 eq). The mixture was stirred at 20° C. for 5 h to give a colorless solution. LC-MS showed the reaction was complete. The reaction mixture was concentrated and the product purified by prep-HPLC column: Phenomenex Gemini 150×25 mm×10 um; mobile phase: [A: water (0.1% TFA)-B: ACN]; B %: 15%-45%, 10 min). The separated layers were lyophilized to give K101-C1336 (6.00 mg, 9.84 μmol, 51.55% yield, 100% purity, TFA salt) as a white solid.

LC-MS (m/z): 518.2 $[M+Na]^+$ $^1H$ NMR (400 MHz, MeOD) δ=7.59 (s, 1H), 7.48-7.29 (m, 5H), 5.63 (s, 1H), 4.37 (dd, J=5.9, 8.2 Hz, 1H), 4.04-3.89 (m, 2H), 3.42-3.37 (m, 1H), 3.25-3.00 (m, 3H), 2.61-2.35 (m, 2H), 2.23 (dd, J=7.0, 15.1 Hz, 1H), 2.05 (s, 1H), 1.78 (d, J=1.5 Hz, 3H), 1.64 (dd, J=10.4, 14.7 Hz, 2H), 1.08 (d, J=7.8 Hz, 6H), 1.01-0.90 (m, 4H)

Example 34: Synthesis Scheme of K101-C1337

The scheme for synthesis of compound K101-C1337 is illustrated below.

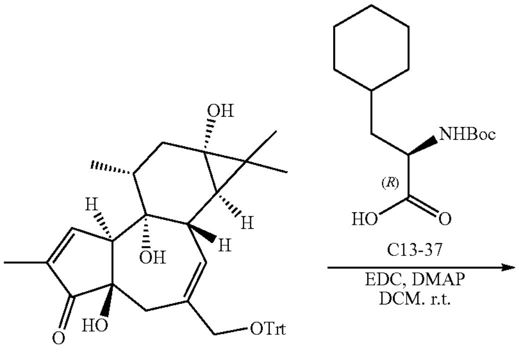

K101-C20Tr-B

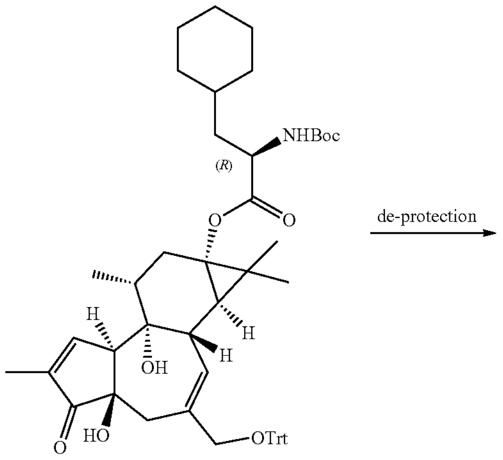

K101-C1337-A

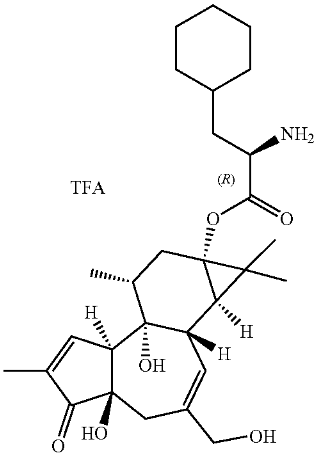

K101-C1337

Preparation of Compound K101-C1337-A. To a solution of K101-C20Tr-B (30.00 mg, 50.78 μmol, 1.00 eq) in DCM (2.00 mL) were added (2R)-2-(tert-butoxycarbonylamino)-3-cyclohexyl-propanoic acid (C13-37) (27.56 mg, 101.56 μmol, 2.00 eq), DMAP (24.82 mg, 203.12 mol, 4.00 eq), HOBt (13.72 mg, 101.56 μmol, 2.00 eq) and EDC (19.47 mg, 101.56 μmol, 2.00 eq). The mixture was stirred at 20° C. for 12 h to give a yellow solution. LC-MS and TLC (eluting with: PE/EtOAc=2/1) showed the reaction was complete. The mixture was combined with a second preparation of K101-C1337-A, the mixture quenched with $H_2O$ (10 mL) and then extracted with DCM (20 mL×3). The organic layers were dried over $Na_2SO_4$ and concentrated to give the crude product. The product was purified by prep-TLC (eluting with: PE/EtOAc=2/1) to give K101-C1337-A (18.00 mg, 21.32 μmol, 41.99% yield) as a white solid.

Preparation of Compound K101-C1337. To a solution of K101-C1337-A (18.00 mg, 21.32 mol, 1.00 eq) in THF (2.00 mL) were added TFA (770.00 mg, 6.75 mmol, 500.00 uL, 316.75 eq) and $Et_3SiH$ (7.44 mg, 63.96 μmol, 10.19 uL, 3.00 eq). The mixture was stirred at 20° C. for 2 h to give a yellow solution. LC-MS showed the reaction was complete. The reaction mixture was concentrated by $N_2$, and the product purified by prep-HPLC (column: Phenomenex Gemini 150×25 mm×10 um; mobile phase: [A: water (0.1% TFA)-B: ACN]; B %: 25%-55%, 10 min) to give K101-C1337 (5.20 mg, 10.37 μmol, 48.62% yield, 100% purity) as a white solid.

LC-MS (m/z): 524.3 $[M+Na]^+$ $^1H$ NMR (400 MHz, $CD_3OD$) δ 7.58 (s, 1H), 5.64-5.63 (s, 1H), 4.12-4.09 (m, 1H), 4.00-3.94 (m, 2H), 3.18 (s, 1H), 3.08 (s, 1H), 2.53-2.45 (m, 1H), 2.40-2.32 (m, 1H), 2.26-2.24 (m, 1H), 2.05-2.03 (m, 1H), 1.84-1.64 (m, 12H), 1.33-1.31 (m, 3H), 1.20 (s, 3H), 1.11 (s, 3H), 1.01-0.95 (m, 6H).

Example 35: Synthesis Scheme of K101-C1338

The scheme for synthesis of compound K101-C1338 is illustrated below.

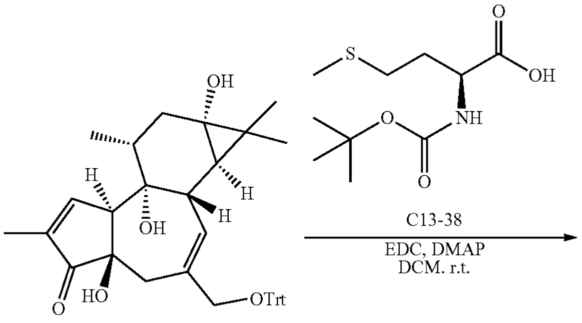

K101-C20Tr-B

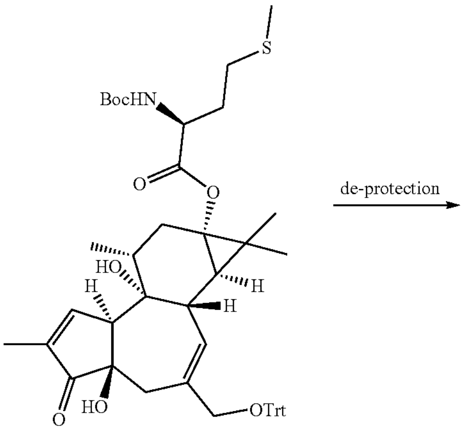

K101-C1338-A

-continued

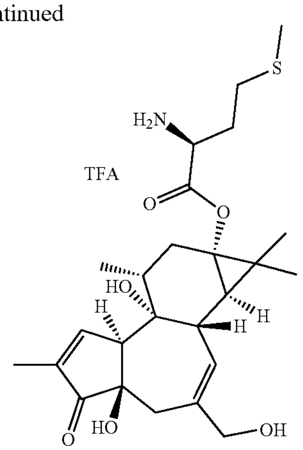

K101-C1338

Preparation of compound K101-C1338-A. To a solution of K101-C20Tr-B (30.00 mg, 50.78 μmol, 1.00 eq) in DCM (2.00 mL) were added (2S)-2-(tert-butoxycarbonylamino)-4-methylsulfanyl-butanoic acid (C13-38) (25.32 mg, 101.56 μmol, 2.00 eq), DMAP (24.82 mg, 203.12 μmol, 4.00 eq), HOBt (13.72 mg, 101.56 μmol, 2.00 eq) and EDC (19.47 mg, 101.56 μmol, 2.00 eq). The mixture was stirred at 20° C. for 12 h to give a yellow solution. LC-MS and TLC (eluting with: PE/EtOAc=2/1) showed the reaction was complete. The mixture was combined with as second preparation of K101-C1338-A, and the mixture quenched with $H_2O$ (10 mL) and extracted with DCM (15 mL×3). The organic layers were dried over $Na_2SO_4$ and concentrated to give the crude product. The product was purified by prep-TLC (eluting with: PE/EtOAc=2/1) to give K101-C1338-A (36.00 mg, 43.79 μmol, 64.84% yield) as a white solid.

Preparation of compound K101-C1338. To a solution of K101-C1338-A (36.00 mg, 43.79 μmol, 1.00 eq) in THF (2.00 mL) was added TFA (1.54 g, 13.51 mmol, 1.00 mL, 308.44 eq). The mixture was stirred at 20° C. for 12 h to give a yellow solution. LC-MS showed the reaction was complete. The reaction mixture was concentrated by $N_2$ and the product purified by prep-HPLC (column: Phenomenex Gemini 150×25 mm×10 um; mobile phase: [A: water (0.1% TFA)-B: ACN]; B %: 20%-50%, 10 min) to give K101-C1338 (13.20 mg, 20.95 μmol, 47.83% yield, 94.2% purity, TFA salt) as a white solid.

LC-MS (m/z): 502.1 $[M+Na]^+$ $^1H$ NMR (400 MHz, $CD_3OD$) δ 7.57 (s, 1H), 5.65-5.64 (m, 1H), 4.26-4.23 (m, 1H), 4.00-3.94 (m, 2H), 3.18 (s, 1H), 3.08 (s, 1H), 2.72-2.69 (m, 2H), 2.53-2.45 (m, 1H), 2.45-2.41 (m, 1H), 2.30-2.24 (m, 2H), 2.15-2.11 (m, 5H), 1.77 (s, 3H), 1.76-1.75 (m, 1H), 1.20 (s, 3H), 1.03 (s, 3H), 0.96-0.94 (m, 4H).

Example 36: Synthesis Scheme of K101-C1339

The scheme for synthesis of compound K101-C1339 is illustrated below.

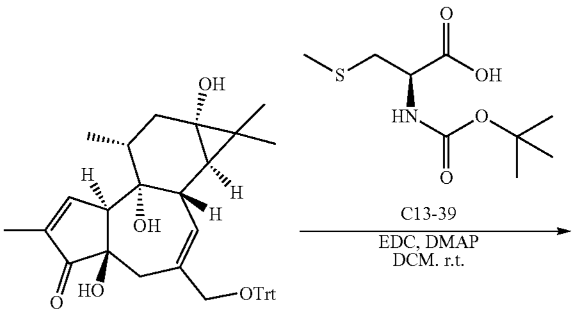

K101-C20Tr-B

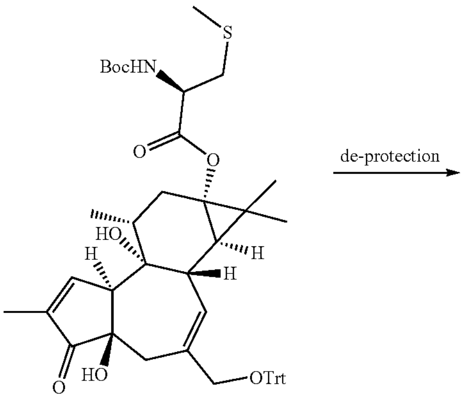

K101-C1339-A

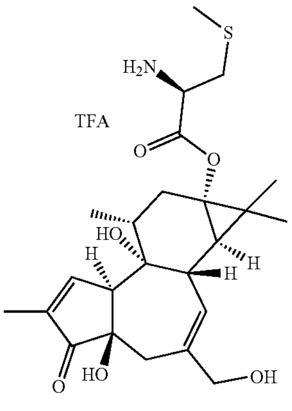

K101-C1339

Preparation of Compound K101-C1339-A. To a solution of K101-C20Tr-B (30.00 mg, 50.78 mol, 1.00 eq) in DCM (2.00 mL) were added (2R)-2-(tert-butoxycarbonylamino)-3-methylsulfanyl-propanoic acid (C13-39) (23.90 mg, 101.56 mol, 2.00 eq), DMAP (24.82 mg, 203.12 mol, 4.00 eq), HOBt (13.72 mg, 101.56 mol, 2.00 eq) and EDC (19.47 mg, 101.56 μmol, 2.00 eq).

The mixture was stirred at 20° C. for 12 hr to give a yellow solution. LC-MS and TLC (eluting with: PE/EtOAc=2/1) showed the reaction was complete. The mixture was combined with a second preparation, which was quenched with $H_2O$ (10 mL) and then extracted with DCM (15 mL). The organic layers were dried over $Na_2SO_4$ and concentrated to give the crude product. The product was purified by prep-TLC (eluting with: PE/EtOAc=2/1) to give K101-C1339-A (35.00 mg, 43.32 μmol, 85.30% yield) as a white solid.

Preparation of Compound K101-C1339. To a solution of K101-C1339-A (35.00 mg, 43.32 μmol, 1.00 eq) in THF (2.00 mL) was added TFA (4.94 mg, 43.32 mol, 3.21 uL, 1.00 eq). The mixture was stirred at 20° C. for 3 h to give a yellow solution. LC-MS showed the reaction was complete. The reaction mixture was concentrated by $N_2$ and the product purified by prep-HPLC (column: Phenomenex Gemini 150x25 mmx10 um; mobile phase: [A: water (0.1% TFA)-B: ACN]; B %: 18%-48%, 10 min) to give K101-C1339 (4.40 mg, 7.11 μmol, 16.41% yield, 93.63% purity, TFA salt) as a white solid.

LC-MS (m/z): 488.1 $[M+Na]^+$ $^1H$ NMR (400 MHz, $CD_3OD$) δ 7.57 (s, 1H), 5.65-5.64 (m, 1H), 4.33-4.30 (m, 1H), 4.00-3.97 (m, 2H), 3.19-3.14 (m 2H), 3.07 (s, 1H), 3.00-2.97 (m, 1H), 2.53-2.45 (m, 1H), 2.40-2.32 (m, 1H), 2.25-2.23 (m, 4H), 2.10-2.05 (m, 1H), 1.77 (s, 3H), 1.20 (s, 3H), 1.11 (s, 3H), 1.05-1.03 (m, 1H), 0.96-0.94 (m, 3H).

Example 37: Synthesis Scheme of K101-C1340

The scheme for synthesis of compound K101-C1340 is illustrated below.

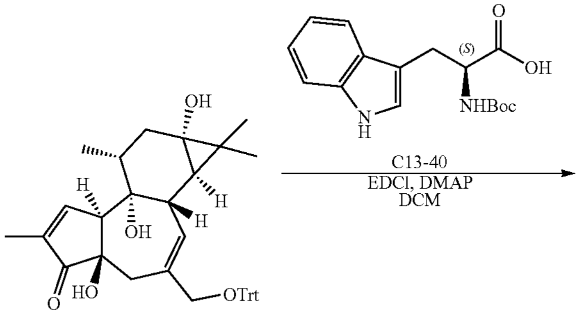

K101-C20Tr-B

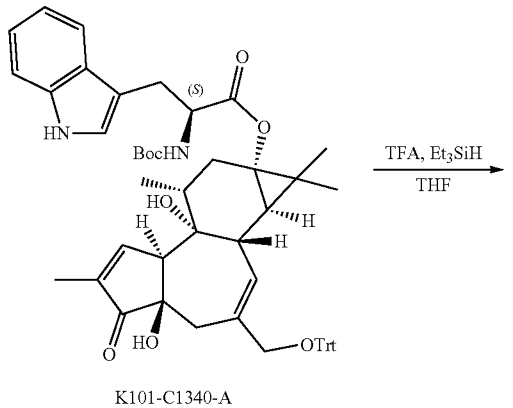

K101-C1340-A

-continued

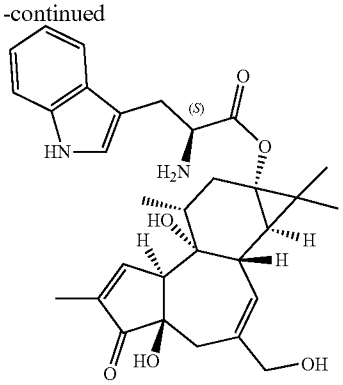

K101-C1340

Preparation of compound K101-C1340-A. To a solution of K101-C20Tr-B (30.00 mg, 50.78 mol, 1.00 eq) and C13-40 in DCM (3.00 mL) were added EDC (19.47 mg, 101.56 μmol, 2.00 eq) and DMAP (37.22 mg, 304.68 μmol, 6.00 eq). The reaction solution was stirred at 20° C. for 14 hours to give colorless solution. TLC (PE/EtOAc=1/1, $SiO_2$) and LC-MS showed the reaction was complete. The reaction solution was combined with a second preparation, and then diluted with $H_2O$ (5 mlx2) followed by extraction with DCM (10 mlx5). The combined organic layers were dried over anhydrous $Na_2SO_4$, filtered, and concentrated under reduced pressure to give crude product as a pale yellow solid. The product was purified by prep-TLC (PE/EtOAc=1/1, $SiO_2$) to give K101-C1340-A (20.30 mg, 23.15 μmol, 39.29% yield) as a white solid.

Preparation of Compound K101-C1340. To a solution of K101-C1343-A (20.00 mg, 22.80 mol, 1.00 eq) in THF (2.00 mL) were added sequentially TFA (770.00 mg, 6.75 mmol, 500.00 uL, 296.19 eq) followed by $Et_3SiH$ (2.65 mg, 22.80 μmol, 3.63 uL, 1.00 eq). The mixture was stirred at 20° C. for 18 hours to give a pale yellow solution. The reaction was complete detected by LC-MS. The reaction was concentrated under reduced pressure to give a yellow solid, and the product purified by prep-HPLC (column: Phenomenex Gemini 150x25 mmx10 um; mobile phase: [A: water (0.1% TFA)-B: ACN]; B %: 55%-95%, 10 min). The separated layers were lyophilized to give K101-C1340 (3.80 mg, 7.11 μmol, 31.17% yield, 96.78% purity, TFA salt) as a pale yellow solid.

LC-MS (m/z): 557.1 $[M+Na]^+$ $^1H$ NMR (400 MHz, MeOD) δ 7.58 (d, J=7.5 Hz, 1H), 7.54-7.51 (m, 1H), 7.38 (d, J=8.0 Hz, 1H), 7.19 (s, 1H), 7.17-7.12 (m, 1H), 7.10-7.05 (m, 1H), 5.59-5.54 (m, 1H), 4.58 (s, 2H), 4.17-4.09 (m, 1H), 3.99-3.90 (m, 2H), 3.17-3.11 (m, 1H), 3.02-2.96 (m, 1H), 2.55-2.46 (m, 1H), 2.45-2.36 (m, 1H), 2.04-1.92 (m, 2H), 1.78-1.71 (m, 3H), 1.43-1.32 (m, 1H), 1.04-0.97 (m, 6H), 0.83 (d, J=6.0 Hz, 3H), 0.78-0.74 (m, 1H).

Example 38: Synthesis Scheme of K101-C1341

The scheme for synthesis of compound K101-C1341 is illustrated below.

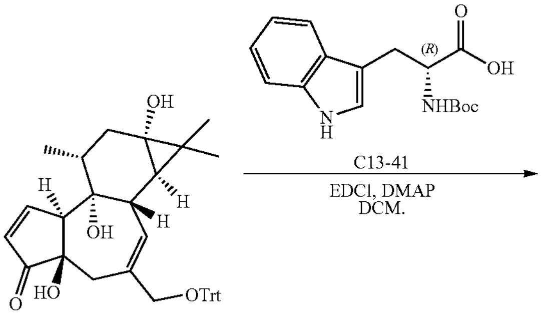

K101-C20Tr-B

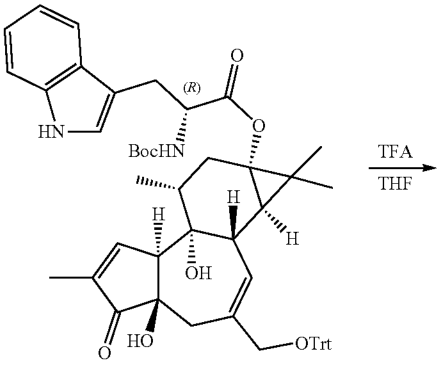

K101-C1341-A

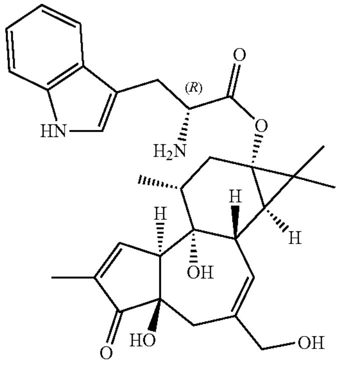

K101-C1341

Preparation of Compound K101-C1341-A. To a solution of K101-C20Tr-B (30.00 mg, 50.78 μmol, 1.00 eq) in DCM (1.00 mL) were added (2R)-2-(tert-butoxycarbonylamino)-3-(1H-indol-3-yl)propanoic acid (C13-41) (154.55 mg, 507.83 μmol, 10.00 eq), EDC (19.47 mg, 101.57 μmol, 2.00 eq) and DMAP (37.22 mg, 304.70 μmol, 6.00 eq). The mixture was stirred at 20° C. for 5 hr to give a colorless solution. LC-MS and TLC showed the reaction was complete. The reaction mixture was quenched with $H_2O$ (15 mL) and extracted with DCM (15 mL×5). The organic layers were dried over $Na_2SO_4$ and concentrated to give a yellow solid. The product was purified by prep-TLC (eluting with Petroleum ether: Ethyl acetate=2/1) to give K101-C1341-A (35.00 mg, 39.91 μmol, 67.35% yield) as a white solid.

Preparation of Compound K101-C1341. To a solution of K101-C1341-A (35.00 mg, 39.91 mol, 1.00 eq) in THF (2.00 mL) were added TFA (770.00 mg, 6.75 mmol, 500.00 uL, 169.21 eq) and Et3SiH (4.64 mg, 39.91 μmol, 6.36 uL, 1.00 eq). The mixture was stirred at 20° C. for 5 hr to give a colorless solution. The reaction mixture was concentrated and the resultant yellow oil dissolved with DCM (2 mL) followed by addition of TFA (0.5 mL). The mixture was stirred at 20° C. for 2 hr to give a yellow solution. The reaction mixture was concentrated and dissolved with DCM (2 mL) followed by addition of TFA (0.5 mL). This reaction mixture was stirred at 20° C. for 1 hr to give a yellow solution. LC-MS showed the reaction was complete. The reaction mixture was concentrated to give a yellow oil, which was then dissolved in MeOH (4 mL) and stirred at 20° C. for 14 hr to give a yellow liquid. The product was purified by prep-HPLC (column: Phenomenex Gemini 150×25 mm×10 um; mobile phase: [A: water (0.1% TFA)-B: ACN]; B %: 20%-50%, 10 min). The separated layers were lyophilized to give K101-C1341 (4.00 mg, 5.59 μmol, 14.01% yield, 90.7% purity, TFA salt) as a white solid.

LC-MS (m/z): 557.1 $[M+Na]^+$ $^1H$ NMR (400 MHz, MeOD) δ=7.61 (d, J=7.5 Hz, 1H), 7.57 (s, 1H), 7.42 (d, J=8.3 Hz, 1H), 7.26 (s, 1H), 7.23-7.10 (m, 2H), 5.60-5.50 (m, 1H), 4.33 (t, J=7.4 Hz, 1H), 4.06-3.92 (m, 2H), 3.60-3.45 (m, 1H), 3.22-3.13 (m, 1H), 3.05-2.95 (m, 1H), 2.59-2.38 (m, 2H), 2.17 (dd, J=6.8, 14.6 Hz, 1H), 2.04 (d, J=8.8 Hz, 1H), 1.77 (d, J=1.5 Hz, 3H), 1.63 (dd, J=10.5, 14.8 Hz, 1H), 1.40-1.25 (m, 2H), 1.04 (s, 3H), 0.93 (d, J=6.5 Hz, 3H), 0.87 (s, 3H), 0.69 (d, J=5.8 Hz, 1H)

Example 39: Synthesis Scheme of K101-C1342

The scheme for synthesis of compound K101-C1342 is illustrated below.

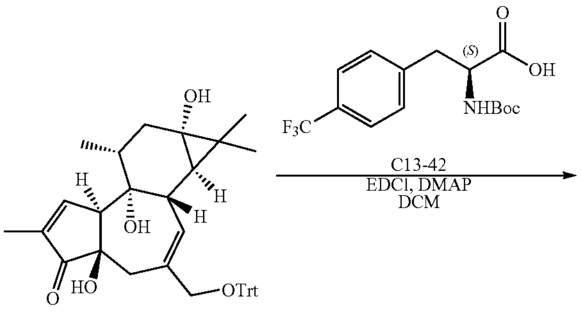

K101-C20Tr-B

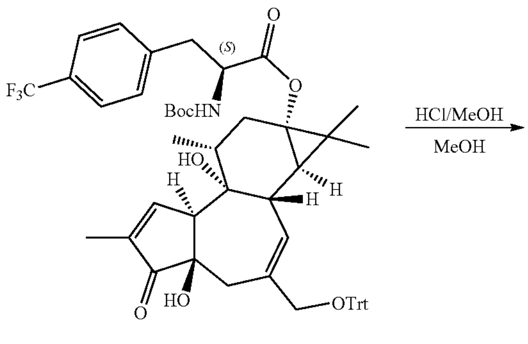

K101-C1342-A

-continued

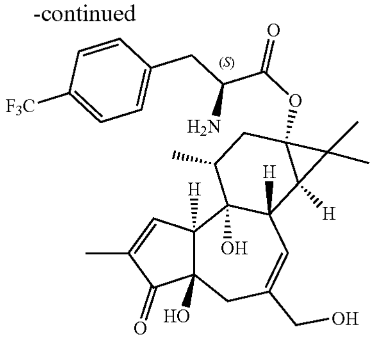

K101-C1342

Preparation of Compound K101-C1342-A. To a solution of K101-C20Tr-B (30.00 mg, 50.78 μmol, 1.00 eq) and C13-42 (25.39 mg, 76.17 μmol, 1.50 eq) in DCM (1.00 mL) were added EDC (58.41 mg, 304.68 μmol, 6.00 eq) and DMAP (18.61 mg, 152.35 μmol, 3.00 eq). The mixture was stirred at 20° C. for 14 h to give a yellow solution. The reaction was complete as detected by LC-MS. The reaction solution was combined with a second preparation, and diluted with $H_2O$ (10 mL) followed by extraction with DCM (10 mL×3). The combined organic layers were dried over $Na_2SO_4$, filtered, and concentrated under reduced pressure to give a yellow solid. The product was purified by prep-TLC (PE/EtOAc=2/1, $SiO_2$) to give K101-C1342-A (50.30 mg, 55.52 μmol, 93.44% yield) as a white solid.

Preparation of Compound K101-C1342. To a solution of K101-C1342-A (50.00 mg, 55.19 mol, 1.00 eq) in MeOH (500.00 uL) was added HCl/MeOH (4 M, 500.00 uL, 36.24 eq). The reaction was stirred at 20° C. for 3.5 hours to give a pale yellow solution. LC-MS showed the reaction was almost complete. The solution was adjusted to pH 8 with saturated aqueous $NaHCO_3$ and then extracted with DCM (2 ml×3). The combined organic layers were concentrated under reduced pressure to give a yellow solid. The product was purified by prep-HPLC (column: Phenomenex Gemini 150×25 mm×10 um; mobile phase: [A: water (0.1% TFA)-B: ACN]; B %: 25%-55%, 10 min) to give K101-C1342 (10.70 mg, 18.99 μmol, 34.40% yield, 98.84% purity, TFA salt) as a white solid.

LC-MS (m/z): 586.1 $[M+Na]^+$ $^1H$ NMR (400 MHz, MeOD) δ 7.71 (d, J=8.0 Hz, 2H), 7.56-7.51 (m, 3H), 5.62-5.57 (m, 1H), 4.47-4.40 (m, 1H), 3.94 (s, 2H), 3.47-4.40 (m, 1H), 3.25-3.18 (m, 1H), 3.18-3.13 (m, 1H), 3.07-2.99 (m, 1H), 2.57-2.47 (m, 1H), 2.45-2.36 (m, 1H), 2.17 (dd, J=7.2, 14.7 Hz, 1H), 2.07-1.98 (m, 1H), 1.78-1.73 (m, 3H), 1.53-1.43 (m, 1H), 1.10 (s, 3H), 1.06 (s, 3H), 0.96 (d, J=5.8 Hz, 1H), 0.91 (d, J=6.5 Hz, 3H).

Example 40: Synthesis Scheme of K101-C1343

The scheme for synthesis of compound K101-C1343 is illustrated below.

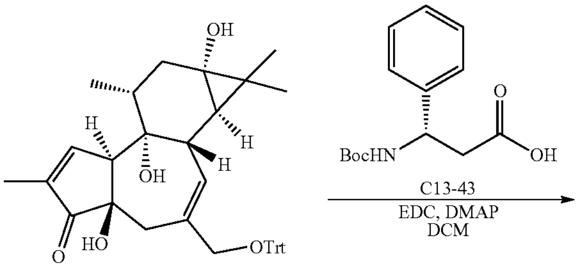

K101-C20Tr-B

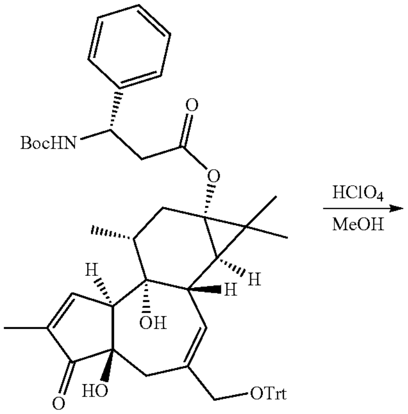

K101-C1343-A

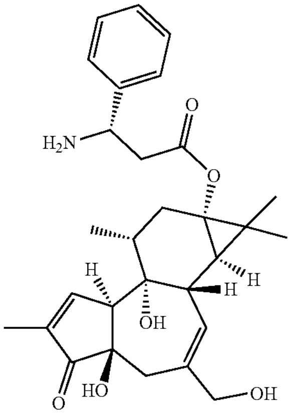

K101-C1343

Preparation of Compound K101-C1343-A. To a solution of K101-C20Tr-B (30.00 mg, 50.78 μmol, 1.00 eq) and C13-43 were added EDC (58.41 mg, 304.68 μmol, 6.00 eq) and DMAP (37.22 mg, 304.68 μmol, 6.00 eq). The reaction solution was stirred at 25° C. for 1 hour to give a brown solution. TLC (PE/EtOAc=1/1, $SiO_2$) showed the reaction was complete. The reaction solution was diluted with DCM (2 mL), washed with brine (1 mL), and dried over anhydrous $Na_2SO_4$.

The product was filtered and concentrated under reduced pressure to give the crude product as a brown gum. The product was purified by prep-TLC (PE/EtOAc=1/1, $SiO_2$) to give K101-C1343-A (33.30 mg, 78.25% yield) as a colorless gum.

Preparation of Compound K101-C1343. To a solution of K101-C1343-A (25.00 mg, 29.83 μmol, 1.00 eq) in MeOH (1.00 mL) was added HCl/MeOH (4 M, 1 mL), and the reaction solution stirred at 20° C. for 2.5 hours to give a clear solution. LC-MS showed the reaction was almost complete so the reaction solution was stirred at 20° C. for an additional 1 hr. The reaction solution was combined with a second preparation of the compound, and then cooled to 0° C. The solution was adjusted to pH 8 with saturated aqueous $NaHCO_3$. The solution was purified by prep-HPLC (column: Phenomenex Gemini 150×25 mm×10 um; mobile phase: [A: water (0.05% HCl)-B: ACN]; B %: 15%-45%, 10 min) to give K101-C1343 (7.60 mg, 47.02% yield, 98.2% purity, HCl salt) as a white solid.

LC-MS (m/z): 518.1 $[M+Na]^+$ $^1H$ NMR (400 MHz, $CD_3OD$) δ 7.53 (s, 1H), 7.50-7.43 (m, 5H), 5.57 (d, J=4.2 Hz, 1H), 4.73 (t, J=7.3 Hz, 1H), 4.00-3.88 (m, 2H), 3.18-3.04 (m, 3H), 3.01 (t, J=5.5 Hz, 1H), 2.56-2.46 (m, 1H), 2.44-2.36 (m, 1H), 2.11-1.93 (m, 2H), 1.78-1.71 (m, 3H), 1.38 (dd, J=10.1, 14.3 Hz, 1H), 1.01 (s, 3H), 0.96 (s, 3H), 0.90-0.80 (m, 4H).

Example 41: Synthesis Scheme of K101-C1344

The scheme for synthesis of compound K101-C1344 is illustrated below.

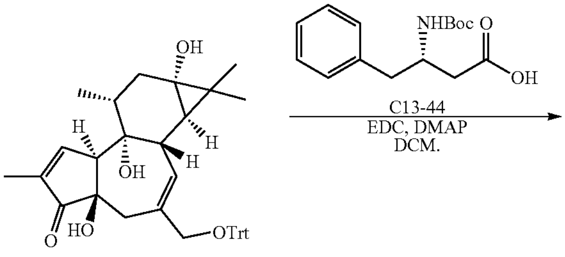

K101-C20Tr-B

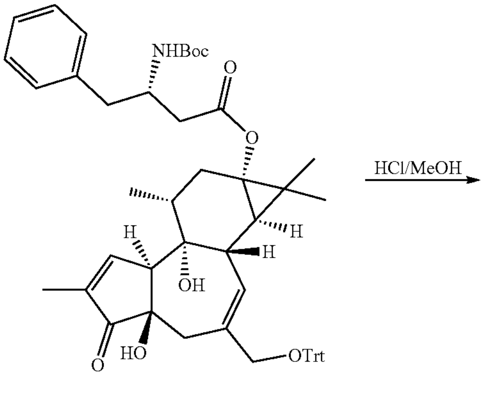

K101-C1344-A

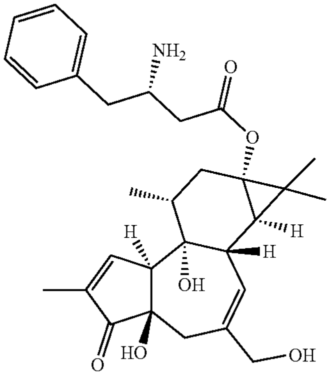

K101-C1344

Preparation of Compound K101-C1344-A. To a solution of K101-C20Tr-B (35.00 mg, 59.25 μmol, 1.00 eq) and C13-44 (41.37 mg, 148.12 μmol, 2.50 eg) in DCM (1.00 mL) were added EDC (68.15 mg, 355.48 μmol, 6.00 eg) and DMAP (21.71 mg, 177.74 μmol, 3.00 eq). The mixture was stirred at 20° C. for 18 hr to give a yellow solution. The reaction was complete as detected by LC-MS. The reaction solution was diluted with $H_2O$ (10 mL), extracted with DCM (10 mL×3), and the combined organic layers dried over $Na_2SO_4$. The solution was concentrated under reduced pressure and purified by prep-TLC ($SiO_2$, PE:EA=3:1). Concentration under reduced pressure yielded K101-C1344-A (43.60 mg, 51.17 μmol, 86.36% yield) as a white solid.

Preparation of Compound K101-C1344. To a solution of K101-C1344-A (35.00 mg, 41.08 μmol, 1.00 eg) in MeOH (500.00 uL) was added HCl/MeOH (4 M, 583.29 uL, 56.80 eq). The solution was stirred at 20° C. for 18 hr to give a yellow solution. The reaction was complete as detected by LC-MS. The reaction solution was diluted with $H_2O$ (10 mL) and extracted with DCM (10 mL×3). The combined organic layers were dried over $Na_2SO_4$ and concentrated under reduced pressure to give a yellow solid. The product was purified by prep-HPLC (column: Phenomenex Gemini 150×25 mm×10 um; mobile phase: [A: water (0.1% TFA)-B: ACN]; B %: 20%-50%, 10 min). The separated layers were lyophilized to give K101-C1344 (5.00 mg, 8.02 μmol, 19.52% yield, TFA salt) as a white solid.

LC-MS (m/z): 532.3 $[M+Na]^+$ $^1H$ NMR (400 MHz, $CD_3OD$) δ 7.53 (s, 1H), 7.40-7.37 (m, 2H), 7.34-7.33 (m, 1H), 7.29-7.27 (m, 2H), 5.59 (s, 1H), 3.98 (s, 2H), 3.88-3.85 (m, 1H), 3.15 (s, 1H), 3.06-3.03 (m, 2H), 2.95-2.93 (m, 1H), 2.72-2.64 (m, 2H), 2.55-2.44 (m, 2H), 2.12-1.98 (m, 2H), 1.75 (s, 3H), 1.59-1.55 (m, 1H), 1.30-1.25 (m, 3H), 1.14 (s, 3H), 1.06 (s, 3H), 0.91-0.89 (m, 3H), 0.84-0.83 (m, 1H).

Example 42: Synthesis Scheme of K101-C1345

The scheme for synthesis of compound K101-C1345 is illustrated below.

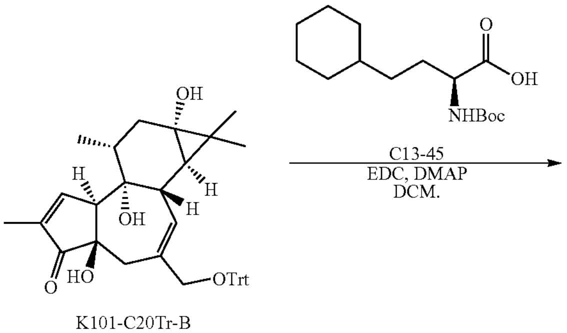

K101-C20Tr-B

-continued

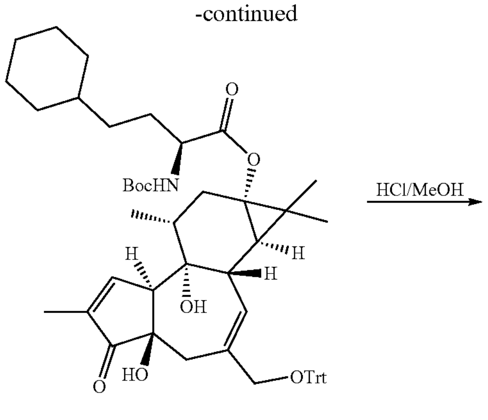

K101-C1345-A

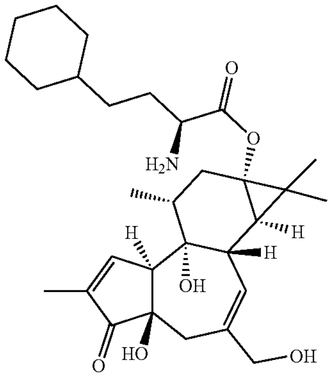

K101-C1345

Preparation of Compound K101-C1345-A. To a solution of K101-C20Tr-B (30.00 mg, 50.78 μmol, 1.00 eq) and C13-45 (36.23 mg, 126.96 μmol, 2.50 eq) in DCM (1.00 mL) were added EDC (48.68 mg, 253.91 μmol, 5.00 eq) and DMAP (18.61 mg, 152.35 μmol, 3.00 eq). The reaction mixture was stirred at 20° C. for 18 hr. The reaction was complete as detected by LC-MS. The reaction solution was diluted with $H_2O$ (10 mL) and extracted with DCM (8 mL×5). The combined organic layers were dried over $Na_2SO_4$ and concentrated under reduced pressure to give pale yellow solution. The product was purified by prep-TLC ($SiO_2$, PE:EA=3:1) to give K101-C1345-A (26.30 mg, 30.65 μmol, 60.36% yield) as a white solid.

Preparation of Compound K101-C1345. To a solution of K101-C1345-A (25.00 mg, 29.13 μmol, 1.00 eq) in MeOH (500.00 uL) was added HCl/MeOH (4 M, 7.28 uL, 1.00 eg). The solution was stirred at 20° C. for 18 hr to give a yellow solution. The reaction was complete as detected by LC-MS. The reaction solution was diluted with $H_2O$ (10 mL), neutralized with $NaHCO_3$ aqueous solution and then extracted with DCM (8 mL×5). The combined organic layers were dried over $Na_2SO_4$ and concentrated under reduced pressure to give a yellow solid. The residue was purified by prep-HPLC (column: Phenomenex Gemini 150×25 mm×10 um; mobile phase: [A: water (0.1% TFA)-B: ACN]; B %: 25%-55%, 10 min), and the separated layers lyophilized to give K101-C1345 (4.30 mg, 8.34 μmol, 28.63% yield) as a white solid.

LC-MS (m/z): 538.3 $[M+Na]^+$ $^1H$ NMR (400 MHz, $CD_3OD$) δ 7.56 (s, 1H), 5.62 (s, 1H), 5.49 (m, 1H), 4.02-3.95 (m, 3H), 3.16-3.06 (m, 2H), 2.56-2.44 (m, 2H), 2.39-2.22 (m, 1H), 2.04-1.94 (m, 3H), 1.76-1.57 (m, 9H), 1.30-1.25 (m, 7H), 1.18 (s, 3H), 1.01 (s, 3H), 0.99-0.93 (m, 5H).

Example 43: Synthesis Scheme of K101-C1346

The scheme for synthesis of compound K101-C1346 is illustrated below.

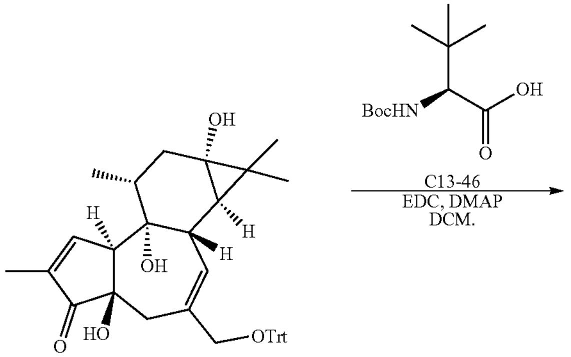

K101-C20Tr-B

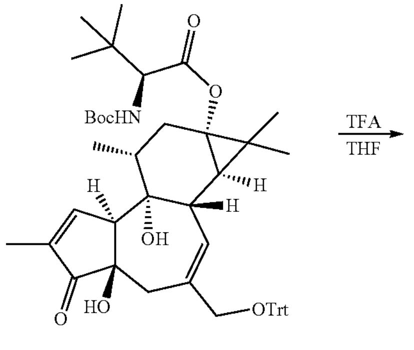

K101-C1346-A

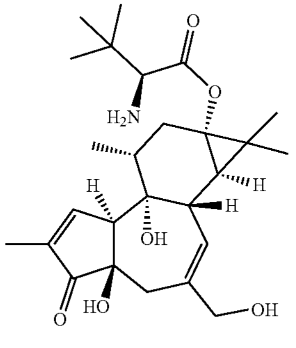

K101-C1346

Preparation of Compound K101-C1346-A. To a solution of K101-C20Tr-B (30.00 mg, 50.78 μmol, 1.00 eq) in DCM (1.00 mL) were added (2S)-2-(tert-butoxycarbonylamino)-3,3-dimethyl-butanoic acid (C13-46) (70.47 mg, 304.68 μmol, 6.00 eq) DMAP (43.43 mg, 355.46 μmol, 7.00 eq) and EDC (58.41 mg, 304.68 μmol, 6.00 eq). The mixture was stirred at 20° C. for 5 hr to give a yellow solution. TLC showed the reaction was complete. The reaction mixture was quenched with $H_2O$ (15 mL) and extracted with DCM (15 mL×5). The organic layers were dried over $Na_2SO_4$ and concentrated to give a yellow solid. The product was purified by prep-TLC (eluting with Petroleum ether: Ethyl acetate=3/1) to give K101-C1346-A (28.00 mg, 34.83 μmol, 68.58% yield) as a colorless solid.

Preparation of Compound K101-C1346. To a solution of K101-C1346-A (28.00 mg, 34.83 mol, 1.00 eq) in MeOH (500.00 uL) was added HCl/MeOH (4 M, 8.71 uL, 1.00 eq). The mixture was stirred at 20° C. for 19 hr to give a yellow solution. LC-MS showed the reaction was complete.

The reaction mixture was adjusted to pH 6 with saturated $NaHCO_3$ and the resultant product purified by prep-HPLC (column: Phenomenex Gemini 150×25 mm×10 um; mobile phase: [A: water (0.1% TFA)-B: ACN]; B %: 20%-50%, 10 min). The organic layers were lyophilized to give K101-C1346 (7.80 mg, 13.55 μmol, 38.91% yield, 100% purity, TFA salt) as a white solid.

LC-MS (m/z): 584.2 $[M+Na]^+$ $^1$H NMR (400 MHz, MeOD) δ=7.60-7.54 (m, 1H), 5.70-5.60 (m, 1H), 4.04-3.92 (m, 2H), 3.86 (s, 1H), 3.33-3.20 (m, 1H), 3.20-3.12 (m, 1H), 2.60-2.38 (m, 2H), 2.26 (dd, J=7.0, 14.6 Hz, 1H), 2.19-2.02 (m, 1H), 1.77 (d, J=1.5 Hz, 3H), 1.60 (dd, J=10.8, 14.6 Hz, 1H), 1.26 (s, 3H), 1.17 (s, 9H), 1.13 (s, 3H), 1.02 (d, J=5.8 Hz, 1H), 0.95 (d, J=6.3 Hz, 3H).

Example 44: Synthesis Scheme of K101-C1347

The scheme for synthesis of compound K101-C1347 is illustrated below.

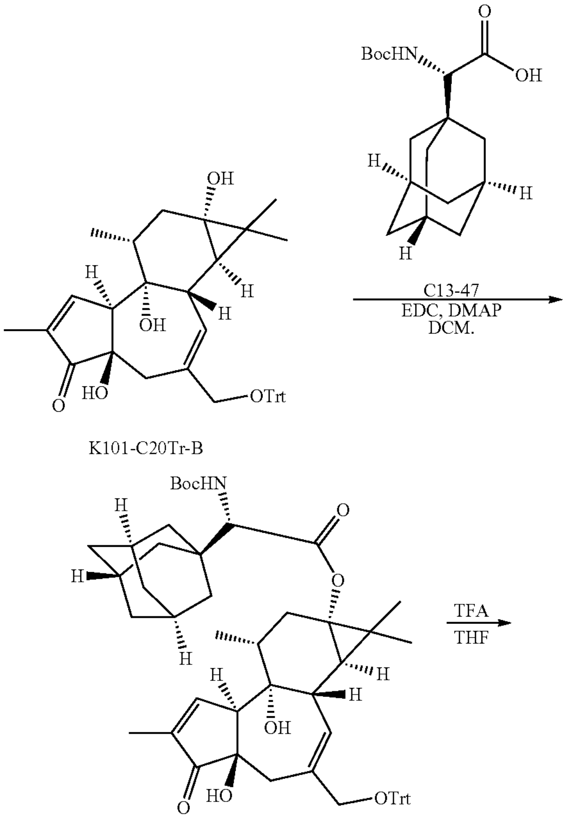

K101-C20Tr-B

K101-C1347-A

-continued

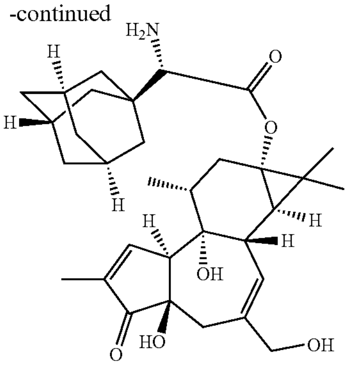

K101-C1347

Preparation of Compound K101-C1347-A. To a solution of K101-C20Tr-B (30.00 mg, 50.78 μmol, 1.00 eq) in DCM (2.00 mL) were added (2S)-2-(1-adamantyl)-2-(tert-butoxycarbonylamino) acetic acid (C13-47) (94.27 mg, 304.68 μmol, 6.00 eq), EDC (58.41 mg, 304.68 μmol, 6.00 eq) and DMAP (43.43 mg, 355.46 μmol, 7.00 eq). The mixture was stirred at 20° C. for 14 h to give a yellow solution. LC-MS and TLC showed the reaction was complete. The reaction mixture was quenched with $H_2O$ (15 mL) and extracted with DCM (15 mL×5). The organic layers were dried over $Na_2SO_4$ and concentrated to give a yellow solid. The product was purified by prep-TLC (eluting with Petroleum ether: Ethyl acetate=3/1) to give K101-C1347-A (13.00 mg, 14.74 μmol, 24.80% yield) as a white solid.

Preparation of Compound K101-C1347. To a solution of K101-C1347-A (13.00 mg, 14.74 mol, 1.00 eq) in THF (1.00 mL) were added TFA (500.55 mg, 4.39 mmol, 325.03 uL, 297.89 eq) and $Et_3SiH$ (1.71 mg, 14.74 μmol, 2.35 uL, 1.00 eq). The mixture was stirred at 20° C. for 3 h to give a colorless solution. The reaction mixture was concentrated, dissolved with DCM (2 mL) and then followed by addition of TFA (0.5 mL). The mixture was stirred at 20° C. for 2 h to give a yellow solution. LC-MS showed the reaction was complete. The reaction mixture was concentrated to give a yellow oil, which was dissolved with MeOH (2 mL) and stirred at 20° C. for 14 h to give a buff liquid. The product was purified by prep-HPLC (column: Phenomenex Gemini 150×25 mm×10 um; mobile phase: [A: water (0.1% TFA)-B: ACN]; B %: 25%-55%, 10 min). The separated layers were lyophilized to give K101-C1347 (6.50 mg, 9.94 μmol, 67.44% yield, 100% purity, TFA salt) as a white solid.

LC-MS (m/z): 562.3 $[M+Na]^+$ $^1$H NMR (400 MHz, MeOD) δ=7.62-7.55 (s, 1H), 5.70-5.60 (m, 1H), 4.05-3.90 (m, 2H), 3.75-3.56 (m, 1H), 3.25-3.15 (m, 1H), 3.16-3.08 (m, 1H), 2.62-2.38 (m, 2H), 2.27 (dd, J=6.9, 14.7 Hz, 1H), 2.15-2.06 (m, 4H), 1.91-1.53 (m, 16H), 1.27 (s, 3H), 1.13 (s, 3H), 1.03 (d, J=5.5 Hz, 1H), 0.96 (d, J=6.5 Hz, 3H)

Example 45: Synthesis Scheme of K101-C1348

The scheme for synthesis of compound K101-C1348 is illustrated below.

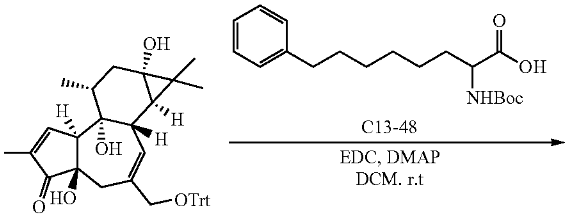

K101-C20Tr-B

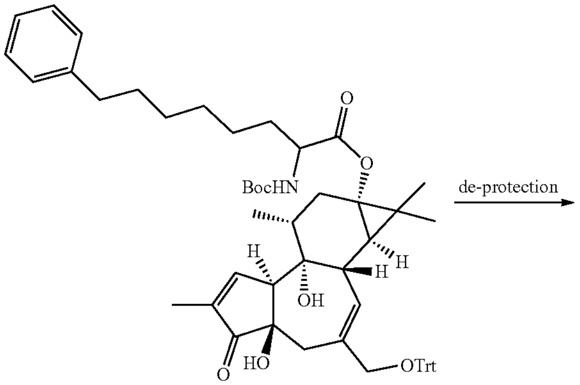

K101-C1348-A

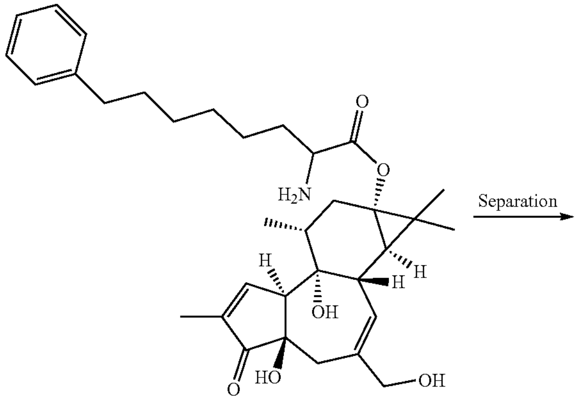

K101-C1348

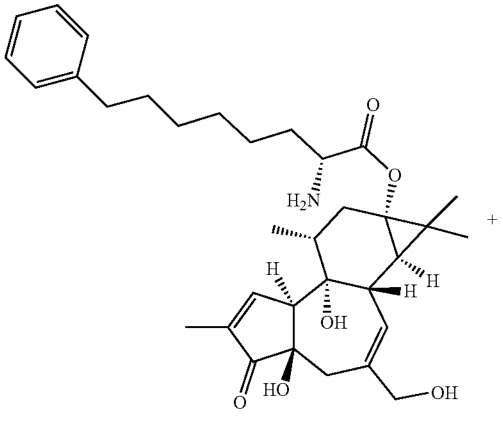

K101-C134801

-continued

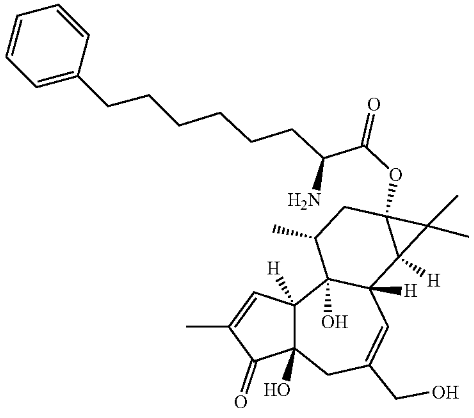

K101-C134802

Preparation of C13-48:

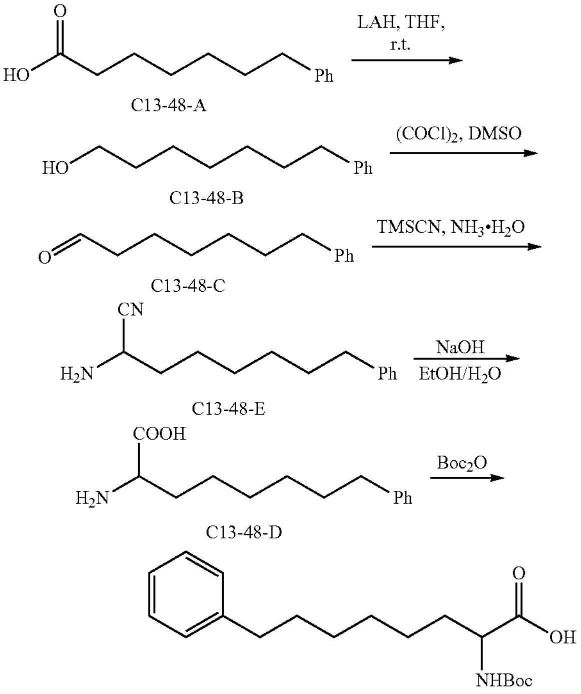

C13-48

Preparation of compound C13-48-B. $LiAlH_4$ (413.84 mg, 10.91 mmol, 1.50 eq) was suspended in THF (10.00 mL) at 0° C., then C13-48-A (1.50 g, 7.27 mmol, 1.00 eq) in THF (10.00 mL) was added dropwise at 0° C. The mixture was allowed to stir at 20° C. for 4 hr to give a brown solution. LC-MS showed the reaction was complete. Following quenching with $H_2O$ (0.5 mL), aqueous NaOH (0.5 mL, 15%) and $H_2O$ (1.5 mL) were added. The mixture was filtered on Celite and the filtrate was concentrated to give the 7-phenylheptan-1-ol (1.30 g, 6.76 mmol, 92.99% yield) as a yellow oil.

Preparation of compound C13-48-C. To a solution of oxalyl dichloride (1.72 g, 13.52 mmol, 1.18 mL, 2.00 eq) in DCM (20.00 mL) was added dropwise DMSO (2.64 g, 33.80 mmol, 2.64 mL, 5.00 eq) at −78° C. The mixture was stirred at −78° C. for 0.5 hr. Compound C13-48-B (1.30 g, 6.76 mmol, 1.00 eq) in DCM (10.00 mL) was added at −78° C. The mixture was stirred at −78° C. for 1 hr, and the $Et_3N$ (3.42 g, 33.80 mmol, 4.68 mL, 5.00 eq) was added dropwise at −78° C. The mixture was allowed to stir at 20° C. for 2.5 hr to give a yellow suspension. LC-MS and TLC (eluting with: PE/EtOAc=5/1) showed the reaction was complete. The reaction mixture was quenched with $H_2O$ (30 mL) and extracted with DCM (50 mLx3). The organic layers were dried over $Na_2SO_4$ and concentrated to give the crude product. The product was purified by column chromatography on silica gel (eluting with: PE/EtOAc=100% PE to 5/1) to give C13-48-C (1.10 g, 5.78 mmol, 85.52% yield) as a yellow oil.

Preparation of compound C13-48-E. To a solution of C13-48-C (1.05 g, 5.52 mmol, 1.00 eq) in EtOH (10.00 mL) were added trimethylsilyl cyanide (TMSCN) (547.46 mg, 5.52 mmol, 692.99 uL, 1.00 eq) and $NH_3 \cdot H_2O$ (851.01 mg, 6.07 mmol, 935.18 uL, 25% purity, 1.10 eq). The mixture was stirred at 20° C. for 7 hr to give a yellow solution. LC-MS showed the reaction was complete. The reaction mixture was quenched with $H_2O$ (30 mL) and extracted with DCM (50 mLx3). The organic layers were dried over $Na_2SO_4$ and concentrated to give C13-48-E (1.10 g, crude) as a yellow oil.

Preparation of compound C13-48-D. To a solution of C13-48-E (1.10 g, 5.09 mmol, 1.00 eq) in EtOH (5.00 mL) was added NaOH (610.21 mg, 15.26 mmol, 3.00 eq). The mixture was stirred at 20° C. for 2 hr followed by the addition of $H_2O$ (1.00 mL). The mixture was stirred at 90° C. for 2 hr to give a yellow solution. LC-MS showed the reaction was complete.

Preparation of Compound C13-48. Boc anhydride ($Boc_2O$) (2.23 g, 10.20 mmol, 2.34 mL, 2.00 eq) was added to the preparation of C13-48-E, and the mixture stirred at 20° C. for 2 hr to give a yellow suspension. LC-MS and TLC (eluting with: 100% EtOAc) showed the reaction was complete. The mixture was combined with a second preparation, and the combined mixture was diluted with $H_2O$ (20 mL) followed by extraction with PE (20 mLx3). The water layer was adjusted to pH 5 with HCl (1N) and extracted with EtOAc (30 mLx3). The organic layers were dried over $Na_2SO_4$ and concentrated to give the crude product. The product was purified by column chromatography on silica gel (eluting with: PE/EtOAc=1/1 to 100% EtOAc) to give C13-48 (700.00 mg, 2.09 mmol, 40.92% yield) as a yellow oil.

Preparation of Compound K101-C1348-A. To a solution of K101-C20Tr-B (30.00 mg, 50.78 μmol, 1.00 eq) in DCM (2.00 mL) were added C13-48 (34.07 mg, 101.56 μmol, 2.00 eq), DMAP (24.82 mg, 203.12 μmol, 4.00 eq), HOBt (13.72 mg, 101.56 μmol, 2.00 eq) and EDC (19.47 mg, 101.56 μmol, 2.00 eq). The mixture was stirred at 10° C. for 12 hr to give a yellow solution. LC-MS and TLC (eluting with: PE/EtOAc=2/1) showed the reaction was complete. The mixture was combined with a second preparation, and the combined mixture was quenched with saturated $NaHCO_3$ (10 mL) followed by extraction with DCM (20 mLx3). The organic layers were dried over $Na_2SO_4$ and concentrated to give the crude product. The product was purified by prep-TLC (eluting with: PE/EtOAc=2/1) to give K101-C1348-A (18.00 mg, 19.82 μmol, 39.03% yield) as a white solid.

$^1H$ NMR (400 MHz, $CDCl_3$) δ 7.57 (s, 1H), 7.44-7.42 (m, 5H), 7.31-7.29 (m, 7H), 7.24-7.18 (m, 8H), 5.59-5.58 (m, 1H), 3.51-3.50 (m, 2H), 3.28 (s, 1H), 2.93 (s, 1H), 2.60-2.56 (m, 2H), 2.50-2.42 (m, 1H), 2.05-1.99 (m, 2H), 1.97-1.95 (m, 3H), 1.77 (s, 2H), 1.55-1.54 (m, 2H), 1.34 (s, 9H), 1.25-1.19 (m, 12H), 1.08 (s, 3H), 0.87-0.79 (m, 4H).

Preparation of Compound K101-C1348 (as a mixture of K101-C134801 and K101-C134802). To a solution of K101-C1348-A (48.00 mg, 52.85 μmol, 1.00 eg) in THF (2.00 mL) was added TFA (6.03 mg, 52.85 μmol, 3.91 uL, 1.00 eq). The mixture was stirred at 10° C. for 12 hr to give a yellow solution. LC-MS and TLC (eluting with: EtOAc/MeOH=10/1) showed the reaction was complete. The reaction mixture was concentrated by $N_2$ and the resultant product dissolved in MeOH (30 mL). The reaction mixture was stirred at 20° C. for 12 hr. After the mixture was concentrated, the product of K101-C1348 was purified by prep- TLC (eluting with: EtOAc/MeOH=10/1) to give K101-C1348 as a mixture of stereoisomers of K101-C134801 (11.10 mg, 19.62 μmol, 37.12% yield, 100% purity) and K101-C134802 (10.30 mg, 17.73 μmol, 33.55% yield, 97.4% purity), each as a white solid.

K101-C134801: LC-MS (m/z): 588.2 $[M+Na]^+$

K101-C134801: $^1H$ NMR (400 MHz, $CD_3OD$) δ 7.53 (s, 1H), 7.30-7.10 (m, 5H), 5.65-5.55 (m, 1H), 4.00-3.90 (m, 2H), 3.50-3.45 (m, 1H), 3.25-3.20 (m, 1H), 3.15-3.05 (m, 1H), 2.65-2.55 (m, 2H), 2.55-2.40 (m, 2H), 2.20-1.95 (m, 2H), 1.807-1.55 (m, 8H), 1.40-1.25 (m, 6H), 1.20 (s, 3H), 1.10 (s, 3H), 0.95-0.85 (m, 4H).

K101-C134802: LC-MS (m/z): 588.3 $[M+Na]^+$

K101-C134802: $^1H$ NMR (400 MHz, $CD_3OD$) δ 7.53 (s, 1H), 7.30-7.10 (m, 5H), 5.65-5.55 (m, 1H), 4.0-3.85 (m, 2H), 3.70-3.60 (m, 1H), 3.20-3.10 (m, 1H), 3.05-3.0 (m, 1H), 2.70-2.55 (m, 2H), 2.55-2.40 (m, 2H), 2.15-2.15 (m, 2H), 1.85-1.45 (m, 8H), 1.45-1.30 (m, 6H), 1.20 (s, 3H), 1.09 (s, 3H), 0.95-0.90 (m, 4H).

Example 45A: Synthesis Scheme of K101-C134801

The scheme for synthesis of compound K101-C134801 is illustrated below.

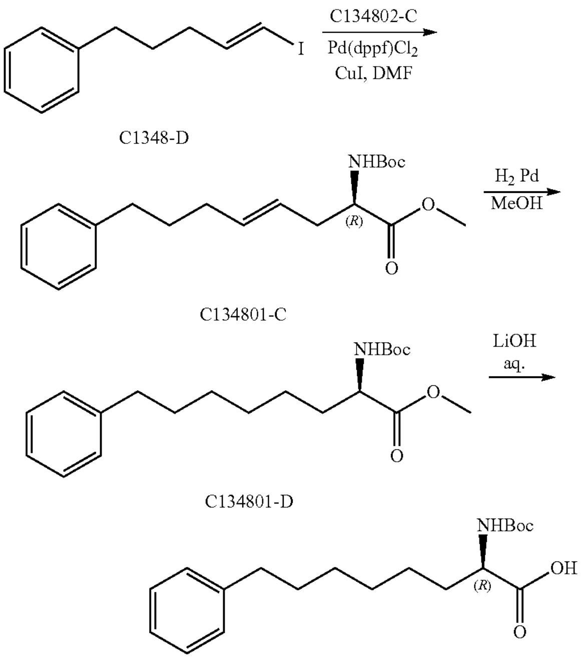

C1348-D

C134801-C

C134801-D

BB-C134801

-continued

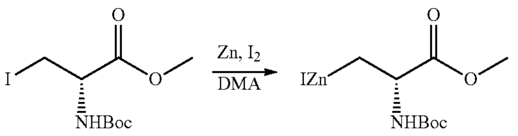

C134801-A C134801-B

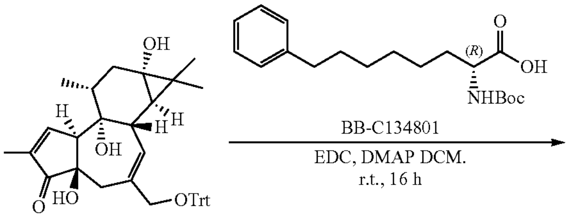

K101-C20Tr-B

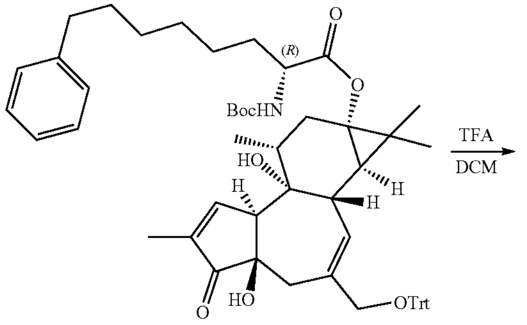

K101-C134801-A

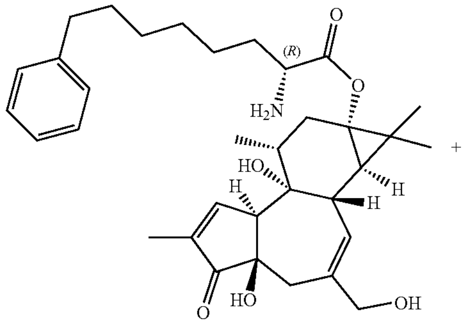

K101-C134801

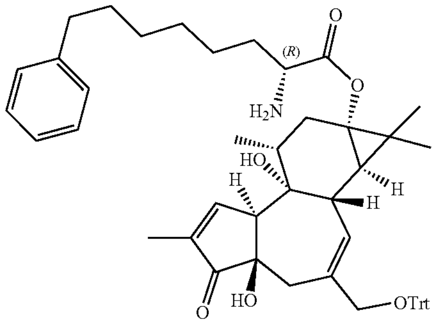

K101-C134801-C

-continued

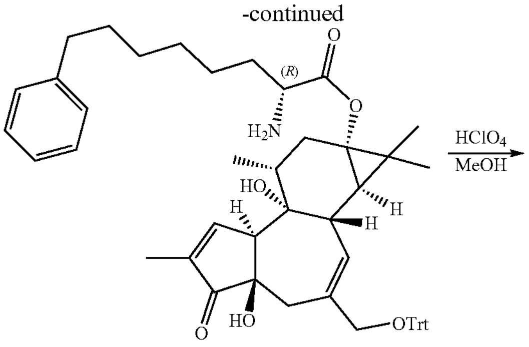

K101-C134801-C

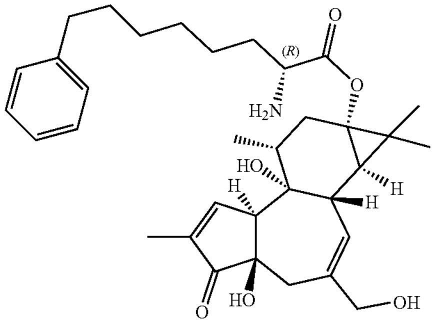

K101-C134801

Preparation of compound C134801-C. To a solution of C1348-D (2 g, 7.35 mmol, 1 eq) in DMA (2 mL) were added CuI (139.97 mg, 734.96 μmol, 0.1 eq) and C134801-B (4.06 g, 10.29 mmol, 1.4 eq) and Pd(dppf)$Cl_2$ (537.77 mg, 734.96 μmol, 0.1 eq) under $N_2$. The mixture was stirred under $N_2$ at 90° C. for 5 hr to give a black suspension. LCMS and TLC (eluting with: PE/EtOAc=3/1) showed the reaction was complete. The reaction mixture was quenched with $H_2O$ (100 mL) and extracted with MBTE (40 mL×3). The organic layers were dried over $Na_2SO_4$ and concentrated to give the crude product. The crude product was purified by a flash column (eluting with: PE/EtOAc=100% PE to 20%) to give C134801-C (750 mg, 2.16 mmol, 29.37% yield) as a yellow oil.

$^{1}$H NMR (400 MHz, $CDCl_3$): δ 7.30-7.20 (m, 2H), 7.20-7.16 (m, 3H), 5.58-5.51 (m, 1H), 5.34-5.27 (m, 1H), 5.02-5.00 (m, 1H), 4.37-4.33 (m, 1H), 3.73 (s, 3H), 2.62-2.58 (m, 2H), 2.46-2.44 (m, 2H), 2.07-2.02 (m, 2H), 1.70-1.66 (m, 2H), 1.44 (s, 9H).

Preparation of compound C134801-D. To a solution of C134801-C (0.75 g, 2.16 mmol, 1 eq) in MeOH (15 mL) was added Pd/C (500 mg, 2.16 mmol, 50% purity, 1 eq) under $N_2$. The suspension was degassed under vacuum and purged with $H_2$ several times. The mixture was stirred under $H_2$ (15 psi) at 20° C. for 12 hours. LCMS showed the reaction was complete. The reaction mixture was filtered on celite. The filtrate was concentrated to give C134801-D (750 mg, 2.15 mmol, 99.42% yield) as a black oil, which was used for next step without further purification.

$^{1}$H NMR (400 MHz, $CDCl_3$): δ 7.29-7.26 (m, 2H), 7.19-7.16 (m, 3H), 4.99-4.84 (m, 1H), 4.29-4.28 (m, 1H), 3.73 (s, 3H), 2.61-2.51 (m, 2H), 1.78-1.60 (m, 4H), 1.45 (s, 9H), 1.33-1.28 (m, 6H).

Preparation of compound BB-C134801. To a solution of C134801-D (750 mg, 2.15 mmol, 1 eq) in THF (5 mL)/$H_2O$ (1 mL) was added LiOH·$H_2O$ (90.06 mg, 2.15 mmol, 1 eq) at 0° C. The mixture was allowed to stir at 20° C. for 12 hr to give a yellow solution. LCMS showed the reaction was complete. The reaction mixture was acidified to pH=4 with HCl (1N) and extracted with MBTE (20 mL×3). The organic layers were dried over $Na_2SO_4$ and concentrated to give BB-C134801 (700 mg, 2.09 mmol, 97.24% yield) as a yellow oil, which was used for next step without further purification.

Preparation of compound C134801-B. Zinc (6 g) was treated with 1N HCl aqueous (30 mL) with stirring for 10 min. Then it was filtered and washed with water (30 mL), EtOH (30 mL) and toluene (30 mL) in sequence, dried in vacuum to afford the zinc powder for next step. A mixture of activated Zn (2.62 g, 40.11 mmol, 4 eq) and I2 (127.24 mg, 501.32 μmol, 100.98 uL, 0.05 eq) in DMA (10 mL) was stirred at 20° C. for 5 min. Then C134801-A (3.3 g, 10.03 mmol, 1 eq) in DMA (10 mL) was added dropwise. The reaction mixture was stirred at 20° C. for 25 min to give a black suspension. The reaction mixture (about 0.5015 mmol/mL) was used for next step without further purification.

Preparation of compound K101-C134801-A. To a solution of K101-C20Tr-B (200 mg, 338.55 μmol, 1 eq) in DCM (3 mL) were added BB-C134801 (193.06 mg, 575.54 μmol, 1.7 eq), DMAP (165.44 mg, 1.35 mmol, 4 eq), HOBt (50.32 mg, 372.41 μmol, 1.1 eq) and EDCI (110.33 mg, 575.54 μmol, 1.7 eq). The mixture was stirred at 20° C. for 12 hr to give a yellow solution. LCMS showed the desired mass was found, and K101-C20Tr-B was remained. The mixture was stirred at 20° C. for 12 hr again. LCMS showed the desired mass was found, and K101-C20Tr-B was remained. The mixture was stirred at 20° C. for 12 hr to give a yellow solution again. LCMS and TLC (eluting with: PE/EtOAc=2/1) showed the reaction was complete. The reaction mixture was quenched with $H_2O$ (10 mL) and extracted with MBTE (15 mL×3). The organic layers were dried over $Na_2SO_4$ and concentrated to give the crude product. The crude product was purified by flash column (eluting with: PE/EtOAc=100% PE to 40%) to give K101-C134801-A (210 mg, 231.23 μmol, 68.30% yield) as a yellow solid.

$^1$H NMR (400 MHz, $CDCl_3$) δ 7.58 (s, 1H), 7.44-7.42 (m, 6H), 7.31-7.26 (m, 7H), 7.26-7.17 (m, 7H), 5.60-5.59 (m, 1H), 5.26-5.17 (m, 1H), 5.95-5.93 (m, 1H), 4.28-4.27 (m, 1H), 3.52 (s, 2H), 3.27 (s, 1H), 2.94 (s, 1H), 2.61-2.43 (m, 5H), 2.09-2.05 (m, 1H), 2.04-1.99 (m, 1H), 1.78-1.77 (m, 4H), 1.58-1.56 (m, 1H), 1.54-1.52 (m, 1H), 1.44 (s, 9H), 1.33-1.28 (m, 6H), 1.19 (s, 3H), 1.08 (s, 3H), 0.88-0.78 (m, 4H).

Preparation of compound K101-C134801 and K101-C134801-C. To a solution of K101-C134801-A (610.00 mg, 671.68 μmol, 1.00 eq) in DCM (5 mL) was added TFA (2.76 g, 24.23 mmol, 1.79 mL, 36.08 eq). The mixture was stirred at 20° C. for 1 hr to give a yellow solution. LCMS and TLC (eluting with: EtOAc/MeOH=10/1) showed the reaction was complete. The reaction mixture was concentrated by purging with $N_2$. The residue from concentration was dissolved in MeOH (50 mL). The reaction mixture was stirred at 40° C. for 12 hr. LCMS showed the reaction was complete. The reaction mixture was concentrated to give K101-C134801 (158 mg, 255.88 μmol, 38.10% yield, 91.62% purity) as a white solid, which was the final product, and K101-C134801-C (130 mg, 160.88 μmol, 23.95% yield) as a yellow solid, which was an intermediate.

K101-C134801: LC-MS (m/z): 588.2 $[M+Na]^+$

K101-C134801: $^1$H NMR (400 MHz, $CD_3OD$) δ 7.56 (s, 1H), 7.30-7.10 (m, 5H), 5.65-5.55 (m, 1H), 4.00-3.90 (m, 2H), 3.50-3.45 (m, 1H), 3.25-3.20 (m, 1H), 3.15-3.05 (m, 1H), 2.65-2.40 (m, 4H), 2.20-1.95 (m, 2H), 1.807-1.55 (m, 8H), 1.40-1.25 (m, 6H), 1.20 (s, 3H), 1.10 (s, 3H), 0.95-0.85 (m, 4H).

K101-C134801-C: $^1$H NMR (400 MHz, $CDCl_3$) δ 7.51 (s, 1H), 7.36-7.35 (m, 6H), 7.24-7.22 (m, 7H), 7.18-7.10 (m, 7H), 5.54 (s, 1H), 5.26 (brs, 1H), 3.45-3.42 (m, 2H), 3.36-3.34 (m, 1H), 3.21 (s, 1H), 2.87 (s, 1H), 2.54-2.36 (m, 4H), 1.99-1.97 (m, 3H), 1.71 (s, 3H), 1.27-1.21 (m, 6H), 1.13 (s, 3H), 1.01 (s, 3H), 0.81-0.71 (m, 4H).

Preparation of compound K101-C134801. To a solution of K101-C134801-C (130 mg, 160.88 μmol, 1 eq) in MeOH (5 mL) was added $HClO_4$ (32.32 mg, 321.76 μmol, 19.47 uL, 2 eq) at 0° C. The mixture was stirred at 0° C. for 0.5 hr to give a yellow solution. LCMS and TLC (eluting with: EtOAc=10/1) showed the reaction was complete. The reaction mixture was quenched with saturated $NaHCO_3$ (10 mL) and extracted with EtOAc (20 mL×3). The organic layers were dried over $Na_2SO_4$ and concentrated to give the crude product. The crude product was purified by prep-TLC (eluting with: EtOAc=10/1) to give K101-C134801 (20.5 mg, 30.07 μmol, 18.69% yield, 82.99% purity) as a white solid LC-MS (m/z): 588.2 [M+Na]+

$^1$H NMR (400 MHz, $CD_3OD$): δ 7.56 (s, 1H), 7.30-7.10 (m, 5H), 5.65-5.55 (m, 1H), 4.00-3.90 (m, 2H), 3.50-3.45 (m, 1H), 3.25-3.20 (m, 1H), 3.15-3.05 (m, 1H), 2.65-2.40 (m, 4H), 2.20-1.95 (m, 2H), 1.807-1.55 (m, 8H), 1.40-1.25 (m, 6H), 1.20 (s, 3H), 1.10 (s, 3H), 0.95-0.85 (m, 4H).

Example 45B: Synthesis Scheme of K101-C134802

The scheme for synthesis of compound K101-C134802 is illustrated below.

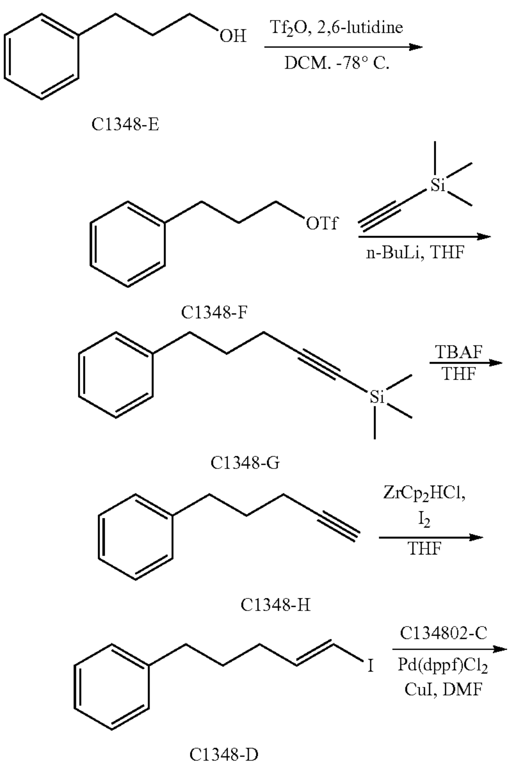

C1348-E

C1348-F

C1348-G

C1348-H

C1348-D

-continued

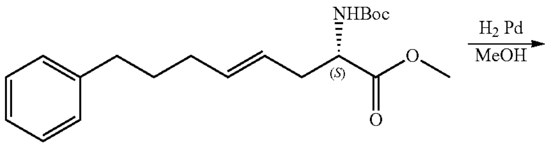

C134802-D

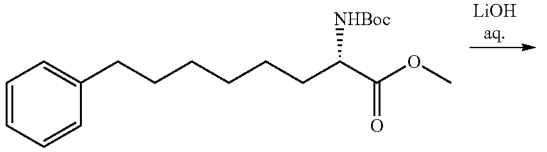

C134802-E

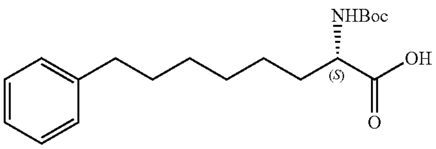

BB-C134802

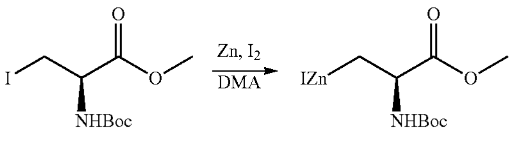

C134802-B C134802-C

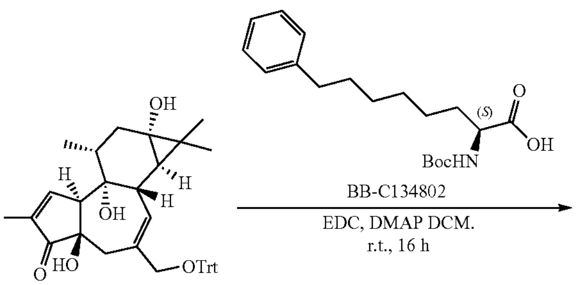

K101-C20Tr-B

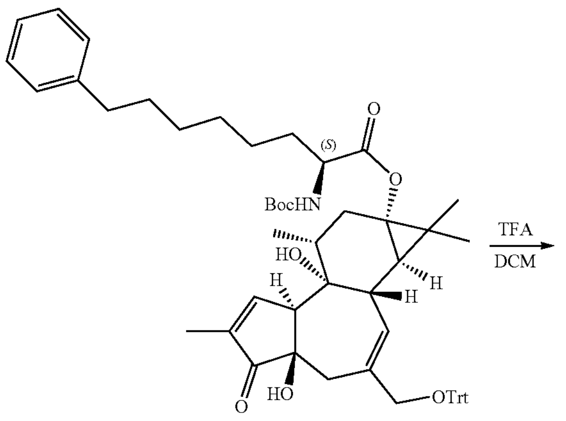

K101-C134802-A

-continued

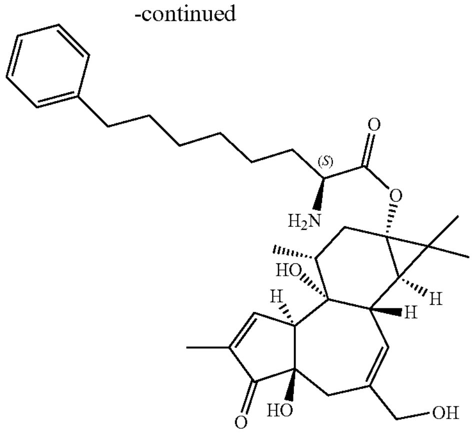

K101-C134802

Preparation of compound C1348-F. To a solution of C1348-E (20 g, 146.85 mmol, 20.00 mL, 1 eq) in DCM (200 mL) was added 2,4-lutidine (25.18 g, 234.96 mmol, 27.16 mL, 1.6 eq) at −78° C. Then triflic anhydride ($Tf_2O$) (45.58 g, 161.54 mmol, 26.65 mL, 1.1 eq) was added dropwise at −78° C. The mixture was stirred at −78° C. for 0.5 hr to give a yellow suspension. TLC (eluting with: PE/EtOAc=3/1) showed the reaction was complete. The reaction mixture was diluted with PE (40 mL). The mixture was poured into silica gel and washed with PE/EtOAc (4 L, 4/1) to give C1348-F (30.5 g, 113.70 mmol, 77.42% yield) as yellow oil.

Preparation of compound C1348-G. To a solution of ethynyl(trimethyl)silane (15.25 g, 155.30 mmol, 21.51 mL, 1.49 eq) in THF (200 mL) was added dropwise n-BuLi (2.5 M, 51.67 mL, 1.24 eq) at −78° C. The mixture was warmed to 0° C. for 30 min. Then C1348-F (28 g, 104.38 mmol, 1 eq) was added dropwise at −78° C. The mixture was warmed to 0° C. for 1 hr to give a yellow solution. TLC (eluting with: PE/EtOAc=10/1) showed the reaction was complete. The reaction mixture was quenched with saturated $NH_4Cl$ (200 mL) and extracted with MBTE (150 mL×2). The organic layers were dried over $Na_2SO_4$ and concentrated to give C1348-G (25 g, crude) as a yellow oil, which was used for next step without further purification.

$^1H$ NMR (400 MHz, $CDCl_3$): δ 7.30-7.18 (m, 5H), 3.80-3.70 (m, 1H), 2.80-2.69 (m, 2H), 2.26-2.22 (m, 2H), 1.89-1.84 (m, 2H), 0.23-0.09 (m, 9H).

Preparation of compound C1348-H. To a solution of C1348-G (25 g, 115.53 mmol, 1 eq) in THF (50 mL) was added tetra-n-butylammonium fluoride (TBAF) (1 M, 150.19 mL, 1.3 eq). The mixture was stirred at 20° C. for 1 hr to give a yellow solution. TLC (eluting with: PE/EtOAc=10/1) showed the reaction was complete. The reaction mixture was quenched with $H_2O$ (300 mL) and extracted with EtOAc (150×3). The organic layers were dried over $Na_2SO_4$ and concentrated to give the crude product. The crude product was purified by a flash column (eluting with: PE/EtOAc=100% PE to 5%) to give C1348-H (9.5 g, 65.88 mmol, 57.02% yield) as a colorless oil.

$^1H$ NMR (400 MHz, $CDCl_3$): δ 7.32-7.13 (m, 5H), 2.74-2.65 (m, 2H), 2.14-2.11 (m, 5H), 1.93 (s, 1H), 1.80-1.67 (m, 2H).

Preparation of compound C1348-D. To a solution of C1348-H (3 g, 20.80 mmol, 1 eq) in THF (50 mL) was added $ZrCp_2HCl$ (8.88 g, 33.28 mmol, 1.6 eq) at 0° C. The mixture was stirred at 0° C. for 2.5 hr, then stirred at 20° C. for 1 hr. $I_2$ (6.34 g, 24.96 mmol, 5.03 mL, 1.2 eq) in THF (10 mL)

was added at −78° C. The mixture was stirred at −78° C. for 1 hr. The mixture was allowed to stir at 0° C. for 1 hr to give a brown suspension. TLC (eluting with: PE=100%) showed the reaction was completed. The reaction mixture was quenched with HCl (0.1N, 200 mL). The mixture was extracted with EtOAc (30 mL×3). The organic layers were dried over $Na_2SO_4$ and concentrated to give the crude product. The crude product was purified by column silica (eluting with: PE=100%) to give C1348-D (3.8 g, 13.96 mmol, 67.13% yield) as a yellow oil.

$^1$H NMR (400 MHz, $CDCl_3$): δ 7.34-7.21 (m, 2H), 7.19-7.15 (m, 3H), 6.55-6.51 (m, 1H), 6.02-5.99 (m, 1H), 2.64-2.60 (m, 2H), 2.10-2.07 (m, 2H), 1.73-1.71 (m, 2H).

Preparation of compound C134802-D. To a solution of C134802-C (4.35 g, 11.02 mmol, 1.5 eq) in DMA (10 mL) were added CuI (139.97 mg, 734.96 μmol, 0.1 eq) and C1348-D (2 g, 7.35 mmol, 1 eq) and Pd(dppf)$Cl_2$ (537.77 mg, 734.96 μmol, 0.1 eq) under $N_2$. The mixture was stirred under $N_2$ at 90° C. for 12 hr to give a black suspension. LCMS and TLC (eluting with: PE/EtOAc=4/1) showed the reaction was complete. The reaction mixture was quenched with $H_2O$ (200 mL) and extracted with MBTE (100 mL×3). The organic layers were dried over $Na_2SO_4$ and concentrated to give the crude product. The crude product was purified by flash column (eluting with: PE/EtOAc=100% PE to 10%) to give C134802-D (1 g, 2.88 mmol, 39.16% yield) as a yellow oil.

$^1$H NMR (400 MHz, $CDCl_3$) δ 7.30-7.27 (m, 1H), 7.20-7.16 (m, 1H), 5.58-5.1 (m, 1H), 5.34-5.26 (m, 1H), 5.02-5.00 (m, 2H), 4.37-4.32 (m, 1H), 3.73 (s, 3H), 2.62-2.58 (m, 2H), 2.48-2.44 (m, 2H), 2.07-2.02 (m, 2H), 1.71-1.66 (m, 2H), 1.44 (s, 9H).

Preparation of compound C134802-E. To a solution of C134802-D (1 g, 2.88 mmol, 1 eq) in MeOH (20 mL) was added Pd/C (200 mg, 2.88 mmol, 50% purity, 1 eq) under $N_2$. The suspension was degassed under vacuum and purged with $H_2$ several times. The mixture was stirred under $H_2$ (15 psi) at 20° C. for 12 hours to give a yellow solution. LCMS and TLC (eluting with: PE/EtOAc=4/1) showed the reaction was complete. The reaction mixture was filtered on celite and washed with MeOH (60 mL). The filtrate was concentrated to give C134802-E (800 mg, 2.29 mmol, 79.54% yield) as a yellow oil, which was used for next step without further purification.

$^1$H NMR (400 MHz, $CDCl_3$): δ 7.31-6.98 (m, 5H), 5.05-4.98 (m, 1H), 4.31-4.26 (m, 1H), 3.73 (s, 3H), 2.61-2.57 (m, 2H), 1.76-1.62 (m, 4H), 1.44 (s, 9H), 1.33-1.22 (m, 4H).

Preparation of compound BB-C134802. To a solution of C134802-E (700 mg, 2.00 mmol, 1 eq) in THF (10 mL)/$H_2O$ (1.4 mL) was added LiOH·$H_2O$ (84.06 mg, 2.00 mmol, 1 eq) at 0° C. The mixture was allowed to stir at 25° C. for 12 hr to give a yellow solution. LCMS and TLC (eluting with: EtOAc=100%) showed the reaction was complete. The reaction mixture was extracted with MBTE (20 mL). The water layer was acidified to pH=3 with HCl (0.5N) and extracted with EtOAc (30 mL×3). The organic layers were dried over $Na_2SO_4$ and concentrated to give BB-C134802 (560 mg, 1.61 mmol, 80.54% yield, 96.63% purity, 98.7% ee %) as a yellow oil.

$^1$H NMR (400 MHz, $CDCl_3$): δ 7.28-7.16 (m, 5H), 7.05-7.03 (m, 1H), 3.87-3.81 (m, 1H), 2.57-2.55 (m, 2H), 1.61-1.53 (m, 4H), 1.37 (s, 9H), 1.32-1.18 (m, 6H).

Preparation of compound K101-C134802-A. To a solution of K101-C20Tr-B (200 mg, 338.55 μmol, 1.00 eq) in DCM (5 mL) were added BB-C134802 (136.28 mg, 406.27 μmol, 1.2 eq), DMAP (165.45 mg, 1.35 mmol, 4.00 eq), HOBt (48.03 mg, 355.48 μmol, 1.05 eq) and EDCI (77.88 mg, 406.27 μmol, 1.2 eq). The mixture was stirred at 20° C. for 12 hr to give a yellow solution. LCMS showed desired mass was found and K101-C20Tr-B was remained. The reaction was stirred at 20° C. for 16 hr again to give yellow solution. LCMS and TLC (eluting with: PE/EtOAc=2/1) showed the reaction was complete. The mixture was quenched with saturated $NaHCO_3$ (50 mL) and extracted with DCM (80 mL×3). The organic layers were dried over $Na_2SO_4$ and concentrated to give the crude product. The crude product was purified by prep-TLC (eluting with: PE/EtOAc=2/1) to give K101-C134802-A (200 mg, 220.22 μmol, 65.05% yield) as a yellow solid.

Preparation of compound K101-C134802. To a solution of K101-C134802-A (340.00 mg, 374.38 μmol, 1.00 eq) in DCM (5 mL) was added TFA (1.54 g, 13.51 mmol, 1 mL, 36.08 eq). The mixture was stirred at 20° C. for 1 hr to give a yellow solution. LCMS showed the reaction was complete. The reaction mixture was concentrated by purging with $N_2$. The residue was dissolved in MeOH (50 mL). The reaction mixture was stirred at 40° C. for 12 hr. LCMS showed the reaction was complete. The reaction mixture was concentrated to give K101-C134802 (107 mg, 170.84 μmol, 45.63% yield, 90.33% purity) as a white solid.

LC-MS (m/z): 566.4 [M+H]+

$^1$H NMR (400 MHz, $CD_3OD$): δ 7.56 (s, 1H), 7.30-7.10 (m, 5H), 5.70-5.60 (m, 1H), 4.0-3.90 (m, 2H), 3.50-3.40 (m, 1H), 3.20-3.0 (m, 2H), 2.70-2.55 (m, 2H), 2.55-2.40 (m, 2H), 2.15-2.05 (m, 2H), 1.85-1.45 (m, 8H), 1.45-1.30 (m, 6H), 1.20 (s, 3H), 1.09 (s, 3H), 0.95-0.90 (m, 4H).

Example 46: Synthesis Scheme of K101-C1349

The scheme for synthesis of compound K101-C1349 is illustrated below.

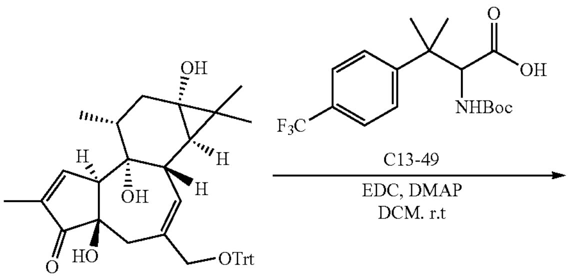

K101-C20Tr-B

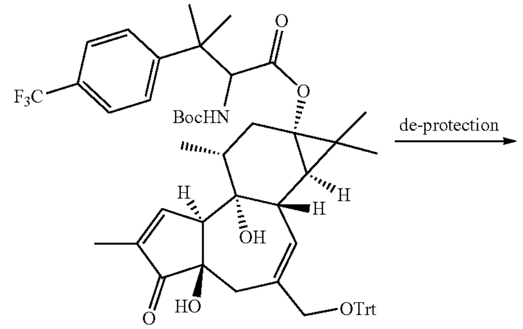

K101-C1349-A

-continued

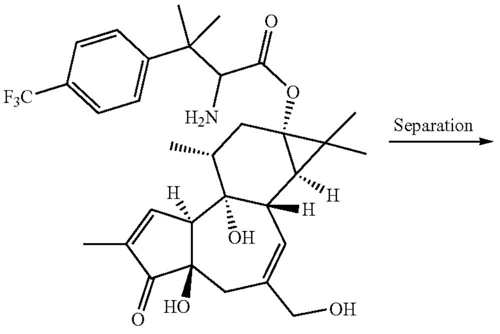

K101-C1349

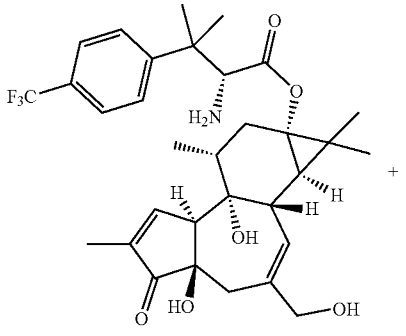

+

K101-C134901

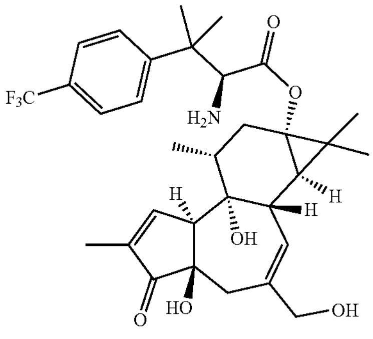

K101-C134902

Preparation of C13-49:

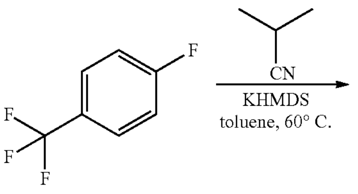

C13-49-A

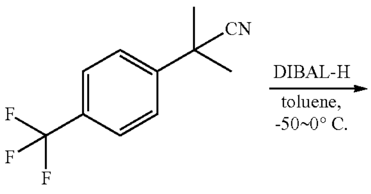

C13-49-B

-continued

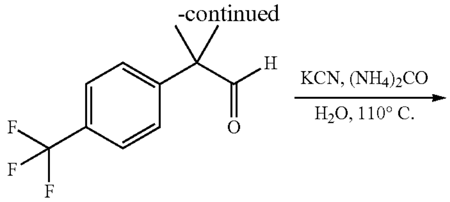

C13-49-C

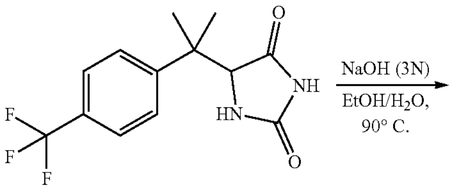

C13-49-F

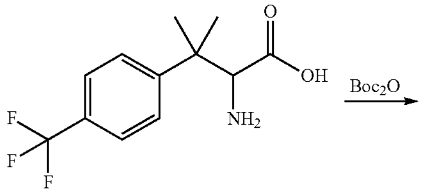

C13-49-E

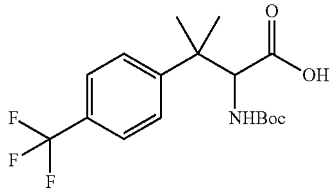

C13-49

Preparation of Compound C13-49-B. To a solution of C13-49-A (1.00 g, 6.09 mmol, 775.19 uL, 1.00 eq) in toluene (5.00 mL) were added 2-methylpropanenitrile (1.68 g, 24.36 mmol, 4.00 eq) and KHMDS (1 M, 9.14 mL, 1.50 eq). The mixture was stirred at 60° C. for 12 hr to give a black solution. LC-MS and TLC (eluting with: PE/EtOAc=5/1) showed the reaction was complete. The reaction mixture was quenched with Sat.$NH_4Cl$ (50 mL) and extracted with EtOAc (30 mL×3). The organic layers were dried over $Na_2SO_4$ and concentrated to give the crude product. The product was purified by column chromatography on silica gel (eluting with: PE/EtOAc=100% PE to 10/1) to give C13-49-B (1.10 g, 5.16 mmol, 84.72% yield) as a colorless oil.

Preparation of Compound C13-49-C. To a solution of C13-49-B (1.10 g, 5.16 mmol, 1.00 eq) in toluene (10.00 mL) was added dropwise diisobutylaluminium hydride (1 M, 6.71 mL, 1.30 eq) at −50° C. The mixture was stirred at −50° C. for 0.5 hr and then stirred at 0° C. for 0.5 hr to give a colorless solution. LC-MS showed the reaction was complete. The reaction mixture was quenched with $H_2SO_4$ (1.5M, 9 mL), stirred at 0° C. for 3 hr, and allowed to stand for 12 hr. The mixture was extracted with MTBE (30 mL×3), the combined organic layers dried over $Na_2SO_4$ and then concentrated to give C13-49-C (1.30 g, crude) as a colorless oil.

Preparation of Compound C13-49-F. To a solution of C13-49-C (1.60 g, 7.40 mmol, 1.00 eq) in $H_2O$ (20.00 mL) were added $(NH_4)_2CO_3$ (1.42 g, 14.80 mmol, 1.58 mL, 2.00 eq) and KCN (481.92 mg, 7.40 mmol, 317.05 uL, 1.00 eq). The mixture was stirred at 110° C. for 12 hr to give a yellow suspension. LC-MS showed the reaction was complete. The reaction mixture was concentrated to give the crude product, which was washed with PE/$H_2O$ (3:1, 50 mL) and filtered to give C13-49-F (1.40 g, 4.89 mmol, 66.09% yield) as a yellow solid.

Preparation of Compound C13-49-E. To a solution of C13-49-F (900.00 mg, 3.14 mmol, 1.00 eq) in EtOH (2.00 mL) was added NaOH (3 M, 5.23 mL, 5.00 eq). The mixture was stirred at 100° C. for 12 hr to give a yellow suspension. LC-MS showed the reaction was complete. The reaction mixture was used for next step without further purification.

Preparation of Compound C13-49. $Boc_2O$ (1.37 g, 6.28 mmol, 1.44 mL, 2.00 eq) was added to the preparation of C13-49-E and the mixture stirred at 10° C. for 12 hr to give a yellow suspension. LC-MS showed the reaction was complete. The reaction mixture was diluted with $H_2O$ (20 mL) and extracted with PE (30 mL×3). The water layer was adjusted to pH 4 with HCl (1N) and extracted with EtOAc (30 mL×3). The organic layers were dried over $Na_2SO_4$ and concentrated to give C13-49 (1.05 g, 2.91 mmol, 92.54% yield) as a yellow gum. The product was used for next step without further purification.

Preparation of Compound K101-C1349-A. To a solution of K101-C20Tr-B (50.00 mg, 84.64 μmol, 1.00 eq) in DCM (2.00 mL) were added C13-49 (91.75 mg, 253.92 μmol, 3.00 eq), DMAP (41.36 mg, 338.56 μmol, 4.00 eq), HOBt (13.72 mg, 101.57 μmol, 1.20 eq) and EDC (32.45 mg, 169.28 μmol, 2.00 eq). The mixture was stirred at 10° C. for 12 hr to give a yellow solution. LC-MS and TLC (eluting with: PE/EtOAc=2/1) showed the reaction was complete. The reaction mixture was combined with a second preparation, and quenched with saturated $NaHCO_3$ (20 mL). The mixture was extracted with DCM (20 mL×3) and the combined organic layers dried over $Na_2SO_4$ and concentrated to give the crude product. The product was purified by prep-TLC (eluting with: PE/EtOAc=2/1) to give K101-C1349-A (60.00 mg, 64.23 μmol, 63.24% yield) as a white solid.

Preparation of Compound K101-C1349. To a solution of K101-C1349-A (60.00 mg, 64.23 μmol, 1.00 eq) in tetrahydrofuran (THF) (3.00 mL) was added TFA (1.54 g, 13.51 mmol, 1.00 mL, 210.28 eq), and the mixture stirred at 10° C. for 12 hr to give a yellow solution. LC-MS showed the reaction was complete. The reaction mixture was concentrated, dissolved in MeOH (30 mL), and the stirred at 40° C. for 12 hr. The mixture was concentrated to give the crude product, which was then dissolved in saturated $NaHCO_3$ (10 mL) and extracted with EtOAc (20 mL×3). The organic layers were dried over $Na_2SO_4$ and concentrated to give the crude product. The product was purified by prep-TLC (eluting with: EtOAc/MeOH=10/1) to give K101-C134901 (11.50 mg, 18.45 μmol, 28.72% yield, 94.9% purity) and K101-C134902 (10.60 mg, 15.28 μmol, 23.79% yield, 85.3% purity) as white solids.

K101-C134901 LC-MS (m/z): 614.3 $[M+Na]^+$

K101-134901 $^1H$ NMR (400 MHz, $CD_3OD$) δ7.65 (s, 4H), 7.53 (s, 1H), 5.55-5.53 (m, 1H), 3.99-3.92 (m, 2H), 3.68 (s, 1H), 3.15 (s, 1H), 3.01 (s, 1H), 2.54-2.41 (m, 2H), 2.04-1.98 (m, 2H), 1.76-1.75 (m, 3H), 1.52-1.45 (m, 6H), 1.31-1.28 (m, 1H), 1.01 (s, 3H), 0.89-0.86 (m, 6H), 0.57-0.55 (m, 1H).

K101-C134902 LC-MS (m/z): 614.3 $[M+Na]^+$

K101-C134902 $^1H$ NMR (400 MHz, $CD_3OD$) δ7.65 (s, 4H), 7.53 (s, 1H), 5.55-5.53 (m, 1H), 3.93-3.89 (m, 2H), 3.67 (s, 1H), 3.16 (s, 1H), 3.00 (s, 1H), 2.48-2.40 (m, 2H), 1.94-1.93 (m, 1H), 1.75-1.69 (m, 4H), 1.49-1.48 (m, 6H), 1.04-1.01 (m, 4H), 0.97-0.96 (m, 3H), 0.84-0.80 (m, 4H).

Example 47: Synthesis Scheme of K101-C1350

The scheme for synthesis of compound K101-C1350 is illustrated below.

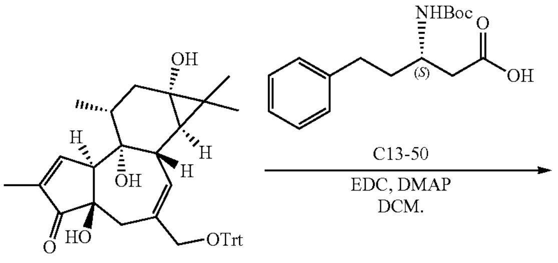

K101-C20Tr-B

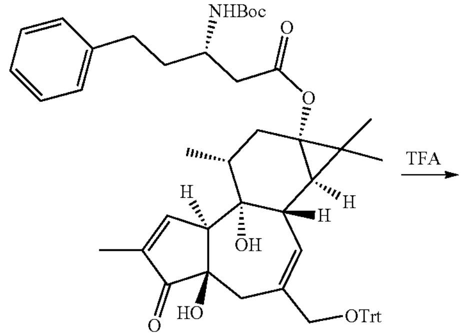

K101-C1350-A

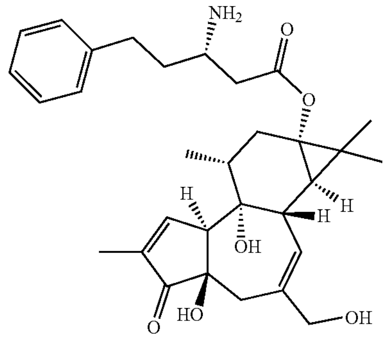

K101-C1350

Preparation of Compound K101-C1350-A. To a solution of K101-C20Tr-B (30.00 mg, 50.78 μmol, 1.00 eq) in DCM (1.00 mL) were added C13-50 (74.49 mg, 253.91 μmol, 5.00 eq), EDC (58.41 mg, 304.70 mol, 6.00 eq) and DMAP (37.22 mg, 304.70 μmol, 6.00 eq). The mixture was stirred at 20° C. for 14 hr to give a yellow solution. LC-MS showed the reaction was complete. The reaction mixture was quenched with $H_2O$ (15 mL) and extracted with DCM (15 mL×3). The organic layers were dried over $Na_2SO_4$ and concentrated to give a yellow oil. The product was purified by prep-TLC (eluting with Petroleum ether: Ethyl acetate=3/1) to give K101-C1350-A (25.00 mg, 28.87 mol, 56.84% yield) as a white solid.

Preparation of Compound K101-C1350. To a solution of K101-C1350-A (25.00 mg, 28.87 mol, 1.00 eq) in THF (1.00 mL) were added TFA (770.00 mg, 6.75 mmol, 500.00 uL, 233.92 eq) and $Et_3SiH$ (3.36 mg, 28.87 μmol, 4.60 uL, 1.00 eq). The mixture was stirred at 20° C. for 5 hr and then concentrated to give a yellow oil. The product was dissolved with DCM (1 mL), followed by addition of TFA (0.5 mL). The mixture stirred at 20° C. for 1 hr to give a yellow oil. LC-MS showed the reaction was complete. Following concentration, the resultant yellow oil was dissolved with MeOH (2 mL), and the mixture stirred at 20° C. for 14 hr. The product was purified by prep-HPLC (column: Phenomenex Gemini 150x25 mmx10 um; mobile phase: [A: water (0.1% TFA)-B: ACN]; B %: 23%-53%, 10 min), and the organic layers lyophilized to give K101-C1350 (6.00 mg, 9.41 μmol, 32.59% yield, 100% purity, TFA) as a white solid.

LC-MS (m/z): 546.2 $[M+Na]^+$ $^1H$ NMR (400 MHz, $CD_3OD$) δ 7.56 (s, 1H), 7.35-7.22 (m, 5H), 5.64 (s, 1H), 4.00-3.96 (m, 2H), 3.59-3.56 (m, 1H), 3.19 (s, 1H), 3.08 (s, 1H), 2.87-2.86 (m, 1H), 2.77-2.74 (m, 3H), 2.52-2.46 (m, 2H), 2.19-2.18 (m, 1H), 2.03-1.99 (m, 3H), 1.77 (s, 3H), 1.68-1.64 (m, 1H), 1.19 (s, 3H), 1.10 (s, 3H), 0.98-0.93 (m, 3H).

Example 48: Synthesis Scheme of K101-C1351

The scheme for synthesis of compound K101-C1351 is illustrated below.

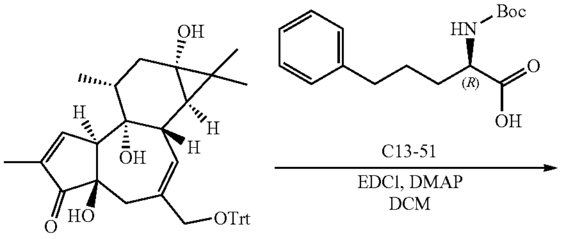

K101-C20Tr-B

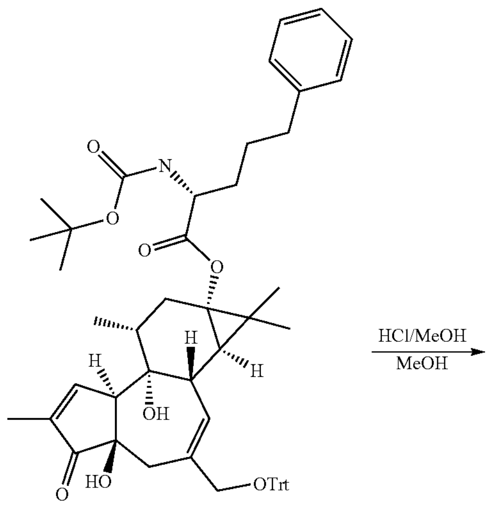

K101-C1351-A

-continued

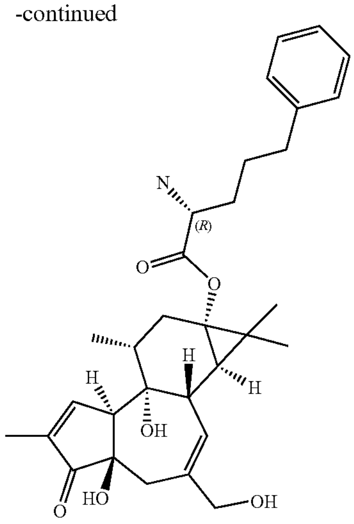

K101-C1351

Preparation of Compound K101-C1351-A. To a solution of K101-C20Tr-B (30.00 mg, 50.78 μmol, 1.00 eq) and C13-51 (72.31 mg, 152.34 μmol, 3.00 eq) in DCM (1.00 mL) were added EDC (38.94 mg, 203.12 μmol, 4.00 eq) and DMAP (24.82 mg, 203.12 μmol, 4.00 eq). The mixture was stirred at 20° C. for 18 h to give a yellow solution. The reaction was complete as detected by LC-MS. The reaction solution was diluted with $H_2O$ (15 mL), and extracted with DCM (10 mLx5). The combined organic layers were dried over anhydrous $Na_2SO_4$, filtered, and then concentrated under reduced pressure to give a white solid. The product was purified by prep-TLC (PE/EtOAc=3/1, $SiO_2$) to give K101-C1351-A (30.30 mg, 34.98 μmol, 59.39% yield) as a pale yellow solid.

Preparation of Compound K101-C1351. To a solution of K101-C1351-A (30.00 mg, 34.64 mol, 1.00 eq) in MeOH (500.00 uL) was added HCl/MeOH (4 M, 500.03 uL, 57.74 eq). The solution was stirred at 20° C. for 14 h to give a colorless solution. The reaction was complete as detected by LC-MS. The reaction solution was diluted with $H_2O$ (10 mL), neutralized with saturated aqueous $NaHCO_3$, and then extracted with DCM (8 mLx5). The combined organic layers were dried over anhydrous $Na_2SO_4$, filtered, and then concentrated under reduced pressure to give a yellow solid. The product was purified by prep-HPLC (column: Phenomenex Gemini 150x25 mmx10 um; mobile phase: [A: water (0.1% TFA)-B: ACN]; B %: 23%-53%, 10 min) to give K101-C1351 (3.80 mg, 7.26 μmol, 20.95% yield, 100% purity, TFA salt) as a white solid.

LC-MS (m/z): 546.1 $[M+Na]^+$ $^1H$ NMR (400 MHz, MeOD) δ 7.58-7.53 (m, 1H), 7.31-7.25 (m, 2H), 7.22-7.15 (m, 3H), 5.63-5.58 (m, 1H), 4.00-3.90 (m, 2H), 3.89-3.85 (m, 1H), 3.18-3.14 (m, 1H), 3.09-3.03 (m, 1H), 2.68 (t, J=6.8 Hz, 2H), 2.57-2.49 (m, 1H), 2.45-2.38 (m, 1H), 2.17 (dd, J=6.9, 14.7 Hz, 1H), 2.10-2.01 (m, 1H), 1.95-1.86 (m, 1H), 1.83-1.73 (m, 5H), 1.72-1.65 (m, 1H), 1.58 (dd, J=10.3, 14.6 Hz, 1H), 1.11 (s, 3H), 1.07 (s, 3H), 0.95-0.88 (m, 4H).

Example 49: Synthesis Scheme of K101-C1352

The scheme for synthesis of compound K101-C1352 is illustrated below.

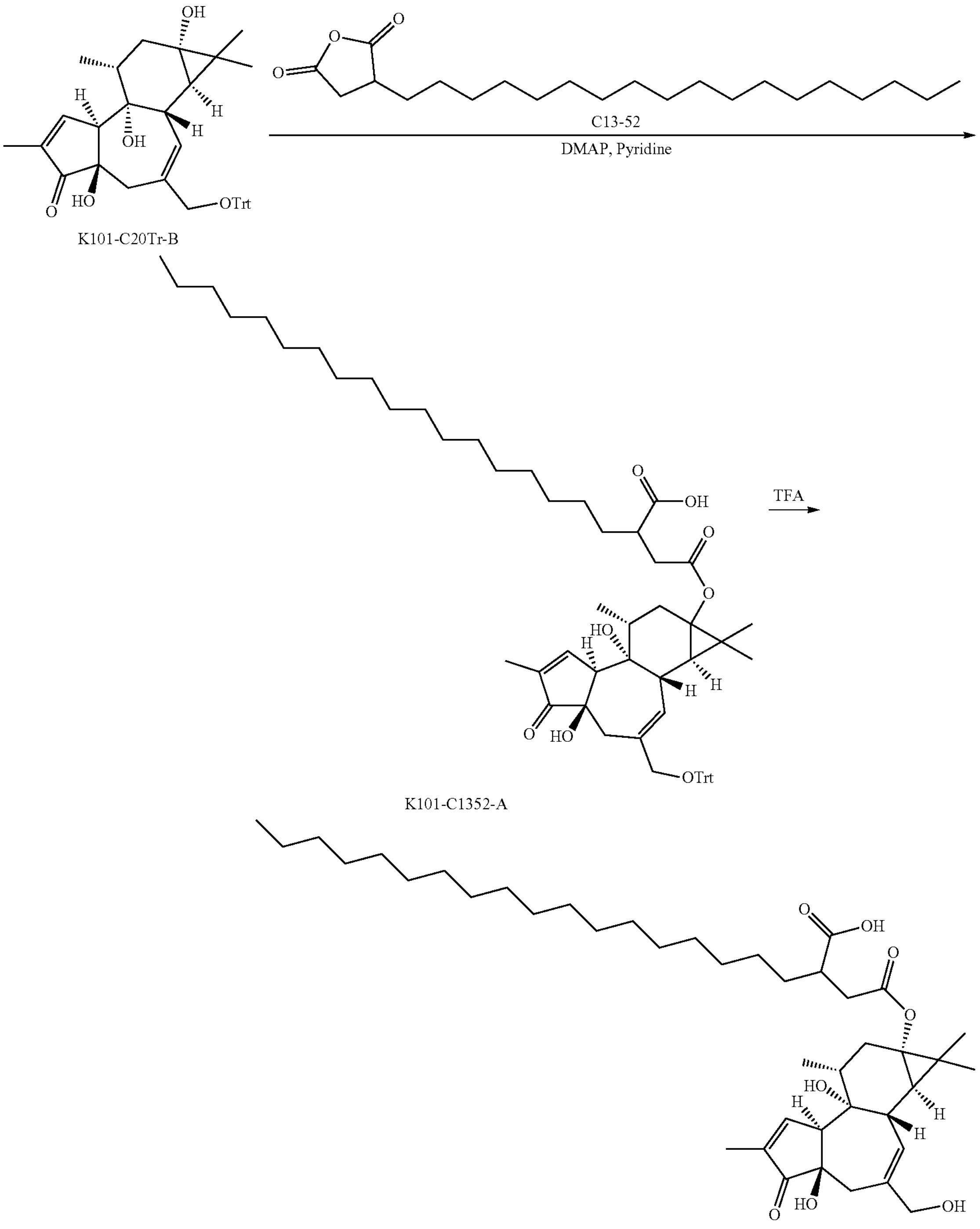

K101-C20Tr-B

K101-C1352-A

K101-C1352

Preparation of Compound K101-C1352-A: To a solution of K101-C20Tr-B (30.00 mg, 50.78 μmol, 1.00 eq) in Py (1.00 mL) were added C13-52 (179.04 mg, 507.80 μmol, 10.0 eg) and DMAP (12.41 mg, 101.56 μmol, 2.00 eq). The mixture was stirred at 90° C. for 14 hr in sealed tube to give a brown solution. LCMS showed the reaction was completed. The reaction mixture was concentrated to give a black oil. The black oil was dissolved by DCM (5 mL) and was adjusted to pH=4 with HCl (0.1 M) to give a yellow liquid. The yellow liquid was dried over $Na_2SO_4$ and concentrated to give a yellow oil. The yellow oil was purified by prep-TLC (eluting with Dichloromethane: Methanol=10/1) to give K101-C1352-A (15.00 mg, 15.90 μmol, 31.31% yield) as a white solid.

Preparation of Compound K101-C1350: To a solution of K101-C1352-A (15.00 mg, 15.90 mol, 1.00 eq) in THF (2.00 mL) were added TFA (770.00 mg, 6.75 mmol, 500.00 uL, 424.73 eq) and $Et_3SiH$ (1.85 mg, 15.90 μmol, 2.53 uL, 1.00 eq). The mixture was stirred at 20° C. for 5 hr to give a colorless solution. LCMS showed the mass of K101-

C1352-A was remained, then DCM (1 mL) was added. The mixture was stirred at 20° C. for 14 hr to give a colorless solution. LCMS and TLC (eluting with Dichloromethane: Methanol=8/1) showed the reaction was completed. The reaction mixture was concentrated to give a yellow solid. The yellow solid was purified by prep-TLC (eluting with Dichloromethane: Methanol=8/1). The organic layers were concentrated to give a white solid.

The white solid was dissolved with MeCN (1 mL) and $H_2O$ (5 mL), then was lyophilized to give K101-C1352 (2.00 mg, 2.11 μmol, 13.28% yield, 74% purity) as a white solid.

LC-MS (m/z): 724.1 $[M+Na]^+$ $^1H$ NMR (400 MHz, $CD_3OD$) δ 7.53 (s, 1H), 5.59 (s, 1H), 3.95 (s, 2H), 3.15 (s, 1H), 3.06 (m, 1H), 2.64-2.44 (m, 4H), 2.08-2.02 (m, 3H), 1.72 (s, 3H), 1.60-1.57 (m, 4H), 1.27 (s, 30H), 1.18 (s, 3H), 1.06 (s, 3H), 0.89-0.86 (m, 7H).

-continued

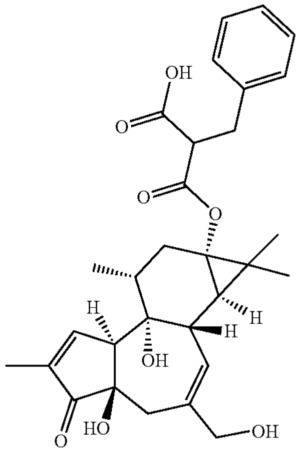

K101-C1353

Example 50: Synthesis Scheme of K101-C1353

The scheme for synthesis of compound K101-C1353 is illustrated below.

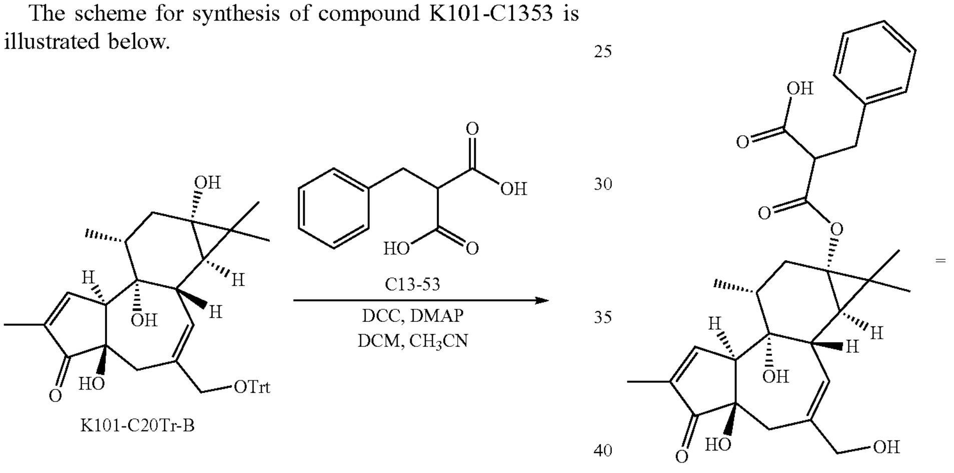

K101-C20Tr-B

C13-53

K101-C1353

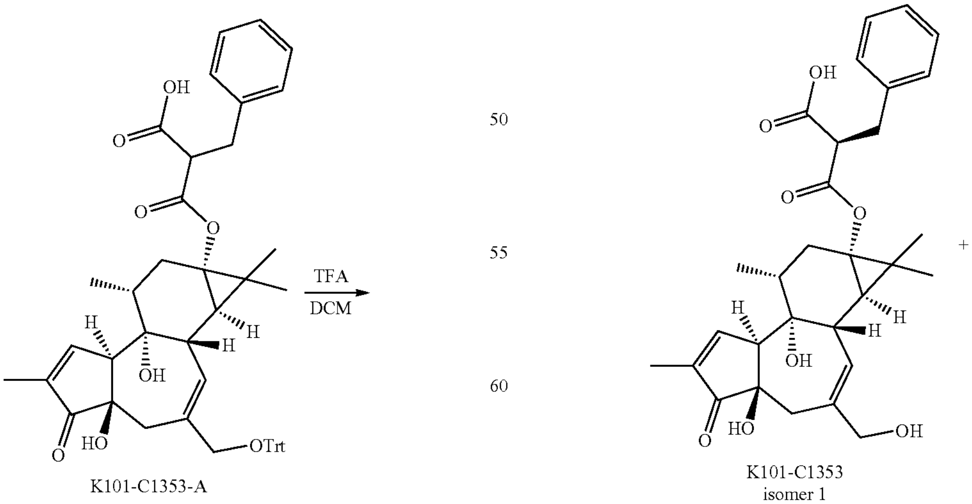

K101-C1353-A

K101-C1353
isomer 1

-continued

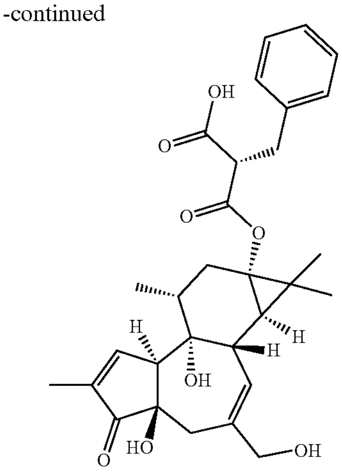

K101-C1353
isomer 2

Preparation of Compound K101-C1353-A: To a solution of K101-C20Tr-B (30.00 mg, 50.78 μmol, 1.00 eq), 2-benzylpropanedioic acid (59.17 mg, 304.68 μmol, 6.00 eq) and DMAP (6.20 mg, 50.78 μmol, 1.00 eq) in a mixed solvent of DCM (1.50 mL) and $CH_3CN$ (1.50 mL) was added a solution of DCC (31.43 mg, 152.34 μmol, 30.81 uL, 3.00 eq) in DCM (1.50 mL) at 0° C. dropwise. Then the reaction solution was stirred at 0° C. for 15 minutes and 15° C. for 2 hours to give a brown solution. LCMS showed the reaction was completed and the desired MS was observed. The reaction solution was combined with ES5329-254 (10 mg of K101-C20Tr-B was used in this batch) and diluted with DCM (5 mL), washed with 0.1 M HCl solution (5 mL×2), brine (1 mL), dried over anhydrous $Na_2SO_4$, filtered, concentrated under reduced pressure to give the crude product as a brown gum. The crude product was purified by prep-TLC (PE/EtOAc=1/1, $SiO_2$) to give K101-C1353-A (30.50 mg, 78.32% yield) as a colorless gum. The structure would be confirmed in the next step.

Preparation of Compound K101-C1353: To a solution of K101-C1353-A (25.00 mg, 32.60 μmol, 1.00 eq) in DCM (2.50 mL) was added TFA (500.00 uL) at 0° C. Then the reaction solution was stirred at 0° C. for 1 hour to give a clear solution. The reaction solution was quenched by water (2 mL) and then sat. aq. $NaHCO_3$ solution was added at 0° C. to render pH to 6-7. Then the mixture was extracted with DCM (5 mL×2). The combined extract was washed with brine (5 mL), dried over $Na_2SO_4$, filtered, concentrated under reduced pressure to give 22.1 mg of brown gum as the crude product. The crude product was purified by prep-TLC (DCM/MeOH=10/1) to give 15 mg of product.

The product was purified by prep-HPLC (column: Phenomenex Gemini 150*25 mm*10 um; mobile phase: [water (0.1% TFA)-ACN]; B %: 35%-65%, 10 min) to give K101-C1353 (5.30 mg, 30.74% yield, 99.2% purity) as a white solid after lyophilization. Note: the product is a mixture of two isomers as shown in the synthetic scheme with a ratio of about 1:1 based on NMR and HPLC.

LC-MS (m/z): 547.7 $[M+Na]^+$ $^1H$ NMR (400 MHz, $CD_3OD$) δ 7.57-7.50 (m, 1H), 7.33-7.18 (m, 5H), 5.62-5.51 (m, 1H), 3.99-3.87 (m, 2H), 3.79-3.68 (m, 1H), 3.26-3.07 (m, 3H), 3.06-2.96 (m, 1H), 2.56-2.37 (m, 2H), 2.07-1.89 (m, 2H), 1.77-1.71 (m, 2H), 1.77-1.70 (m, 1H), 1.49-1.27 (m, 1H), 1.07 (s, 1H), 1.01 (d, J=4.0 Hz, 3H), 0.92-0.80 (m, 5H), 0.59 (d, J=5.8 Hz, 1H).

Example 51: Synthesis Scheme of K101-C1354

The scheme for synthesis of compound K101-C1354 is illustrated below.

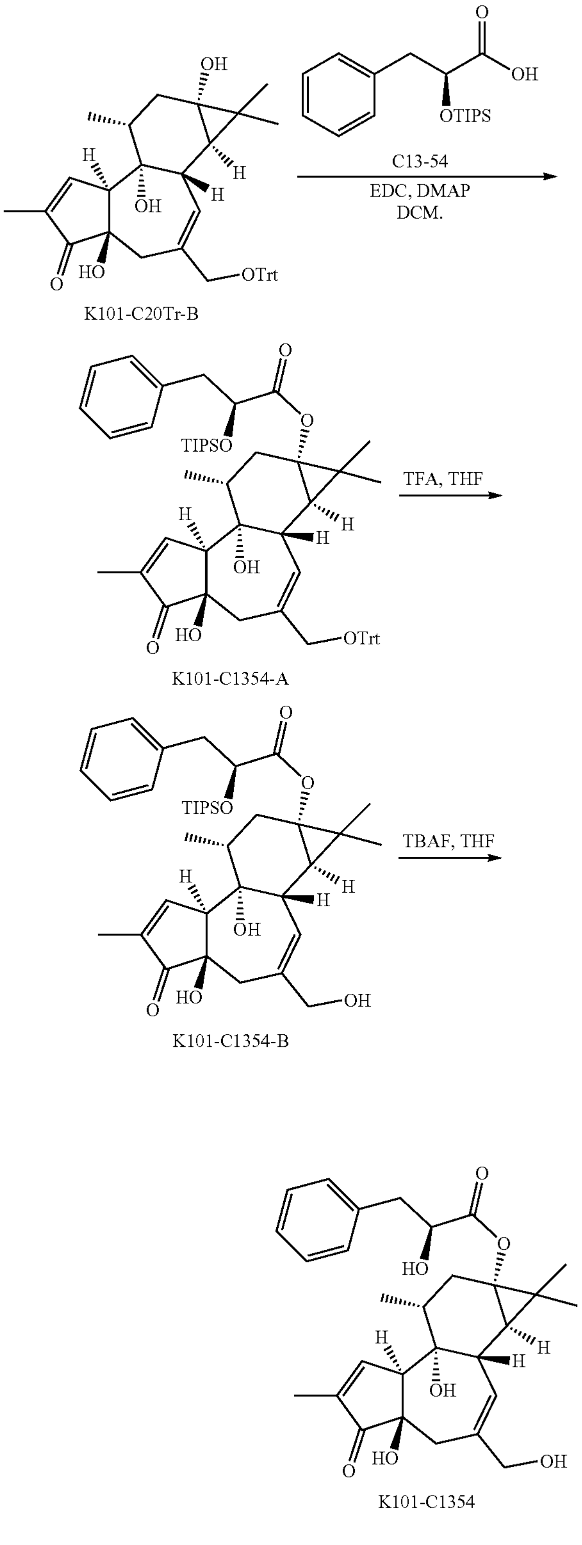

K101-C20Tr-B

K101-C1354-A

K101-C1354-B

K101-C1354

Preparation of C13-54:

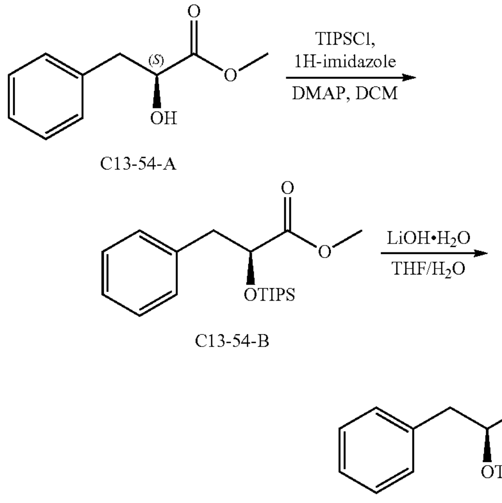

C13-54-A

C13-54-B

C13-54

Preparation of Compound C13-54-B: To a solution of methyl C13-54-A (499.15 mg, 2.77 mmol, 1.00 eq) in DCM (2.00 mL) was added triisopropylsilyl chloride (TIPSCl) (640.87 mg, 3.32 mmol, 712.08 uL, 1.20 eq), imidazole (565.74 mg, 8.31 mmol, 3.00 eq) and DMAP (33.84 mg, 277.00 μmol, 0.10 eq). The mixture was stirred at 20° C. for 14 hr to give a white suspension. LCMS and TLC showed the reaction was completed. The reaction mixture was combined with ES5890-138, then was quenched with $H_2O$ (20 mL) and extracted with DCM (20 mL*5). The organic layers were dried over $Na_2SO_4$ and then was purified by flash chromatography (eluting with Petroleum ether: Ethyl acetate=0/1-3/1) to give C13-54-B (900 mg, 2.67 mmol, 96.54% yield) as a colorless oil.

$^1H$ NMR (400 MHz, $CDCl_3$) δ=7.26 (s, 2H), 7.24-7.18 (m, 3H), 4.53 (dd, J=5.8, 7.0 Hz, 1H), 3.65 (s, 3H), 3.10-2.91 (m, 2H), 1.56 (s, 4H), 1.06-1.02 (m, 3H), 1.02-0.94 (m, 18H).

Preparation of Compound C1354: To a solution of C13-54-B (800.00 mg, 2.38 mmol, 1.00 eq) in THF (5.00 mL) and $H_2O$ (1.00 mL) was added $LiOH{\cdot}H_2O$ (499.32 mg, 11.90 mmol, 5.00 eq). The mixture was stirred at 45° C. for 14 hr to give a white suspension. LCMS showed the reaction was completed. The reaction mixture was quenched with $H_2O$ (20 mL) and extracted with PE (20 mL*3). The water layers were adjusted to pH 6 with HCl (1N), then was extracted with DCM (20 mL*3). The organic layer was dried over $Na_2SO_4$ and filtered on silica gel. The filtrate was concentrated to give C1354 (500 mg, 1.55 mmol, 65.14% yield) as a buff oil.

$^1H$ NMR (400 MHz, $CDCl_3$) δ=7.31-7.27 (m, 2H), 7.26-7.19 (m, 3H), 4.66 (t, J=5.0 Hz, 1H), 3.10 (d, J=5.0 Hz, 2H), 1.09-0.98 (m, 21H)

Preparation of Compound K101-C1354-A: To a solution of (2S)-3-phenyl-2-triisopropylsilyloxy-propanoic acid (87.35 mg, 270.84 μmol, 4 eq) in DCM (1.00 mL) was added DCC (55.88 mg, 270.84 μmol, 54.79 uL, 4 eq). The mixture was stirred at 20° C. for 0.5 hr to give a solution. Then K101-C20Tr-B (40 mg, 67.71 μmol, 1.00 eq) and DMAP (66.18 mg, 541.69 μmol, 8 eq) in DCM (1.00 mL) were added. The mixture was stirred at 20° C. for 14 hr to give a white suspension. LCMS and TLC showed the reaction was completed. The reaction mixture was combined with ES5890-150, then was quenched with $H_2O$ (15 mL) and extracted with DCM (15 mL*5). The organic layers were dried over $Na_2SO_4$ and concentrated to give yellow oil. The yellow oil was purified by prep-TLC (eluting with Petroleum ether: Ethyl acetate=4/1) to give K101-C1354-A (15.00 mg, 15.90 μmol, 31.31% yield) as a white solid.

$^1H$ NMR (400 MHz, $CDCl_3$) δ=7.58 (s, 1H), 7.45 (d, J=7.5 Hz, 6H), 7.33-7.27 (m, 6H), 7.25-7.15 (m, 8H), 5.65-5.55 (m, 1H), 5.42 (s, 1H), 4.61 (t, J=5.3 Hz, 1H), 3.52 (s, 2H), 3.30-3.20 (m, 1H), 3.05 (d, J=5.8 Hz, 2H), 2.86 (s, 1H), 2.53-2.28 (m, 2H), 1.99-1.82 (m, 3H), 1.77 (d, J=1.5 Hz, 3H), 1.03-0.96 (m, 21H), 0.91-0.80 (m, 6H), 0.55 (d, J=5.0 Hz, 1H)

Preparation of Compound K101-C1354-B: To a solution of K101-C1354-A (25 mg, 27.93 μmol, 1 eq) in THF (1 mL) was added TFA (770.00 mg, 6.75 mmol, 500.00 uL, 241.82 eq). The mixture was stirred at 20° C. for 14 hr to give a yellow solution. LCMS (ES5890-154-P1A) showed the reaction was completed. The reaction mixture was concentrated to give a yellow oil, the yellow oil was dissolved with MeOH (10 mL). The mixture was stirred at 40° C. for 14 hr to give a yellow solution. The yellow solution was concentrated to give K101-C1354-B as yellow oil. The yellow oil was used next step without further purification.

Preparation of Compound K101-C1354: To a solution of K101-C1354-B (18.23 mg, 27.92 μmol, 1 eq) in THF (1 mL) was added TBAF (1 M, 55.84 uL, 2 eq). The mixture was stirred at 10° C. for 14 hr to give a yellow solution. LCMS and TLC showed the reaction was completed. The reaction mixture was concentrated to give a yellow oil. The yellow oil was purified by prep-TLC (eluting with Ethyl acetate: Petroleum ether=3/1) to give K101-C1354 (3.5 mg, 7.05 μmol, 25.24% yield, 100% purity) as a white solid. 3.5 mg was delivered.

LC-MS (m/z): 519.1 $[M+Na]^+$ $^1H$ NMR (400 MHz, MeOD) δ=7.56 (s, 1H), 7.35-7.18 (m, 5H), 5.62 (s, 1H), 4.40 (dd, J=4.6, 7.7 Hz, 1H), 4.01-3.88 (m, 2H), 3.22-2.91 (m, 4H), 2.60-2.37 (m, 2H), 2.12-1.95 (m, 3H), 1.76 (d, J=1.5 Hz, 3H), 1.09 (d, J=18.1 Hz, 6H), 0.92-0.82 (m, 4H)

Example 52: Synthesis Scheme of K101-C1355

The scheme for synthesis of compound K101-C1355 is illustrated below.

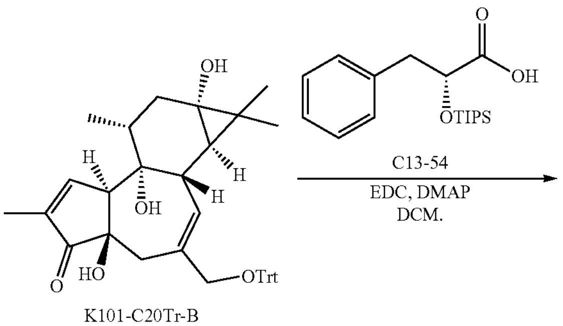

C13-54

K101-C20Tr-B

-continued

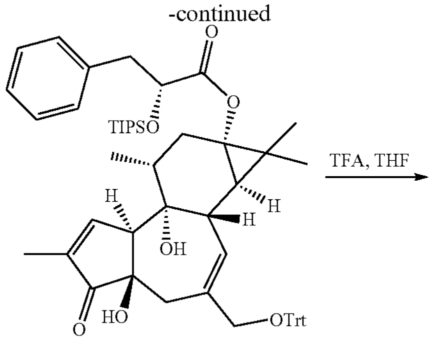

K101-C1355-A

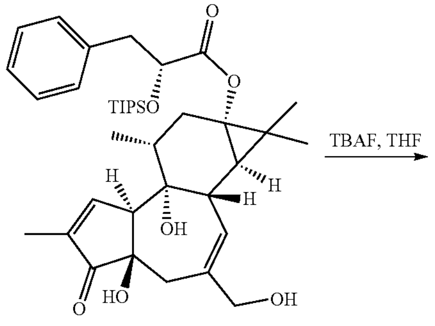

K101-C1355-B

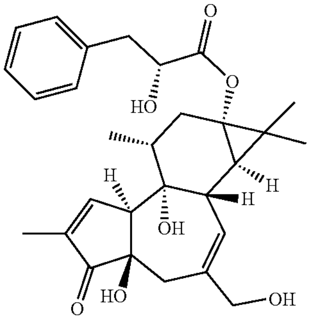

K101-C1355

Preparation of C13-55:

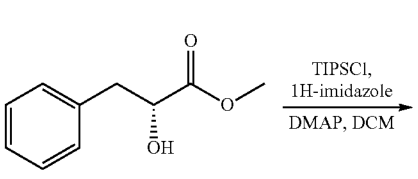

C13-55-A

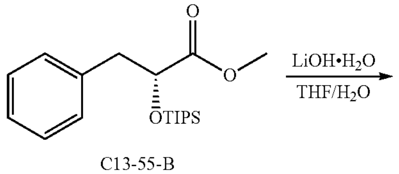

C13-55-B

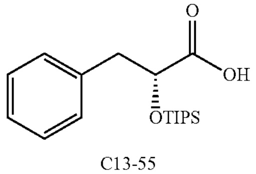

C13-55

Preparation of Compound C13-55-B: To a solution of C13-55-B (100.00 mg, 601.79 μmol, 1.00 eq) in DCM (1.00 mL) was added imidazole (122.91 mg, 1.81 mmol, 3.00 eq), DMAP (73.52 mg, 601.79 μmol, 1.00 eq) and TIPSCl (139.23 mg, 722.15 μmol, 154.70 uL, 1.20 eq). The mixture was stirred at 10° C. for 12 hr to give a yellow suspension. LCMS and TLC (eluting with: PE/EtOAc=5/1) showed the reaction was completed. The reaction mixture was quenched with saturated $NaHCO_3$ (15 mL) and extracted with DCM (20 mL*3). The organic layers were dried over $Na_2SO_4$ and concentrated to give the crude product. The crude product was purified by prep-TLC (eluting with: PE/EtOAc=5/1) to give C13-55-B (150.00 mg, 465.10 μmol, 77.29% yield) as a colorless oil.

$^1H$ NMR (400 MHz, $CDCl_3$) δ 7.41-7.26 (m, 5H), 4.54-4.51 (t, J=6.0 Hz, 1H), 3.65 (s, 3H), 3.09-2.95 (m, 2H), 1.06-0.98 (m, 21H).

Preparation of Compound C13-55: To a solution of C13-55-B (1.90 g, 5.65 mmol, 1.00 eq) in THF (10.00 mL)/$H_2O$ (2.00 mL) was added $LiOH{\cdot}H_2O$ (1.19 g, 28.25 mmol, 5.00 eq). The mixture was stirred at 40° C. for 12 hr to give a yellow suspension. LCMS showed the reaction was completed. The reaction mixture was concentrated to give the residue. The residue was acidified to pH=4 with HCl (1N) and extracted with EtOAc (20 mL*3). The organic layers were dried over $Na_2SO_4$ and concentrated to give C13-55 (1.10 g, 3.41 mmol, 60.37% yield) as a yellow oil. Used for next step without further purification.

$^1H$ NMR (400 MHz, DMSO): δ 7.29-7.19 (m, 5H), 4.59-4.13 (m, 1H), 3.01-2.80 (s, 2H), 3.09-2.95 (m, 2H), 1.22-1.02 (m, 1H), 1.01-0.84 (m, 20H).

Preparation of Compound K101-C1355-A: Preparation of Compound K101-C1355-A: To a solution of K101-C20Tr-B (30.00 mg, 50.78 μmol, 1.00 eq) in DCM (1.00 mL) were added C13-55 (32.76 mg, 101.57 μmol, 2.00 eq) and DMAP (6.20 mg, 50.78 μmol, 1.00 eq), DCC (20.96 mg, 101.57 μmol, 20.55 uL, 2.00 eq). The mixture was stirred at 10° C. for 12 hr to give yellow solution. LCMS and TLC (eluting with: PE/EtOAc=2/1) showed 61.484% of desired mass was found, and 23.129% of K101-C20Tr-B was remained. The reaction mixture was combined with ES5350-274. The mixture was quenched with $H_2O$ (10 mL) and extracted with DCM (20 mL*3). The organic layers were dried over $Na_2SO_4$ and concentrated to give the crude product. The crude product was purified by prep-TLC (eluting with: PE/EtOAc=2/1) to give K101-C1355-A (0.03 g, 33.51 μmol, 65.99% yield) as a white solid.

$^1H$ NMR (400 MHz, $CDCl_3$) δ 7.60 (s, 1H), 7.46-7.37 (m, 6H), 7.30-7.28 (m, 6H), 7.25-7.22 (m, 8H), 5.59 (s, 1H), 4.49-4.46 (m, 1H), 3.52 (s, 2H), 3.27 (s, 1H), 3.10-2.86 (m, 3H), 2.46-2.38 (m, 2H), 2.09-2.05 (m, 2H), 1.77 (s, 3H), 1.28-1.25 (m, 3H), 1.03-1.02 (m, 18H), 0.97-0.84 (m, 11H), 0.56-0.54 (m, 1H).

Preparation of Compound K101-C1355-B: To a solution of K101-C1355-A (0.03 g, 33.51 μmol, 1 eq) in THF (3 mL) was added TFA (3.82 mg, 33.51 μmol, 2.48 uL, 1 eq). The mixture was stirred at 10° C. for 12 hr to give yellow solution. LCMS showed the reaction was completed. The reaction mixture was concentrated to give the residue by purging with $N_2$. The residue was dissolved in MeOH (20 mL). The mixture was stirred at 40° C. for 12 hr. The mixture was concentrated to give K101-C1355-B (0.022 g, crude) as a yellow solid. Used for next step without further purification.

Preparation of Compound K101-C1355: To a solution of K101-C1355-B (0.022 g, 33.69 μmol, 1 eq) in THF (3 mL) was added TBAF (1 M, 67.39 uL, 2 eq). The mixture was stirred at 10° C. for 12 hr to give a yellow solution. LCMS and TLC (eluting with: EtOAc/PE=2/1) showed the reaction was completed. The reaction mixture was concentrated to give the crude product by purging with $N_2$. The crude product was prep-TLC (eluting with: EtOAc/PE=3/1) and lyophilized to give K101-C1355 (5.3 mg, 10.67 μmol, 31.68% yield) as a white solid. 5.3 mg was delivered.

LC-MS (m/z): 519.1 $[M+Na]^+$ $^1H$ NMR (400 MHz, $CD_3OD$) δ 7.57 (s, 1H), 7.31-7.23 (m, 5H), 5.61 (s, 1H), 4.37-4.34 (m, 1H), 4.00-3.96 (s, 2H), 3.18 (s, 1H), 3.12-3.06 (m, 2H), 2.98-2.94 (m, 1H), 2.51-2.46 (m, 2H), 2.12-2.03 (m, 2H), 1.77 (s, 3H), 1.57-1.54 (m, 1H), 1.06 (s, 3H), 1.00 (s, 3H), 0.93-0.91 (m, 3H), 0.78-0.76 (m, 1H).

Example 53: Synthesis Scheme of K101-C1356

The scheme for synthesis of compound K101-C1356 is illustrated below.

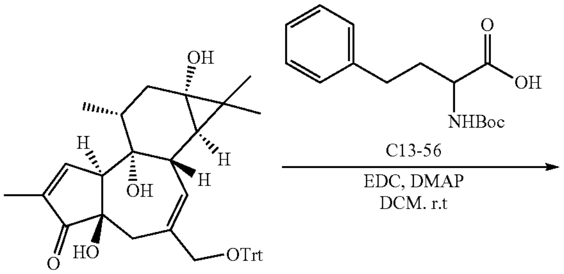

K101-C20Tr-B

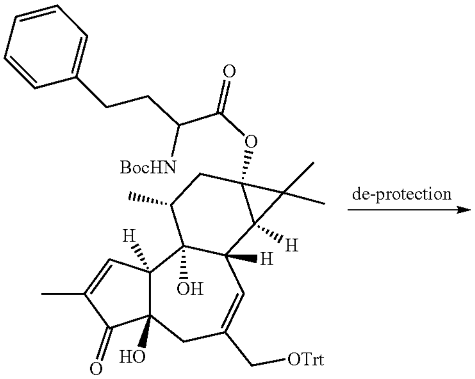

K101-C1356-A

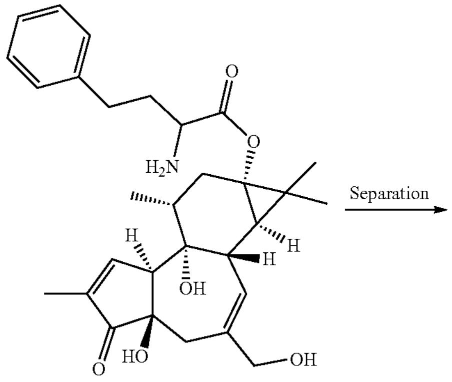

K101-C1356

-continued

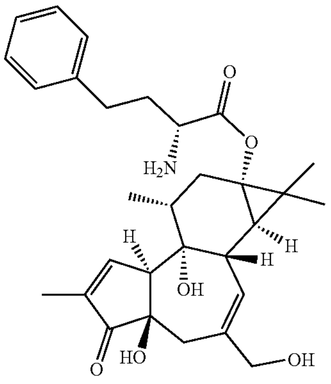

+

K101-C135601

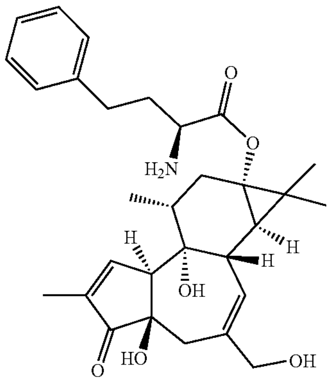

K101-C135602

Preparation of C13-56:

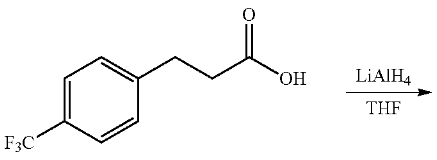

C13-56-A

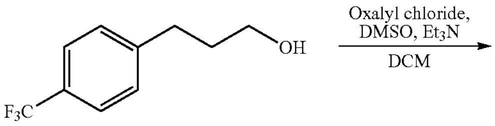

C13-56-B

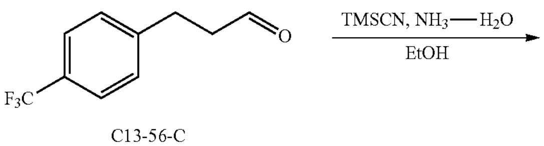

C13-56-C

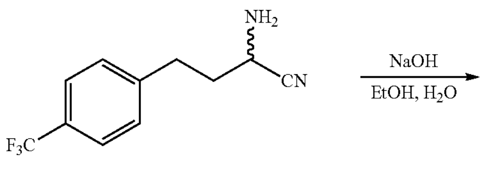

C13-56-D

-continued

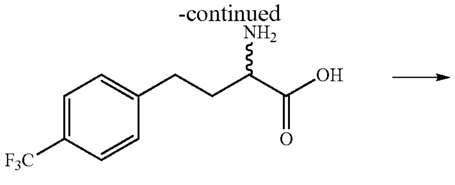

C13-56-E

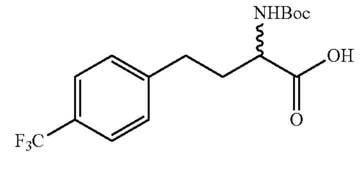

C13-56

Preparation of Compound C13-56-B: To a solution containing $LiAlH_4$ (469.66 mg, 12.38 mmol, 1.50 eq) in THF (10.00 mL) was added dropwise 3-[4-(trifluoromethyl)phenyl]propanoic acid (1.80 g, 8.25 mmol, 1.00 eq) in THF (10.00 mL) at 0° C. The mixture was allowed to stir at 10° C. for 12 hr to give a yellow suspension. LCMS showed the reaction was completed. The reaction mixture was quenched with $H_2O$ (0.47 mL), NaOH (15%, 0.47 mL) and $H_2O$ (1.41 mL). The mixture was stirred at 0° C. for 20 min. The mixture was filtered on celite. The filtrate was dried over $Na_2SO_4$ and concentrated to give C1356-B (1.40 g, 6.86 mmol, 83.11% yield) as a yellow oil. Used for next step without further purification.

$^1$H NMR (400 MHz, $CDCl_3$): δ 7.55-7.43 (m, 2H), 7.33-7.28 (m, 2H), 3.69-3.68 (m, 2H), 2.76-2.70 (m, 2H), 1.96-1.89 (m, 2H).

Preparation of Compound C13-56-C: To a solution of oxalyl dichloride (1.74 g, 13.72 mmol, 1.20 mL, 2.00 eq) in DCM (15.00 mL) was added dropwise at −78° C. The mixture was stirred at −78° C. for 0.5 hr. Then C13-56-B (1.40 g, 6.86 mmol, 1.00 eq) in DCM (15.00 mL) was added dropwise at −78° C. The mixture was stirred at −78° C. for 1 hr. Then $Et_3N$ (3.47 g, 34.30 mmol, 4.75 mL, 5.00 eq) was added dropwise at −78° C. The mixture was stirred at −78° C. for 2.5 hr to give a yellow suspension. LCMS and TLC (eluting with: PE/EtOAc=2/1) showed the reaction was completed. The reaction mixture was quenched with $H_2O$ (30 mL) and extracted with DCM (30 mL*3). The organic layers were dried over $Na_2SO_4$ and concentrated to give the crude product. The crude product was purified by column chromatography on silica gel (eluting with: PE/EtOAc=100% PE to 10/1) to give C13-56-C (1.10 g, 5.44 mmol, 79.31% yield) as a yellow oil.

$^1$H NMR (400 MHz, $CDCl_3$): δ 9.85 (s, 1H), 7.72-7.56 (m, 2H), 7.35-7.28 (m, 2H), 3.06-3.01 (m, 2H), 2.86-2.81 (m, 2H).

Preparation of Compound C13-56-D: To a solution of C13-56-C (100.00 mg, 494.63 μmol, 1.00 eq) in EtOH (2.00 mL) were added $NH_3{\cdot}H_2O$ (208.04 mg, 1.48 mmol, 228.62 uL, 25% purity, 3.00 eq) and TMSCN (58.89 mg, 593.56 μmol, 74.54 uL, 1.20 eq). The mixture was stirred at 10° C. for 70 hr to give yellow solution. LCMS showed the reaction was completed. The reaction mixture was quenched with $H_2O$ (10 mL) and extracted with DCM (30 mL*3). The organic layers were dried over $Na_2SO_4$ and concentrated to give C13-56-D (0.11 g, 482.01 μmol, 97.45% yield) as a yellow oil. Used for next step without further purification.

$^1$H NMR (400 MHz, $CDCl_3$): δ 7.59-7.54 (m, 2H), 7.35-7.30 (m, 2H), 3.66-3.58 (m, 1H), 2.99-2.86 (m, 2H), 2.15-2.05 (m, 2H), 1.66-1.64 (m, 2H).

Preparation of Compound C13-56-E: To a solution of C13-56-D (0.11 g, 482.00 μmol, 1 eq) in EtOH (2 mL) were added NaOH (96.39 mg, 2.41 mmol, 5 eq). The mixture was stirred at 40° C. for 2 hr. Then $H_2O$ (0.4 mL) was added. The mixture was stirred at 90° C. for 3 hr to give a yellow solution. LCMS showed the reaction was completed. The reaction mixture was used for next step without further purification.

Preparation of Compound C13-56: $Boc_2O$ (194.22 mg, 889.92 μmol, 204.44 uL, 2 eq) was added the mixture of C13-56-E (0.11 g, 444.96 μmol, 1 eq) from ES5350-284. The mixture was stirred at 10° C. for 12 hr to give a yellow suspension. LCMS showed the reaction was completed. The reaction mixture was diluted with $H_2O$ (10 mL) and extracted with PE (15 mL*3). The water layers was acidified to pH=4 with HCl (1N) and extracted with EtOAc (20 mL*3). The organic layers were dried over $Na_2SO_4$ and concentrated to give C13-56 (0.11 g, 316.70 μmol, 71.18% yield) as a yellow oil. Used for next step without further purification.

$^1$H NMR (400 MHz, DMSO): δ 12.50 (brs, 1H), 7.66-7.64 (m, 2H), 7.49-7.48 (m, 2H), 6.14 (brs, 1H), 3.71 (s, 1H), 2.72-2.71 (m, 2H), 1.95-1.85 (m, 2H), 1.40 (s, 9H).

Preparation of Compound K101-C1356-A: To a solution of K101-C20Tr-B (0.05 g, 84.64 μmol, 1 eq) in DCM (2 mL) were added C13-56 (58.79 mg, 169.28 μmol, 2 eq), DMAP (41.36 mg, 338.55 μmol, 4 eq), HOBt (13.72 mg, 101.57 μmol, 1.2 eq) and EDCI (32.45 mg, 169.28 μmol, 2 eq). The mixture was stirred at 40° C. for 12 hr to give a yellow solution. LCMS and TLC (eluting with: PE/EtOAc=2/1) showed the reaction was completed. The reaction was combined with ES5350-289. The reaction mixture was quenched with $H_2O$ (15 mL) and extracted with DCM (30 mL*3). The organic layers were dried over $Na_2SO_4$ and concentrated to give the crude product. The crude product was purified by prep-TLC (eluting with: PE/EtOAc=2/1) to give K101-C1356-A (0.039 g, 42.39 μmol, 41.73% yield) as a white solid.

Preparation of Compound K101-C1356: To a solution of K101-1356-A (0.039 g, 42.39 μmol, 1 eq) in THF (3 mL) were added TFA (1.54 g, 13.51 mmol, 1 mL, 318.63 eq) and $Et_3SiH$ (4.93 mg, 42.39 μmol, 6.77 uL, 1 eq). The mixture was stirred at 10° C. for 12 hr to give a yellow solution.

LCMS and TLC (eluting with: EtOAc/MeOH=10/1) showed the reaction was completed. The reaction mixture was concentrated to give the residue by purging with $N_2$. The residue was dissolved MeOH (20 mL). The mixture was stirred at 40° C. for 12 hr. The mixture was concentrated to give the crude product. The crude product was purified by prep-TLC (eluting with: EtOAc/MeOH=10/1) and lyophilized to give K101-C135601 (4.7 mg, 7.03 μmol, 16.59% yield, 86.45% purity) as a white solid and K101-C135602 (3.4 mg, 5.24 μmol, 12.35% yield, 88.96% purity) as a white solid. 4.7 mg and 3.4 mg were delivered.

K101-C135601 LC-MS (m/z): 600.2 $[M+Na]^+$

K101-C135601 $^1$H NMR (400 MHz, $CD_3OD$) δ 7.62-7.58 (m, 3H), 7.46-7.38 (m, 2H), 5.63 (s, 1H), 3.97 (s, 2H), 3.54-3.53 (m, 1H), 3.19-3.09 (m, 2H), 2.84-2.82 (m, 2H), 2.57-2.42 (m, 2H), 2.20-2.08 (m, 4H), 1.77 (s, 3H), 1.64-1.61 (m, 1H), 1.21 (s, 3H), 1.10 (s, 3H), 0.95-0.93 (m, 4H).

K101-C135602 LC-MS (m/z): 600.0 $[M+Na]^+$

K101-C135602 $^1$H NMR (400 MHz, $CD_3OD$) δ 7.62-7.57 (m, 3H), 7.46-7.38 (m, 2H), 5.63-5.60 (m, 1H), 3.96 (s, 2H), 3.49-3.46 (m, 1H), 3.19 (s, 1H), 3.09 (s, 1H), 2.86-2.82 (m, 2H), 2.52-2.42 (m, 2H), 2.20-1.91 (m, 4H), 1.77 (s, 3H), 1.61-1.57 (m, 1H), 1.20 (s, 3H), 1.11 (s, 3H), 0.97-0.93 (m, 4H).

Example 54: Synthesis Scheme of K101-C1357

The scheme for synthesis of compound K101-C1357 is illustrated below.

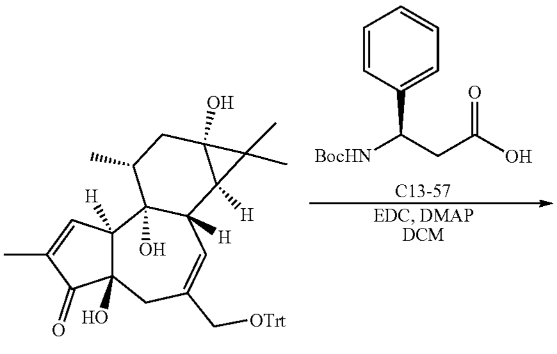

K101-C20Tr-B

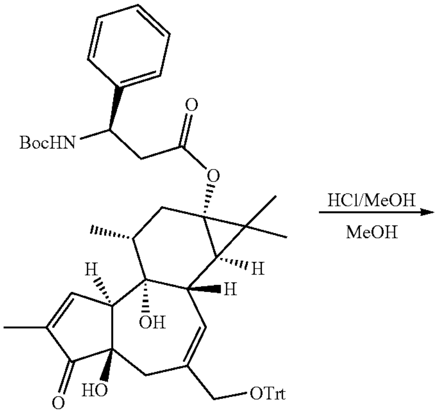

K101-C1357-A

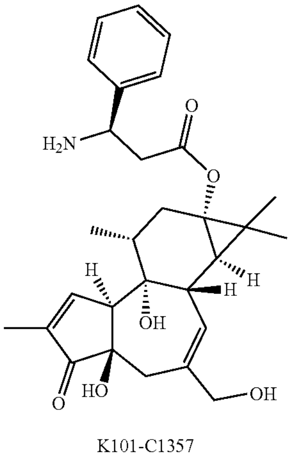

K101-C1357

Preparation of Compound K101-C1357-A. To a solution of K101-C20Tr-B (30.00 mg, 50.78 μmol, 1.00 eq) and C13-57 (40.42 mg, 152.35 μmol, 3 eq) in DCM (1 mL) were added EDC (58.41 mg, 304.70 μmol, 6 eq) and DMAP (37.22 mg, 304.70 μmol, 6 eq). The mixture was stirred at 20° C. for 16 hours to give a yellow solution. The reaction was complete detected by LC-MS. The reaction solution was diluted with $H_2O$ (20 mL) and extracted with DCM (10 mL×5). The combined organic layers were dried over $Na_2SO_4$ and concentrated under reduced pressure to give a yellow solid. The product was purified by prep-TLC (PE/EtOAc=3/1, $SiO_2$) to give K101-C1357-A (16.00 mg, 19.09 μmol, 37.60% yield) as a white solid.

Preparation of Compound K101-C1357. To a solution of K101-C1357-A (16.00 mg, 19.09 μmol, 1 eq) in MeOH (0.50 mL) was added HCl/MeOH (4 M, 0.50 mL, 104.75 eq). The solution was stirred at 20° C. for 12 hours to give a black solution. The reaction was complete as detected by LC-MS. The reaction solution was concentrated under $N_2$ to give yellow solid, which was then purified by prep-HPLC (column: Phenomenex Gemini 150×25 mm×10 um; mobile phase: [A: water (0.1% TFA)-B: ACN]; B %: 20%-50%, 10 min) to give K101-C1357 (1.2 mg, 1.97 μmol, 10.31% yield, 91.34% purity, TFA salt) as a white solid.

LC-MS (m/z): 518.1 $[M+Na]^+$ $^1H$ NMR (400 MHz, $CD_3OD$) δ 7.53 (s, 1H), 7.40-7.33 (m, 2H), 7.33-7.27 (m, 3H), 5.67 (s, 1H), 5.57-5.58 (m, 1H), 5.22 (s, 1H), 4.29-4.32 (m, 1H), 3.92 (s, 2H), 3.16-3.04 (m, 3H), 3.01-3.08 (m, 1H), 2.54-2.45 (m, 1H), 2.41-2.33 (m, 1H), 2.17 (dd, J=7.0, 14.8 Hz, 1H), 2.06-1.95 (m, 1H), 1.71-1.72 (m, 3H), 1.64-1.54 (m, 1H), 1.03 (s, 3H), 1.01 (s, 3H), 0.93-0.86 (m, 5H).

Example 55: Synthesis Scheme of K101-C1358

The scheme for synthesis of K101-C1358 is illustrated below.

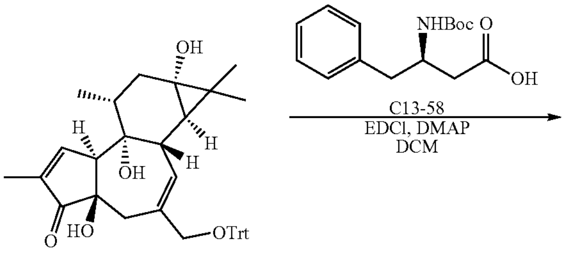

K101-C20Tr-B

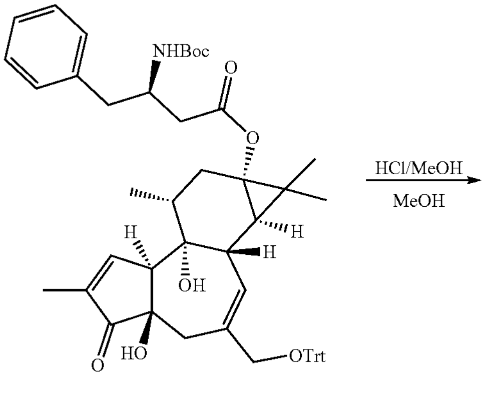

K101-C1358-A

-continued

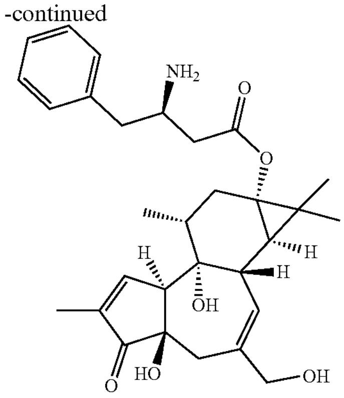

K101-C1358

Preparation of Compound K101-C1358-A. To a solution of K101-C20Tr-B (30.00 mg, 50.78 μmol, 1.00 eq) and C13-58 (35.46 mg, 126.96 μmol, 2.50 eq) in DCM (1.00 mL) were added EDC (58.41 mg, 304.70 μmol, 6 eq) and DMAP (18.61 mg, 152.35 μmol, 3 eq). The mixture was stirred at 15° C. for 18 hours to give a yellow solution. The reaction was complete as detected by LC-MS. The reaction solution was combined with a second preparation, which was then diluted with $H_2O$ (20 mL) and extracted with DCM (10 mL×5). The organic layers were dried over $Na_2SO_4$, filtered and concentrated under reduced pressure to give a yellow solution. The product was purified by prep-TLC (PE/EtOAc=3/1, SiO2) to give K101-C1358-A (39 mg, 45.77 μmol, 90.13% yield) as a yellow solid.

Preparation of Compound K101-C1358. To a solution of K101-C1358-A (39.00 mg, 45.77 μmol, 1.00 eq) in MeOH (0.5 mL) was added HCl/MeOH (4 M, 500 uL, 43.70 eq). The solution was stirred at 10° C. for 16 hours to give a black solution. LC-MS showed the reaction was complete. The reaction solution was diluted with $H_2O$ (25 mL) and extracted with DCM (10 mL×5). The combined organic layers were dried over $Na_2SO_4$ and concentrated under reduced pressure to give a yellow solid. The product was purified by prep-HPLC (column: Phenomenex Gemini 150×25 mm×10 um; mobile phase: [A: water (0.1% TFA)-B: ACN]; B %: 20%-50%, 10 min). The separated layers were lyophilized to give K101-C1358 (5.00 mg, 9.81 μmol, 21.43% yield, 92.55% purity, TFA salt) as a light yellow solid.

LC-MS (m/z): 532.1 $[M+Na]^+$ $^1H$ NMR (400 MHz, $CD_3OD$) δ 7.54 (s, 1H), 7.40-7.36 (m, 2H), 7.34-7.31 (m, 1H), 7.30-7.27 (m, 2H), 5.61-5.59 (m, 1H), 4.10 (q, J=7.0 Hz, 1H), 3.94 (s, 1H), 3.88-3.85 (m, 1H), 3.16-3.15 (m, 1H), 3.06-3.02 (m, 2H), 2.98-2.92 (m, 1H), 2.77-2.71 (m, 1H), 2.68-2.61 (m, 1H), 2.55-2.49 (m, 1H), 2.44-2.38 (m, 1H), 2.16 (s, 1H), 2.01 (s, 1H), 1.75-1.74 (m, 3H), 1.55-1.48 (m, 1H), 130-1.22 (m, 3H), 1.12 (s, 3H), 1.06 (s, 3H), 0.92-0.89 (m, 4H).

Example 56: Synthesis Scheme of K101-C1359

The scheme for synthesis of K101-C1359 is illustrated below.

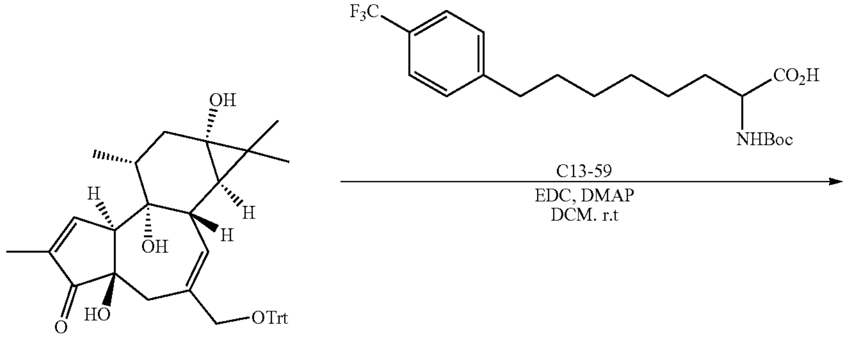

K101-C20Tr-B

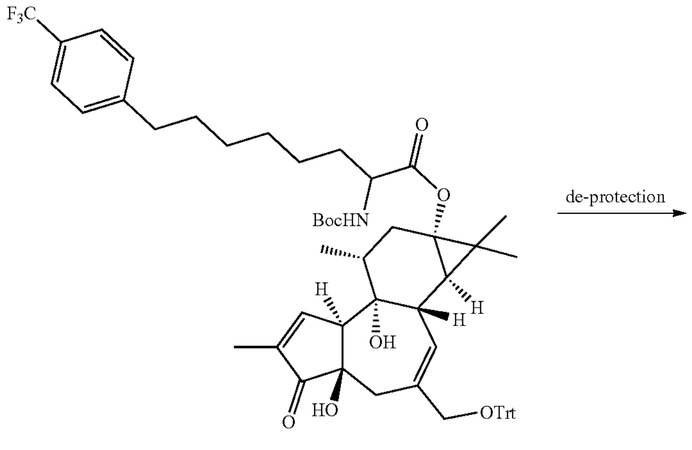

K101-C1359-A

-continued
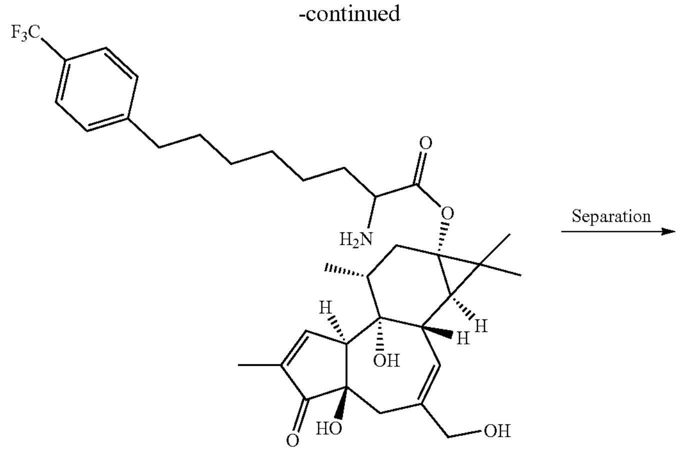
K101-C1359
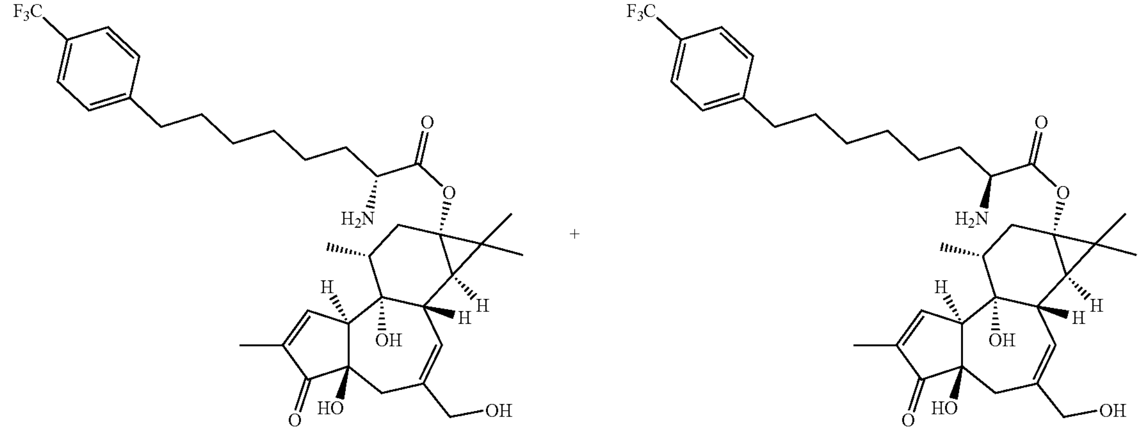
K101-C135901
K101-C135902
Preparation of C13-59:
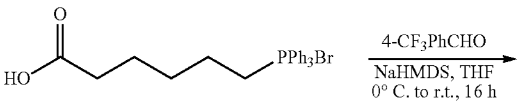
13A
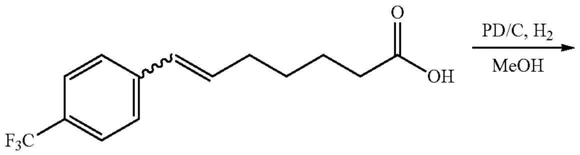
C13-59A
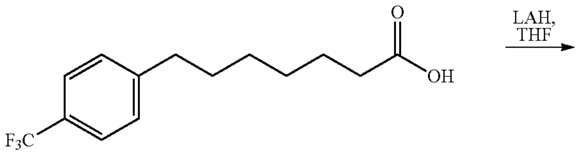
C13-59B
-continued
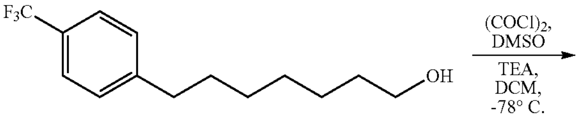
C13-59C
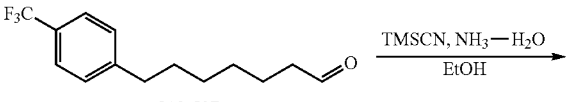
C13-59D
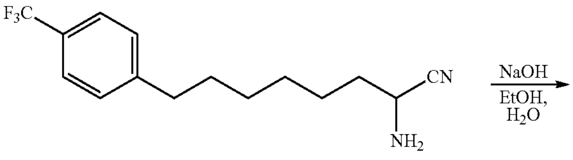
C13-59E
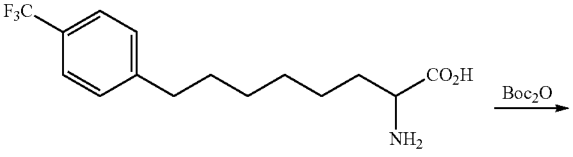
C13-59F -continued

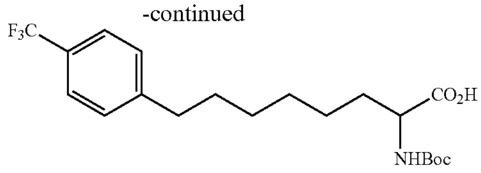

C13-59

Preparation of Compound C13-59A. To a solution of 13A (13.13 g, 28.72 mmol, 1 eq) in THF (40 mL) was added dropwise NaHMDS (1 M, 57.43 mL, 2 eq) at 0° C. The mixture was stirred at 0° C. for 0.5° C., followed by addition of 4-(trifluoromethyl)benzaldehyde (5 g, 28.72 mmol, 3.85 mL, 1 eq) in THF (20 mL) at 0° C. The mixture was allowed to stir at 10° C. for 15.5 hr to give a yellow suspension. LC-MS and TLC (eluting with: EtOAc/PE=2/1) showed the reaction was complete. The reaction mixture was quenched with $H_2O$ (40 mL) and extracted with PE (50 mL×3). The water layer was adjusted to pH 4 with HCl (1N) and extracted with EtOAc (50 mL×3). The organic layers were dried over $Na_2SO_4$ and concentrated to give the crude product. The product was purified by a flash column (eluting with: PE/EtOAc=10% to 50%) to give C13-59A (5.9 g, 21.67 mmol, 75.46% yield) as a yellow solid.

Preparation of Compound C13-59B. To a solution of C13-59A (5.9 g, 21.67 mmol, 1 eq) in MeOH (80 mL) was added Pd—C(10%, 590 mg) under $N_2$. The suspension was degassed under vacuum and purged with $H_2$ several times. The mixture was stirred under $H_2$ (15 psi) at 10° C. for 12 hours to give a black suspension. HPLC showed the reaction was complete. The reaction mixture was filtered on Celite, and the filtrate concentrated to give C13-59B (5.7 g, 20.78 mmol, 95.90% yield) as a yellow solid.

Preparation of Compound C13-59C. To a solution containing $LiAlH_4$ (1.58 g, 41.56 mmol, 2 eq) in THF (30 mL) was added dropwise C13-59B (5.7 g, 20.78 mmol, 1 eq) in THF (30 mL) at 0° C. The mixture was stirred at 10° C. for 16 hr to give a black suspension. LC-MS showed the reaction was complete. The reaction mixture was quenched with $H_2O$ (1.58 mL) and aqueous NaOH (1.58 mL) followed by additional $H_2O$ (4.74 mL). The mixture was filtered and concentrated to give C13-59C (4.7 g, 18.06 mmol, 86.89% yield) as a colorless oil.

Preparation of Compound C13-59D. To a solution of oxalyl dichloride (4.58 g, 36.11 mmol, 3.16 mL, 2 eq) in DCM (30 mL) was added dropwise DMSO (7.05 g, 90.28 mmol, 7.05 mL, 5 eq) at −78° C. The mixture was stirred at −78° C. for 0.5 hr followed by addition of C13-59C (4.7 g, 18.06 mmol, 1 eq) in DCM (20 mL) at −78° C. Following stirring of the mixture at −78° C. for 1 hr, $Et_3N$ (9.14 g, 90.28 mmol, 12.57 mL, 5 eq) was added dropwise at −78° C. The mixture was allowed to stir at 20° C. for 2.5 hr to give a yellow suspension. TLC (eluting with: PE/EtOAc=5/1) showed the reaction was complete. The reaction mixture was quenched with $H_2O$ (40 mL) and extracted with DCM (50 mL×3). The organic layers were dried over $Na_2SO_4$ and concentrated to give the crude product. The product was purified by column chromatography on silica gel (eluting with: PE/EtOAc=100% PE to 5/1) to give C13-59D (2.6 g, 10.07 mmol, 55.75% yield) as a colorless oil.

Preparation of Compound C13-59E. To a solution of C13-59D (2.6 g, 10.07 mmol, 1 eq) in EtOH (30 mL) were added $NH_3 \cdot H_2O$ (14.11 g, 100.67 mmol, 15.51 mL, 25% purity, 10 eq) and TMSCN (2.00 g, 20.13 mmol, 2.52 mL, 2 eq). The mixture was stirred at 10° C. for 16 hr to give a yellow solution. LC-MS showed the presence of desired mass but that some reactant remained. The mixture was stirred at 10° C. for an additional 70 hr. LC-MS showed the reaction was complete. The reaction mixture was quenched with $H_2O$ (30 mL) and extracted with DCM (40 mL×3). The organic layers were dried over $Na_2SO_4$ and concentrated to give C13-59E (3.1 g, crude) as a yellow oil.

Preparation of Compound C13-59F. To a solution of C13-59E (3.1 g, 10.90 mmol, 1 eq) in EtOH (30 mL) was added NaOH (1.31 g, 32.71 mmol, 3 eq). The mixture was stirred at 40° C. for 2 hr followed by the addition of $H_2O$ (6 mL). The mixture was stirred at 90° C. for 4 hr to give a yellow solution. LC-MS showed the reaction was complete.

Preparation of Compound C13-59. $Boc_2O$ (4.76 g, 21.82 mmol, 5.01 mL, 2 eq) was added to a preparation of C13-59E (3.31 g, 10.91 mmol, 1 eq) in THF (20 mL), and the mixture stirred at 10° C. for 16 hr to give a yellow suspension. LC-MS and TLC (eluting with: EtOAc/PE=2/1, 50 uL AcOH) showed the reaction was complete. The reaction mixture was concentrated, and the resultant residue diluted with $H_2O$ (30 mL) and extracted with PE/MTBE (5/1, 40 mL×3). The water layer was adjusted to pH 4 with HCl (1N) and extracted with EtOAc (50 mL×3). The organic layers were dried over $Na_2SO_4$, concentrated, and the product purified by a flash column (eluting with: PE/EtOAc=100% PE to 40%) to give C13-59 (1.6 g, 3.97 mmol, 36.35% yield) as a yellow oil.

Preparation of Compound K101-C1359-A. To a solution of K101-C20Tr-B (50 mg, 84.64 μmol, 1 eq) in DCM (3 mL) were added C13-59 (68.29 mg, 169.28 μmol, 2 eq), DMAP (41.36 mg, 338.55 μmol, 4 eq), HOBt (13.72 mg, 101.57 μmol, 1.2 eq) and EDC (32.45 mg, 169.28 μmol, 2 eq). The mixture was stirred at 40° C. for 12 hr. LC-MS showed that K101-C20Tr-B remained. The mixture was stirred at 40° C. for an additional 16 hr to give a yellow solution. LC-MS and TLC (eluting with: PE/EtOAc=2/1) showed the reaction was complete. The mixture was combined with a second preparation of K101-C1359-A, and the combined mixture quenched with saturated $NaHCO_3$ (15 mL). Following extraction with DCM (30 mL×3), the organic layers were dried over $Na_2SO_4$ and concentrated to give the crude product. The product was purified by prep-TLC (eluting with: PE/EtOAc=2/1) to give K101-C1359-A (53 mg, 54.29 μmol, 53.46% yield) as a white solid.

Preparation of Compound K101-C1359. To a solution of K101-C1359-A (53 mg, 54.29 μmol, 1 eq) in THF (3 mL) were added TFA (1.54 g, 13.51 mmol, 1 mL, 248.76 eq) and Et3SiH (6.31 mg, 54.29 μmol, 8.67 uL, 1 eq). The mixture was stirred at 10° C. for 12 hr to give a yellow solution. LC-MS showed the reaction was complete. The reaction mixture was concentrated by $N_2$. The resultant residue dissolved in MeOH (20 mL), and the mixture stirred at 40° C. for 12 hr. LC-MS showed the reaction was complete. The mixture was concentrated, and the product dissolved in DCM (20 mL) and adjusted to pH 8 with saturated $NaHCO_3$. The water layer was extracted with DCM (20 mL×3), and the organic layers dried over $Na_2SO_4$ and concentrated to give the crude product. The product was purified by prep-TLC (eluting with: DCM/MeOH=10/1) to give 13 mg of P1 and 14 mg of P2. The P1 and P2 products were purified by prep-HPLC (column: Phenomenex Gemini 150×25 mm×10 um; mobile phase: [A: water (0.1% TFA)-B: ACN]; B %: 30%-60%, 10 min) to give K101-C135901 (10.2 mg, 13.64 μmol, 25.12% yield, 100% purity, TFA) and K101-C135902 (9.8 mg, 12.53 μmol, 23.07% yield, 95.59% purity, TFA) also as white solids. The preparation contained byproduct: [(21R,22S,23S,24R,32S,33R,34R)-33,34-dihydroxy-26-

(hydroxymethyl)-21,25,31,31-tetramethyl-27-oxo-32-tetracyclopentadeca-10(26),11(25)-dienyl]2-amino-8-[4-(difluoromethyl)phenyl]octanoate (about 1.0 mg, TFA) and [(21R,22S,23S,24R,32S,33R,34R)-33,34-dihydroxy-26-(hydroxymethyl)-21,25,31,31-tetramethyl-27-oxo-32-tetracyclopentadeca-10(26),11(25)-dienyl] 2-amino-8-[4-(difluoromethyl)phenyl]octanoate (about 0.8 mg, TFA) as yellow oils.

K101-C135901: LC-MS (m/z): 656.2 [M+Na]$^+$

K101-C135901: $^1$H NMR (400 MHz, $CD_3OD$) δ7.58-7.56 (m, 3H), 7.40-7.38 (m, 2H), 5.62-5.61 (m, 1H), 3.99-3.92 (m, 2H) 3.58 (s, 1H), 3.18 (s, 1H), 3.09 (s, 1H), 2.74-2.71 (m, 2H), 2.52-2.42 (m, 2H), 2.19-2.05 (m, 2H), 1.77-1.67 (m, 7H), 1.40-1.39 (m, 6H), 1.19 (s, 3H), 1.10 (s, 3H), 0.93-0.90 (m, 4H).

K101-C135902: LC-MS (m/z): 656.2 [M+Na]$^+$

K101-C135902: $^1$H NMR (400 MHz, $CD_3OD$) δ7.58-7.56 (m, 3H), 7.41-7.39 (m, 2H), 5.63-5.62 (m, 1H), 3.99-3.95 (m, 2H) 3.50 (s, 1H), 3.19-3.15 (m, 2H), 3.09 (s, 1H), 2.75-2.71 (m, 2H), 2.57-2.42 (m, 2H), 2.13-2.05 (m, 1H), 1.77-1.68 (m, 7H), 1.41-1.40 (m, 6H), 1.19 (s, 3H), 1.09 (s, 3H), 0.96-0.90 (m, 4H).

Example 57: Synthesis Scheme of K101-C1361

The scheme for synthesis of K101-C1361 is illustrated below.

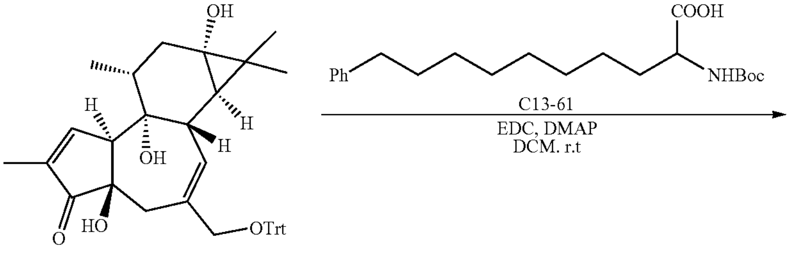

K101-C20Tr-B

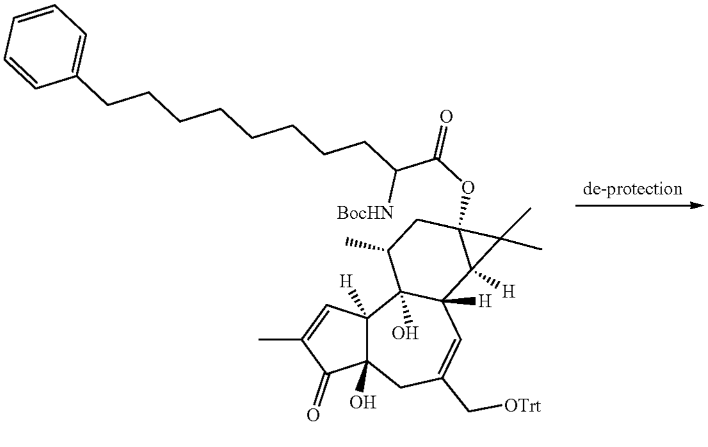

K101-C1361-A

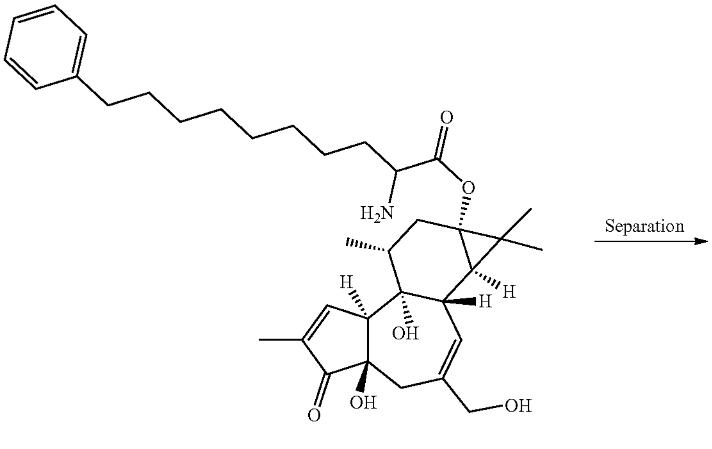

K101-C1361

-continued

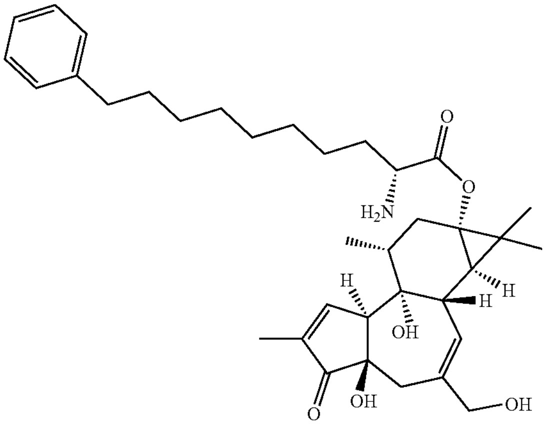

K101-C136101

+

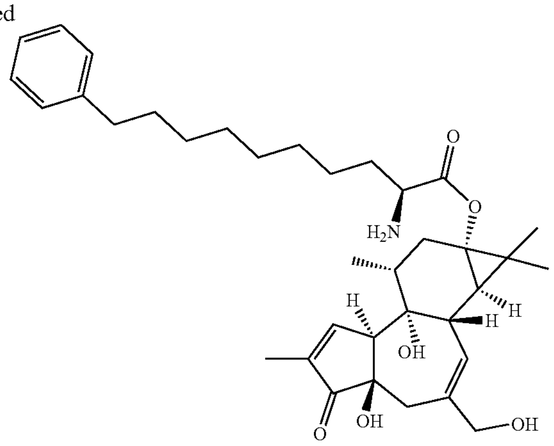

K101-C136102

Preparation of C13-61:

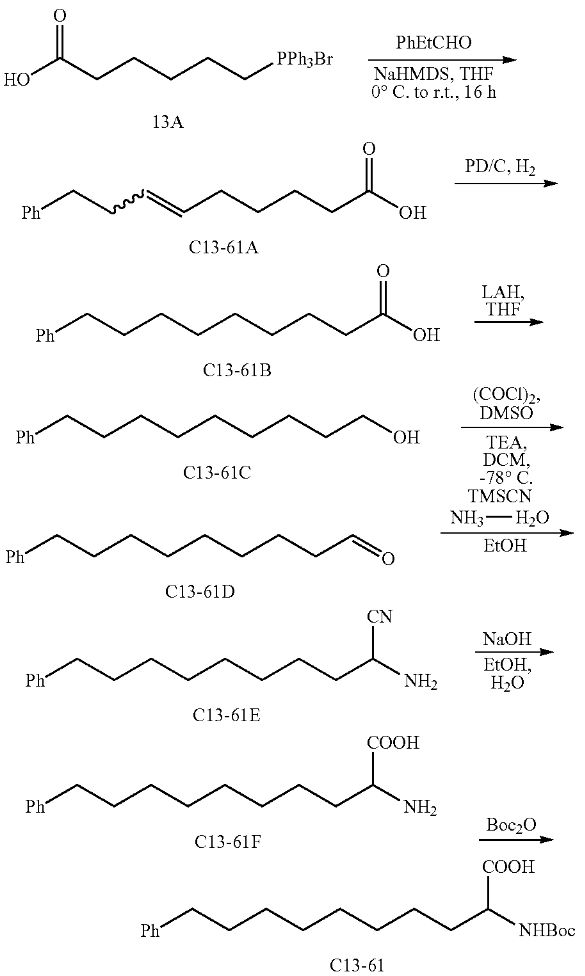

Preparation of Compound C13-61A. To a solution of C13A (13.63 g, 29.81 mmol, 1 eq) in THF (50 mL) was added NaHMDS (1 M, 59.62 mL, 2 eq) at 0° C. Following stirring at 0° C. for 0.5 hr, 3-phenylpropanal (4 g, 29.81 mmol, 3.92 mL, 1 eq) in THF (50 mL) was added dropwise at 0° C. The mixture was allowed to stir at 10° C. for 64.5 hr to give a yellow suspension. LC-MS and TLC (EtOAc: PE=2:1) showed the reaction was complete. The reaction mixture was quenched with $H_2O$ (50 mL) and extracted with PE (50 mL×3). The water layer was adjusted to pH 3 with HCl (1N) and extracted with EtOAc (50 mL×3). The organic layers were dried over $Na_2SO_4$, concentrated, and then purified by flash column (PE/EtOAc=5% to 40%) to give C13-61A (5.55 g, 23.90 mmol, 80.18% yield) as a yellow oil.

Preparation of Compound C13-61B. To a solution of K13-61A (5.55 g, 23.90 mmol, 1 eq) was added Pd/C (550 mg) under $H_2$ (48.28 mg, 23.90 mmol). The suspension was degassed under vacuum and purged with $H_2$ several times. The mixture was stirred under $H_2$ (15 psi) at 10° C. for 16 hours to give a black suspension. HPLC showed the reaction was complete. The reaction mixture was filtered on Celite and then concentrated to give C13-61B (5.27 g, 22.49 mmol, 94.09% yield) as a white gum.

Preparation of Compound C13-61C. To a solution containing $LiAlH_4$ (1.71 g, 44.98 mmol, 2 eq) in THF (100 mL) was added dropwise the preparation of C1361-B (5.27 g, 22.49 mmol, 1 eq) in THF (100 mL) at 0° C. The mixture was stirred at 10° C. for 16 hr to give a black suspension. LC-MS showed the reaction was complete. The reaction mixture was quenched with $H_2O$ (1.7 mL) and aqueous NaOH (1.7 mL), following by additional $H_2O$ (5.1 mL). The mixture was filtered and concentrated to give C13-61C (3.63 g, 16.47 mmol, 73.26% yield) as a colorless oil.

Preparation of Compound C13-61D. To a solution of $(COCl)_2$ (3.46 g, 27.23 mmol, 2.38 mL, 2 eq) in DCM (100 mL) was added dropwise DMSO (5.32 g, 68.07 mmol, 5.32 mL, 5 eq) at −78° C. The mixture was stirred at −78° C. for 0.5 hr. The preparation of C1361-C (3 g, 13.61 mmol, 1 eq) in DCM (100 mL) was added at −78° C., and the resultant mixture stirred at −78° C. for 1 hr. TEA (6.89 g, 68.07 mmol, 9.48 mL, 5 eq) was added dropwise at −78° C. and the mixture was allowed to stir at 20° C. for 2.5 hr to give a yellow suspension. TLC (eluting with: PE/EtOAc=5/1) showed the reaction was complete. The reaction mixture was quenched with $H_2O$ (40 mL) and extracted with DCM (40 mL×3). The organic layers were dried over $Na_2SO_4$ and concentrated to give the crude product. The product was purified by column chromatography on silica gel (eluting with: PE/EtOAc=100% PE to 20/1) to give C13-61D as a yellow oil.

Preparation of Compound C13-61E. To a solution of C13-61D (1.7 g, 7.79 mmol, 1 eq) in EtOH (20 mL) were added $NH_3 \cdot H_2O$ (10.91 g, 77.86 mmol, 11.99 mL, 25% purity, 10 eq) and TMSCN (1.16 g, 11.68 mmol, 1.46 mL, 1.5 eq). The mixture was stirred at 15° C. for 12 hr to give a yellow solution. LC-MS showed desired mass was found, but some C13-61D remained unreacted. The mixture was stirred at 15° C. for an additional 18 hr. LC-MS showed the reaction was complete. The reaction mixture was diluted with $H_2O$ (20 mL) and extracted with DCM (25 mL×3). The organic layers were dried over $Na_2SO_4$ and concentrated to give C13-61E (1.6 g, 6.55 mmol, 84.09% yield) as a yellow oil. The preparation was used without further purification.

Preparation of Compound C13-61F. To a solution of C13-61E (270 mg, 1.10 mmol, 1 eq) in EtOH (2 mL) was added NaOH (132.57 mg, 3.31 mmol, 3 eq) and the mixture stirred at 40° C. for 2 hr. Following addition of $H_2O$ (0.1 mL), the mixture was stirred at 90° C. for 4 hr to give a yellow solution. LC-MS showed the reaction was complete. The preparation was used without further purification.

Preparation of Compound C13-61. $Boc_2O$ (482.26 mg, 2.21 mmol, 507.64 uL, 2 eq) was added to the preparation of C13-61F (290.99 mg, 1.10 mmol, 1 eq) in THF (5 mL), and the mixture stirred at 15° C. for 4 hr to give a yellow solution. LC-MS and TLC (eluting with: EtOAc/PE=2/1) showed the reaction was complete. The reaction mixture was diluted with $H_2O$ (10 mL) and PE (10 mL×3), and the water layer adjusted to pH 3 with HCl (1N). The mixture was extracted with EtOAc (20 mL×3), and the organic layers dried over $Na_2SO_4$ and concentrated to give the crude product. The product was purified by a flash column (eluting with: PE/EtOAc=0% to 50%) to give C13-61 (150 mg, 412.67 μmol, 37.35% yield) as a yellow oil.

Preparation of Compound K101-C1361-A. To a solution of K101-C20Tr-B (70 mg, 118.49 μmol, 1 eq) in DCM (2 mL) were added C13-61 (86.14 mg, 236.99 μmol, 2 eq), DMAP (57.90 mg, 473.98 μmol, 4 eq), HOBt (16.01 mg, 118.49 μmol, 1 eq) and EDC (45.43 mg, 236.99 μmol, 2 eq). The mixture was stirred at 40° C. for 12 hr to give a yellow solution. LC-MS and TLC (eluting with: PE/EtOAc=2/1) showed the reaction was complete. The reaction mixture was quenched with saturated $NaHCO_3$ (10 mL) and extracted with DCM (20 mL×3). The organic layers were dried over $Na_2SO_4$, concentrated, and the resultant product purified by prep-TLC (eluting with: PE/EtOAc=2/1) to give K101-C1361-A (62 mg, 66.22 μmol, 55.89% yield) as a white solid.

Preparation of Compound K101-C1361. To a solution of K101-C1361-A (62 mg, 66.22 μmol, 1 eq) in THF (3 mL) were added TFA (1.54 g, 13.51 mmol, 1 mL, 203.95 eq) and Et3SiH (7.70 mg, 66.22 μmol, 10.58 uL, 1 eq). The mixture was stirred at 15° C. for 12 hr to give a yellow solution. LC-MS showed the reaction was complete. The reaction mixture was concentrated by $N_2$, and the resultant residue dissolved in MeOH (20 mL). The mixture was stirred at 30° C. for 12 hr. LC-MS showed the reaction was complete. The reaction mixture was concentrated, dissolved in DCM (30 ml) and the solution adjusted to pH 8 with saturated $NaHCO_3$. The organic layer was separated, dried over $Na_2SO_4$ and concentrated to give the crude product. The product was purified by prep-TLC (eluting with: DCM/MeOH=10/1) to give K101-C136101 (12.2 mg, 20.19 μmol, 30.49% yield, 98.26% purity) and K101-C136102 (15.6 mg, 25.77 μmol, 38.91% yield, 98.09% purity) as white solids.

K101-C136101: LC-MS (m/z): 616.2 $[M+Na]^+$

K101-C136101: $^1H$ NMR (400 MHz, $CD_3OD$) δ7.56 (s, 1H), 7.28-7.13 (m, 5H), 5.6-5.61 (m, 1H), 3.98-3.91 (m, 2H), 3.51-3.50 (m, 1H), 3.19 (s, 1H), 3.09 (s, 1H), 2.64-2.62 (m, 2H), 2.60-2.47 (m, 2H), 2.18-2.06 (m, 2H), 1.76-1.60 (m, 8H), 1.35-1.31 (m, 10H), 1.21 (s, 3H), 1.10 (s, 3H), 0.94-0.89 (m, 4H).

K101-C136102: LC-MS (m/z): 616.3 $[M+Na]^+$

K101-C136102: $^1H$ NMR (400 MHz, $CD_3OD$) δ7.56 (s, 1H), 7.28-7.13 (m, 5H), 5.6-5.61 (m, 1H), 3.99-3.92 (m, 2H), 3.46-3.45 (m, 1H), 3.19 (s, 1H), 3.09 (s, 1H), 2.64-2.62 (m, 2H), 2.60-2.47 (m, 2H), 2.14-2.03 (m, 2H), 1.77-1.61 (m, 8H), 1.36-1.26 (m, 10H), 1.21 (s, 3H), 1.10 (s, 3H), 0.95-0.92 (m, 4H).

Example 58: Synthesis Scheme of K101-C1364

The scheme for synthesis of K101-C1364 is illustrated below.

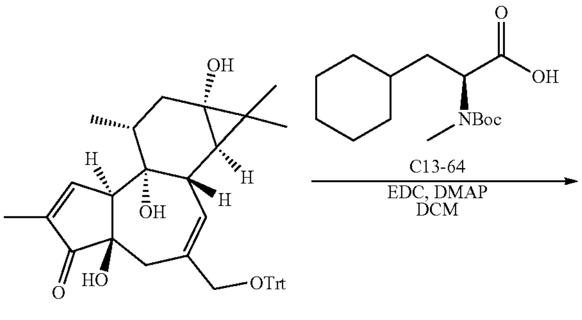

K101-C20Tr-B

C13-64

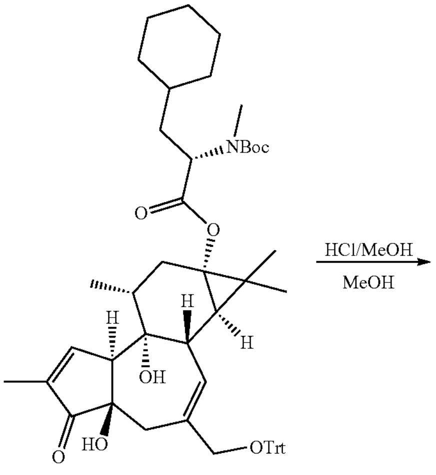

K101-C1364-A

-continued

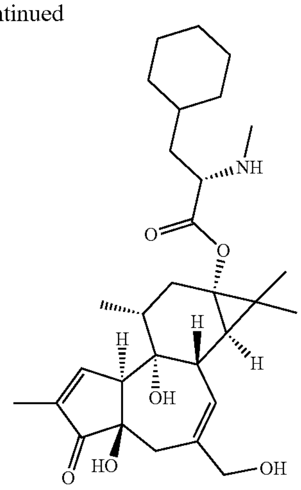

K101-C1364

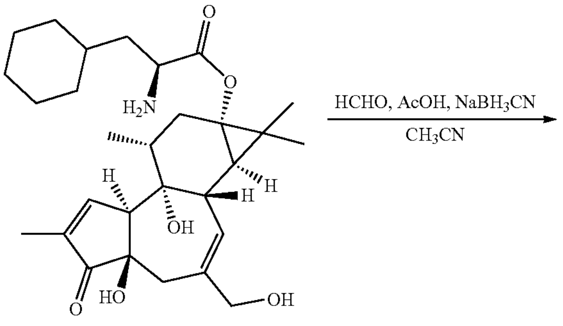

K101-C1327

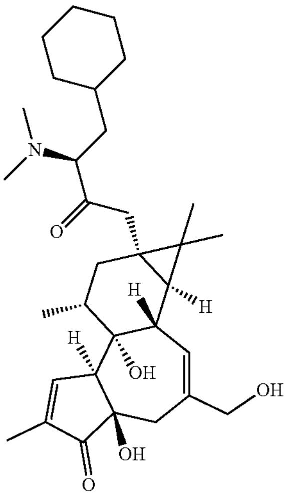

K101-C1365

Preparation of Compound K101-C1364-A. To a solution of K101-C20Tr-B (30 mg, 50.78 mol, 1 eq) and C13-64 (36.23 mg, 126.96 μmol, 2.5 eq) in DCM (1 mL) were added EDC (48.68 mg, 253.92 μmol, 5 eq) and DMAP (18.61 mg, 152.35 mol, 3 eq). The mixture was stirred at 20° C. for 5 hr to give a pale yellow solution. The reaction was complete as detected by LC-MS. The reaction solution was combined with K101-C20Tr-B (5 mg), diluted with $H_2O$ (10 mL), and extracted with DCM (10 mL×3). The combined organic layers were dried over $Na_2SO_4$ and concentrated under reduced pressure to give a yellow gum. The product was purified by prep-TLC (PE/EtOAc=3/1, $SiO_2$) to give K101-C1364-A (23.6 mg, 27.50 mol, 54.16% yield) as a yellow solid.

Preparation of Compound K101-C1364. To a solution of K101-C1364-A (23.6 mg, 27.50 μmol, 1 eq) in MeOH (0.5 mL) was added HCl/MeOH (4 M, 0.5 mL, 72.72 eq), and the mixture stirred at 20° C. for 2 hours to give a yellow solution. The reaction was complete as detected by LC-MS. The reaction solution was diluted with $H_2O$ (2 mL), neutralized with saturated aqueous $NaHCO_3$ until pH 7, and the extracted with DCM (5 mL×5). The combined organic layers were dried over $Na_2SO_4$ and concentrated under reduced pressure to give a yellow solid. The product was purified by prep-TLC (DCM/MeOH=10/1, $SiO_2$) to give K101-C1364 (3.5 mg, 6.79 μmol, 24.68% yield, 100% purity) as a white solid.

LC-MS (m/z): 538.1 $[M+Na]^+$ $^1H$ NMR (400 MHz, $CD_3OD$) δ 7.55 (s, 1H), 5.60-5.61 (m, 1H), 4.62 (s, 1H), 4.00-3.88 (m, 2H), 3.26 (t, J=7.4 Hz, 1H), 3.20-3.15 (m, 1H), 3.07-3.10 (m, 1H), 2.57-2.39 (m, 2H), 2.34 (s, 3H), 2.20-2.11 (m, 1H), 2.11-2.01 (m, 1H), 1.79-1.82 (m, 1H), 1.74-1.75 (m, 4H), 1.69-1.71 (m, 3H), 1.59-1.46 (m, 3H), 1.31-1.22 (m, 3H), 1.21 (s, 3H), 1.09 (s, 3H), 0.94-0.87 (m, 5H).

Example 59: Synthesis Scheme of K101-C1365

The scheme for synthesis of K101-C1365 is illustrated below.

Preparation of Compound K101-C1365. To a solution of K101-C1327 (5.00 mg, 9.97 μmol, 1 eq) in $CH_3CN$ (0.5 mL) were added formaldehyde (8.09 mg, 99.67 μmol, 7.42 uL, 10 eq) and AcOH (598.54 ug, 9.97 μmol, 0.57 uL, 1 eq). After stirred at 20° C. for 5 minutes, $NaBH_3CN$ (3.76 mg, 59.80 μmol, 6 eq) was added in portions, and the mixture stirred at 20° C. for 14 hr to give a colorless solution. LC-MS showed the presence of the desired MS species. The reaction solution was quenched with saturated $NaHCO_3$ (10 mL) and extracted with EtOAc (10 mL×2). The combined organic layers were washed with brine (10 mL), dried over anhydrous $Na_2SO_4$, filtered, and then concentrated under reduced pressure to give crude product as a yellow solid. The product was purified by prep-TLC ($SiO_2$, DCM:MeOH=10:1) to give a yellow solid. The product was further purified by prep-HPLC (column: Phenomenex Gemini 150×25 mm×10 um; mobile phase: [A: water (0.05% HCl)-B: ACN]; B %: 20%-50%, 10 min) to give K101-C1365 (1.5 mg, 2.83 μmol, 20.29% yield) as a white solid.

LC-MS (m/z): 552.2 $[M+Na]^+$ $^1H$ NMR (400 MHz, $CD_3OD$) δ 7.56 (s, 1H), 5.64 (s, 1H), 4.21-4.18 (m, 1H), 3.96 (s, 2H), 3.17 (s, 1H), 3.06 (s, 1H), 2.94 (s, 6H), 2.56-2.43 (m, 3H), 2.30-2.28 (m, 1H), 1.94-1.45 (m, 15H), 1.32-1.29 (m, 9H), 1.20 (s, 3H), 1.11 (s, 3H), 0.95-0.90 (m, 4H).

Example 60: Synthesis Scheme of K101-C1370

The scheme for synthesis of K101-C1370 is illustrated below.

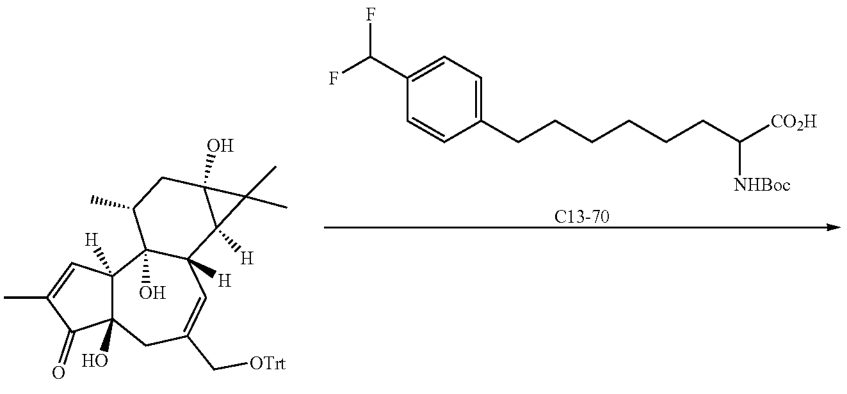
K101-C20Tr-B
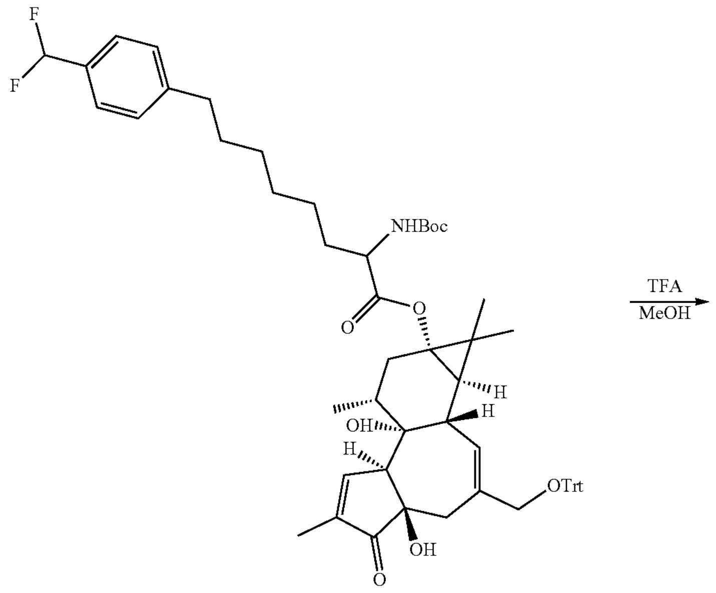
K101-C1370-A
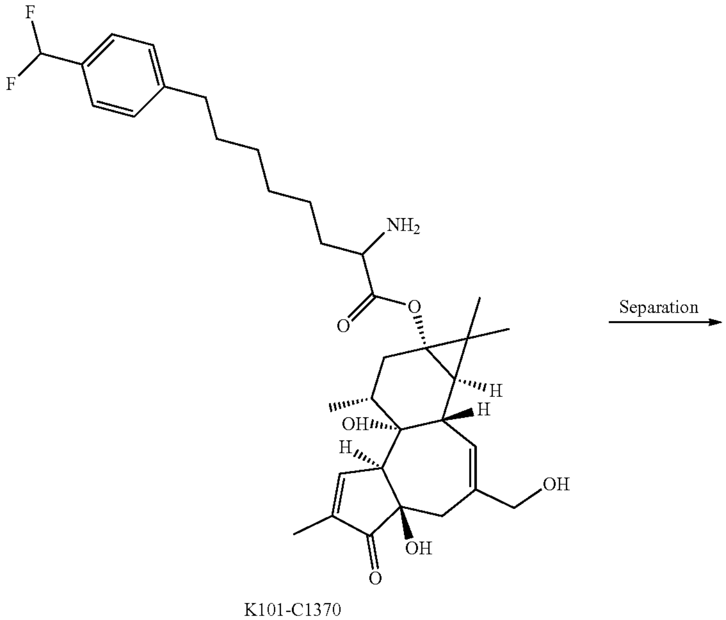
K101-C1370

-continued

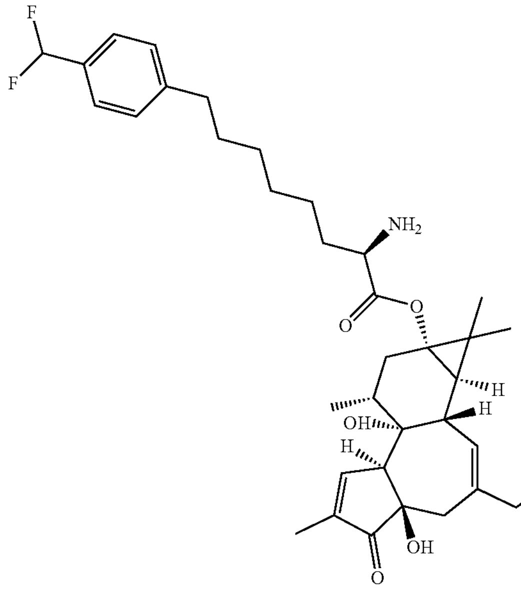

K101-C137001

+

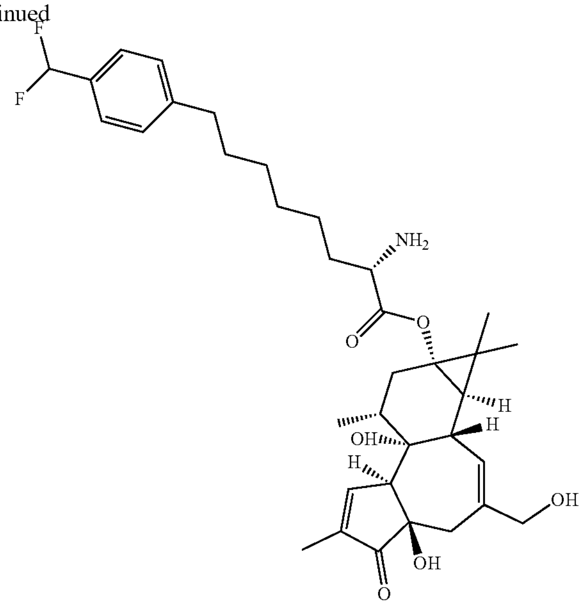

K101-C137002

Preparation of Compound K101-C1370-A. To a solution of K101-C20Tr-B (30 mg, 50.78 mol, leq) and K101-C13-70 (29.36 mg, 76.17 μmol, 1.5 eq) in DCM (1 mL) were added DMAP (3.10 mg, 25.39 μmol, 0.5 eq) and EDC (19.47 mg, 101.57 μmol, 2 eq). The mixture was stirred at 10° C. for 1 hr to give a yellow solution. LC-MS showed the reaction was complete. DCM (3 mL) was added and the mixture filtered and concentrated. The product was purified by prep-TLC (SiO2, PE:EtOAc=2:1) to give K101-C1370-A (42 mg, 43.83 μmol, 86.31% yield) as a yellow oil.

Preparation of Compound K101-C1370. To a solution of K101-C1370-A (40 mg, 41.75 μmol, 1 eq) in THF (1 mL) was added TFA (3.08 g, 27.01 mmol, 2 mL, 647.06 eq). The mixture was stirred at 10° C. for 2 hr to give a yellow solution. The mixture was concentrated with $N_2$ to give a brown gum. The residue was diluted with MeOH (20 mL) and the mixture stirred at 15° C. for 72 hr to give a yellow solution. The final mixture was concentrated, and the product was purified by prep-HPLC (column: Phenomenex Gemini 150×25 mm×10 um; mobile phase: [A: water (0.1% TFA)-B: ACN]; B %: 35%-45%, 10 min) to give K101-C137001 (6.5 mg, 8.91 μmol, TFA salt) and K101-C137002 as white solids. K101-C137002 was purified by prep- TLC (eluting with: EtOAc/MeOH=10/1) to give K101-C137002 (6.1 mg, 9.91 μmol) as a white solid.

K101-C137001 LC-MS (m/z): 638.3 $[M+Na]^+$

K101-C137001 $^1H$ NMR (400 MHz, $CD_3OD$) δ 7.56 (s, 1H), 7.46-7.44 (m, 2H), 7.33-7.31 (m, 2H), 6.87-6.59 (m, 1H), 5.61 (s, 1H), 3.96 (s, 2H), 3.54-3.53 (m, 1H), 3.18 (s, 1H), 3.09 (s, 1H), 2.71-2.67 (m, 2H), 2.57-2.42 (m, 2H), 2.18-2.06 (m, 3H), 1.77 (s, 3H), 1.67-1.58 (m, 4H), 1.39-1.29 (m, 6H), 1.19 (s, 3H), 1.10 (s, 3H), 0.93-0.89 (m, 4H).

K101-C137002 LC-MS (m/z): 638.6 $[M+Na]^+$

K101-C137002 $^1H$ NMR (400 MHz, $CD_3OD$) δ 7.56 (s, 1H), 7.46-7.44 (m, 2H), 7.33-7.31 (m, 2H), 6.87-6.58 (m, 1H), 5.63 (s, 1H), 3.99 (s, 2H), 3.54-3.50 (m, 1H), 3.19 (s, 1H), 3.09 (s, 1H), 2.71-2.67 (m, 2H), 2.52-2.47 (m, 2H), 1.76-1.39 (m, 11H), 1.20 (s, 3H), 1.09 (s, 3H), 0.95-0.90 (m, 4H).

Example 61: Synthesis Scheme of K101-C1373

The scheme for synthesis of K101-C1373 is illustrated below.

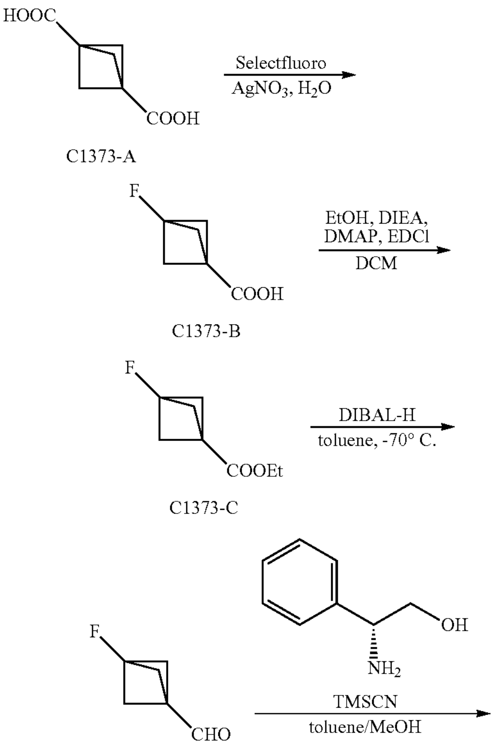

C1373-A

C1373-B

C1373-C

C1373-D

-continued

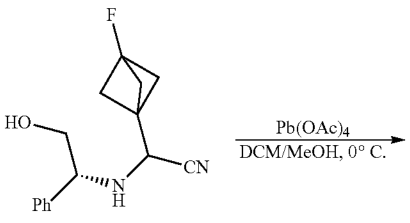

C1373-E

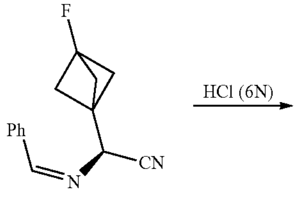

C1373-F

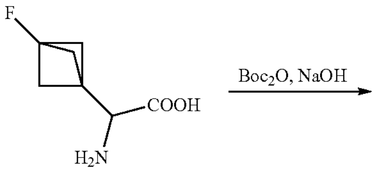

C1373-G

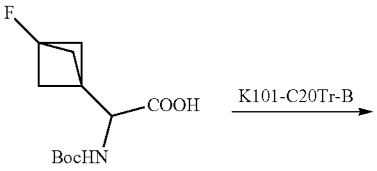

BB-C1373

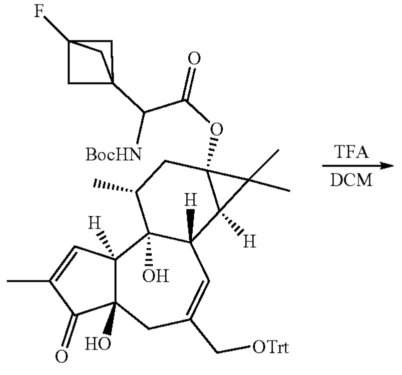

K101-C1373-A

-continued

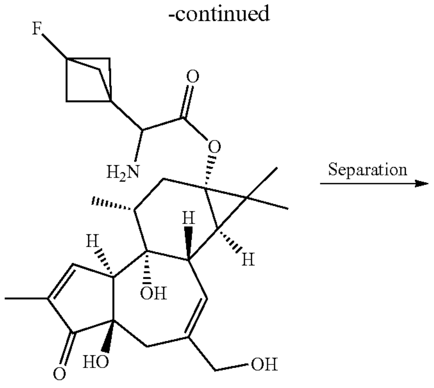

K101-C1373

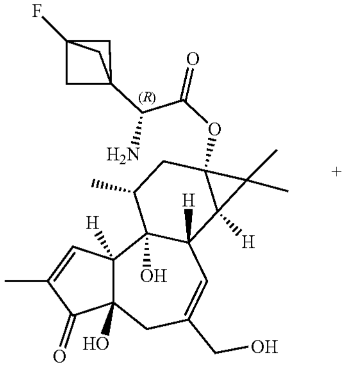

K101-C137301

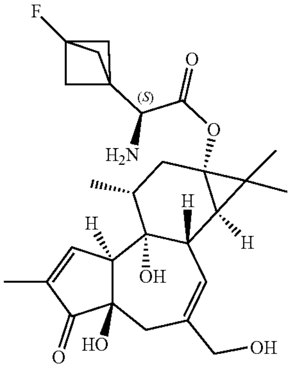

K101-C137302

Preparation of Compound C1373-B. Compound C1373-A (1.5 g, 9.61 mmol, 1 eq) was dissolved in $H_2O$ (40 mL), and the mixture purged with $N_2$. 1-(chloromethyl)-4-fluoro-1,4-diazoniabicyclo [2.2.2] octane ditetrafluoroborate (6.13 g, 17.29 mmol, 1.8 eq) and $AgNO_3$ (326.39 mg, 1.92 mmol, 323.16 uL, 0.2 eq) were added, and the mixture stirred at 55° C. for 12 hr under $N_2$ to give a brown suspension. TLC (eluting with: EtOAc=100%) showed the reaction was complete. The reaction mixture was filtered, extracted with MTBE (50 mL×3), and the organic layers dried over $Na_2SO_4$ and concentrated to give C1373-B (680 mg, 5.23 mmol, 54.40% yield) as a yellow solid. The preparation was used without further purification.

Preparation of Compound C1373-C. To a solution of C1373-B (680 mg, 5.23 mmol, 1 eq) in DCM (10 mL) were added EtOH (481.51 mg, 10.45 mmol, 611.06 uL, 2 eq), DIEA (945.61 mg, 7.32 mmol, 1.27 mL, 1.4 eq), DMAP (127.69 mg, 1.05 mmol, 0.2 eq) and EDC (1.30 g, 6.79 mmol, 1.3 eq). The mixture was stirred at 20° C. for 12 hr to give a yellow solution. TLC (eluting with: PE/EtOAc=3/1) showed the reaction was complete. The reaction mixture was washed with HCl (1N, 30 mL), and extracted with DCM (30 ml×3). The organic layers were dried over $Na_2SO_4$ and concentrated to give C1373-C (560 mg, 3.54 mmol, 67.75% yield) as a yellow oil.

Preparation of Compound C1373-D. To a solution of C1373-C (560 mg, 3.54 mmol, 1 eq) in toluene (5 mL) was added dropwise Diisobutylaluminium hydride (DIBAL-H) (1 M, 4.25 mL, 1.2 eq) at −70° C. The mixture was stirred at −70° C. for 1.5 hr to give a yellow solution. TLC (eluting with: PE/EtOAc=3/1) showed the reaction was complete. The reaction mixture was quenched with MeOH (5 mL), and used for next step without further purification.

Preparation of Compound C1373-E. To (2R)-2-amino-2-phenyl-ethanol (582.77 mg, 4.25 mmol, 1.2 eq) was added C1373-D (404 mg, 3.54 mmol, 1 eq), and the mixture stirred at 0° C. for 3 hr. TMSCN (1.05 g, 10.62 mmol, 1.33 mL, 3 eq) was added, and the mixture stirred at 20° C. for 12 hr to give a yellow solution. LC-MS and TLC (eluting with: PE/EtOAc=2/1) showed the reaction was complete. The reaction was quenched with saturated KF (20 mL) and extracted with EtOAc (20 mL×3). The organic layers were dried over $Na_2SO_4$ and concentrated to give the crude product. The product was purified by a flash column (eluting with: PE/EtOAc=1/2) to give C1373-E (480 mg, 1.84 mmol, 52.09% yield) as a yellow oil.

Preparation of Compound C1373-F. To a solution of C1373-E (480 mg, 1.84 mmol, 1 eq) in DCM (10 mL)/MeOH (10 mL) was added $Pb(OAc)_4$ (1.23 g, 2.77 mmol, 1.5 eq). The mixture was stirred at 0° C. for 15 min to give a yellow solution. TLC (eluting with: PE/EtOAc=2/1) showed the reaction was complete. The reaction mixture was quenched with saturated $NaHCO_3$ (20 mL) and extracted with DCM (15 mL×3). The organic layers were dried over $Na_2SO_4$ and concentrated to give C1373-F (400 mg, 1.75 mmol, 95.03% yield) as a yellow oil.

Preparation of Compound C1373-G. Compound C1373-F (0.4 g, 1.75 mmol, 1 eq) was dissolved in HCl (6 M, 292.06 uL, 1 eq), and the mixture stirred at 100° C. for 12 hr to give a yellow solution. LC-MS showed the reaction was complete. The product was concentrated to give C1373-G (342 mg, 1.75 mmol, 99.77% yield, HCl) as a yellow solid.

Preparation of Compound BB-C1373. To a solution of C1373-G (342 mg, 2.15 mmol, 1 eq) in H2O (3 mL)/dioxane (5 mL) were added NaOH (859.46 mg, 21.49 mmol, 10 eq) and $Boc_2O$ (703.45 mg, 3.22 mmol, 740.48 uL, 1.5 eq), and the mixture stirred at 20° C. for 12 hr to give a yellow solution. LC-MS showed the reaction was complete. The reaction mixture was extracted with MBTE (20 mL×2), and the water layer extracted with EtOAc (20 mL×3). The combined organic layers were dried over $Na_2SO_4$ and concentrated to give BB-C1373 (200 mg, 771.39 μmol, 35.90% yield) as a yellow solid.

Preparation of Compound K101-C1373-A. To a solution of K101-C20Tr-B (60 mg, 101.57 μmol, 1 eq) in DCM (3 mL) were added BB-C1373 (39.50 mg, 152.35 μmol, 1.5 eq), DMAP (49.63 mg, 406.27 μmol, 4 eq) and EDC (29.21 mg, 152.35 μmol, 1.5 eq). The mixture was stirred at 20° C. for 12 hr to give a yellow solution. LC-MS showed the desired mass was found, but some K101-C20Tr-B remained unreacted. The mixture was stirred at 20° C. for an additional 12 hr. LC-MS and TLC (eluting with: PE/EtOAc=2/1) showed the reaction was complete. The reaction mixture was quenched with $H_2O$ (10 mL) and extracted with DCM (15 mL×3). The organic layers were dried over $Na_2SO_4$ and concentrated to give the crude product. The product was purified by a flash column (eluting with: PE/EtOAc=100% PE to 50%) to give K101-C1373-A (70 mg, 84.13 μmol, 82.84% yield) as a brown solid.

Preparation of Compound K101-C1373. To a solution of K101-C1373-A (70 mg, 84.13 μmol, 1 eq) in DCM (5 mL) was added TFA (770.00 mg, 6.75 mmol, 500.00 uL, 80.26 eq). The mixture was stirred at 20° C. for 12 hr to give a yellow solution. LC-MS showed the reaction was complete. The reaction mixture was concentrated by $N_2$, dissolved in MeOH (20 mL) and the mixture stirred at 20° C. for 12 hr. LC-MS showed the reaction was complete. The reaction mixture was concentrated by $N_2$ and then dissolved in DCM (20 mL) and adjusted to pH 8 with saturated $NaHCO_3$ (10 mL). The organic layer was separated, and the water layer extracted with DCM (20 mL×3). The combined organic layers were concentrated to give the crude product. The product was purified by prep-TLC (eluting with: EtOAc/MeOH=10/1) to give K101-C137301 (13.6 mg, 26.76 μmol, 31.81% yield, 96.33% purity) and K101-C137302 (11.6 mg, 22.28 μmol, 26.48% yield, 94.03% purity) as white solids.

K101-C137301 LC-MS (m/z): 512.1 $[M+Na]^+$

K101-C137301 $^1$H NMR (400 MHz, $CDCl_3$) δ 7.51 (s, 1H), 5.60-5.59 (m, 1H), 5.23 (brs, 1H), 4.00-3.91 (m, 2H), 3.67 (s, 1H), 3.20 (s, 1H), 2.95 (s, 1H), 2.48-2.40 (m, 2H), 2.21-2.18 (m, 1H), 2.00-1.95 (m, 8H), 1.71 (s, 3H), 1.46-1.45 (m, 1H), 1.15 (s, 3H), 1.01 (s, 3H), 0.83-0.76 (m, 4H).

K101-C137302 LC-MS (m/z): 512.2 $[M+Na]^+$

K101-C137302 $^1$H NMR (400 MHz, $CDCl_3$) δ 7.51 (s, 1H), 5.59-5.58 (m, 1H), 5.27 (brs, 1H), 3.99-3.90 (m, 2H), 3.65 (s, 1H), 3.21 (s, 1H), 2.95 (s, 1H), 2.48-2.41 (m, 2H), 2.05-1.99 (m, 9H), 1.71 (s, 3H), 1.43-1.42 (m, 1H), 1.12 (s, 3H), 1.02 (s, 3H), 0.83-0.79 (m, 4H).

Example 62: Synthesis Scheme of K101-C1375

The scheme for synthesis of K101-C1375 is illustrated below.

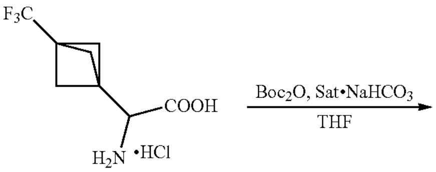

C1375-A

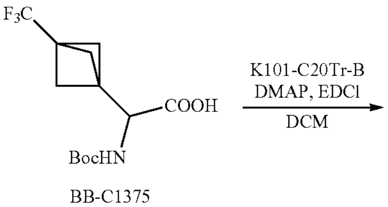

BB-C1375

-continued

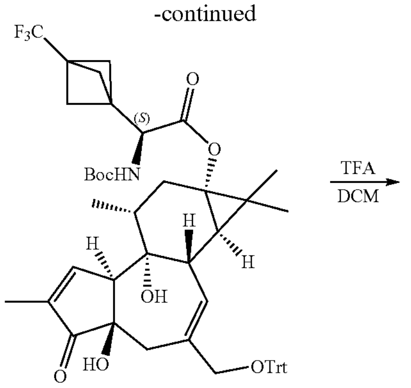

K101-C1375-A

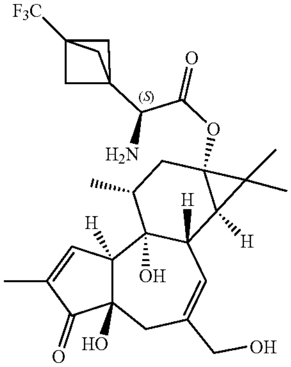

K101-C1375

Preparation of Compound BB-C1375. To a solution of C1375-A (50 mg, 203.56 μmol, 1 eq, HCl) in THF (2 mL)/H2O (1 mL) were added $NaHCO_3$ (42.75 mg, 508.90 μmol, 19.79 uL, 2.5 eq) and $Boc_2O$ (53.31 mg, 244.27 μmol, 56.12 uL, 1.2 eq) at 0° C. The mixture was stirred at 20° C. for 12 hr to give a yellow solution. LC-MS showed the reaction was complete. The reaction mixture was adjusted to pH 4 with HCl (1N) and extracted with MBTE (10 mL×3). The organic layers were dried over $Na_2SO_4$ and concentrated to give the crude product. The product was washed with PE (10 mL) to give BB-C1375 (75 mg, crude) as a white solid.

Preparation of Compound K101-C1375-A. To solution of K101-C20Tr-B (40 mg, 67.71 μmol, 1 eq) in DCM (2 mL) were added BB-C1375 (41.88 mg, 135.42 μmol, 2 eq), DMAP (33.09 mg, 270.84 μmol, 4 eq), HOBt (10.06 mg, 74.48 μmol, 1.1 eq), and EDC (25.96 mg, 135.42 μmol, 2 eq). The mixture was stirred at 20° C. for 12 hr to give a yellow solution. LC-MS showed the desired mass was found, but some K101-C20Tr-B remained unreacted. The mixture was stirred at 20° C. for an additional 12 hr. LC-MS and TLC (eluting with: PE/EtOAc=2/1) showed the reaction was complete. The reaction was quenched with $H_2O$ (5 mL) and extracted with DCM (10 mL×3). The organic layers were dried over $Na_2SO_4$ and concentrated to give the crude product. The product was purified by prep-TLC (eluting with: PE/EtOAc=2/1) to give K101-C1375-A (44 mg, 49.89 μmol, 73.67% yield) as a white solid.

Preparation of Compound K101-C1375. To a solution of K101-C1375-A (44 mg, 49.89 μmol, 1 eq) in DCM (3 mL) was added TFA (770.00 mg, 6.75 mmol, 0.5 mL, 135.37 eq) at 0° C., and the mixture stir at 20° C. for 12 hr to give a yellow solution. LC-MS and TLC (eluting with: PE/EtOAc=2/1) showed the reaction was complete. The reaction mixture was concentrated by $N_2$, and the resultant residue dissolved in MeOH (20 mL). The mixture was stirred at 20° C. for 12 hr. LC-MS showed the reaction was complete. The mixture was concentrated to give the crude product, which was dissolved in MBTE (20 mL) and washed with saturated $NaHCO_3$ (10 mL). The organic layer was separated, and the water layer extracted with MBTE (20 mL×3). The combined organic layers were dried over $Na_2SO_4$ and concentrated to give the crude product. The product was purified by prep-TLC (eluting with: PE/EtOAc=10/1) to give K101-C1375 (11.7 mg, 20.18 μmol, 40.45% yield, 93.05% purity) as a white solid.

LC-MS (m/z): 562.2 $[M+Na]^+$ $^1H$ NMR (400 MHz, $CD_3OD$) δ 7.58 (s, 1H), 5.64-5.63 (m, 1H), 4.00-3.92 (m, 2H), 3.60 (s, 1H), 3.21 (s, 1H), 3.10 (s, 1H), 2.52-2.43 (m, 2H), 2.21-2.01 (m, 8H), 1.77 (s, 3H), 1.58-1.55 (m, 1H), 1.22 (s, 3H), 1.11 (s, 3H), 0.98-0.93 (m, 4H).

Example 63: Synthesis Scheme of K101-C134801C2003

The scheme for synthesis of K101-C134801C2003 is illustrated below.

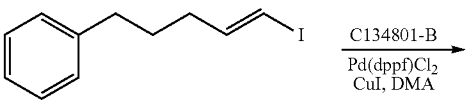

C1348-D

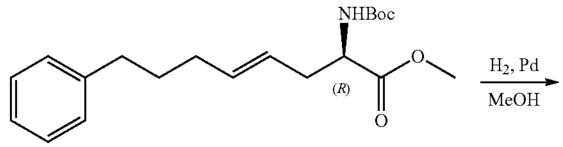

C134801-C

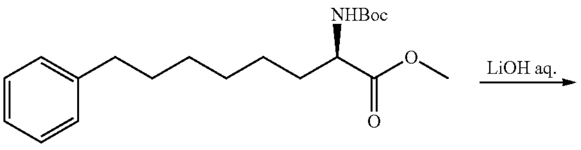

C134801-D

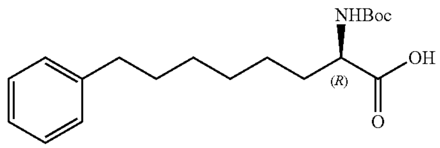

BB-C134801

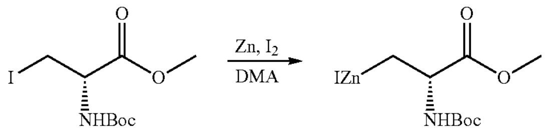

C134801-A C134801-B

-continued

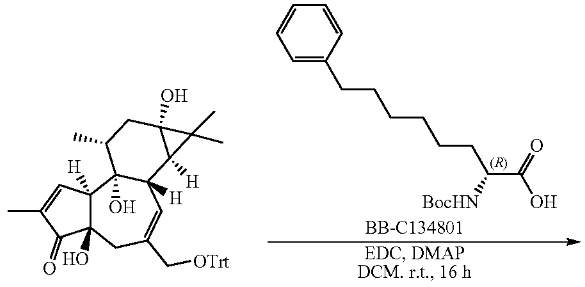

K101-C20Tr-B

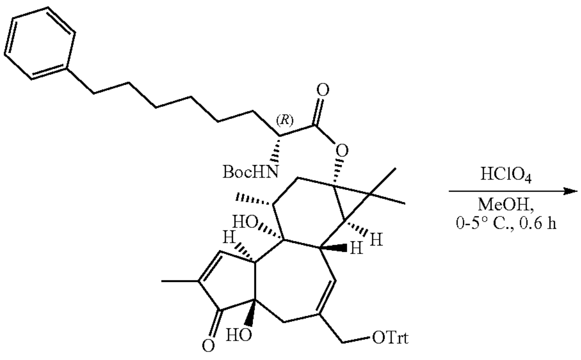

K101-C134801-A

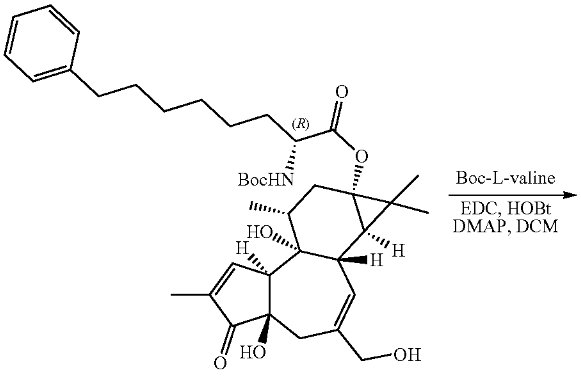

K101-C134801-B

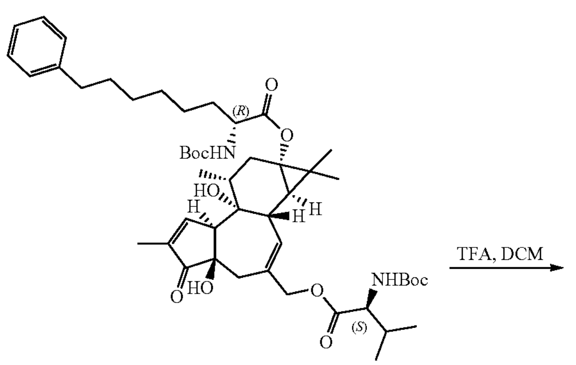

K101-C134801C2003-A

-continued

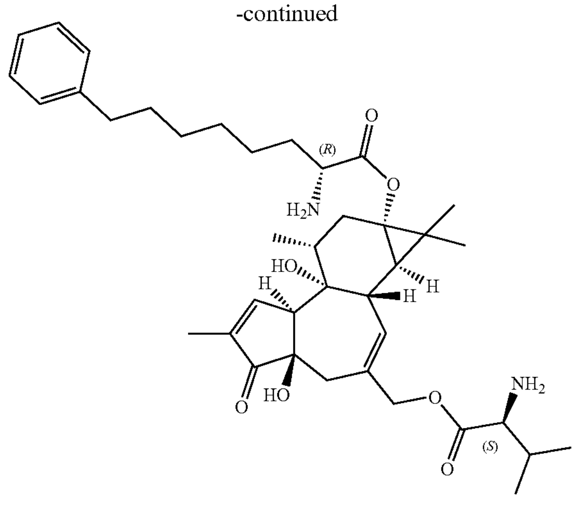

K101-C134801C2003

Preparation of Compound C134801-C. To a solution of C1348-D (2 g, 7.35 mmol, 1 eq) in DMA (2 mL) were added CuI (139.97 mg, 734.96 μmol, 0.1 eq) and C134801-B (4.06 g, 10.29 mmol, 1.4 eq) and Pd(dppf)$Cl_2$ (537.77 mg, 734.96 μmol, 0.1 eq) under $N_2$. The mixture was stirred under $N_2$ at 90° C. for 5 hr to give a black suspension. LC-MS and TLC (eluting with: PE/EtOAc=3/1) showed the reaction was complete. The reaction mixture was quenched with $H_2O$ 100 mL) and extracted with MBTE (40 mL×3). The organic layers were dried over $Na_2SO_4$ and concentrated to give the crude product. The product was purified by a flash column (eluting with: PE/EtOAc=100% PE to 20%) to give C134801-C (750 mg, 2.16 mmol, 29.37% yield) as a yellow oil.

Preparation of Compound C134801-D. To a solution of C134801-C (0.75 g, 2.16 mmol, 1 eq) in MeOH (15 mL) was added Pd/C (500 mg, 2.16 mmol, 50% purity, 1 eq) under $N_2$. The suspension was degassed under vacuum and purged with $H_2$ several times. The mixture was stirred under $H_2$ (15 psi) at 20° C. for 12 hours. After LC-MS showed the reaction was complete, the mixture was filtered on Celite and then concentrated to give C134801-D (750 mg, 2.15 mmol, 99.42% yield) as a black oil.

Preparation of Compound BB-C134801. To a solution of C134801-D (750 mg, 2.15 mmol, 1 eq) in THF (5 mL)/H2O (1 mL) was added LiOH·$H_2O$ (90.06 mg, 2.15 mmol, 1 eq) at 0° C. The mixture was allowed to stir at 20° C. for 12 hr to give a yellow solution. LC-MS showed the reaction was complete. The reaction mixture was adjusted to pH 4 with HCl (1N) and extracted with MBTE (20 mL×3). The organic layers were dried over $Na_2SO_4$ and concentrated to give BB-C134801 (700 mg, 2.09 mmol, 97.24% yield) as a yellow oil.

Preparation of Compound C134801-B. Zinc (6 g) was treated with 1N HCl aqueous (30 mL) with stirring for 10 min. The mixture was filtered and washed with water (30 mL), EtOH (30 mL) and toluene (30 mL) in sequence, and the dried in vacuum to afford the activated zinc powder. A mixture of activated Zn (2.62 g, 40.11 mmol, 4 eq) and $I_2$ (127.24 mg, 501.32 μmol, 100.98 uL, 0.05 eq) in DMA (10 mL) was stirred at 20° C. for 5 min and C134801-A (3.3 g, 10.03 mmol, 1 eq) in DMA (10 mL) added dropwise. The reaction mixture was stirred at 20° C. for 25 min to give a black suspension.

Preparation of Compound K101-C134801-A. To a solution of K101-C20Tr-B (200 mg, 338.55 μmol, 1 eq) in DCM (3 mL) were added BB-C134801 (193.06 mg, 575.54 μmol, 1.7 eq), DMAP (165.44 mg, 1.35 mmol, 4 eq), HOBt (50.32 mg, 372.41 μmol, 1.1 eq) and EDC (110.33 mg, 575.54 μmol, 1.7 eq). The mixture was stirred at 20° C. for 12 hr to give a yellow solution. LC-MS showed the presence of the desired mass, but some K101-C20Tr-B remained unreacted. The mixture was stirred at 20° C. for an additional 12 hr followed by a second 12 hr to give a yellow solution. LC-MS and TLC (eluting with: PE/EtOAc=2/1) showed the reaction was complete. The reaction mixture was quenched with $H_2O$ (10 mL) and extracted with MBTE (15 mL×3). The organic layers were dried over $Na_2SO_4$ and concentrated to give the crude product. The product was purified by a flash column (eluting with: PE/EtOAc=100% PE to 40%) to give K101-C134801-A (210 mg, 231.23 μmol, 68.30% yield) as a yellow solid.

Preparation of Compound K101-C134801-B. To a solution of K101-C134801-A (210 mg, 231.23 μmol, 1 eq) in MeOH (5 mL) was added $HClO_4$ (46.46 mg, 462.47 μmol, 27.99 uL, 2 eq) at 0° C. The mixture was stirred at 0° C. for 0.5 hr to give a yellow solution. LC-MS showed the reaction was complete. The reaction mixture was quenched with saturated $NaHCO_3$ (10 mL) and extracted with MBTE (15 mL×3). The organic layers were dried over $Na_2SO_4$ and concentrated to give the crude product. The product was purified by flash column (eluting with: PE/EtOAc=100% to 50%) to give K101-C134801-B (120 mg, 180.22 μmol, 77.94% yield) as a yellow solid.

Preparation of Compound K101-C134801C2003-A. To a solution of K101-C134801-B (120 mg, 180.22 μmol, 1 eq) in DMF (3 mL) were added Boc-L-valine (78.31 mg, 360.44 μmol, 2 eq), DMAP (88.07 mg, 720.88 μmol, 4 eq), DIEA (46.58 mg, 360.44 μmol, 62.78 uL, 2 eq) and HATU (137.05 mg, 360.44 μmol, 2 eq). The mixture was stirred at 20° C. for 12 hr to give a yellow solution. LC-MS and TLC (eluting with: PE/EtOAc=1/1) showed the reaction was complete. The reaction mixture was quenched with $H_2O$ (15 mL×3), the combined organic layers dried over $Na_2SO_4$ and then concentrated to give the crude product. The product was purified by a flash column (eluting with: PE/EtOAc=100% to 40%) to give K101-C134801C2003-A (120 mg, 138.71 μmol, 76.97% yield) as a yellow solid.

Preparation of Compound K101-C134801C2003. To a solution of K101-C134801C2003-A (120 mg, 138.71 μmol, 1 eq) in DCM (3 mL) was added TFA (770.00 mg, 6.75 mmol, 500.00 uL, 48.68 eq). The mixture was stirred at 0° C. for 3 hr to give a yellow solution. LC-MS showed the desired mass was found but some K101-C134801C2003-A remained unreacted. The mixture was allowed to stir at 20° C. for an additional 12 hr. LC-MS showed the reaction was complete. The reaction mixture was concentrated by $N_2$ and the resultant product dissolved in DCM (20 mL). Following adjustment of the solution to pH 8 with saturated $NaHCO_3$, the organic layer was separated, and the water layer extracted with DCM (20 mL×3). The combined organic layers were dried over $Na_2SO_4$ and concentrated to give K101-C134801C2003 (72.6 mg, 103.89 μmol, 74.89% yield, 95.14% purity) as a white solid.

LC-MS (m/z): 665.4 $[M+H]^+$ $^1H$ NMR (400 MHz, $CD_3OD$): δ 7.56 (s, 1H), 7.30-7.10 (m, 5H), 5.75 (d, 1H, J=3.6 Hz), 4.70-4.50 (m, 3H), 3.55-3.45 (m, 1H), 3.20-3.10 (m, 2H), 2.70-2.40 (m, 4H), 2.20-1.95 (m, 3H), 1.80-1.55 (m, 8H), 1.45-1.30 (m, 6H), 1.21 (s, 3H), 1.10 (s, 3H), 1.0-0.90 (m, 10H).

Example 64: Synthesis Scheme of K101-C134802C2003

The scheme for synthesis of K101-C134802C2003 is illustrated below.

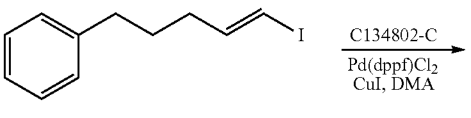

C1348-D

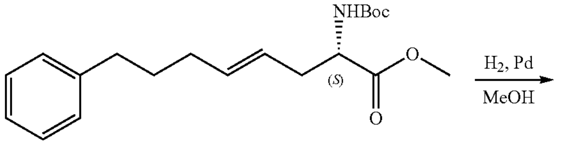

C134802-D

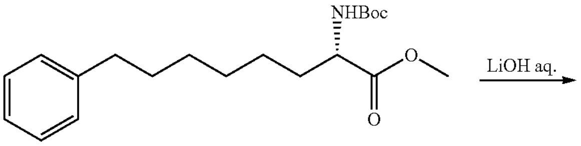

C134802-E

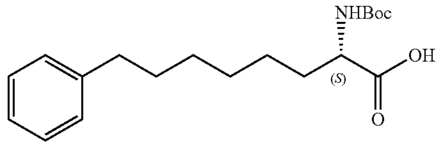

BB-C134802

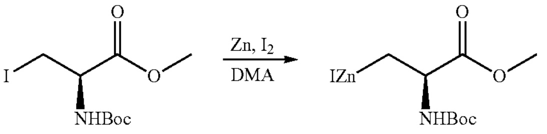

C134802-B C134802-C

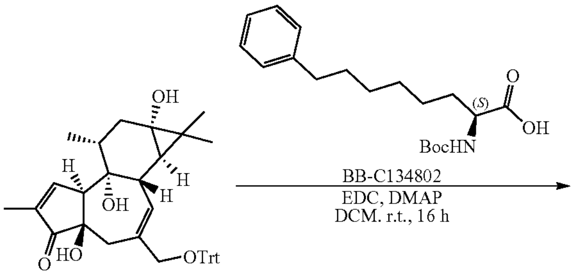

K101-C20Tr-B

-continued

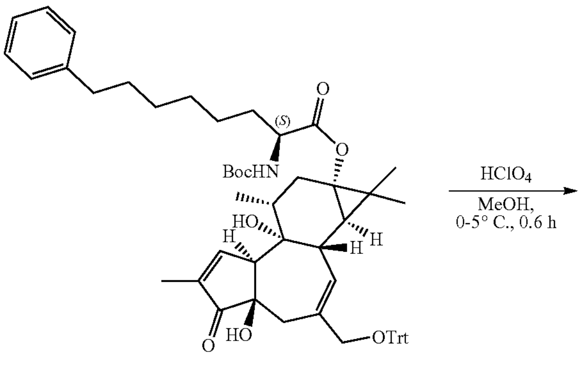

K101-C134802-A

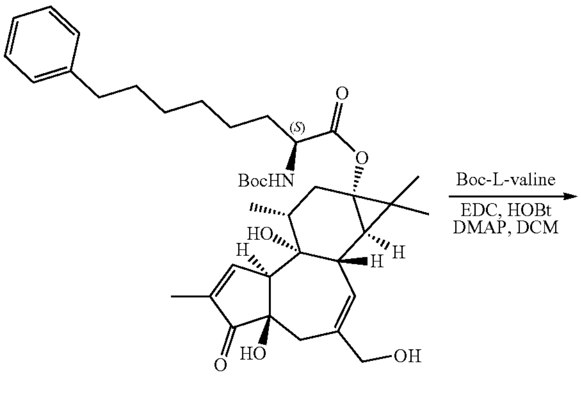

K101-C134802-B

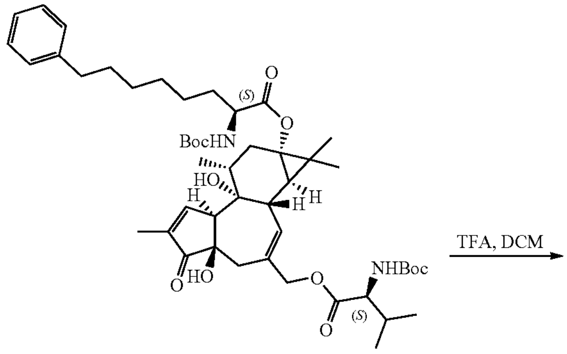

K101-C134802C2003-A

-continued

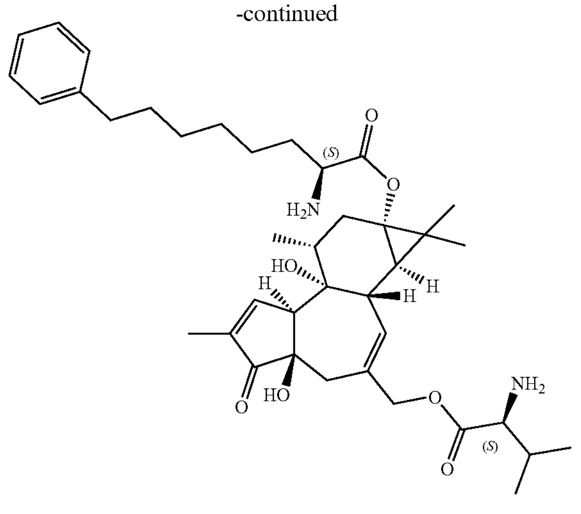

K101-C134802C2003

Preparation of Compound C134802-D. To a solution of C134802-C (4.35 g, 11.02 mmol, 1.5 eq) in DMA (10 mL) were added CuI (139.97 mg, 734.96 μmol, 0.1 eq) and C1348-D (2 g, 7.35 mmol, 1 eq) and Pd(dppf)$Cl_2$ (537.77 mg, 734.96 μmol, 0.1 eq) under $N_2$. The mixture was stirred under $N_2$ at 90° C. for 12 hr to give a black suspension. LC-MS and TLC (eluting with: PE/EtOAc=4/1) showed the reaction was complete. The reaction mixture was quenched with $H_2O$ 200 mL) and extracted with MBTE (100 mL×3). The organic layers were dried over $Na_2SO_4$ and concentrated to give the crude product. The product was purified by a flash column (eluting with: PE/EtOAc=100% PE to 10%) to give C134802-D (1 g, 2.88 mmol, 39.16% yield) as a yellow oil.

$^1$H NMR (400 MHz, $CDCl_3$) δ 7.30-7.27 (m, 1H), 7.20-7.16 (m, 1H), 5.58-5.1 (m, 1H), 5.34-5.26 (m, 1H), 5.02-5.00 (m, 2H), 4.37-4.32 (m, 1H), 3.73 (s, 3H), 2.62-2.58 (m, 2H), 2.48-2.44 (m, 2H), 2.07-2.02 (m, 2H), 1.71-1.66 (m, 2H), 1.44 (s, 9H).

Preparation of Compound C134802-E. To a solution of C134802-D (1 g, 2.88 mmol, 1 eq) in MeOH (20 mL) was added Pd/C (200 mg, 2.88 mmol, 50% purity, 1 eq) under $N_2$. The suspension was degassed under vacuum and purged with $H_2$ several times. The mixture was stirred under $H_2$ (15 psi) at 20° C. for 12 hours. After LC-MS showed the reaction was complete, the mixture was filtered on Celite, washed with MeOH (60 mL), then concentrated to give C134802-E (800 mg, 2.29 mmol, 79.54% yield) as a yellow oil.

$^1$H NMR (400 MHz, $CDCl_3$): δ 7.31-6.98 (m, 5H), 5.05-4.98 (m, 1H), 4.31-4.26 (m, 1H), 3.73 (s, 3H), 2.61-2.57 (m, 2H), 1.76-1.62 (m, 4H), 1.44 (s, 9H), 1.33-1.22 (m, 4H).

Preparation of Compound BB-C134802. To a solution of C134802-E (700 mg, 2.00 mmol, 1 eq) in THF (10 mL)/H2O (1.4 mL) was added LiOH·$H_2O$ (84.06 mg, 2.00 mmol, 1 eq) at 0° C. The mixture was allowed to stir at 20° C. for 12 hr to give a yellow solution. LC-MS showed the reaction was complete. The reaction mixture was extracted with MBTE (20 mL). The water layer was acidified to pH=3 with HCl (0.5N) and extracted with EtOAc (30 mL×3). The organic layers were dried over $Na_2SO_4$ and concentrated to give BB-C134802 (560 mg, 1.61 mmol, 80.54% yield, 96.63% purity, 98.7% ee %) as a yellow oil.

$^1$H NMR (400 MHz, $CDCl_3$): δ 7.28-7.16 (m, 5H), 7.05-7.03 (m, 1H), 3.87-3.81 (m, 1H), 2.57-2.55 (m, 2H), 1.61-1.53 (m, 4H), 1.37 (s, 9H), 1.32-1.18 (m, 6H).

Preparation of Compound C134802-C. Zinc (6 g) was treated with 1N HCl aqueous (30 mL) with stirring for 10 min. The mixture was filtered and washed with water (30 mL), EtOH (30 mL) and toluene (30 mL) in sequence, and the dried in vacuum to afford the activated zinc powder. A mixture of activated Zn (3.18 g, 48.61 mmol, 4 eq) and $I_2$ (154.23 mg, 607.66 μmol, 122.40 μL, 0.05 eq) in DMA (90 mL) was stirred at 20° C. for 5 min. Then C134802-B (4 g, 12.15 mmol, 1 eq) in DMA (30 mL) added dropwise. The reaction mixture was stirred at 20° C. for 25 min to give a black suspension and used for the next step without further purification.

Preparation of Compound K101-C134802-A. To a solution of K101-C20Tr-B (200 mg, 338.55 μmol, 1 eq) in DCM (5 mL) were added BB-C134802 (136.28 mg, 406.27 μmol, 1.2 eq), DMAP (165.44 mg, 1.35 mmol, 4 eq), HOBt (48.03 mg, 355.48 μmol, 1.05 eq) and EDC (77.88 mg, 406.27 μmol, 1.2 eq). The mixture was stirred at 20° C. for 12 hr to give a yellow solution. LC-MS showed the presence of the desired mass, but some K101-C20Tr-B remained unreacted. The mixture was stirred at 20° C. for an additional 16 hr to give a yellow solution. LC-MS and TLC (eluting with: PE/EtOAc=2/1) showed the reaction was complete. The reaction mixture was quenched with saturated $NaHCO_3$ (50 mL) and extracted with DCM (80 mL×3). The organic layers were dried over $Na_2SO_4$ and concentrated to give the crude product. The product was purified by a preparative TLC (eluting with: PE/EtOAc=2/1) to give K101-C134802-A (200 mg, 220.22 μmol, 65.05% yield) as a yellow solid.

$^1$H NMR (400 MHz, $CDCl_3$) δ 7.60 (s, 1H), 7.47-7.44 (m, 6H), 7.33-7.28 (m, 7H), 7.24-7.20 (m, 7H), 5.62-5.61 (m, 1H), 5.14 (m, 1H), 4.25 (brs 1H), 3.54 (s, 2H), 3.29 (s, 1H), 2.95 (s, 1H), 2.64-2.60 (m, 2H), 2.52-2.40 (m, 2H), 2.07-1.99 (m, 6H), 1.80 (s, 4H), 1.64-1.60 (m, 2H), 1.46 (s, 9H), 1.37-1.29 (m, 5H), 1.23 (s, 3H), 1.007 (s, 3H), 0.90-0.86 (m, 4H).

Preparation of Compound K101-C134802-B. To a solution of K101-C134802-A (190 mg, 209.21 μmol, 1 eq) in MeOH (5 mL) was added $HClO_4$ (42.03 mg, 418.42 μmol, 25.32 uL, 2 eq) at 0° C. The mixture was stirred at 0° C. for 0.5 hr to give a yellow solution. LC-MS showed the reaction was complete. The reaction mixture was quenched with saturated $NaHCO_3$ (4 mL) and extracted with DCM (20 mL×3). The organic layers were dried over $Na_2SO_4$ and concentrated to give the crude product. The crude product was purified by a flash column (eluting with: PE/EtOAc=100% to 50%) to give K101-C134802-B (150 mg) as a yellow solid.

$^1$H NMR (400 MHz, $CDCl_3$) δ 7.58 (s, 1H), 7.30-7.27 (m, 2H), 7.19-7.16 (m, 3H), 5.66-5.65 (m, 1H), 4.94-4.92 (m, 1H), 4.30-4.24 (m, 1H), 4.10-4.02 (m, 1H), 3.27 (s, 1H), 3.00 (s, 1H), 2.62-2.48 (m, 4H), 2.24 (s, 1H), 2.05-1.95 (m, 2H), 1.90-1.85 (m, 1H), 1.78 (s, 4H), 1.49-1.44 (m, 10H), 1.34-1.26 (m, 6H), 1.21 (s, 3H), 1.07 (s, 3H), 0.88-0.87 (m, 4H).

Preparation of Compound K101-C134802C2003-A. To a solution of K101-C134802-B (150 mg, 225.27 μmol, 1 eq) in DMF (5 mL) were added Boc-L-valine (97.89 mg, 450.55 μmol, 2 eq), DMAP (110.09 mg, 901.10 μmol, 4 eq), DIEA (58.23 mg, 450.55 μmol, 78.48 uL, 2 eq) and HATU (170.31 mg, 450.55 μmol, 2 eq). The mixture was stirred at 20° C. for 28 hr to give a yellow solution. LC-MS showed the reaction was complete. The reaction mixture was quenched with $H_2O$ (30 mL), the organic layer was dried over $Na_2SO_4$ then concentrated to give the crude product. The product was purified by a flash column (eluting with: PE/EtOAc=100% to 30%) to give K101-C134802C2003-A (150 mg, 173.39 μmol, 76.97% yield) as a yellow solid.

$^1$H NMR (400 MHz, $CDCl_3$) δ 7.61 (s, 1H), 7.32-7.29 (m, 2H), 7.21-7.18 (m, 2H), 5.75 (m, 1H), 5.03-5.00 (m, 2H), 4.59-4.52 (m, 2H), 4.25-4.16 (m, 2H), 3.29 (s, 1H), 3.01-3.00 (m, 1H), 2.64-2.38 (m, 4H), 2.21-2.07 (m, 2H), 2.00-1.95 (m, 1H), 1.81 (s, 3H), 1.63-1.47 (m, 21H), 1.37-1.24 (m, 6H), 1.10 (s, 3H), 1.03 (s, 3H), 0.98-0.96 (m, 5H), 0.90-0.87 (m, 7H).

Preparation of Compound K101-C134802C2003. To a solution of K101-C134802C2003-A (150 mg, 173.39 mol, 1 eq) in DCM (5 mL) was added TFA (770.00 mg, 6.75 mmol, 500.00 uL, 38.95 eq). The mixture was stirred at 20° C. for 1 hr to give a yellow solution. LC-MS showed the reaction was complete. The reaction mixture was concentrated by $N_2$ and the resultant product dissolved in MTBE (20 mL). Following adjustment of the solution to pH 8 with saturated $NaHCO_3$, the organic layer was separated, and the water layer extracted with MTBE (20 mL×3). The combined organic layers were dried over $Na_2SO_4$ and concentrated to give K101-C134802C2003 (85.2 mg, 123.43 μmol, 71.19% yield, 96.32% purity) as a yellow solid.

LC-MS (m/z): 687.4 $[M+Na]^+$ $^1$H NMR (400 MHz, $CD_3OD$): δ 7.56 (s, 1H), 7.30-7.10 (m, 5H), 5.80-5.75 (m, 1H), 4.70-4.50 (m, 3H), 3.55-3.45 (m, 1H), 3.20-3.05 (m, 2H), 2.70-2.50 (m, 3H), 2.50-2.40 (m, 1H), 2.20-1.95 (m, 3H), 1.85-1.45 (m, 8H), 1.45-1.25 (m, 6H), 1.21 (s, 3H), 1.10 (s, 3H), 1.0-0.90 (m, 10H).

Example 65: Compound Binding to C1b Domain of PKC Isoforms

Compounds described in this disclosure were tested for binding affinity to C1b domain of PKC isoforms. Compound binding affinity to C1b domain of PKC isoforms was derived from competitive binding assay using radioactive tracer $^3$H-PDBu and recombinant GST-C1b or full-length of human PKC proteins based on modified procedures from Methods in Molecular Biology, vol. 233: Protein Kinase C Protocols Edited by: A. C. Newton, Humana Press Inc., Totowa, N.J. (2003) and Beans et al., Proc Natl Acad Sci USA. 2013, 110(29):11698-703.

Genes encoding C1b domains of human PKCα, δ, ε, θ, and PKD1 (PKCμ) were synthesized and inserted into pGEX-2TK or pGEX-4T1 vectors for expression and production of GST-C1b proteins in *E. coli* BL21(DE3) via IPTG induction. The target proteins were purified by glutathione sepharose 4B and followed by ion exchange chromatography if needed to achieve purity >70%. Aliquots of the purified proteins were stored at −80 degree for binding assay (storage buffer: 20 mM Tris pH 8.0, 200 mM NaCl, 10% glycerol, 1 mM DTT). Full-length PKCδ was purchased from Millipore (cat #14-504).

Competitive binding assay was performed in 96-well plate (Agilent-5042-1385). 300 μL reaction contains 60 μL of 1 mg/mL phosphatidylserine (Sigma-P7769), 1 μL DMSO, testing compound (10-point 3-fold or 4-fold serial dilution) or PDBu (Sigma-P1269) (final concentration of 5 or 10M as the nonspecific binding control), 19 μL of assay buffer (50 mM Tris-HCl pH7.4, 100 mM KCl, 0.15 mM $CaCl_2$ and 0.2% BSA), 200 μL of protein (final concentration of 1-10 nM), and 20 μL $^3$H-PDBu (ARC-ART 0485) (final concentration of 1-10 nM). The plate was incubated at 37° C. on a shaker at 300 rpm for 10 minutes and then put on ice for 20 minutes. The reaction mixtures were filtered through the GF/B filter plate (PE-6005177) and the plate was washed with the wash buffer (20 mM Tris-HCl pH7.4, stored at 4° C.) for 6 times before drying at 50° C. for 1 hour. The bottom of the filter plate was sealed and 50 μL of MicroScint-20 (PerkinElmer) cocktail was added to each well. $^{3}$H-PDBu trapped in each well was counted using PerkinElmer MicroBeta2 Reader. Data were analyzed using GraphPad Prism5 with the model "log(inhibitor) vs. response-variable slope" to fit the IC50, and then IC50 was transformed to Ki using Cheng-Prusoff equation: Ki=IC50/(1+added radio ligand/Kd). Kd is the binding affinity of each protein preparation to $^{3}$H-PDBu, determined experimentally. Unrelated protein made in similar expression system did not have specific binding to $^{3}$H-PDBu. Ki values of Diterpenoid compounds for human PKCα, δ, ε, θ, and PKD1 (PKCμ) were reported in Table 3.

As shown in Table 3, in general, binding affinity of new diterpenoid compounds in this disclosure to C1b domain of novel PKC isoforms or PKD1 (PKCμ) is much higher than that to conventional PKCα (up to >100-fold difference). The Ki values of the diterpenoid compounds for C1b domain of human PKC δ, α, ε, θ, and PKD1 (PKCμ) are as follows: A=≤5 nM, B=>5 nM and ≤10 nM, C=>1 nM and ≤30 nM; D=>30 nM and ≤60 nM; E=>60 nM and ≤10 nM, F=>100 nM and ≤200 nM; G=>200 nM and ≤400 nM; H=>400 nM and ≤800 nM; I=>800 nM and ≤1000 nM; J=>1000 nM and ≤2000 nM, K=>2000 nM and ≤4000 nM; L=>4000 nM and ≤6000 nM; M=>6000 nM and ≤8000 nM; N=>8000 nM.)

TABLE 3

| Compound | PKCδ | PKCα | PKCθ | PKCε | PKD1/ PKCμ |
|---|---|---|---|---|---|
| PBDu (Phorbol 12,13-dibutyrate) | A | G | A | A | A |
| K101A (or K101, Prostratin) | G | M | F | F | D |
| K103 (TPA) | A | B | A | A | A |
| K101-C13OH | M | N | K | K | L |
| K101-C1301 | B | F | C | B | A |
| K101-C1302 | A | D | A | A | A |
| K101-C1303 | D | H | D | F | C |
| K101-C1304 | B | F | B | C | A |
| K101-C1305 | H | N | G | J | F |
| K101-C1306 | F | J | F | G | C |
| K101-C1308 | C | I | D | C | B |
| K101-C1311 | C | H | C | D | A |
| K101-C1312 | B | F | C | C | A |
| K101-C1313 | C | G | C | C | A |
| K101-C1315 | F | N | NT | NT | D |
| K101-C1316 | F | M | NT | NT | D |
| K101-C1317 | C | I | NT | NT | A |
| K101-C1318 | B | F | C | D | A |
| K101-C1319 | A | E | B | D | A |
| K101-C1320 | D | K | NT | NT | C |
| K101-C1321 | A | E | NT | NT | A |
| K101-C1322 | D | I | NT | NT | B |
| K101-C1323 | G | N | NT | NT | F |
| K101-C1324 | A | F | A | A | A |
| K101-C1325 | D | L | NT | NT | D |
| K101-C1326 | H | N | NT | NT | G |
| K101-C1327 | A | E | B | C | A |
| K101-C1328 | C | G | NT | NT | A |
| K101-C1329 | A | D | B | C | A |
| K101-C1330 | E | J | NT | NT | D |
| K101-C1331 | B | F | NT | NT | A |
| K101-C1332 | B | F | NT | NT | B |
| K101-C1333 | A | E | A | C | A |
| K101-C1334 | H | N | NT | NT | D |
| K101-C1335 | G | N | NT | NT | E |
| K101-C1336 | F | K | NT | NT | D |
| K101-C1337 | C | J | NT | NT | B |
| K101-C1338 | F | K | NT | NT | D |
| K101-C1339 | G | L | NT | NT | E |

TABLE 3-continued

| Compound | PKCδ | PKCα | PKCθ | PKCε | PKD1/ PKCμ |
|---|---|---|---|---|---|
| K101-C1340 | C | G | NT | NT | B |
| K101-C1341 | D | J | NT | NT | C |
| K101-C1342 | B | F | NT | NT | A |
| K101-C1343 | D | J | NT | NT | C |
| K101-C1344 | D | J | NT | NT | C |
| K101-C1345 | A | D | C | C | A |
| K101-C1346 | C | G | D | E | B |
| K101-C1347 | A | C | A | B | A |
| K101-C134801 | B | H | C | C | A |
| K101-C134802 | A | D | A | C | A |
| K101-C134901 | C | G | C | C | B |
| K101-C134902 | A | D | B | C | A |
| K101-C1350 | C | H | NT | NT | A |
| K101-C1351 | D | J | NT | NT | C |
| K101-C1352 | G | L | NT | NT | G |
| K101-C1353 | H | N | NT | NT | L |
| K101-C1354 | D | J | NT | NT | C |
| K101-C1355 | F | NT | NT | NT | D |
| K101-C135601 | D | J | NT | NT | C |
| K101-C135602 | C | G | NT | NT | A |
| K101-C1357 | G | N | NT | NT | D |
| K101-C1358 | C | G | NT | NT | B |
| K101-C135901 | D | J | D | E | C |
| K101-C135902 | B | E | C | C | B |
| K101-C136101 | C | H | C | C | B |
| K101-C136102 | C | D | A | B | A |
| K101-C1364 | C | G | NT | NT | NT |
| K101-C1365 | F | L | NT | NT | D |
| K101-C137001 | C | I | D | D | C |
| K101-C137002 | C | G | C | D | B |

TPA = 12-O-Tetradecanoylphorbol-13-acetate (TPA), also commonly known as tetradecanoylphorbol acetate, tetradecanoyl phorbol acetate, and phorbol 12-myristate 13-acetate (PMA).
NT = Not tested

Example 66: Western Blot to Assess Activation of PKC and Downstream Target Protein by the Diterpenoid Compounds According to the methods described in patent (WO/2017/083783) A549 lung cancer cells (~3 million cells) were seeded in 10 cm tissue culture dishes (or ~1 million cells in 6 cm dish) and grown overnight. Cells were then treated with different drugs at indicated concentrations for 30 minutes. Cell lysate preparation, protein quantitation, SDS-PAGE, and Western blotting procedures are described (WO/2017/083783). β-actin or Vinculin was used as loading controls. Imagequant LAS4000 (GE) was used to scan membranes if secondary antibodies anti-mouse IgG HRP conjugate or anti-rabbit IgG HRP conjugate (dilutions from 1:2000-1:10000) were used. For ProteinSimple Wes system, manufacture's procedure was followed (ProteinSimple 12-230 kDa Wes Separation Module) for sample preparation, loading, running, and data analysis.

Results: 1 μM Prostratin (K101) and 0.3 μM the diterpenoid compounds disclosed herein, such as K101-C1319, -C1321, -C1327, and -C1329, induced high levels of phosphorylation of PKC (detected by phospho-specific antibodies P-PKD/PKC (S916), Cell Signaling Technology cat #2051 and P-PKD/PKC (S744/748), Cell Signaling Technology cat #2054), PKCδ (detected by phospho-specific antibody P-PKCδ (T505), Cell Signaling Technology cat #9374), and one of the PKC downstream targets Erk1/2 (detected by phospho-specific antibody P-Erk1/2 (T202/Y204), Cell Signaling Technology cat #9106) in A549 cells (FIG. 1). Phosphorylation of these sites has been linked to acute activation or catalytic activity of the PKC isoforms and Erk1/2. High level of phosphorylation indicates strong activation. Surprisingly, K101-C1337, an enantiomer of K101-C1327, induced much lower levels of phosphorylation on these proteins, indicating that the stereochemistry of the moiety on the C12 is very important in determining the potency of the compound. Other less potent compounds, such as K101-C1303, -C1315, -C1316, and -C1336, induced phosphorylation at 3 μM.

A subset of the diterpenoid compounds with good binding affinity to novel PKC isoforms and PKC was tested at two different concentrations in A549 cells to assess activation of PKCμ, PKCδ, and Erk1/2 by Western blot analysis. In addition to the phospho-specific antibodies described above, an additional phospho-specific antibody P-PKCδ (S299) (Abcam cat #133456) was also used. This antibody has been shown in the literature (Durgan et al., FEBS Lett. 2007, 581(18):3377-81, Novel phosphorylation site markers of protein kinase C delta activation) to be able to detect activation of PKCδ. K-101 (prostratin, 1 μM) was included as reference compounds.

The results are shown in FIGS. 2, 3, 4A, and 4B. In summary, all of these compounds demonstrated activation of PKCμ, PKCδ, and Erk1/2 in a dose-dependent manner in the concentration range tested. The relative strength of cellular PKC activation correlated well with that of binding affinity of these compounds to PKC isoforms.

Example 67: Effect of Compounds on CaMKii Phosphorylation in PANC1 Cell Line

Figure 5:
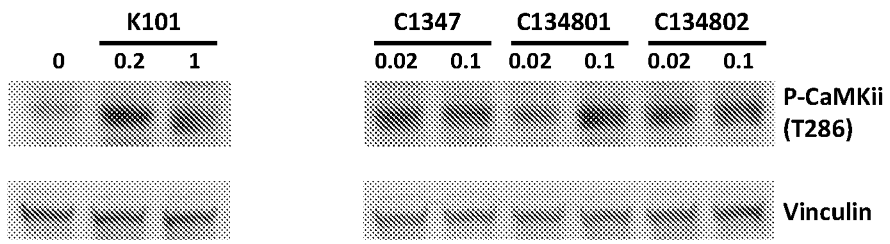
FIG. 5 shows effect of selected diterpenoid compounds on levels of phosphorylated CaMKii (p-CaMKii), a marker of K-Ras stemness pathway inhibition, in Panc1 pancreatic cancer cell line.
Figure 6A:
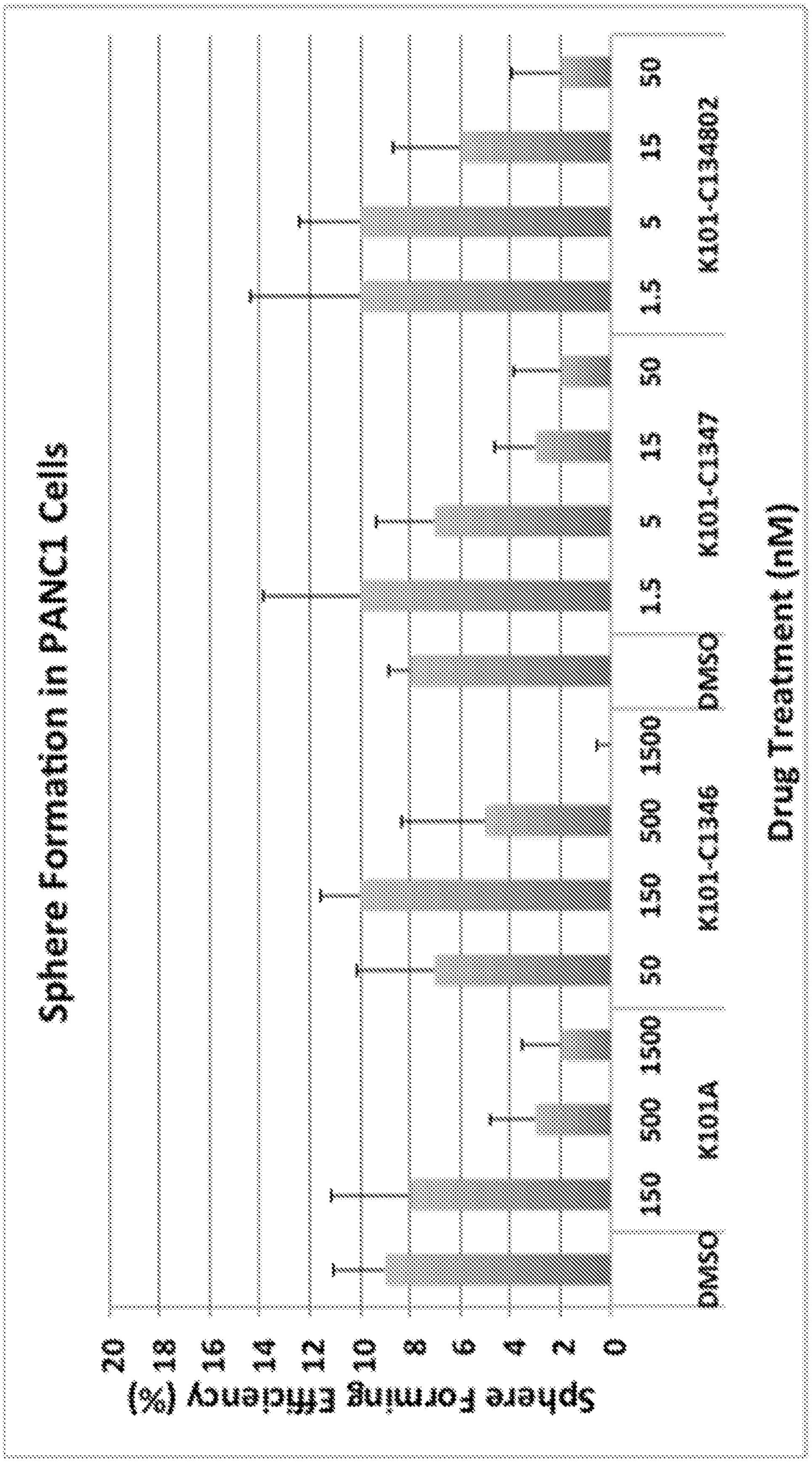
FIGS. 6A-6D show sphere formation by Panc1 pancreatic cancer cell line treated with different diterpenoid compounds.
Figure 6B:
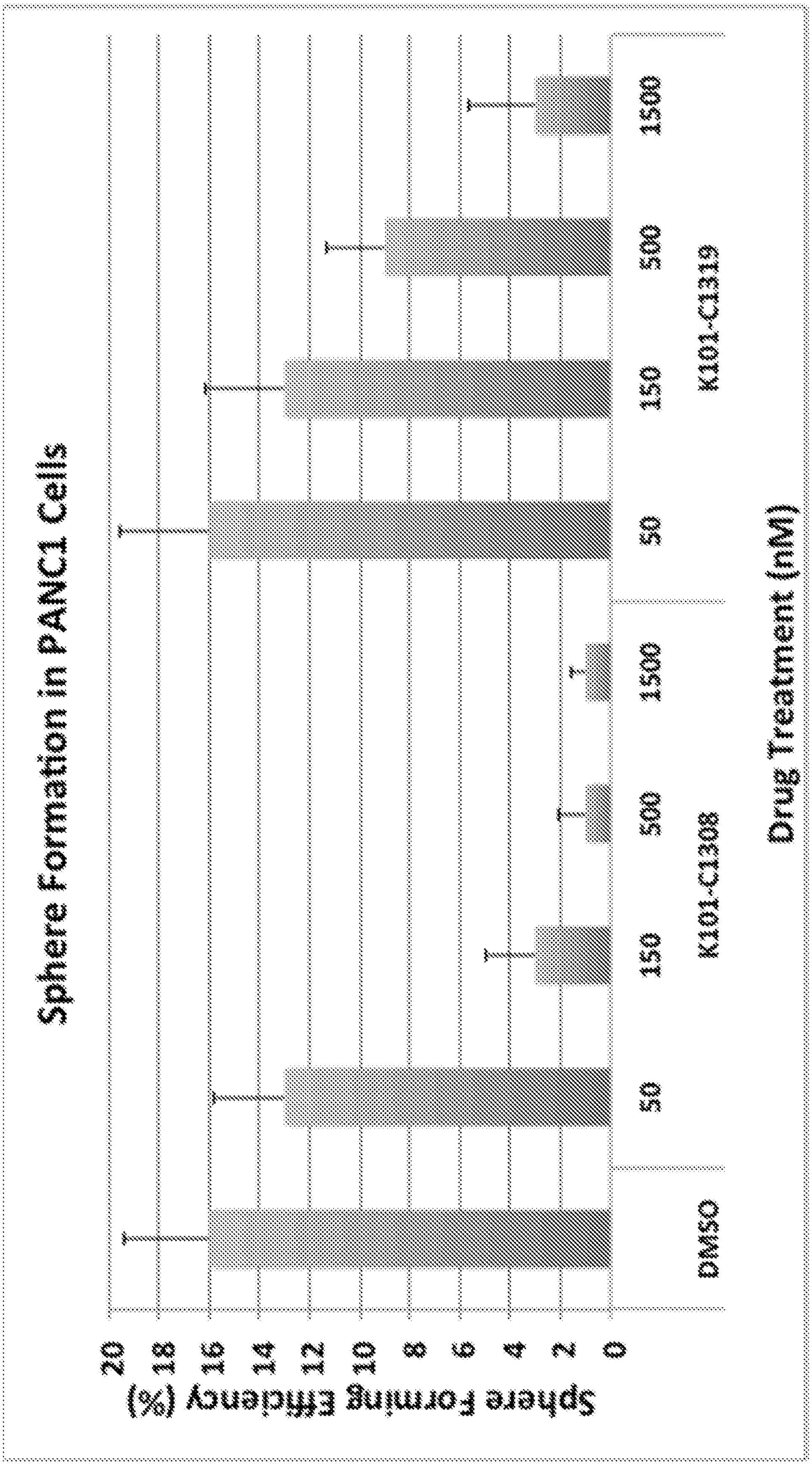
Figure 6C:
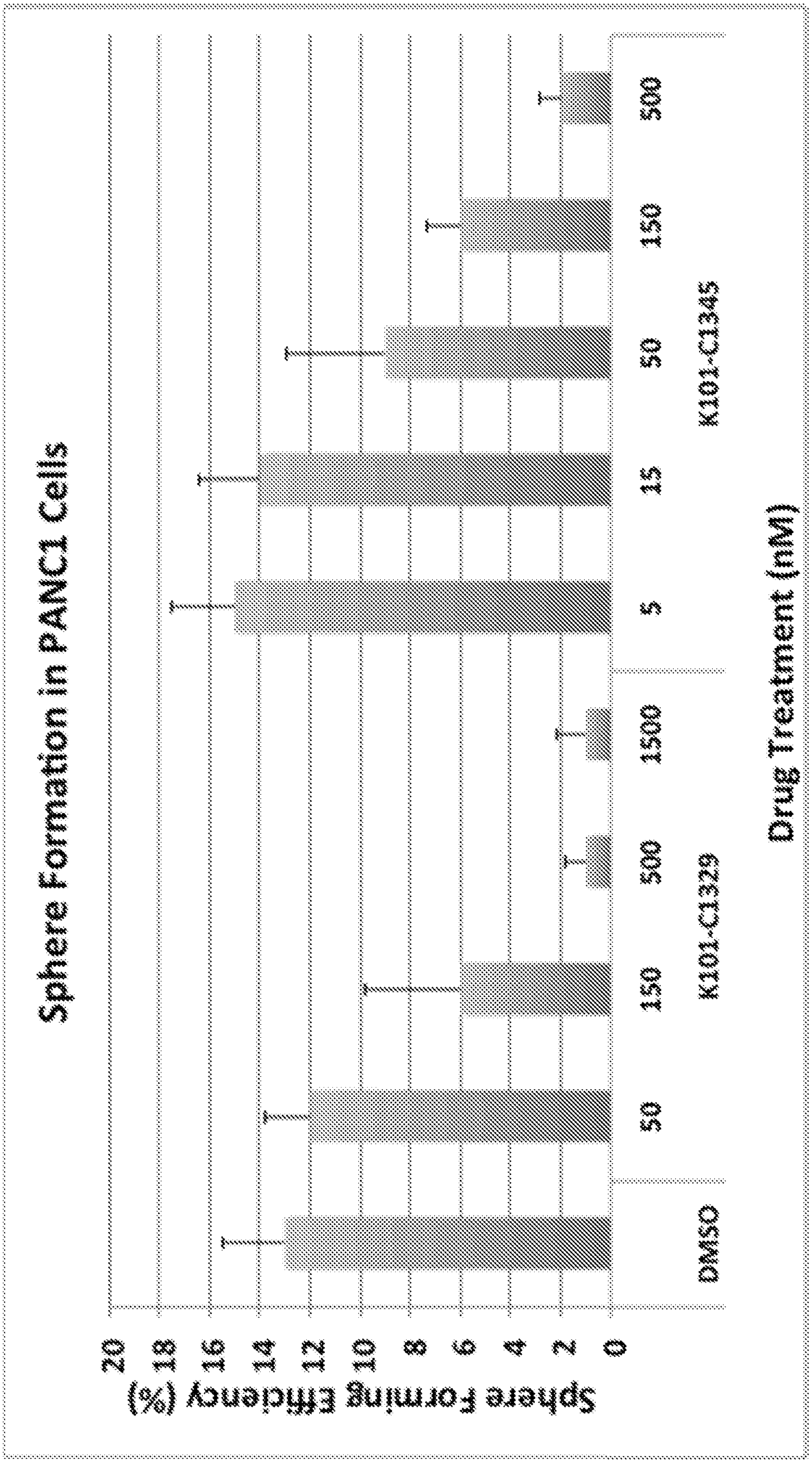
Figure 6D:
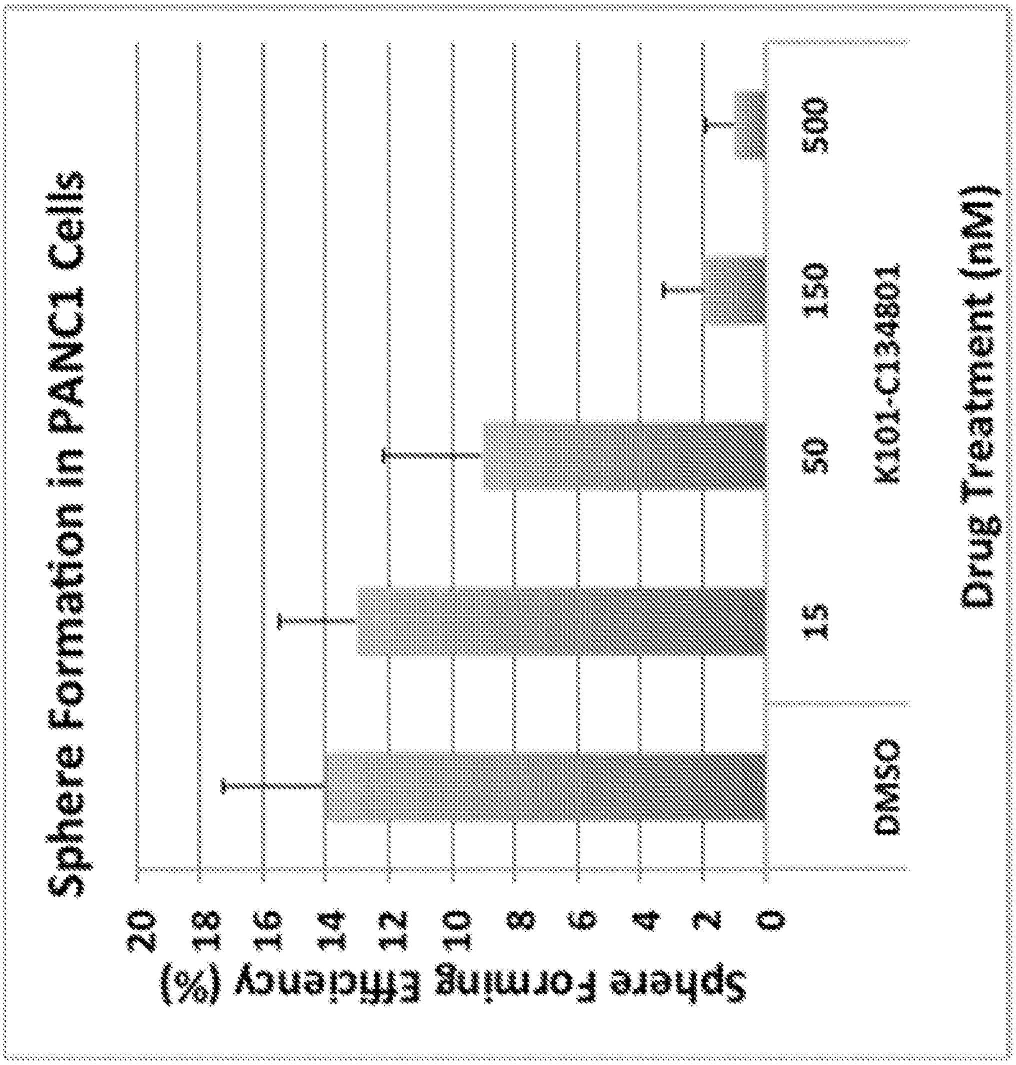

Panc1 (a pancreatic cancer cell line) cells (~5-8 millions) were seeded in 10 cm dishes (or ~2 millions in 6 cm dishes) and treated next day with prostratin (K-101, 0.2 μM and 1 μM) or 0.02 μM and 0.1 M of K101-C1347, -C134801, and -C134802 for 48 hours. Cells were then collected/lysed for Western blot analysis. Protein quantification, SDS-PAGE, and Western blot procedures were performed as described in Example 65, except that a different lysis buffer (1 ml of 10×TNE [20 mL 1M Tris pH7.5; 30 mL 5M NaCl; 2 mL 0.5M EDTA; 48 mL d2$H_2O$], 1 ml of 10% NP40, 7.7 mL of d$H_2O$, 100 μL of 10× Protease inhibitors, 100 μL of 10× Phosphatase inhibitors, and 10 μl DTT) was used. To assess the effect of diterpenoid compounds on CaMKii phosphorylation, a phospho-specific antibody P-CaMKii (T286) (Abcam, cat #32678) was used for detection. Phosphorylation of CaMKii at T286 is a marker for activation of CaMKii kinase in the Wnt/$Ca^{2+}$ signaling pathway when and CaM are dissociated and thus a downstream marker for inhibition of K-Ras stemness (Wang et al., Cell. 2015, 163(5):1237-51). As shown in FIG. 5, all compounds induced phosphorylation of CaMKii at T286. This result indicated that PKC activators activate CaMKii via inhibition of K-Ras stemness.

Example 68: Effect of Compounds on Proliferation of A549

The diterpenoid compounds were tested in A549, a non-small cell lung cancer cell line harboring a K-Ras activating mutation. Briefly, A549 cells at a density of 1,000 cells/well were seeded in 96-well plates and incubated at 37° C. for 24 hours. A series of different concentrations of compound stocks (500×) were prepared by 3-fold serial dilution in DMSO. These compounds were further diluted in culture media and then added to cells so that the final DMSO concentration was not exceeding 0.25%. After 96 hours of incubation, 50 μL of CellTiter Glo reagent (Promega) was added to each well and luminescence was measured after 10 minutes using EnVision (PerkinElmer). Luminescence from cells treated with DMSO alone was set as Max and % of inhibition was calculated as follows: Inhibition %=(Max−Sample value)/Max×100. Data was analyzed using XL-fit software (ID Business Solutions Ltd.) and IC50, relative IC50, and % of top inhibition was calculated. The IC50 for growth inhibition of A549 lung cancer cell line is shown in Table 4. Some of the compounds in this disclosure were very potent in blocking proliferation of A549 lung cancer cells at low nM range. In addition, potency of inhibiting A549 proliferation correlated well with its binding affinity to PKCs for this series of compounds. In other words, higher affinity binders had stronger inhibitory effects on A549 proliferation. This further support the notion that activation, rather than inhibition, of certain PKC isoforms is required to block proliferation of cancer cells, some of which may harbor K-Ras mutations. This is in sharp contrast to previous literature and common belief that inhibition of PKC is necessary to block cancer cell growth (Kang, 2014, New Journal of Science, 2014:1-36). Data presented here is in agreement with recent findings that many loss-of-function but not gain-of-function mutations of PKC isoforms have been identified in many human cancers (Antal et al., 2015, Cell, 160:489-502). The IC50 values of the diterpenoid compounds against A549 cell line are as follows: A=≤0.001 uM, B=>0.001 uM and ≤0.01 uM, C=>0.01 uM, and ≤0.03 uM, D=>0.03 uM and ≤0.06 uM, E=>0.06 uM and ≤0.1 uM, F=>0.1 uM and ≤0.2 uM, G=>0.2 uM and ≤0.6 uM, H=>0.6 uM and ≤1.0 uM, I=>1.0 uM and ≤2.0 uM, J=>2 uM and ≤5 uM, K=>5 uM and ≤10 uM, L=>10 uM and ≤30 uM, and M=>30 uM).

TABLE 4

| Compound | IC50 μM (A549 Cell Line) |
|---|---|
| K101 or K101A (prostratin) | D |
| K103 (TPA) | A |
| K101-C13OH | M |
| K101-Epoxide | M |
| K101-DI-OH | M |
| K101-C1301 | D |
| K101-C1302 | C |
| K101-C1303 | H |
| K101-C1304 | D |
| K101-C1305 | M |
| K101-C1306 | M |
| K101-C1308 | E |
| K101-C1311 | F |
| K101-C1312 | D |
| K101-C1313 | E |
| K101-C1315 | I |
| K101-C1316 | H |
| K101-C1317 | H |
| K101-C1318 | F |
| K101-C1319 | E |
| K101-C1320 | G |
| K101-C1321 | D |
| K101-C1322 | J |
| K101-C1323 | J |
| K101-C1324 | C |
| K101-C1325 | I |
| K101-C1326 | M |
| K101-C1327 | E |
| K101-C1328 | G |
| K101-C1329 | E |
| K101-C1329-Cl | E |
| K101-C1330 | J |
| K101-C1331 | E |
| K101-C1332 | F |
| K101-C1333 | B |
| K101-C1334 | L |
| K101-C1335 | L |
| K101-C1336 | I |

TABLE 4-continued

| Compound | IC50 μM (A549 Cell Line) |
|---|---|
| K101-C1337 | G |
| K101-C1338 | K |
| K101-C1339 | K |
| K101-C1340 | L |
| K101-C1341 | L |
| K101-C1342 | E |
| K101-C1343 | I |
| K101-C1344 | I |
| K101-C1345 | C |
| K101-C1346 | G |
| K101-C1347 | B |
| K101-C134802 | B |
| K101-C134801 | C |
| K101-C134902 | D |
| K101-C134901 | G |
| K101-C1350 | H |
| K101-C1351 | G |
| K101-C1352 | K |
| K101-C1353 | I |
| K101-C1354 | G |
| K101-C1355 | J |
| K101-C135602 | F |
| K101-C135601 | G |
| K101-C1357 | J |
| K101-C1358 | I |
| K101-C135902 | C |
| K101-C135901 | E |
| K101-C136102 | B |
| K101-C136101 | C |
| K101-C1364 | G |
| K101-C1365 | H |
| K101-C137002 | F |
| K101-C137001 | F |
| K101-C137302 | L |
| K101-C137301 | L |
| K101-C1375 | E |
| K101-C134801C2003 | D |
| K101-C134802C2003 | C |

Note:
12-O-Tetradecanoylphorbol-13-acetate (TPA), also commonly known as tetradecanoylphorbol acetate, tetradecanoyl phorbol acetate, and phorbol 12-myristate 13-acetate (PMA).

Example 69: Effect of Compounds on Proliferation of Multiple Cancer Cell Lines The compounds in this disclosure were tested for their potency in blocking proliferation of a few other cancer cells lines, including K-Ras mutant pancreatic cell lines Panc2.13 and KP-4, leukemia cell line HL-60, and lymphoma cell lines Namalwa and Mino. Similar procedures as in Example 67 were followed. Initial cell numbers seeded in 96-well plates were different for different cell lines: 3000 cells/well for Panc2.13; 800-1000 cells/well for KP-4; 5000 cells/well for HL-60; 5000-10000 cells/well for Namalwa and Mino. The IC50 data are shown in Table 5 below. A ratio ratio of (IC50 of K01)/(IC50 of compound) (data in parenthesis in Table 5) was used to normalize the compound potency from different assay batches to a common comparator K2.1. The IC50 and Ratio Data for Various Cell Lines are as follows: A=≤0.001 uM, B=>0.001 uM and ≤0.01 uM, C=>0.01 uM, and 0.03 uM, D=>0.03 uM and ≤0.06 uM, E=>0.06 uM and 0.1 uM, F=>0.1 uM and ≤0.2 uM, G=>0.2 uM and ≤0.6 uM, H=>0.6 uM and ≤1.0 uM, I=>1.0 uM and ≤2.0 uM, J=>2 uM and ≤5 uM, K=>5 uM and ≤10 uM, L=>10 uM and ≤30 uM, and M=>30 uM

TABLE 5

| | IC50 in μM (ratio*) | | | | |
|---|---|---|---|---|---|
| Compound ID | Panc2.13 (Pancreatic) | KP-4 (Pancreatic) | HL-60 (Leukemia) | Namalwa (Lymphoma) | Mino (Lymphoma) |
| K101 | H (1) | G (1) | G (1) | E (1) | E (1) |
| K101-C1301 | NT | NT | D (9.23) | D (1.73) | B (11) |
| K101-C1302 | NT | NT | B (72) | B (13.8) | A (75) |
| K101-C1304 | NT | NT | C (18) | C (3.29) | B (15.6) |
| K101-C1321 | NT | NT | E (5.71) | D (1.15) | C (5.36) |
| K101-C1324 | NT | NT | C (32.7) | B (8.63) | B (37.5) |
| K101-C1303 | I (0.75) | H (0.67) | G (0.9) | G (0.19) | F (0.57) |
| K101-C1308 | F (6.29) | F (4.18) | E (5.29) | D (1.38) | C (6.82) |
| K101-C1318 | G (4.28) | F (3.29) | F (3.21) | E (0.93) | C (3.18) |
| K101-C1319 | G (3.65) | F (3.54) | D (1.79) | D (1.53) | C (6) |
| K101-C1327 | F (7.1) | F (4.18) | D (2.32) | D (2.03) | B (7.33) |
| K101-C1329 | F (5.82) | E (4.6) | D (1.79) | D (1.6) | C (5.5) |
| K101-C1333 | B (157) | B (135) | B (80) | B (20.9) | A (82.5) |
| K101-C1342 | F (6.79) | E (5.75) | D (6.43) | D (1.68) | C (6.2) |
| K101-C1345 | D (20.5) | C (20.3) | C (27.7) | B (7.42) | B (33) |
| K101-C1347 | C (71.7) | B (48.4) | B (16.2) | B (18.2) | B (52.2) |
| K101-C134801 | E (13.4) | D (8.52) | C (4.43) | C (4.93) | B (21.3) |
| K101-C134802 | C (57.3) | B (50) | B (12.1) | B (16.1) | B (52.2) |
| K101-C134901 | NT | NT | F (2.75) | F (0.49) | C (3.88) |
| K101-C134902 | NT | NT | C (12) | C (3.5) | B (15.7) |

NT = Not tested

Example 70: Sphere Formation Assay to Assess Effect of Compounds on Cancer Stemness A group of diterpenoid compounds of the present disclosure were tested to assess their effects on blocking formation of spheres from cancer cell lines such as PANC1, a K-Ras mutant pancreatic cell line. Briefly, PANC1 cells were harvested, re-suspended as single cell suspensions, counted and seeded into Ultra Low Attachment Culture 96-well plate (Corning, Cat #3474) at 100 cells/well in 100 μl of complete media (with 10% FBS) containing 2% Matrigel (Corning, Cat #354234) and DMSO or compounds. Six replicates per condition were seeded. The seeded cells were placed in the 37° C. tissue culture incubator. 10 μl of low serum containing media (with 0.1% FBS) was added to each well every week. Spheres formed after 3-4 weeks were counted. Sphere forming efficiency was expressed as percentage of # of spheres/# of cells seeded.

The results are shown in FIGS. 6A-6D. All compounds showed dose-dependent inhibition of sphere formation from PANC1 single cell suspension. K101 or K101A is prostratin. Compounds exhibiting at least 50% inhibition on the sphere forming efficiency: K101-C1347 and K101-C134802 at a concentration of ≤50 nM; K101-C1308, K101-C1329, K101-C1345, and K101-C134801 at a concentration of ≤150 nM; K101 at a concentration of ≤500 nM; and K101-C1346 and K101-C1319 at a concentration of ≤1500 nM.

Example 71: Testing Compounds in Animals—Pharmacokinetic Studies

Pharmacokinetic (PK) studies were conducted for compounds described in this disclosure, and the PK study of K101-C1327 administered by intravenous injection in rats is given as an example. Briefly, K101-C1327 was dissolved in a pH 5 buffer solution at the concentrations of 2.0 mg/mL, and diluted to 0.04 and 0.08 mg/mL to achieve the doses of 0.1 and 0.2 mg/kg with a dosing volume of 2.5 mL/kg, respectively. The K101-C1327 dosing solutions were administered via intravenous bolus injection in 3 rats (Sprague Dawley). Plasma samples were taken at 1 minute, 5 minutes, 15 minutes, 30 minutes, 1 hour, 2 hours, 4 hours, 7 hours, and 24 hours. The drug concentrations at each time point were determined by LC-MS. The results of drug concentrations and pharmacokinetic parameters are presented in the Table 6 and Table 7, respectively, below.

TABLE 6

K101-C1327 Concentration in plasma after bolus injection in rats
K101-C1327 Concentration (ng/mL) in Rat Plasma after Bolus Injection

| Time post dose | Dose 0.1 mg/kg | | Dose 0.2 mg/kg | |
|---|---|---|---|---|
| (hour) | Mean (ng/mL) | SD | Mean (ng/mL) | SD |
| 0.0167 | 216.0 | 50.0 | 334.0 | 107.0 |
| 0.0833 | 49.2 | 9.7 | 102.0 | 31.0 |
| 0.25 | 28.7 | 7.7 | 65.0 | 17.0 |
| 0.5 | 19.4 | 3.7 | 43.6 | 19.9 |
| 1 | 14.6 | 0.6 | 37.6 | 17.1 |
| 2 | 5.0 | 0.8 | 29.1 | 17.8 |
| 4 | 1.0 | NA | 6.0 | NA |
| 7 | <1 | NA | <1 | NA |
| 24 | <1 | NA | <1 | NA |

TABLE 7

PK parameters for K101-C1327 in rat plasma after bolus injection

| Dose | $t_{1/2}$ (hr) | $C_0$ (ng/mL) | $AUC_{last}$ (hr*ng/mL) | $V_z$ (L/kg) | $V_{ss}$ (L/kg) | CL (mL/min/kg) | $MRT_{Inf}$ (hr) |
|---|---|---|---|---|---|---|---|
| 0.1 mg/kg | 0.857 | 314 | 48.3 | 2.44 | 1.73 | 32.9 | 0.873 |
| 0.2 mg/kg | 2.29 | 450 | 119 | 3.25 | 2.77 | 21.5 | 2.93 |

Figure 7:
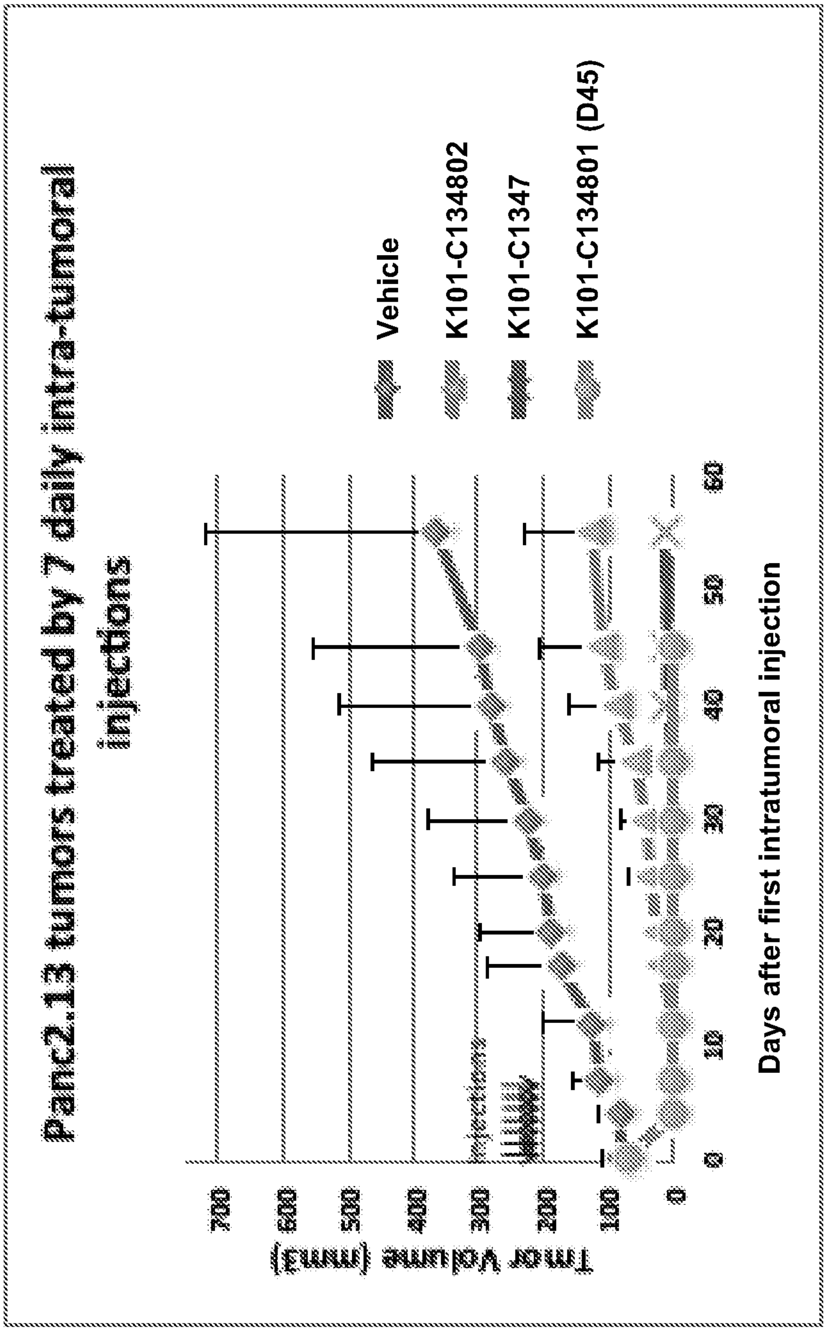
FIG. 7 shows effect of intratumoral administration (7 daily injections) of diterpenoid compounds into Panc2.13 tumors in mice with Panc2.13 pancreatic cancer cell line xenografts.

Example 71: Tumor Clearance in Xenograft Model by Intra-Tumoral (IT) Injected Compounds The antitumor efficacy of the compounds cited in this disclosure was tested in a xenograft model via intra-tumoral injection route. Immunodeficient (athymic) Nu/Nu mice were implanted at one flank subcutaneously with Panc2.13 pancreatic cancer cells. When tumors grew to 50-100 $mm^3$, each group of three mice was treated with seven daily intratumoral (IT) injections of vehicle (50% dimethyl sulfoxide (DMSO)/50% Poly(ethylene glycol) PEG400), K101-C1347 (4 mg/mL, 20 μl), K101-C134801 (20 mg/mL, 20 μl), or K101-C134802 (4 mg/mL, 20 μl). All groups tolerated drug treatments very well. Ulceration of tumor (and the skin covering the tumor) was observed for all compound-treated mice after one or two IT injections. Scabs formed after 1-2 weeks and the skin recovered with minimal scaring after 3-4 weeks. Tumor growth/re-growth on or near the injection site was monitored for up to 55 days. FIG. 7 shows tumor growth curves of various treatment groups. IT injection of K101-K134801 resulted in complete clearance of tumors in mice. K101-C1347 cleared tumors from two out of three mice and K101-C134802 cleared tumors from one out of three mice.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A compound of formula (II):

(II)

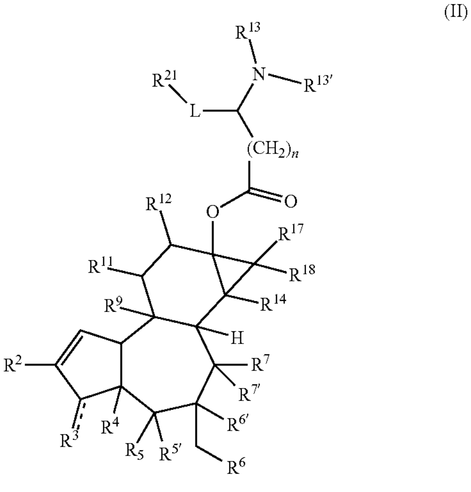

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or -$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^{5'}$ and $R^{6'}$ are H, or $R^{5'}$ and $R^{6'}$ form a bond or are bonded to a common O atom to form an epoxide ring as permitted by valency;

$R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^K$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

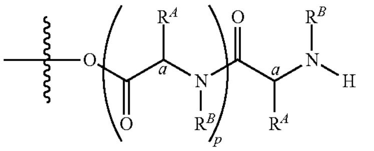

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{6'}$ and $R^{7'}$ are H, or $R^{6'}$ and $R^{7'}$ form a bond or are bonded to a common O atom to form an epoxide ring, as permitted by valency;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{12}$ is H, -OH, -$OC(O)R^f$, wherein $R^f$ is $C_1$-$C_{12}$alkyl, $C_2$-$C_{12}$alkenyl, —$C_0$-$C_{12}$aliphatic-$C_3$-$C_7$cycloalkyl, —$C_0$-$C_{12}$aliphatic-heterocycloalkyl, or —$C_0$-$C_{12}$aliphatic-heteroaryl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$-cycloalkyl, heterocyclyl, aryl, heteroaryl, spiro$C_5$-$C_{12}$ cycloalkyl, bridged bicyclyl, or adamantyl is optionally substituted with 1 to 3 of J1, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of J1;

$R^k$ is H or $M^+$ counterion;

$J^1$ is selected from OH, CN, halo, $C_1$-$C_4$alkyl, and halo$C_1$-$C_4$alkyl; and n is 0 or 1.

2. The compound of claim 1, having the structure of formula (II'):

(II')

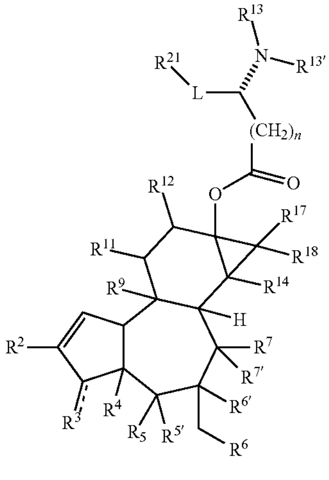

or a pharmaceutically acceptable salt, tautomer, or stereoisomer thereof.

3. The compound of claim 1, having the structure of formula (IIa):

(IIa)

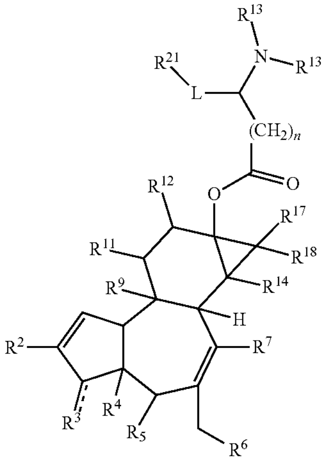

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

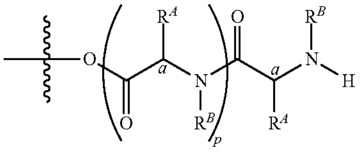

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —$OC(O)R^f$, wherein $R^f$ is $C_1$-$C_{12}$alkyl, $C_2$-$C_{12}$alkenyl, —$C_0$-$C_{12}$aliphatic-$C_3$-$C_7$cycloalkyl, —$C_0$-$C_{12}$aliphatic-heterocycloalkyl, or —$C_0$-$C_{12}$aliphatic-heteroaryl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiroC5-$C_{12}$ cycloalkyl, 5 to 12 membered bridged bicyclyl, adamantyl, or —C(O)OR, wherein the $C_3$-$C_7$cycloalkyl, heterocyclyl, aryl, heteroaryl, spiroC5-$C_{12}$ cycloalkyl, bridged bicyclyl, or adamantyl is optionally substituted with 1 to 3 of $J^1$, and wherein optionally 1 to 2 carbon atoms of the spiroC5-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

4. The compound of claim 3, having the structure of formula (IIa'):

(IIa')

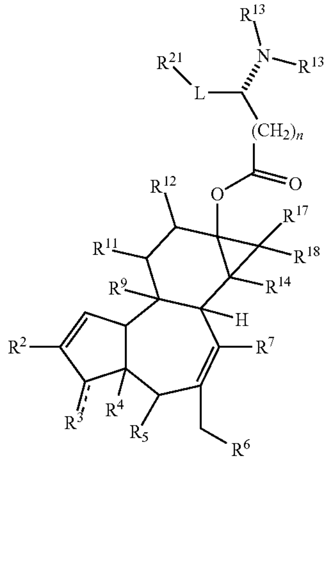

or a pharmaceutically acceptable salt, tautomer, or stereoisomer thereof.

5. The compound of claim 1, having the structure of formula (IIb):

(IIb)

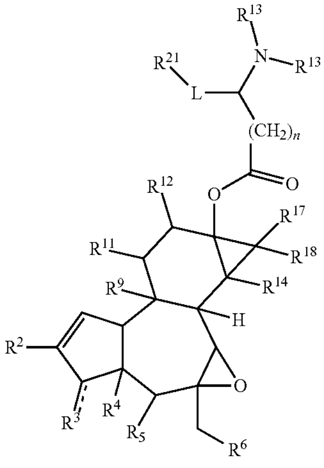

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or -$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —$OC(O)R^c$, wherein $R^e$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

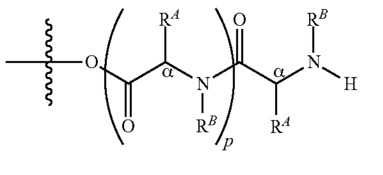

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^9$ is $OR^e$, wherein $R^e$ is H, $C_1$-$C_6$alkyl, or aryl;

$R^{11}$ is $C_1$-$C_4$alkyl;

$R^{12}$ is H, —OH, —$OC(O)R^f$, wherein $R^f$ is $C_1$-$C_{12}$alkyl, $C_2$-$C_{12}$alkenyl, —$C_0$-$C_{12}$aliphatic-$C_3$-$C_7$cycloalkyl, —$C_0$-$C_{12}$aliphatic-heterocycloalkyl, or —$C_0$-$C_{12}$aliphatic-heteroaryl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

6. The compound of claim 3, having the structure of formula (IIc):

(IIc)

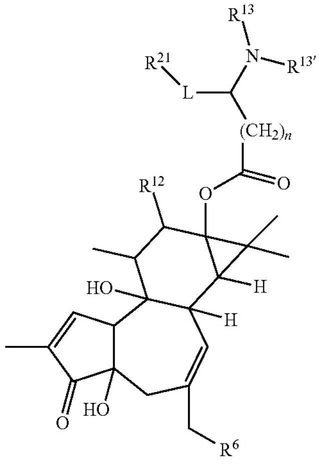

or a pharmaceutically acceptable salt, tautomer, or stereoisomer thereof;

wherein $R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

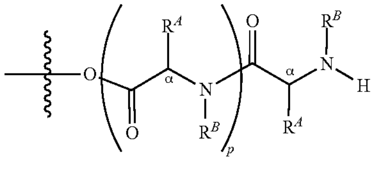

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{12}$ is H, —OH, —OC(O)$R^f$, wherein $R^f$ is $C_1$-$C_{12}$alkyl, $C_2$-$C_{12}$alkenyl, —$C_0$-$C_{12}$aliphatic-$C_3$-$C_7$cycloalkyl, —$C_0$-$C_{12}$aliphatic-heterocycloalkyl, or —$C_0$-$C_{12}$aliphatic-heteroaryl;

$R^{13}$ and $R^{13'}$ are each independently H or $C_1$-$C_4$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)O$R^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$; $R^k$ is H or $M^+$ counterion;

$J^1$ is selected from OH, CN, halo, $C_1$-$C_4$alkyl, and halo$C_1$-$C_4$alkyl; and n is 0 or 1.

7. The compound of claim 1 having the structure of formula (III):

(III)

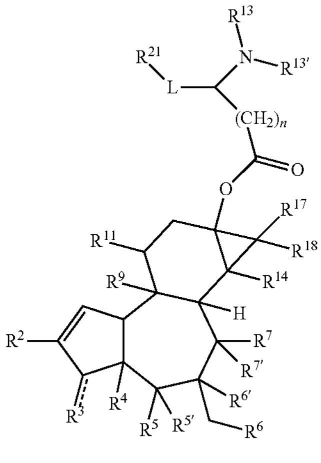

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —O$R^a$; wherein $R^a$ is H or —C(O)$R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —O$R^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^{5'}$ and $R^{6'}$ are H, or $R^{5'}$ and $R^{6'}$ form a bond or are bonded to a common O atom to form an epoxide ring as permitted by valency;

$R^6$ is OH, halo, or —OC(O)$R^c$, wherein $R^c$ is —$C_1$-$C_6$alkyl, —$C_1$-$C_6$alkyl-$(NR^{c1})_2$ or —$C_1$-$C_6$alkylC(O)O$R^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

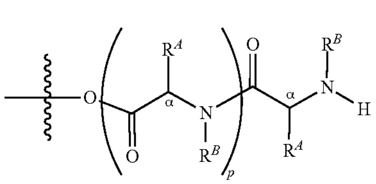

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{6'}$ and $R^{7'}$ are H, or $R^{6'}$ and $R^{7'}$ form a bond or are bonded to a common O atom to form an epoxide ring, as permitted by valency;

$R^7$ is H or OH;

$R^9$ is O$R^e$, wherein $R^e$ is H, $C_1$-$C_6$alkyl, or aryl;

$R^{11}$ is $C_1$-$C_4$alkyl;

$R^{13}$ and $R^{13'}$ are each independently H or $C_1$-$C_4$alkyl;

$R^{14}$ is H or O$R^g$; wherein $R^g$ is H or $C_1$-$C_6$alkyl;

$R^{17}$ and $R^{18}$ are each independently $C_1$-$C_4$alkyl or $C_1$-$C_4$alkyl-O$R^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)O$R^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

8. The compound of claim 7 having the structure of formula (III'):

(III')

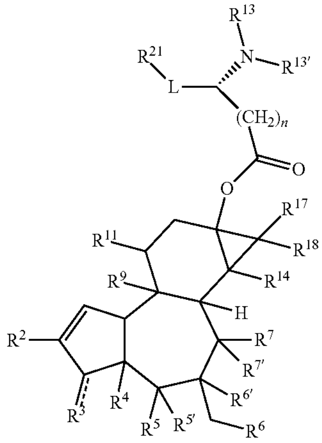

or a pharmaceutically acceptable salt, tautomer, or stereoisomer thereof.

9. The compound of claim 7 having the structure of formula (IIIa):

(IIIa)

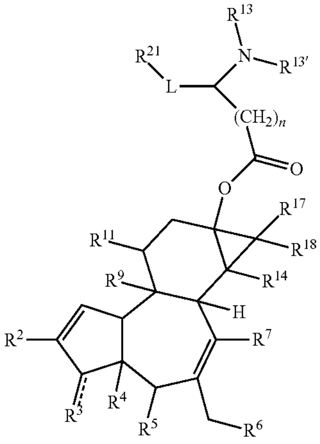

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —C(O)$R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —OC(O)$R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

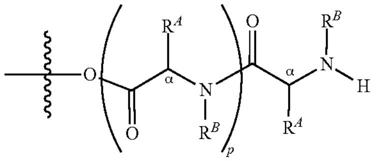

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^7$ is H or OH;

$R^9$ is $OR^e$, wherein $R^e$ is H, $C_1$-$C_6$alkyl, or aryl;

$R^{11}$ is $C_1$-$C_4$alkyl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —C(O)$OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

10. The compound of claim 7 having structure of formula (IIIb):

(IIIb)

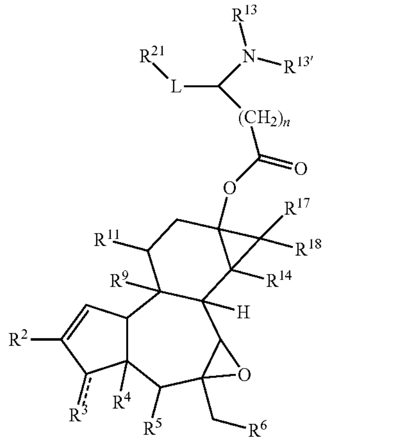

or a pharmaceutically acceptable salt, tautomer, or stereoisomer thereof;

wherein $R^2$ is a $C_1$-$C_4$alkyl;

$R^3$ is O double bonded to the ring carbon when ( - - - ) is a bond, or —$OR^a$; wherein $R^a$ is H or —$C(O)R^{a1}$, wherein $R^{a1}$ is $C_1$-$C_6$alkyl, $C_2$-$C_6$alkenyl, $C_0$-$C_6$alkylaryl, or $C_0$-$C_6$alkylheteroaryl;

$R^4$ and $R^5$ are each independently H or —$OR^b$, wherein $R^b$ is H, $C_1$-$C_6$alkyl, $C_2$-$C_6$alkenyl, $C_0$-$C_6$alkylaryl, or $C_0$-$C_6$alkylheteroaryl;

$R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

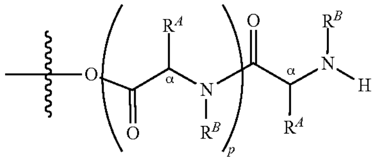

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^9$ is $OR^e$, wherein $R^e$ is H, $C_1$-$C_6$alkyl, or aryl;

$R^{11}$ is $C_1$-$C_4$alkyl;

$R^{13}$ and $R^{13'}$ are each independently H or $C_1$-$C_4$alkyl;

$R^{14}$ is H or $OR^g$; wherein $R^g$ is H or $C_1$-$C_6$alkyl;

$R^{17}$ and $R^{18}$ are each independently $C_1$-$C_4$alkyl or $C_1$-$C_4$alkyl-$OR^h$, wherein $R^h$ is H or $C_1$-$C_6$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

11. The compound of claim 7 having the structure of formula (IIIc):

(IIIc)

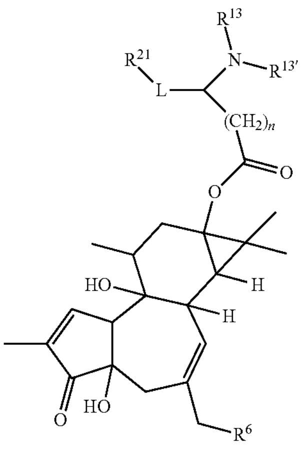

or a pharmaceutically acceptable salt, tautomer, or stereoisomer thereof;

wherein $R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

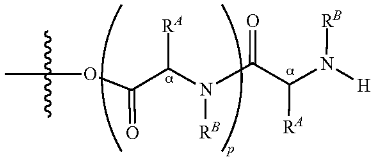

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

$R^{13}$ and $R^{13'}$ are each independently H or $C_1$-$C_4$alkyl;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion;

$J^1$ is selected from OH, CN, halo, $C_1$-$C_4$alkyl, and halo$C_1$-$C_4$alkyl; and n is 0 or 1.

12. The compound of claim 11 having the structure of formula (IIIe):

(IIIe)

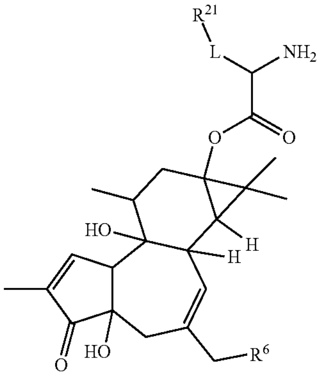

or a pharmaceutically acceptable salt, tautomer, or stereoisomer thereof;

wherein $R^6$ is OH, halo, or —$OC(O)R^c$, wherein $R^c$ is —$C_1$-$C_6$alkyl, —$C_1$-$C_6$alkyl-$(NR^{c1})_2$ or —$C_1$-$C_6$alkylC(O)$OR^k$, $R^{c1}$ is H, $C_1$-$C_6$alkyl, or two $R^{c1}$ together with the N atom form a 5 to 7 membered heterocyclyl containing 1 to 3 heteroatoms selected from N, O, and S; or $R^6$ is

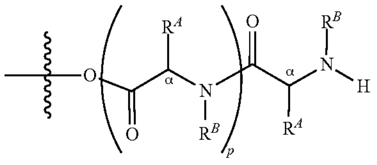

wherein, each occurrence of $R^A$ is independently selected from a side chain of a natural or non-natural amino acid, wherein each occurrence of $R^A$ is same or different;

each occurrence of $R^B$ is independently H, or $R^B$ together with the adjacent $R^A$ and the N atom to which it is attached form a heterocyclic ring of a natural or non-natural amino acid, wherein each occurrence of $R^B$ is same or different; and p is 0, 1, or 2;

L is absent, $C_1$-$C_{12}$alkylene, or $C_2$-$C_{12}$alkenylene, wherein the $C_1$-$C_{12}$alkylene or $C_2$-$C_{12}$alkenylene is optionally substituted with $C_1$-$C_4$alkyl;

$R^{21}$ is H, —$S(O)_2R^j$, —$SR^j$, —$N(R^j)_2$, —$Si(R^j)_3$, $C_3$-$C_7$cycloalkyl, heterocyclyl, aryl, heteroaryl, spiro$C_5$-$C_{12}$ cycloalkyl, 5 to 12 membered bridged bicyclyl, adamantyl, or —$C(O)OR^k$, wherein the $C_3$-$C_7$cycloalkyl, heterocyclyl, aryl, heteroaryl, spiro$C_5$-$C_{12}$ cycloalkyl, bridged bicyclyl, or adamantyl is optionally substituted with 1 to 3 of $J^1$, and wherein optionally 1 to 2 carbon atoms of the spiro$C_5$-$C_{12}$cycloalkyl or bridged bicyclyl is replaced with a heteroatom selected from N, O and S, and optionally substituted with $C_1$-$C_4$alkyl, or when an N atom is present an N-protecting group;

each $R^j$ is independently $C_1$-$C_6$alkyl, $C_2$-$C_6$alkenyl, $C_0$-$C_6$alkyl$C_3$-$C_7$cycloalkyl, $C_0$-$C_6$alkylheterocyclyl, $C_0$-$C_6$alkylaryl, or $C_0$-$C_6$alkylheteroaryl, wherein the $C_3$-$C_7$cycloalkyl, heterocyclyl, alkylaryl, or heteroaryl is optionally substituted with 1 to 3 of $J^1$;

$R^k$ is H or $M^+$ counterion; and $J^1$ is selected from OH, CN, halo, $C_1$-$C_4$alkyl, and halo$C_1$-$C_4$alkyl.

13. The compound of claim 1, wherein $R^{21}$ is $C_3$-$C_7$cycloalkyl, wherein the $C_3$-$C_7$cycloalkyl is optionally substituted with 1 to 3 of $J^1$.

14. The compound of claim 13, wherein the $C_3$-$C_7$cycloalkyl is selected from the group consisting of cyclobutyl, cyclopentyl, cyclohexyl, and cycloheptyl, wherein the $C_3$-$C_7$cycloalkyl is optionally substituted with 1 to 3 of $J^1$.

15. The compound of claim 1, wherein $R^{21}$ is heterocyclyl, wherein the heterocyclyl is optionally substituted with 1 to 3 of $J^1$.

16. The compound of claim 15, wherein the heterocyclyl is selected from the group consisting of oxiranyl, oxetanyl, azetidynyl, oxazolyl, thiazolidinyl, thiazolyl, morpholinyl, pyrrolidinonyl, pyrrolidinyl, piperidinyl, piperazinyl, 2,3-dihydrofuranyl, dihydropyranyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and azapanyl, wherein the heterocyclyl is optionally substituted with 1 to 3 of $J^1$.

17. The compound of claim 1, wherein $R^{21}$ is aryl, wherein the aryl is optionally substituted with 1 to 3 of $J^1$.

18. The compound of claim 17, wherein $R^{21}$ is a phenyl or naphthyl, wherein the phenyl or naphthyl is optionally substituted with 1 to 3 of $J^1$.

19. The compound of claim 1, wherein $R^{21}$ is heteroaryl, wherein the heteroaryl is optionally substituted with 1 to 3 of $J^1$.

20. The compound of claim 19, wherein the heteroaryl is selected from the group consisting of pyrrolyl, pyrazolyl, imidazolyl, pyrazinyl, oxazolyl, isoxazolyl, thiazolyl, furyl, thienyl, pyridyl, pyrimidyl, benzoxazolyl, benzothiazolyl, purinyl, benzimidazolyl, indolyl, isoquinolyl, quinoxalinyl, and quinolyl, wherein the heteroaryl is optionally substituted with 1 to 3 of $J^1$.

21. The compound of claim 1, wherein $R^{21}$ is adamantyl, wherein the adamantyl is optionally substituted with OH, halo, or $C_1$-$C_4$alkyl.

22. The compound of claim 1, wherein $R^{21}$ is spiro$C_5$-$C_{12}$ cycloalkyl, wherein the spiro$C_5$-$C_{12}$ cycloalkyl has 0-2 carbon atoms replaced with 0-2 heteroatoms selected from N, O and S, and is optionally substituted with 1 to 3 of $J^1$ or when an N atom is present an N-protecting group.

23. The compound of claim 1, wherein $R^{21}$ is 5 to 12 membered bridged bicyclyl, wherein the bridged bicyclyl has 0-2 carbon atoms replaced with 0-2 heteroatoms selected from N, O or S, and is optionally substituted with 1 to 3 of $J^1$, or when an N atom is present an N-protecting group.

24. The compound of claim 1, wherein $R^{21}$ is selected from:

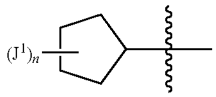,
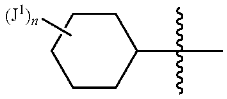,
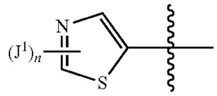,
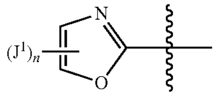,
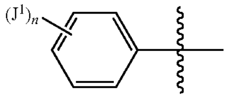,
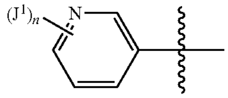,
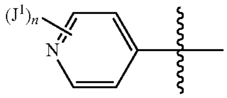,
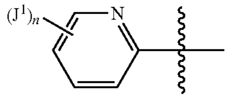,
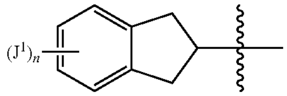,
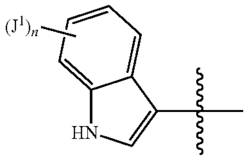,
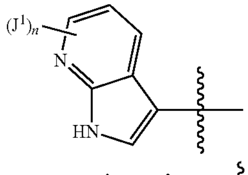,
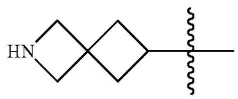,
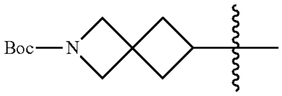,
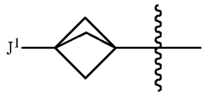,
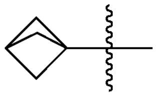
and
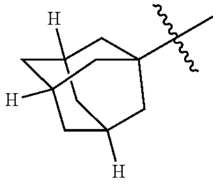, wherein $J^1$ is OH, CN, halo, $C_1$-$C_4$alkyl, and halo$C_1$-$C_4$alkyl, and n is 0-3.

25. The compound of claim 1, wherein L is $C_1$-$C_6$alkylene, $C_3$-$C_6$alkylene or $C_3$-$C_{12}$alkylene.

26. The compound of claim 1, wherein L is $C_1$-$C_6$alkenylene, $C_3$-$C_6$alkenylene or $C_3$-$C_{12}$alkenylene.

27. The compound of claim 1, wherein n is 0.

28. The compound of claim 1, wherein:

$R^6$ is

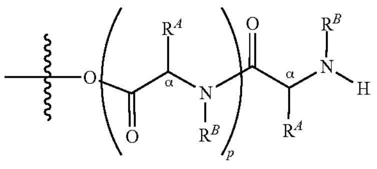

wherein, each occurrence of $R^A$ is independently selected from a side chain of a natural or non-natural amino acid, wherein each occurrence of $R^A$ is same or different;

each occurrence of $R^B$ is independently H, or $R^B$ together with $R^A$ and the N atom to which it is attached form a heterocyclic ring of a natural or non-natural amino acid, wherein each occurrence of $R^B$ is same or different; and p is 0, 1, or 2.

29. The compound of claim 28, wherein each $R^A$ is independently hydrogen (glycine), methyl (alanine), propan-2-yl (valine), propan-1-yl (norvaline), 2-methylpropan-1-yl (leucine), 1-methylpropan-1-yl (isoleucine), butan-1-yl (norleucine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 3-guanidinopropan-1-yl (arginine), or 3-ureido-propan-1-yl (citrulline);

each $R^B$ is H, or $R^B$ together with the adjacent $R^A$ and the N atom form a prolyl side chain:

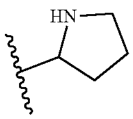;

and p is 0, 1 or 2.

30. The compound of claim 29, wherein:

each $R^A$ is independently methyl (alanine), propan-2-yl (valine), 2-methylpropan-1-yl (leucine), imidazol-4-ylmethyl (histidine), hydroxymethyl (serine), 1-hydroxyethyl (threonine), carbamoylmethyl (asparagine), 2-carbamoylethyl (glutamine), 4-aminobutan-1-yl (lysine), carboxymethyl (aspartic acid), 3-guanidinopropan-1-yl (arginine), benzyl (phenylalanine), or 4-aminobutan-1-yl (lysine);

$R^B$ is H; and p is 0, 1, or 2.

31. The compound of claim 29, wherein each $R^A$ is independently propan-2-yl (valine), 2-methyl-propan-1-yl (leucine), carboxymethyl (aspartic acid), benzyl (phenylalanine), or 4-aminobutan-1-yl (lysine);

each $R^B$ is H; and p is 0, 1, or 2.

32. The compound of claim 29, wherein p is 1;

first of $R^A$ is propan-2-yl (valine) and second of $R^A$ is propan-2-yl (valine); and each of $R^B$ is H (dipeptide Val-Val); or first of $R^A$ is 2-methylpropan-1-yl (leucine), and second of $R^A$ is 2-methylpropan-1-yl (leucine); and each of $R^B$ is H (dipeptide Leu-Leu); or first of $R^A$ is methyl (alanine) and second of $R^A$ is methyl (alanine); and each of $R^B$ is H (dipeptide Ala-Ala); or first of $R^A$ is 4-aminobutan-1-yl (lysine); second of $R^A$ is 4-aminobutan-1-yl (lysine); and each of $R^B$ is H (dipeptide Lys-Lys); or first of $R^A$ is hydrogen; second of $R^A$ is 4-aminobutan-1-yl, and each of $R^B$ is H (dipeptide Gly-Lys).

33. The compound of claim 28, wherein each of the a-carbon of the amino acid other than glycine is in the L or D configuration.

34. A pharmaceutical composition comprising a compound of claim 4, and a pharmaceutically acceptable carrier.

35. The compound of claim 1 selected from the group consisting of the compounds listed below:

K101-C1303

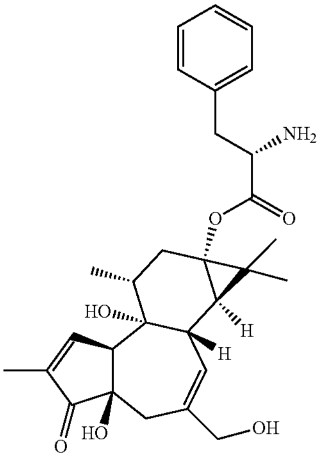

K101-C1317

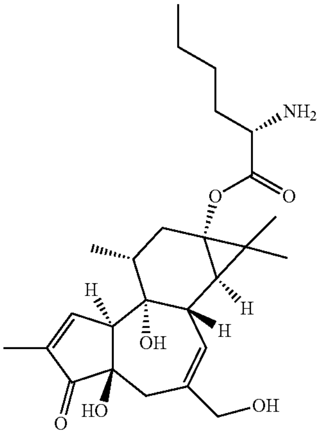

-continued

K101-C1318

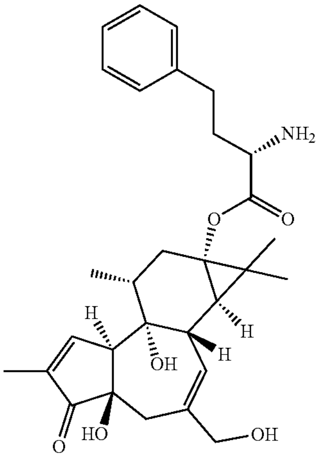

K101-C1319

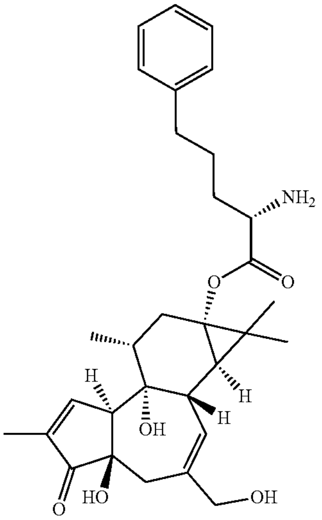

K101-C1325

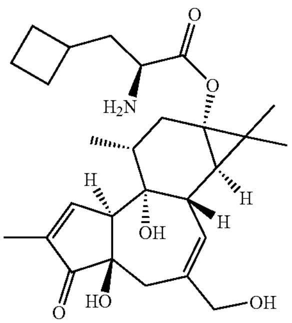

-continued
K101-C1326
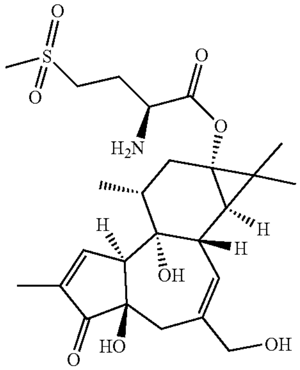
K101-C1327
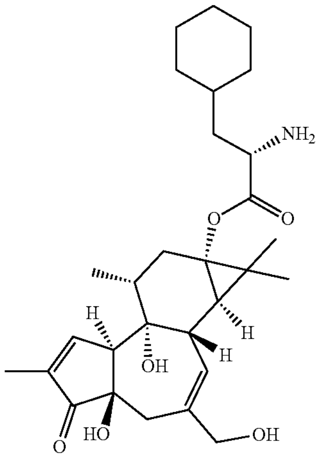
K101-C1328
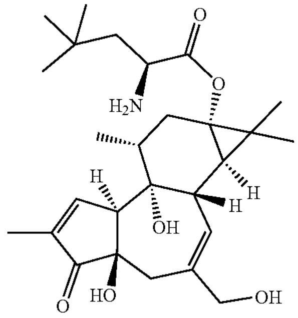
K101-C1329
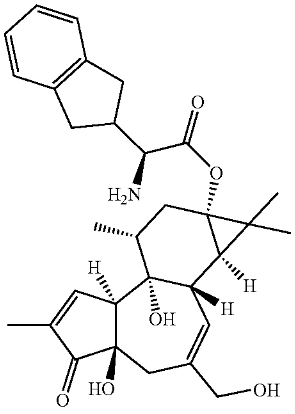
-continued
K101-C1329-Cl
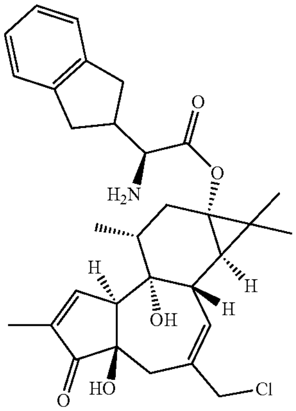
K101-C1330
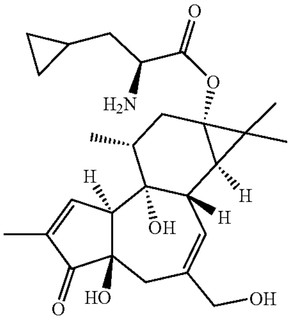
K101-C1331
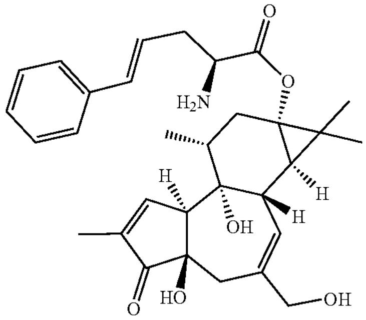
K101-C1332
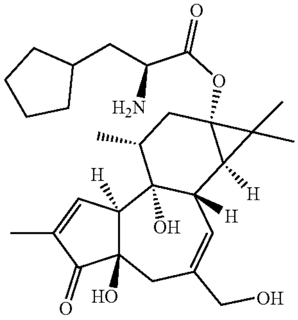

-continued
K101-C1336
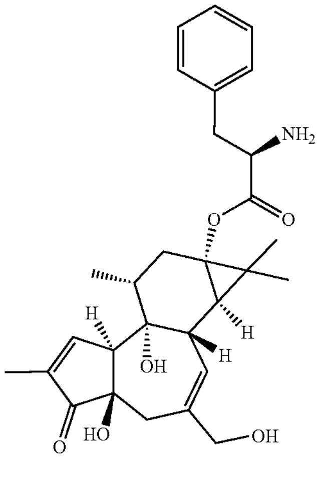
K101-C1337
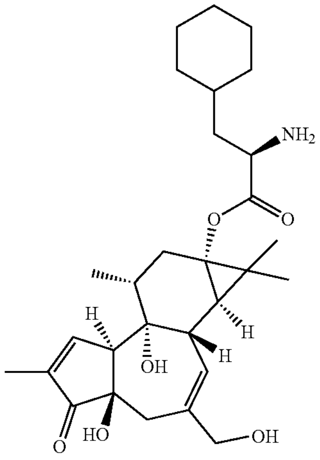
K101-C1338
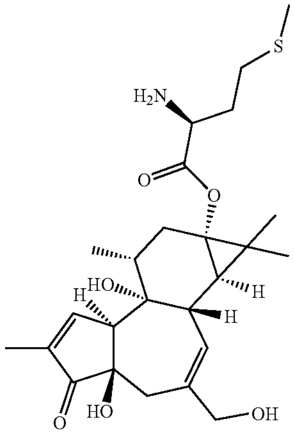
-continued
K101-C1339
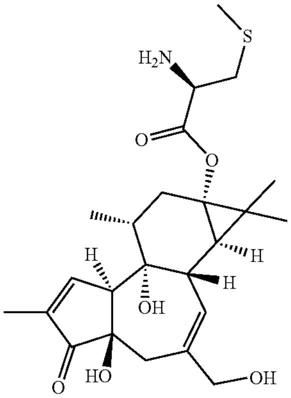
K101-C1340
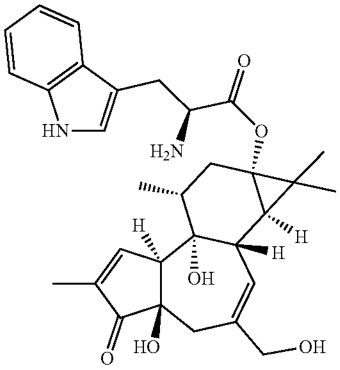
K101-C1341
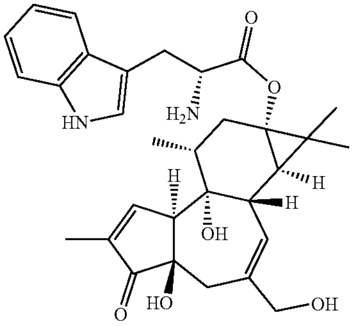
K101-C1342
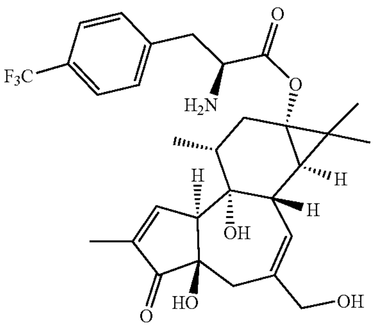

-continued
K101-C1343
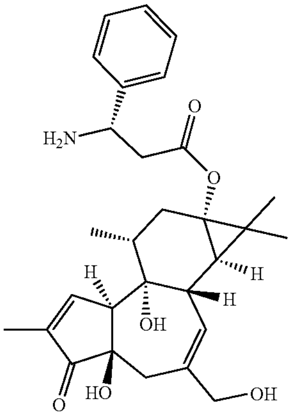
K101-C1344
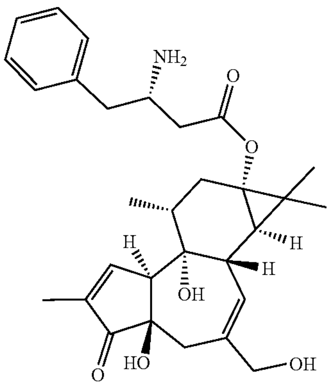
K101-C1345
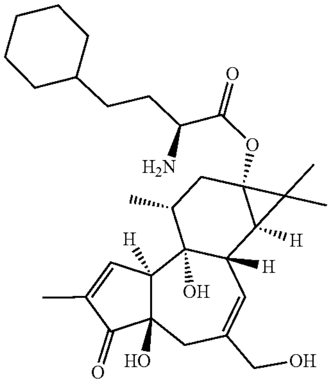
K101-C1346
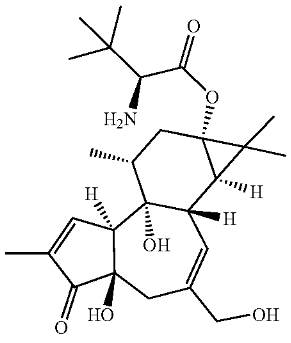
-continued
K101-C1347
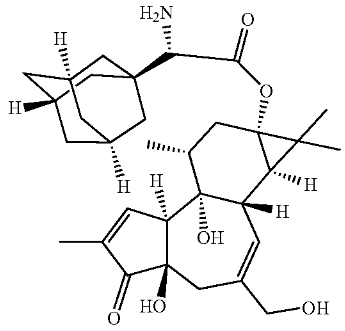
K101-C1348
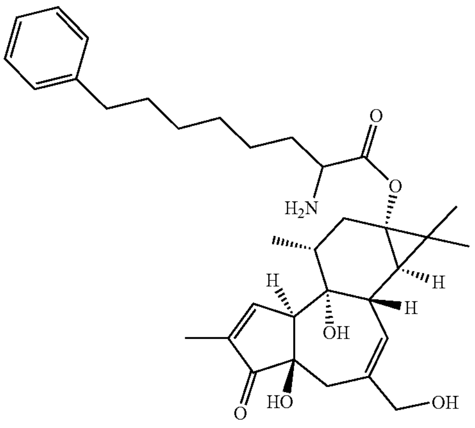
K101-C134802
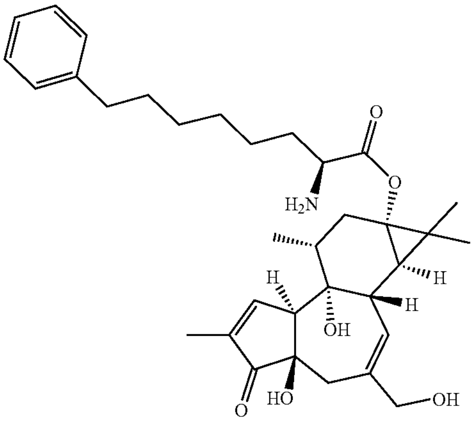

-continued
K101-C134801
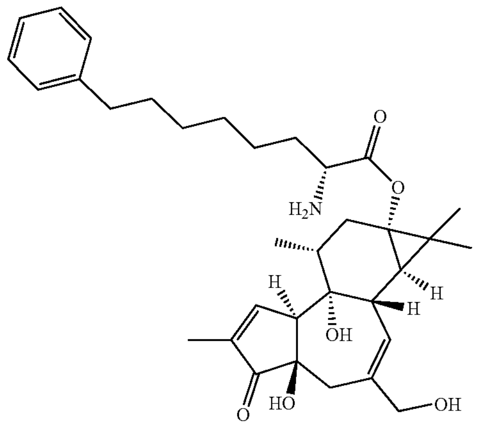
K101-C1349
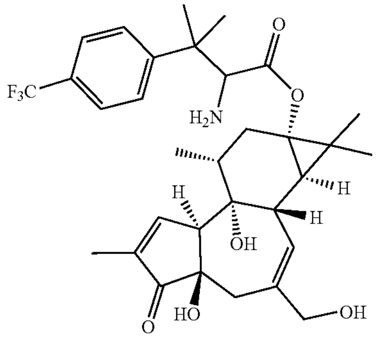
K101-C134901
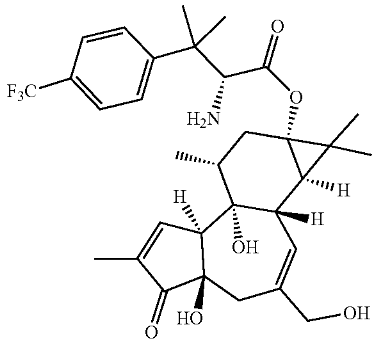
K101-C134902
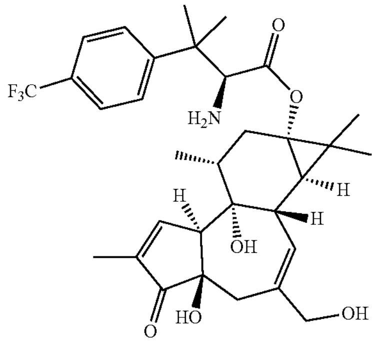
-continued
K101-C1350
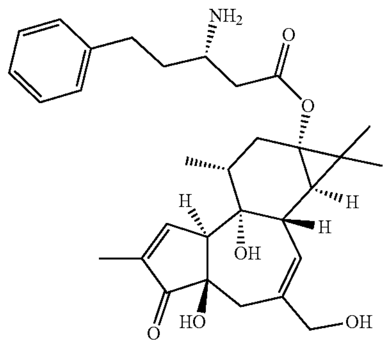
K101-C1351
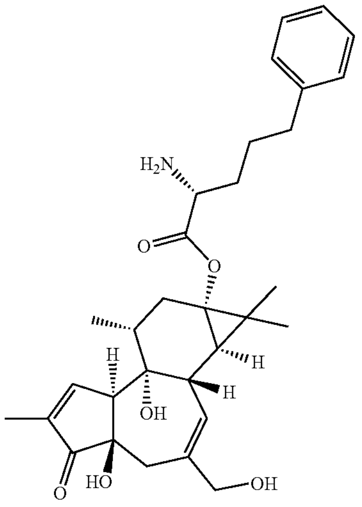
K101-C135601
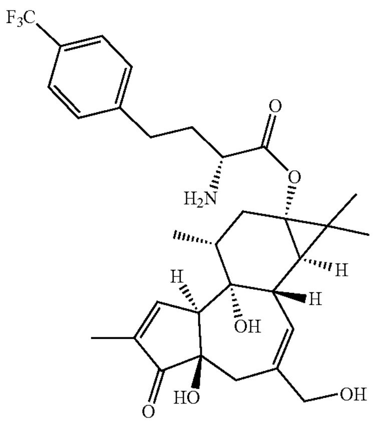

-continued
K101-C135602
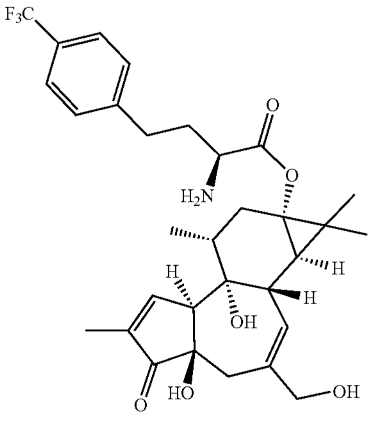
K101-C1357
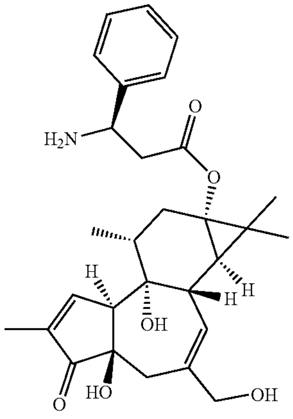
K101-C1358
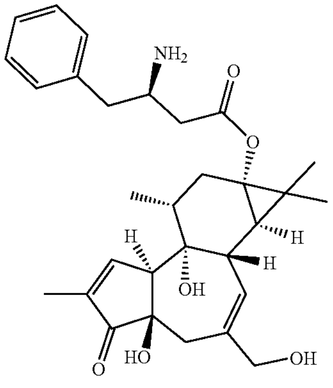
K101-C1359
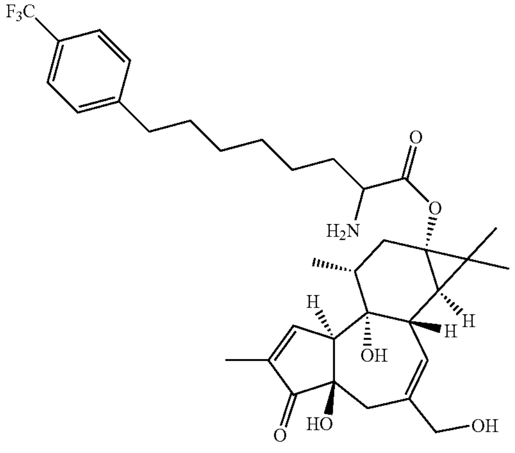
K101-C135901
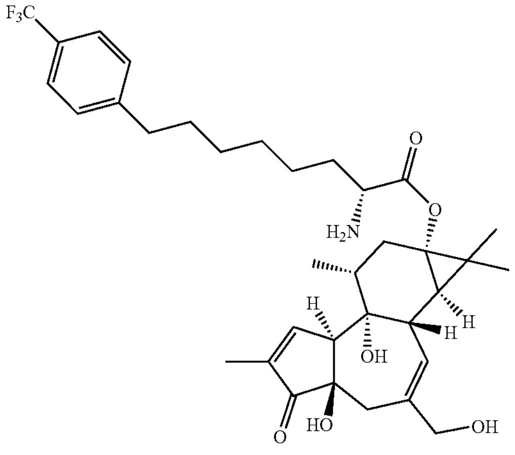
K101-C135902
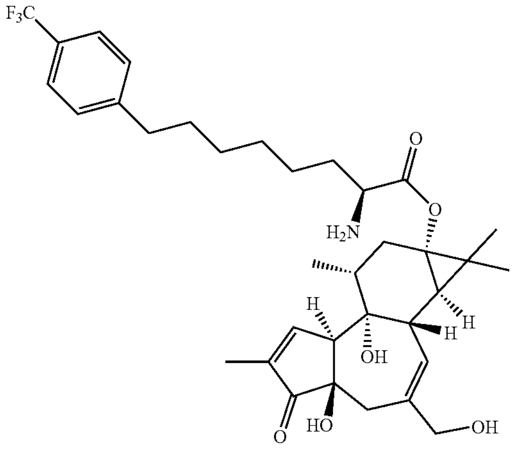

-continued
K101-C1361
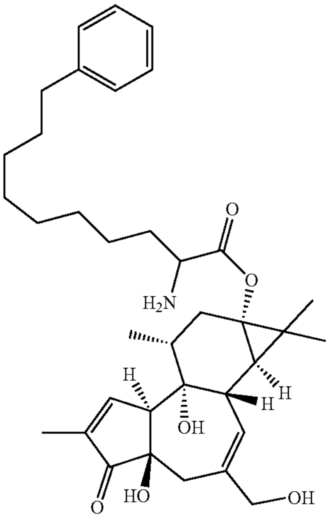
K101-C136101
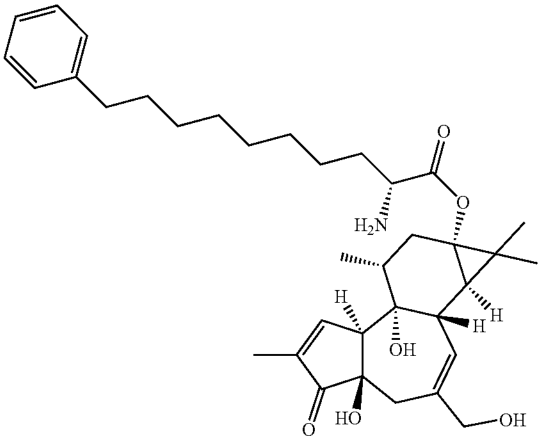
K101-C136102
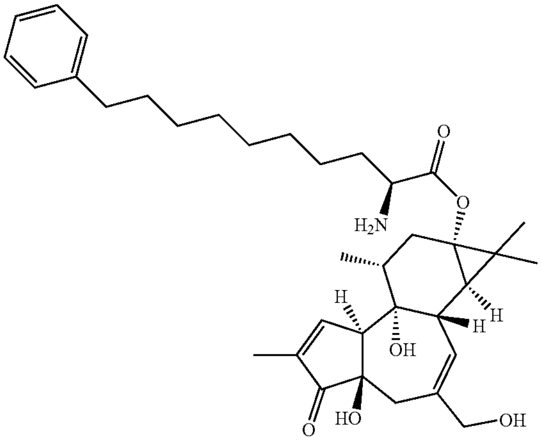
-continued
K101-C1364
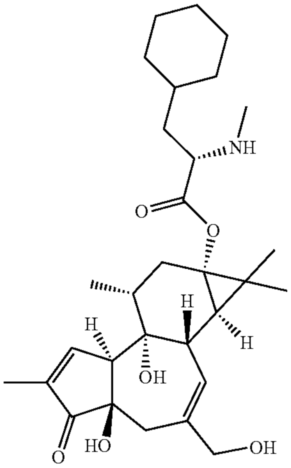
K101-C1365
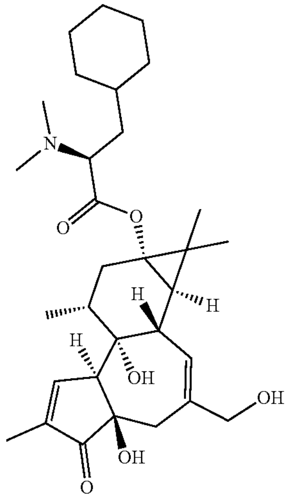
K101-C1370
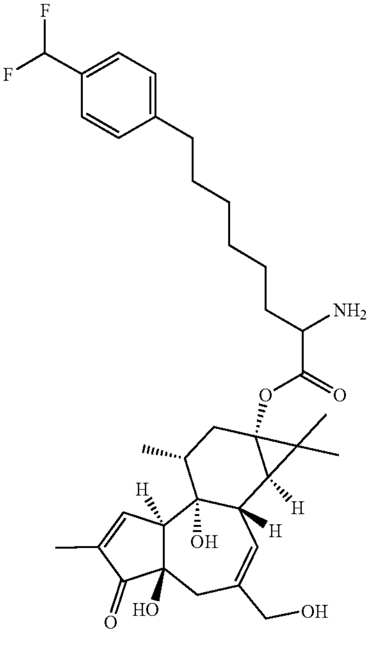

-continued
K101-C137001
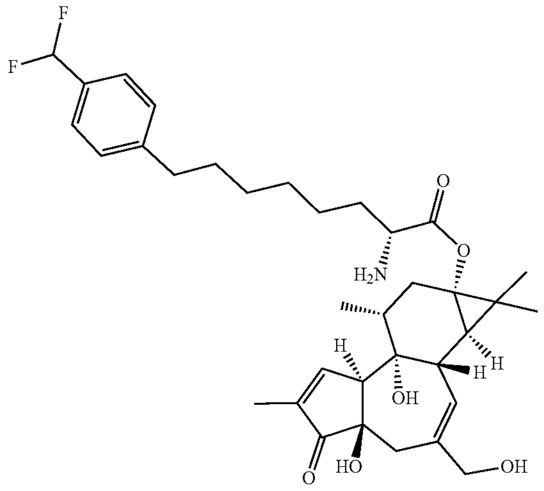
K101-C137002
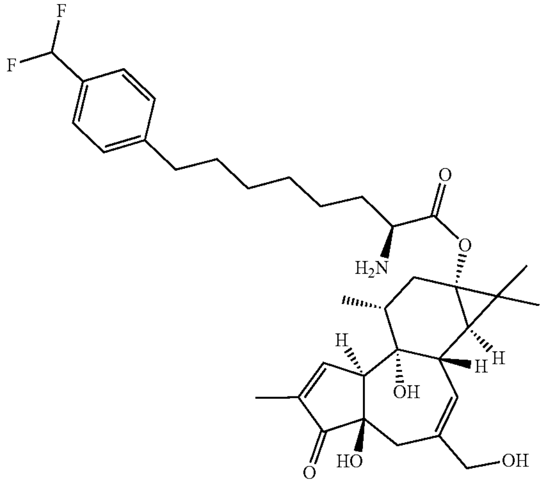
K101-C1373
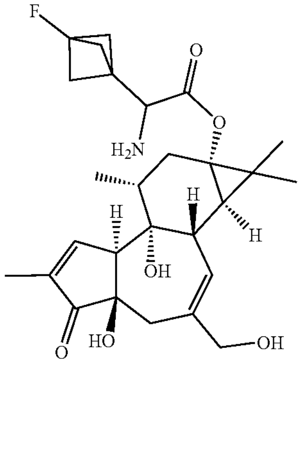
-continued
K101-C137301
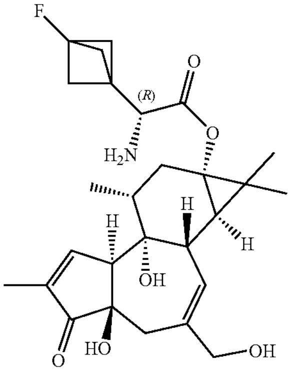
K101-C137302
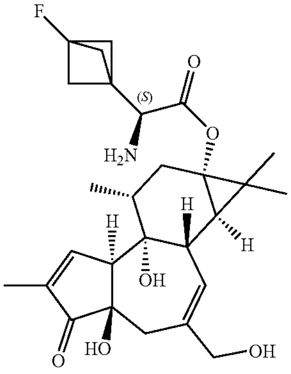
K101-C1375
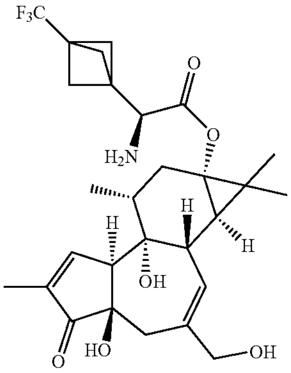

-continued
K101-C134801C2003
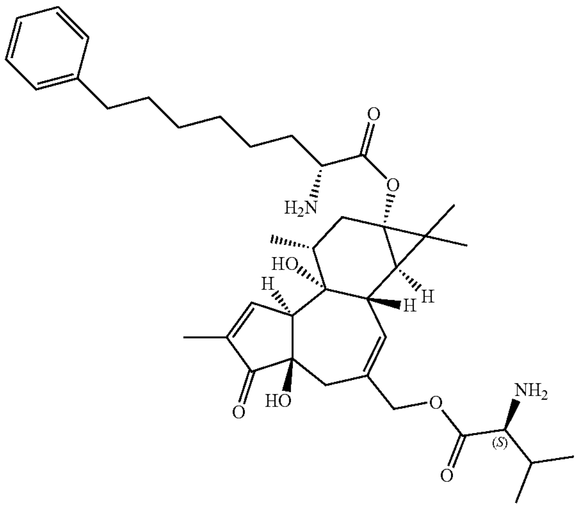
or an amino acid prodrug thereof.
* * * * *